US012661353B2

(12) United States Patent
Dikstein et al.

(10) Patent No.: US 12,661,353 B2
(45) Date of Patent: Jun. 23, 2026

(54) SPT5 INHIBITORS AND USES THEREOF

(71) Applicant: Yeda Research and Development Co. Ltd., Rehovot (IL)

(72) Inventors: Rivka Dikstein, Rehovot (IL); Anat Bahat, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 1139 days.

(21) Appl. No.: 17/401,378

(22) Filed: Aug. 13, 2021

(65) Prior Publication Data

US 2021/0379060 A1 Dec. 9, 2021

Related U.S. Application Data

(63) Continuation of application No. PCT/IL2020/050171, filed on Feb. 14, 2020.

(51) Int. Cl.

| | |
|---|---|
| ***A61K 31/50*** | (2006.01) |
| ***A61K 31/12*** | (2006.01) |
| ***A61K 31/18*** | (2006.01) |
| ***A61K 31/27*** | (2006.01) |
| ***A61K 31/35*** | (2006.01) |
| ***A61K 31/381*** | (2006.01) |
| ***A61K 31/39*** | (2006.01) |
| ***A61K 31/4164*** | (2006.01) |
| ***A61K 31/4196*** | (2006.01) |
| ***A61K 31/422*** | (2006.01) |
| ***A61K 31/423*** | (2006.01) |
| ***A61K 31/4245*** | (2006.01) |
| ***A61K 31/426*** | (2006.01) |
| ***A61K 31/427*** | (2006.01) |
| ***A61K 31/428*** | (2006.01) |
| ***A61K 31/433*** | (2006.01) |
| ***A61K 31/4365*** | (2006.01) |
| ***A61K 31/437*** | (2006.01) |
| ***A61K 31/505*** | (2006.01) |
| ***A61K 31/513*** | (2006.01) |
| ***C07D 311/76*** | (2006.01) |

(52) U.S. Cl.

CPC ............ *A61K 31/50* (2013.01); *A61K 31/381* (2013.01); *A61K 31/39* (2013.01); *A61K 31/427* (2013.01); *A61K 31/428* (2013.01)

(58) Field of Classification Search

None

See application file for complete search history.

(56) References Cited

U.S. PATENT DOCUMENTS

| | | | |
|---|---|---|---|
| 2013/0281462 A1 | 10/2013 | Berglund et al. | |
| 2019/0134007 A1 | 5/2019 | Shakkottai et al. | |

FOREIGN PATENT DOCUMENTS

| | | | |
|---|---|---|---|
| CN | 105481706 | 4/2016 | |
| JP | 2018-131429 | 8/2018 | |
| WO | WO-9524190 A2 * | 9/1995 | ........... C07D 241/52 |
| WO | WO 2007/124171 | 11/2007 | |
| WO | WO 2008/124131 | 10/2008 | |
| WO | WO 2011/045702 | 4/2011 | |
| WO | WO 2012/019113 | 2/2012 | |
| WO | WO 2016/071283 | 5/2016 | |
| WO | WO 2016/087936 | 6/2016 | |
| WO | WO 2016/090371 | 6/2016 | |
| WO | WO 2016/170163 | 10/2016 | |
| WO | WO 2016/176449 | 11/2016 | |
| WO | WO 2016/188828 | 12/2016 | |
| WO | WO 2016/200778 | 12/2016 | |
| WO | WO 2018/149986 | 8/2018 | |
| WO | WO 2018/160356 | 9/2018 | |
| WO | WO 2018/236910 | 12/2018 | |
| WO | WO 2020/165907 | 8/2020 | |
| WO | WO2020/165907 A9 | 6/2021 | |

OTHER PUBLICATIONS

Communication Pursuant to Article 94(3) EPC Dated Sep. 2, 2024 From the European Patent Office Re. Application No. 20713104.6. (4 Pages).
Office Action Dated Sep. 12, 2024 From the Israel Patent Office Re. Application No. 285595. (9 Pages).
International Search Report and the Written Opinion Dated May 14, 2020 From the International Searching Authority Re. Application No. PCT/IL2020/050171. (19 Pages).
Office Action and Search Strategy Dated Oct. 6, 2019 From the Israel Patent Office Re. Application No. 264854. (22 Pages).
Search Report Dated Oct. 6, 2019 From the Israel Patent Office Re. Application No. 264854. (4 Pages).
Ainbinder et al. "Elongation Inhibition by DRB Sensitivity-Inducing Factor Is Regulated by the A20 Promoter Via A Novel Negative Element and NF-KB", Molecular and Cellular Biology, 24(6): 2444-2454, Mar. 2004.
Amir-Zilberstein et al. "Differential Regulation of NF-KB by Elongation Factors Is Determined by Core Promoter Type", Molecular and Cellular Biology, 27(14): 5246-5259, Jul. 2007.
Bahat et al. "Targeting Spt5-Pol II by Small-Molecule Inhibitors Uncouples Distinct Activities and Reveals Additional Regulatory Roles", Molecular Cell, 76(4): 617-631, Published Online Sep. 26, 2019.
Beglinger et al. "Randomized Controlled Trial of Atomoxetine for Cognitive Dysfunction in Early Huntington Disease", Journal of Clinical Psychopharmacology, 29(5): 484-487, Oct. 2009.
Cheng et al. "Effects on Murine Behavior and Lifespan of Selectively Decreasing Expression of Mutant Huntingtin Allele by Supt4h Knockdown", PLOS Genetics, 11(3): e1005043-1-e1005043-17, Published Online Mar. 11, 2015.
Diamant et al. "DSIF Restricts NF-KB Signaling by Coordinating Elongation With mRNA Processing of Negative Feedback Genes", Cell Reports, 2(4): 722-731, Oct. 25, 2012.

(Continued)

*Primary Examiner* — Sun Jae Yoo

(57) ABSTRACT

Provided are compounds which are Spt5 inhibitors and which are for use in the treatment diseases and disorders in which inhibiting one or more activities of Spt5 is beneficial, such as, for example, Trinucleotide repeat disorders, obesity, inflammatory diseases, infectious diseases and cancer. The compounds are represented by Formulae I-VII, as defined in the specification.

Figure 1A:
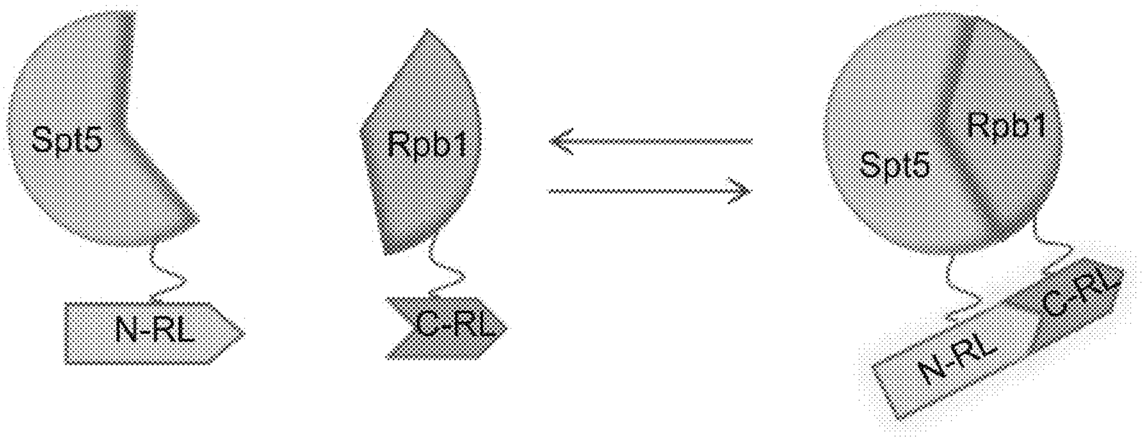

10 Claims, 86 Drawing Sheets
(60 of 86 Drawing Sheet(s) Filed in Color)

Specification includes a Sequence Listing.

(56) References Cited

OTHER PUBLICATIONS

Diamant et al. "The Elongation Factor Spt5 Facilitates Transcription Initiation for Rapid Induction on Inflammatory-Response Genes", Nature Communications, 7(11547): 1-13, Published Online May 16, 2016.
Gupta et al. "Towards Isozyme-Selective HDAC Inhibitors for Interrogating Disease", Current Topics in Medicinal Chemistry, XP055498968, 12(14): 1479-1499, 2012.
Kariya et al. "Cytoprotective Effect of Novel Histone Deacetylase Inhibitors Against Polyglutamine Toxicity", Neuroscience Letters, 392(3): 213-215, Jan. 16, 2006.
Kramer et al. "Spt4 Selectively Regulates the Expression of C9orf72 Sense and Antisense Mutant Transcripts Associated With c9FTD/ALS", Science, 353(6300): 708-712, Aug. 12, 2016.
Liu et al. "Spt4 Is Selectively Required for Transcription of Extended Trinucleotide Repeats", Cell, 148(4): 690-701, Feb. 17, 2012.
Sandi et al. "Prolonged Treatment With Pimelic O-Aminobenzamide HDAC Inhibitors Ameliorates the Disease Phenotype of A Friedreich Ataxia Mouse Model", Neurobiology of Disease, 42(3): 496-505, Available Online Mar. 10, 2011.
Siebzehnruebl et al. "Early Postnatal Behavioral, Cellular, and Molecular Changes in Models of Huntington Disease Are Reversible by HDAC Inhibition", Proc. Natl. Acad. Sci. USA, PNAS, 115(37): E8765-E8774, Published Online Aug. 27, 2018.
Wilke et al. "Identification of Cytotoxic, Glutathione-Reactive Moieties Inducing Accumulation of Reactive Oxygen Species Via Glutathione Depletion", Bioorganic & Medicinal Chemistry, XP055643853, 26(8): 1453-1461, Supplementary Material, P.S1-S19, Available Online Nov. 4, 2017.
Wu et al. "Neuronal Store-Operated Calcium Entry Pathway as A Novel Therapeutic Target for Huntington's Disease Treatment", Chemistry & Biology, 18(6): 777-793, Jun. 24, 2011.
Communication Pursuant to Article 94(3) EPC Dated Jan. 11, 2024 From the European Patent Office Re. Application No. 20713104.6. (8 Pages).
Communication Pursuant to Article 94(3) EPC Dated Sep. 30, 2025 From the European Patent Office Re. Application No. 20713104.6 (5 Pages).

* cited by examiner

| Molecule Name | Structure | Vendor | Cat no. | |
|---|---|---|---|---|
| PCM-0000929 |  | MayBridge | HTS11401 | |
| PCM-0001618 |  | MayBridge | CD07715 | SPI-18 |

| Molecule Name | Structure | Vendor | Cat no. | |
|---|---|---|---|---|
| PCM-0002396 |  | MayBridge | BTB04272 | |
| PCM-0002472 |  | MayBridge | KM10423 | |

| Molecule Name | Structure | Vendor | Cat no. | |
|---|---|---|---|---|
| PCM-0003041 |  | MayBridge | RH01393 | |
| PCM-0003382 |  | MayBridge | NRB00393 | |
| PCM-0003657 |  | MayBridge | NRB04641 | SPI-57 |

| Molecule Name | Structure | Vendor | Cat no. | |
|---|---|---|---|---|
| PCM-0003700 |  | MayBridge | SPB07181 | |
| PCM-0003923 |  | MayBridge | SEW04543 | |

| Molecule Name | Structure | Vendor | Cat no. | |
|---|---|---|---|---|
| PCM-0006316 |  | MayBridge | NRB04162 | |
| PCM-0006700 |  | MayBridge | RH00353 | |
| PCM-0008429 |  | MayBridge | KM06833 | |

| Molecule Name | Structure | Vendor | Cat no. | |
|---|---|---|---|---|
| PCM-0010086 |  | MayBridge | #N/A | SPI-86 |
| PCM-0010465 |  | MayBridge | HTS08977 | |

| Molecule Name | Structure | Vendor | Cat no. | |
|---|---|---|---|---|
| PCM-0011016 |  | MayBridge | JFD00973 | |
| PCM-0011142 |  | MayBridge | KM05953 | |
| PCM-0011654 |  | MayBridge | SPB01965 | |

| Molecule Name | Structure | Vendor | Cat no. | |
|---|---|---|---|---|
| PCM-0047363 |  | ChemBridge | 41954100 | |
| PCM-0064561 |  | SIGMA | A 8423 | |

| Molecule Name | Structure | Vendor | Cat no. | |
|---|---|---|---|---|
| PCM-0064595 |  | SIGMA | C 9511 | |
| PCM-0064686 |  | SIGMA | #N/A | |

| Molecule Name | Structure | Vendor | Cat no. | |
|---|---|---|---|---|
| PCM-0064861 |  | SIGMA | T 4376 | |
| PCM-0064870 |  | SIGMA | #N/A | |

| Molecule Name | Structure | Vendor | Cat no. | |
|---|---|---|---|---|
| PCM-0065089 |  | SIGMA | #N/A | |
| PCM-0065164 |  | SIGMA | PZ0012 | |

| Molecule Name | Structure | Vendor | Cat no. | |
|---|---|---|---|---|
| PCM-0065177 |  | SIGMA | S1228 | |
| PCM-0065368 |  | SIGMA | #N/A | |

| Molecule Name | Structure | Vendor | Cat no. | |
|---|---|---|---|---|
| PCM-0066248 |  | Enamine | Z48854667 | |
| PCM-0067179 |  | Enamine | Z19630528 | |

| Molecule Name | Structure | Vendor | Cat no. | |
|---|---|---|---|---|
| PCM-0069456 |  | Enamine | Z20241837 | |
| PCM-0070430 |  | Enamine | Z46611583 | |
| PCM-0071534 |  | Enamine | Z16550469 | |

| Molecule Name | Structure | Vendor | Cat no. | |
|---|---|---|---|---|
| PCM-0072868 |  | Enamine | Z45967208 | SPI-68 |
| PCM-0073187 |  | Enamine | Z48958429 | |
| PCM-0074419 |  | Enamine | Z195928774 | |

| Molecule Name | Structure | Vendor | Cat no. | |
|---|---|---|---|---|
| PCM-0077217 |  | Enamine | Z729850742 | SPI-17 |
| PCM-0078157 |  | Enamine | #N/A | SPI-157 |
| PCM-0078278 |  | Enamine | Z729849686 | |

| Molecule Name | Structure | Vendor | Cat no. | |
|---|---|---|---|---|
| PCM-0079365 |  | Enamine | Z164208790 | |
| PCM-0079551 |  | Enamine | Z56802351 | |

| Molecule Name | Structure | Vendor | Cat no. | |
|---|---|---|---|---|
| PCM-0081009 |  | Enamine | Z286062738 | |
| PCM-0083146 |  | Enamine | Z144735944 | SPI-46 |
| PCM-0084184 |  | Enamine | Z968456578 | |

| Molecule Name | Structure | Vendor | Cat no. | |
|---|---|---|---|---|
| PCM-0084736 |  | Enamine | Z56771583 | |
| PCM-0084931 |  | Enamine | Z286055298 | SPI-31 |
| PCM-0085849 |  | Prestwick | #N/A | |

| Molecule Name | Structure | Vendor | Cat no. | |
|---|---|---|---|---|
| PCM-0085902 |  | Prestwick | Prestw-304 | |
| PCM-0085955 |  | Prestwick | Prestw-487 | |

| Molecule Name | Structure | Vendor | Cat no. | |
|---|---|---|---|---|
| PCM-0085984 |  | Prestwick | #N/A | |
| PCM-0086032 |  | Prestwick | Prestw-438 | |

| Molecule Name | Structure | Vendor | Cat no. | |
|---|---|---|---|---|
| PCM-0086116 |  | Prestwick | Prestw-1157 | |
| PCM-0086142 |  | Prestwick | #N/A | SPI-42 |

| Molecule Name | Structure | Vendor | Cat no. | |
|---|---|---|---|---|
| PCM-0086160 |  | Prestwick | #N/A | |
| PCM-0086382 |  | Prestwick | S4120 | |

| Molecule Name | Structure | Vendor | Cat no. | |
|---|---|---|---|---|
| PCM-0086397 |  | Prestwick | Prestw-739 | |
| PCM-0087044 |  | Analyticon | NP-009052 | |

| Molecule Name | Structure | Vendor | Cat no. | |
|---|---|---|---|---|
| PCM-0087509 |  | Analyticon | NP-013580 | |
| PCM-0087745 |  | Analyticon | NP-016706 | |

| Molecule Name | Structure | Vendor | Cat no. | |
|---|---|---|---|---|
| PCM-0087798 |  | Analyticon | NP-014476 | |
| PCM-0087848 |  | Analyticon | NP-017375 | |

| Molecule Name | Structure | Vendor | Cat no. | |
|---|---|---|---|---|
| PCM-0088085 |  | Analyticon | #N/A | |
| PCM-0088491 |  | Analyticon | NP-016187 | |

| Molecule Name | Structure | Vendor | Cat no. | |
|---|---|---|---|---|
| PCM-0088631 |  | Analyticon | #N/A | |
| PCM-0088684 |  | Analyticon | NP-017015 | |

| Molecule Name | Structure | Vendor | Cat no. | |
|---|---|---|---|---|
| PCM-0088933 |  | Analyticon | #N/A | |
| PCM-0089205 |  | Analyticon | NP-012882 | |
| PCM-0089376 |  | Analyticon | NP-015550 | |

| Molecule Name | Structure | Vendor | Cat no. | |
|---|---|---|---|---|
| PCM-0089377 |  | Analyticon | NP-001363 | |
| PCM-0089769 |  | Analyticon | NP-003534 | |

| Molecule Name | Structure | Vendor | Cat no. | |
|---|---|---|---|---|
| PCM-0090003 |  | Analyticon | NP-000234 | |
| PCM-0090069 |  | Sellck Chemicals | 1500196 | |

| Molecule Name | Structure | Vendor | Cat no. | |
|---|---|---|---|---|
| PCM-0090084 |  | MicroSource | 1500252 | |
| PCM-0090226 |  | MicroSource | 1501176 | |

| Molecule Name | Structure | Vendor | Cat no. | |
|---|---|---|---|---|
| PCM-0090372 |  | MicroSource | 1504107 | |
| PCM-0090709 |  | Selleck Chemicals | 1503094 | SPI-09 |
| PCM-0090899 |  | MicroSource | #N/A | |

| Molecule Name | Structure | Vendor | Cat no. | |
|---|---|---|---|---|
| PCM-0091121 |  | MicroSource | 1505142 | SPI-21 |
| PCM-0091334 |  | MicroSource | 700024 | |

| Molecule Name | Structure | Vendor | Cat no. | |
|---|---|---|---|---|
| PCM-0094813 |  | Sellck Chemicals | S2260 | |
| PCM-0094872 |  | Sellck Chemicals | S2335 | |

| Molecule Name | Structure | Vendor | Cat no. | |
|---|---|---|---|---|
| PCM-0095018 |  | Sellck Chemicals | #N/A | |
| PCM-0095079 |  | Sellck Chemicals | #N/A | |

| Molecule Name | Structure | Vendor | Cat no. | |
|---|---|---|---|---|
| PCM-0095238 |  | Sellck Chemicals | S2198 | |
| PCM-0095292 |  | Sellck Chemicals | #N/A | SPI-92 |

| Molecule Name | Structure | Vendor | Cat no. | |
|---|---|---|---|---|
| PCM-0095348 |  | Sellck Chemicals | S2781 | |
| PCM-0095392 |  | Sellck Chemicals | #N/A | |

| Molecule Name | Structure | Vendor | Cat no. | |
|---|---|---|---|---|
| PCM-0095469 |  | Sellck Chemicals | #N/A | |
| PCM-0095520 |  | Sellck Chemicals | #N/A | |

| Molecule Name | Structure | Vendor | Cat no. | |
|---|---|---|---|---|
| PCM-0095522 |  | Sellck Chemicals | #N/A | |
| PCM-0095655 |  | Sellck Chemicals | #N/A | |
| PCM-0095674 |  | Sellck Chemicals | #N/A | SPI-74 |

| Molecule Name | Structure | Vendor | Cat no. | |
|---|---|---|---|---|
| PCM-0095675 |  | Sellck Chemicals | #N/A | |
| PCM-0095695 |  | Sellck Chemicals | #N/A | SPI-95 |

| Molecule Name | Structure | Vendor | Cat no. | |
|---|---|---|---|---|
| PCM-0095696 |  | Sellck Chemicals | OutOfStock | SPI-96 |
| PCM-0095706 |  | Sellck Chemicals | OutOfStock | SPI-06 |

Figure 7:
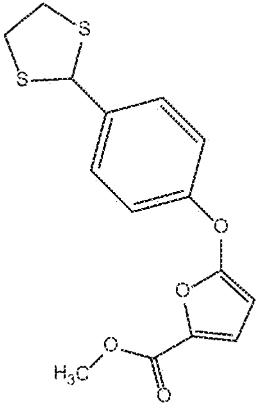
Figure 7:
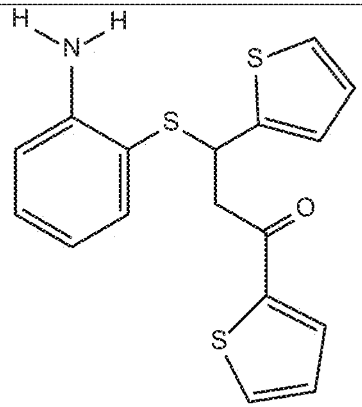
Figure 7:
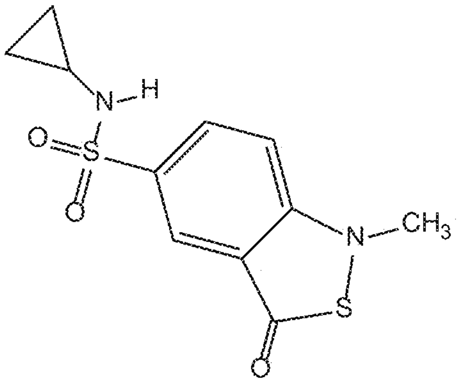
Figure 7:
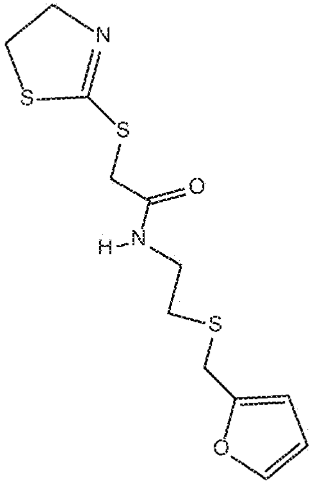
Figure 7:
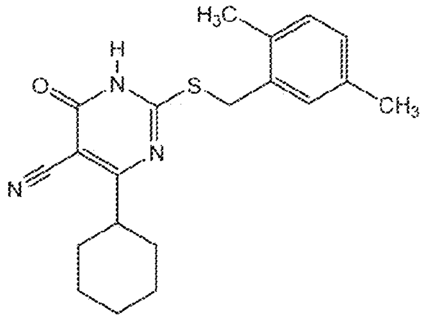
Figure 7:
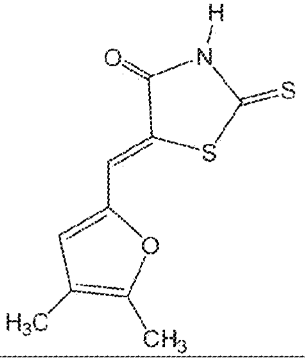
Figure 7:
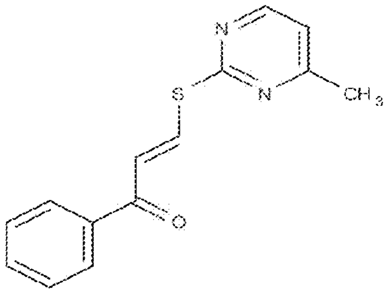
Figure 7:
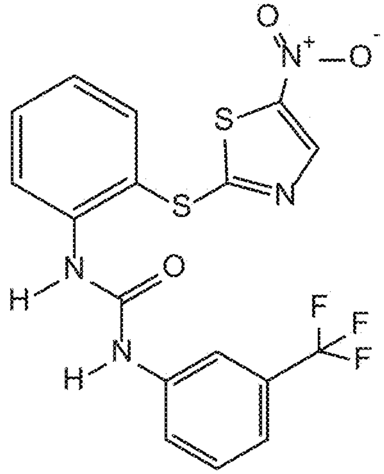
Figure 7:
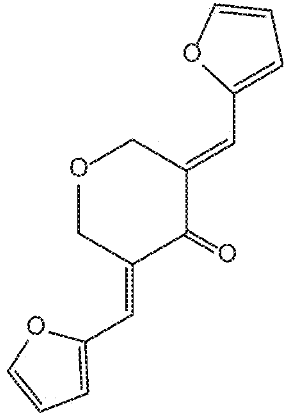
Figure 7:
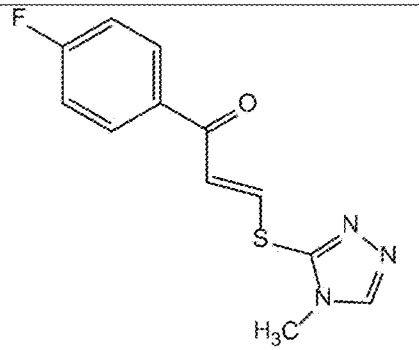
Figure 7:
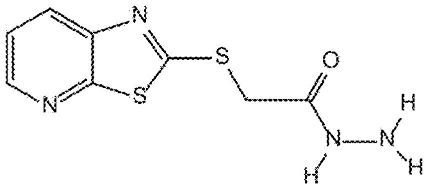
Figure 7:
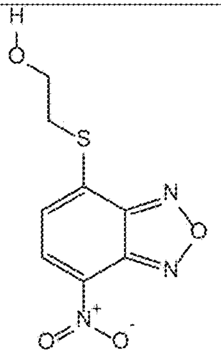
Figure 7:
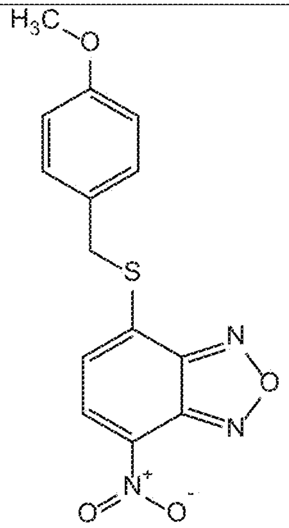
Figure 7:
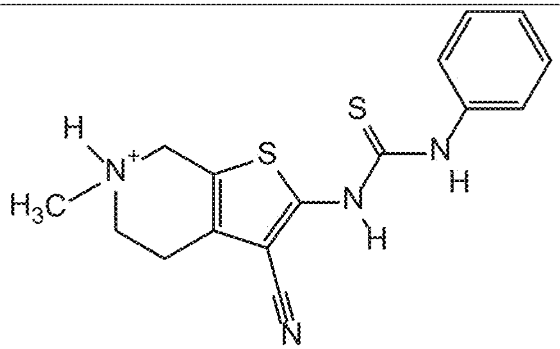
Figure 7:
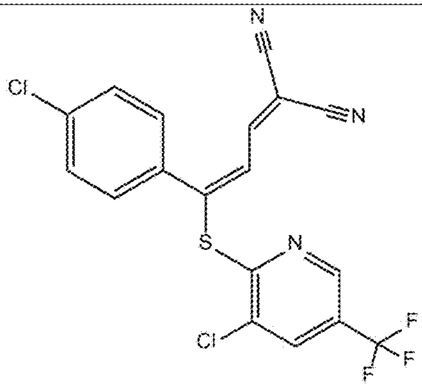
Figure 7:
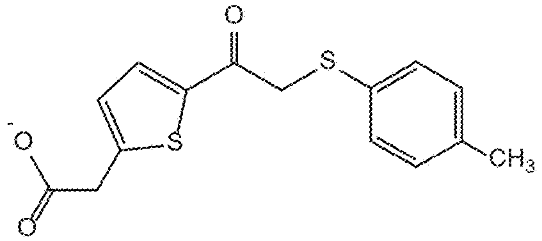
Figure 7:
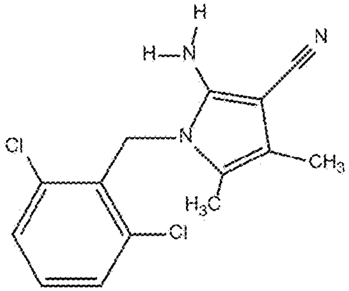
Figure 7:
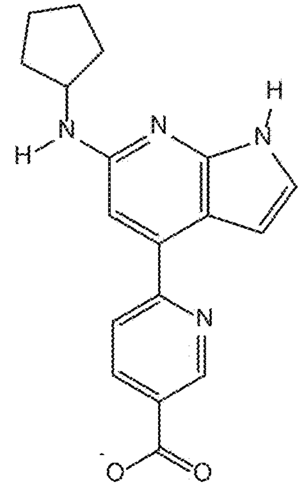
Figure 7:
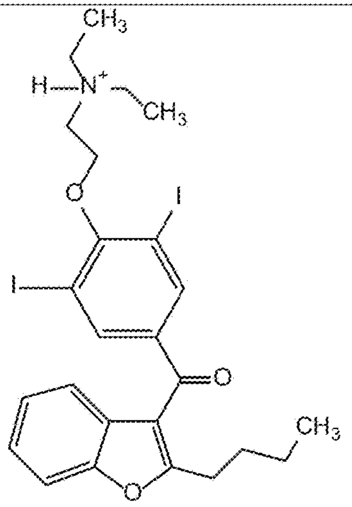
Figure 7:
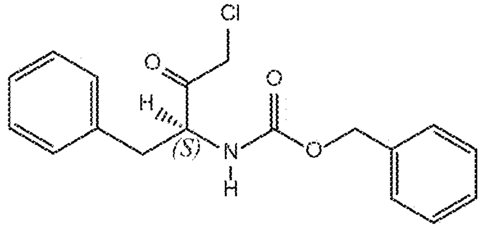
Figure 7:
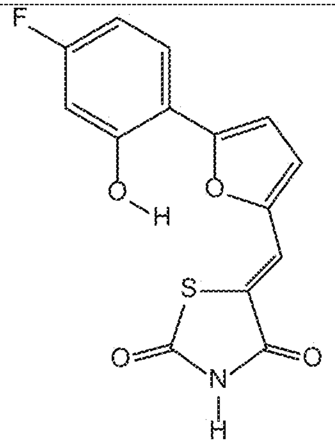
Figure 7:
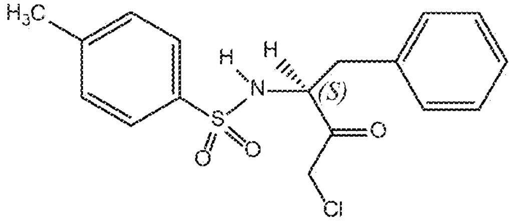
Figure 7:
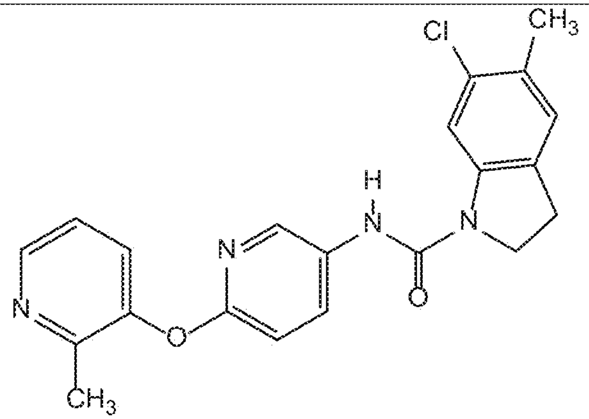
Figure 7:
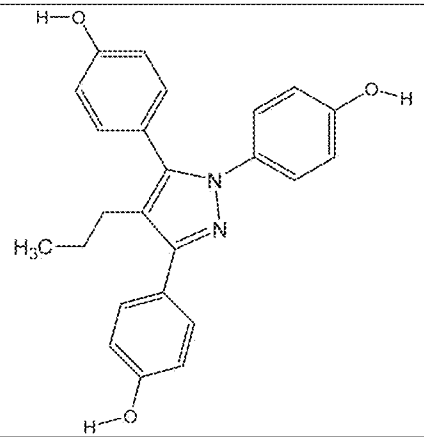
Figure 7:
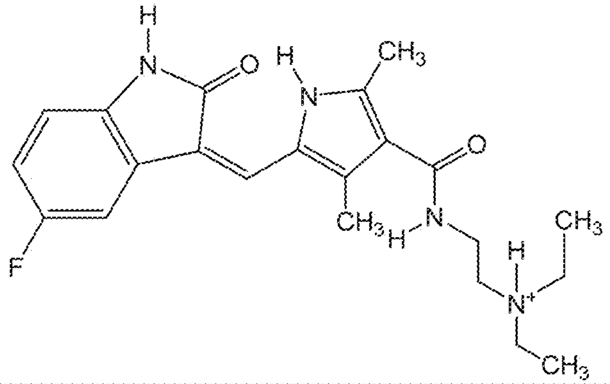
Figure 7:
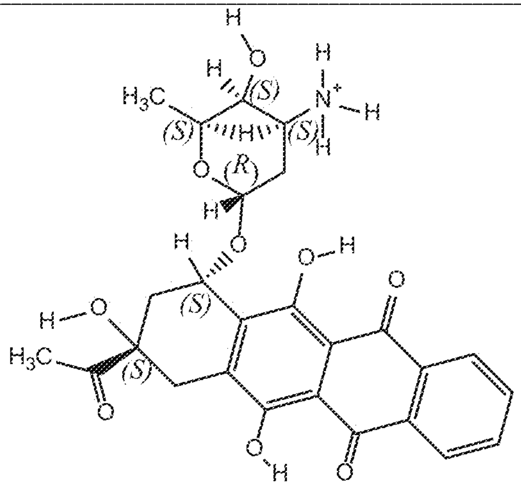
Figure 7:
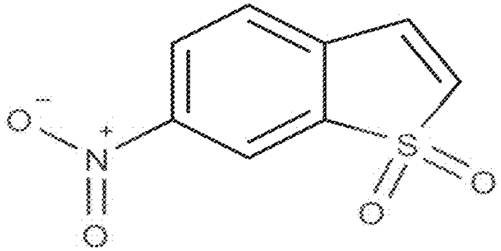
Figure 7:
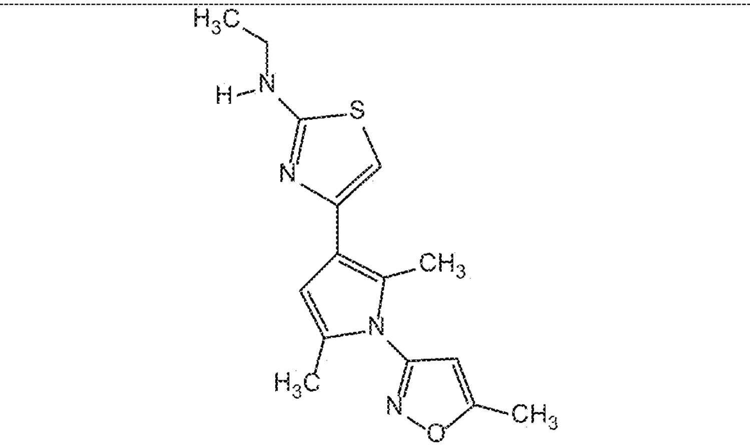
Figure 7:
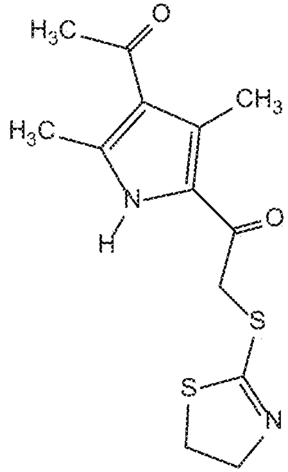
Figure 7:
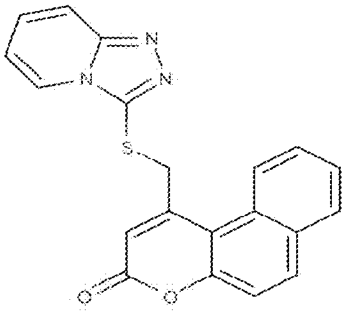
Figure 7:
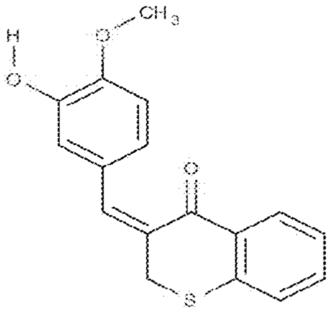
Figure 7:
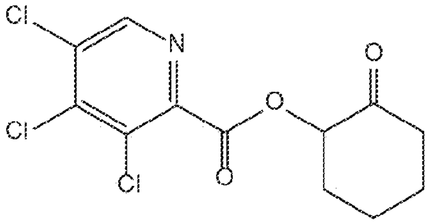
Figure 7:
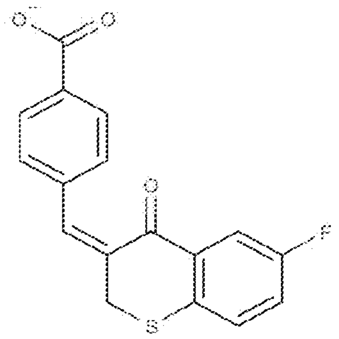
Figure 7:
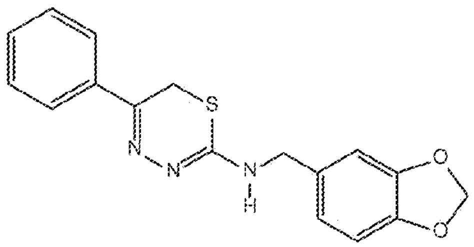
Figure 7:
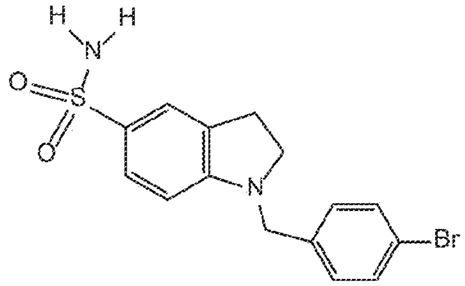
Figure 7:
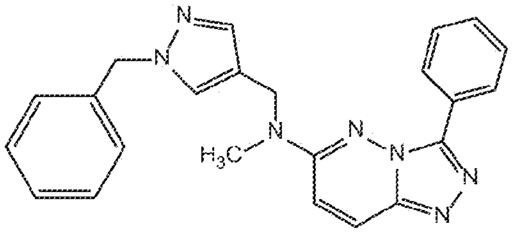
Figure 7:
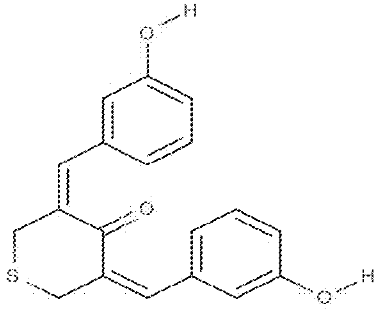
Figure 7:
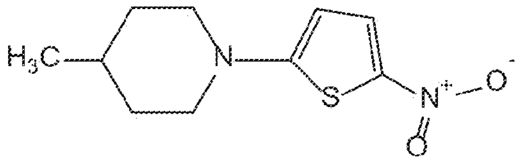
Figure 7:
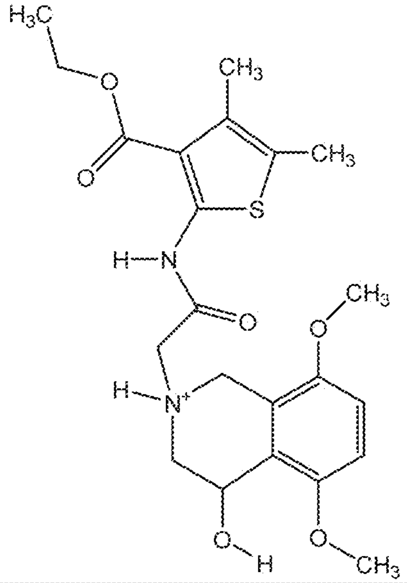
Figure 7:
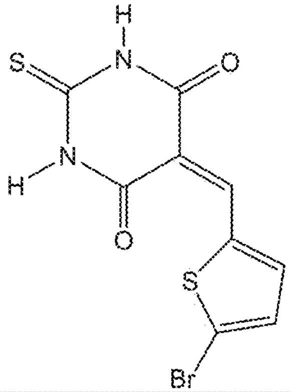
Figure 7:
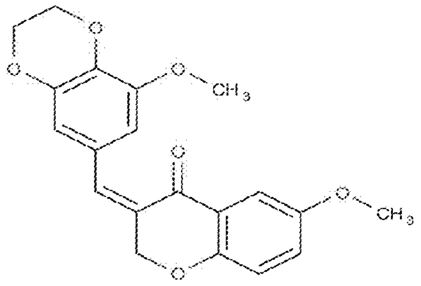
Figure 7:
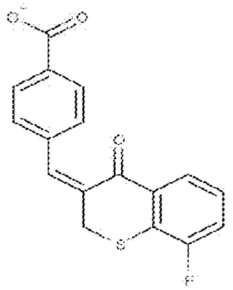
Figure 7:
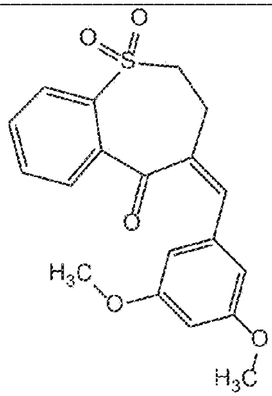
Figure 7:
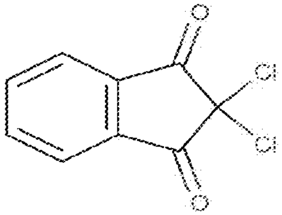
Figure 7:
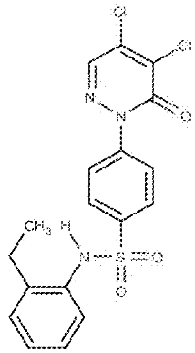
Figure 7:
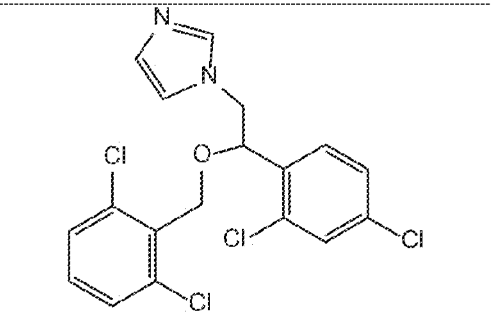
Figure 7:
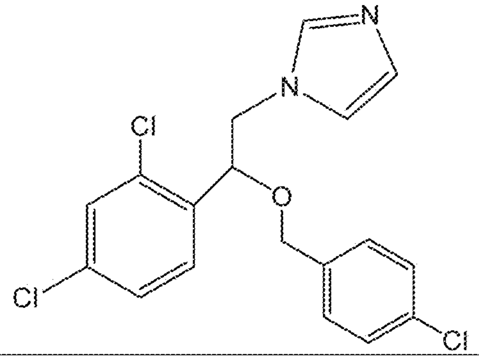
Figure 7:
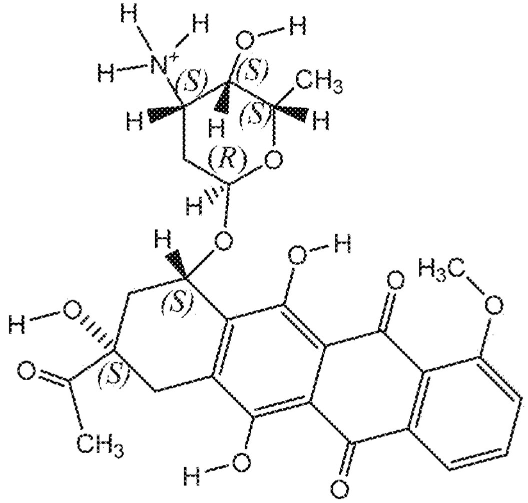
Figure 7:
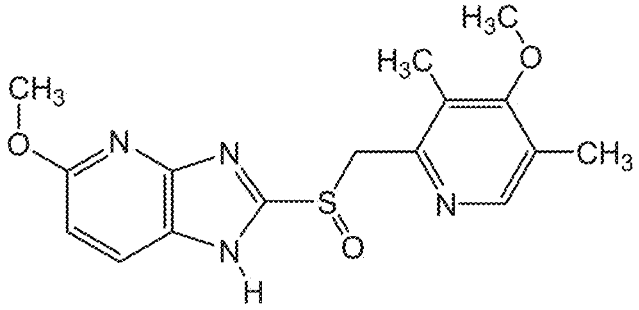
Figure 7:
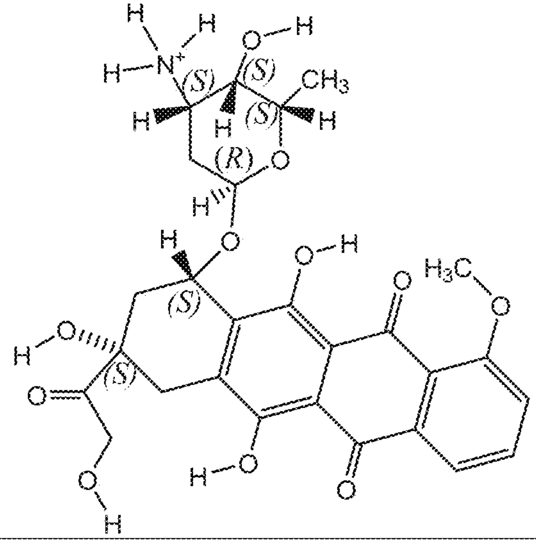
Figure 7:
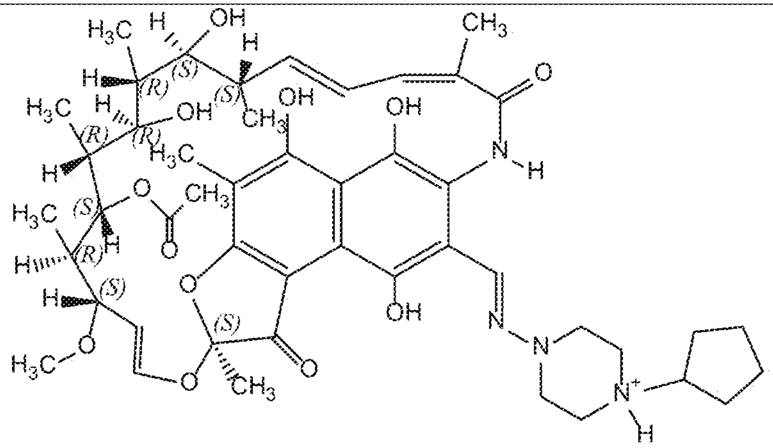
Figure 7:
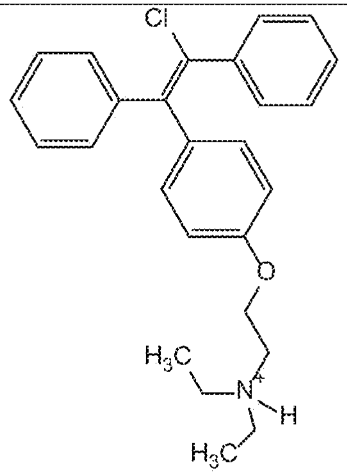
Figure 7:
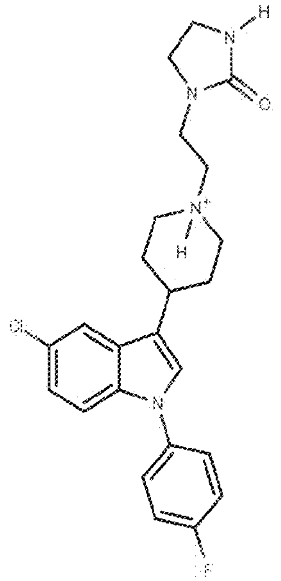
Figure 7:
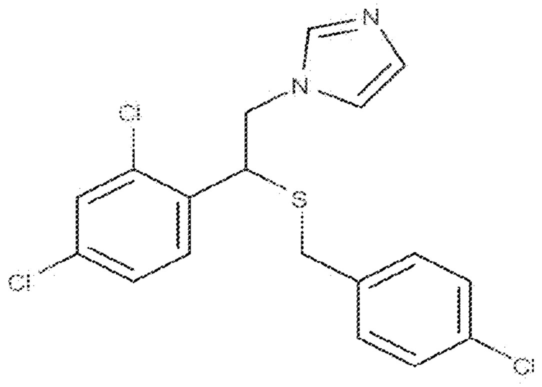
Figure 7:
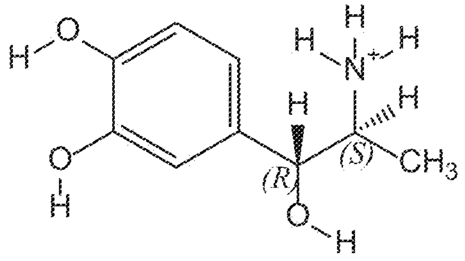
Figure 7:
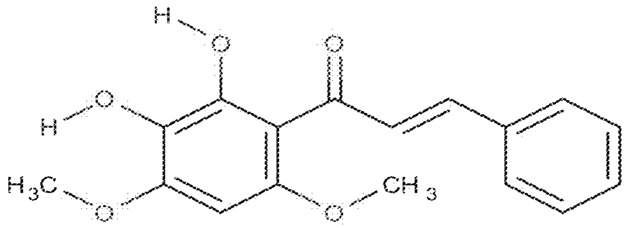
Figure 7:
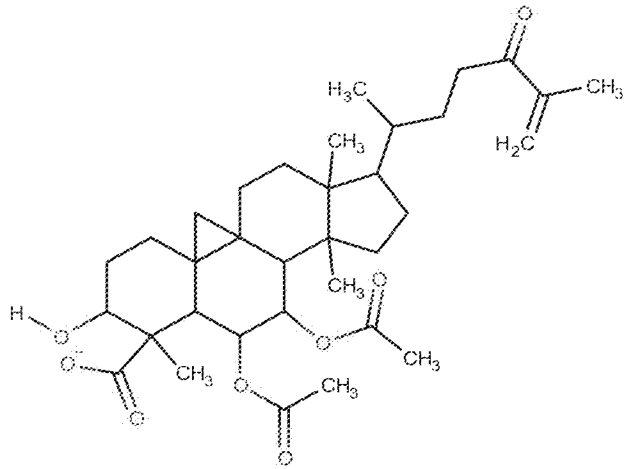
Figure 7:
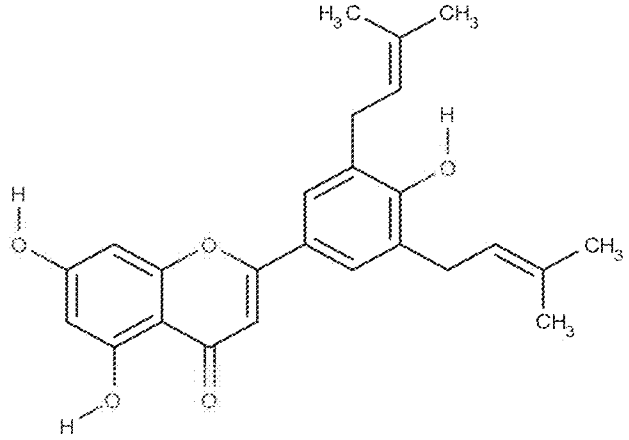
Figure 7:
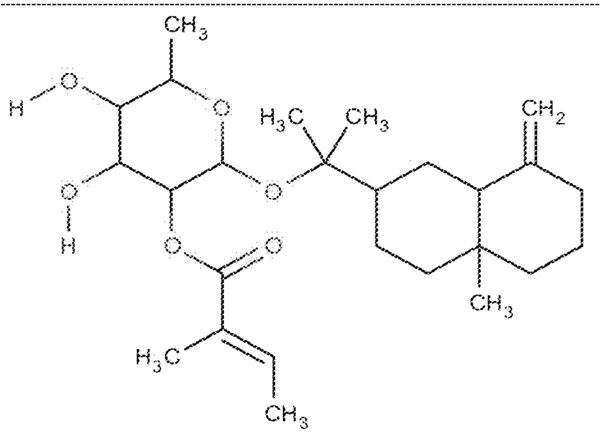
Figure 7:
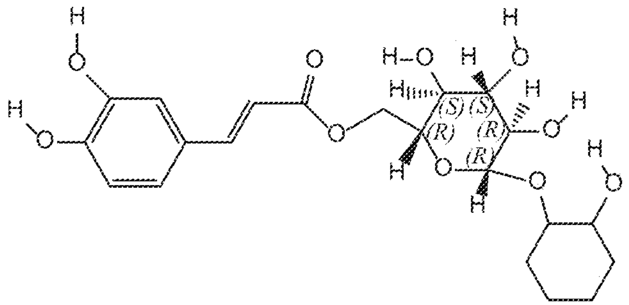
Figure 7:
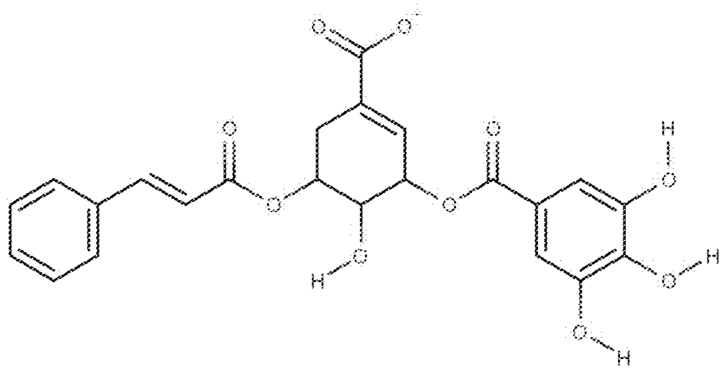
Figure 7:
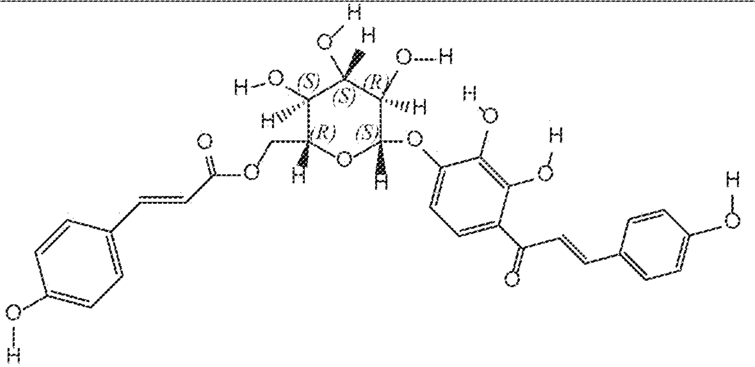
Figure 7:
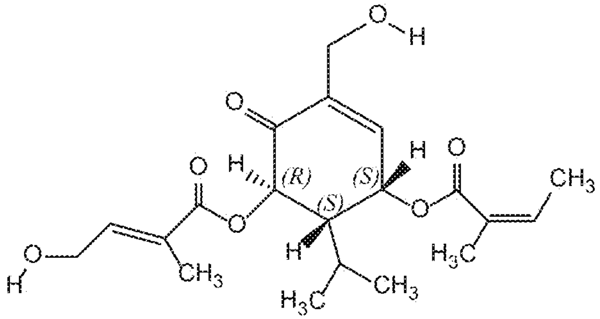
Figure 7:
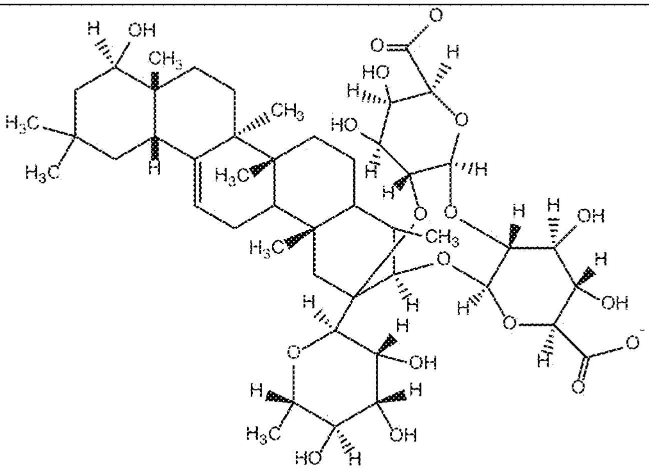
Figure 7:
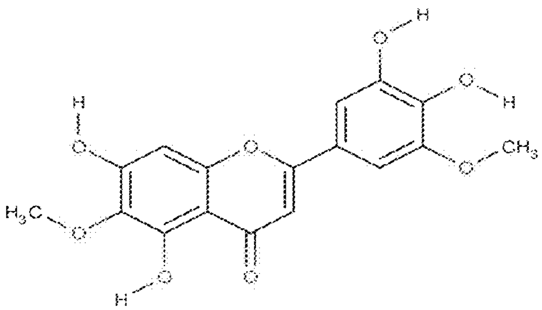
Figure 7:
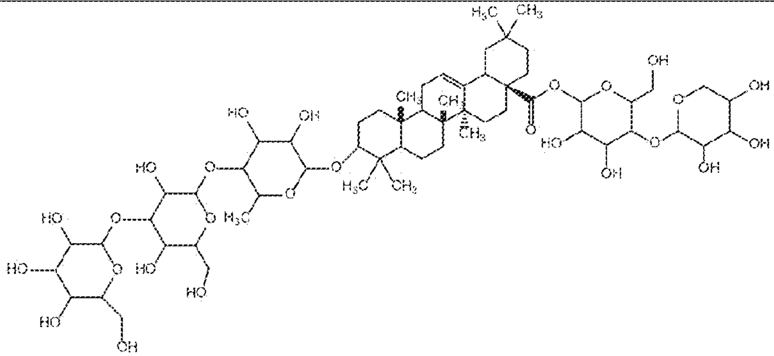
Figure 7:
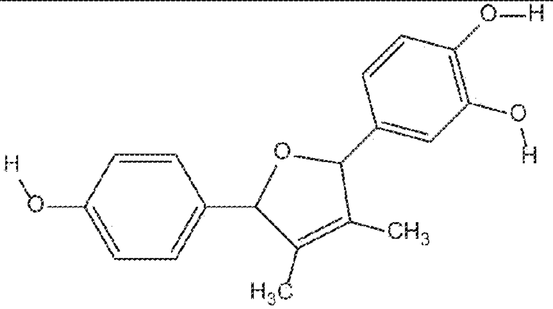
Figure 7:
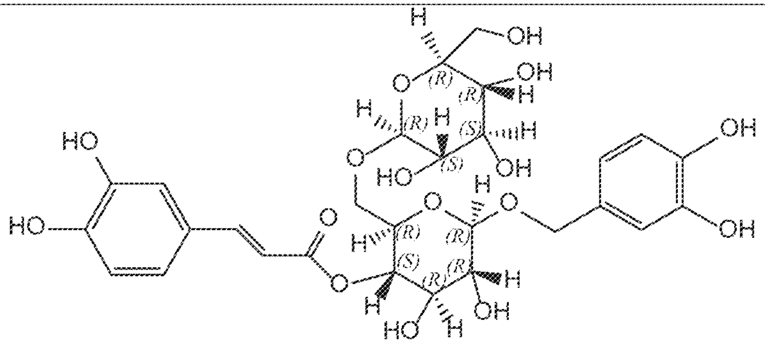
Figure 7:
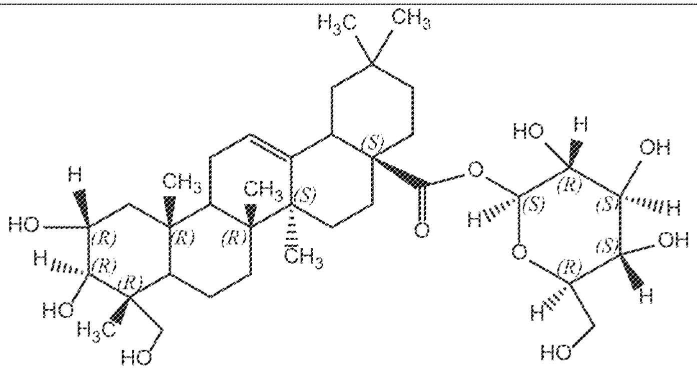
Figure 7:
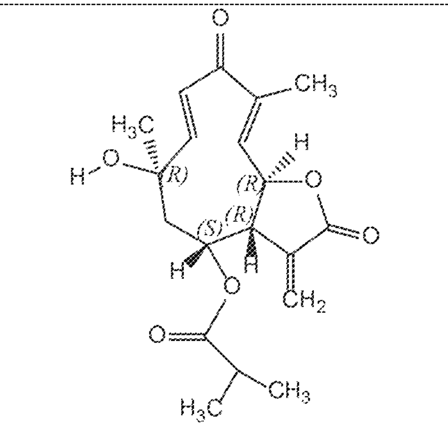
Figure 7:
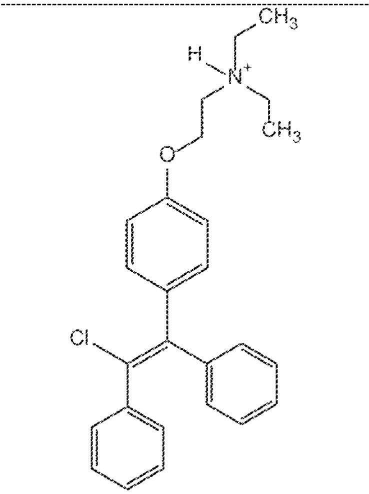
Figure 7:
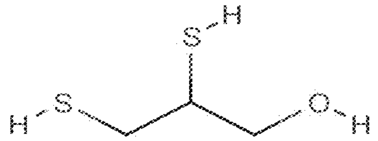
Figure 7:
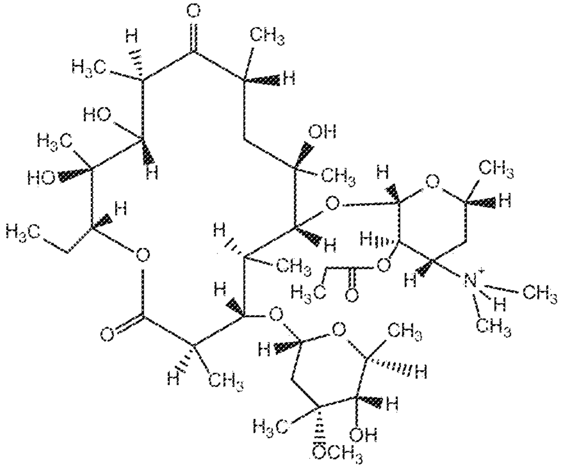
Figure 7:
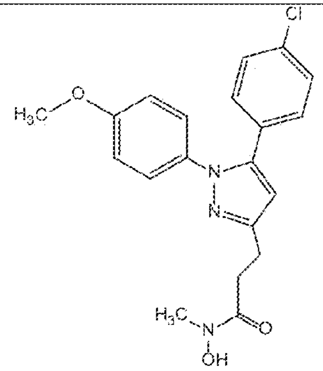
Figure 7:
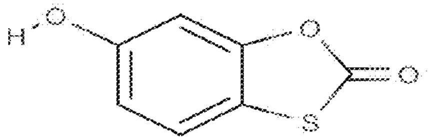
Figure 7:
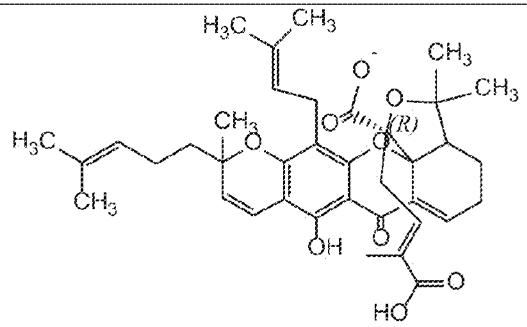
Figure 7:
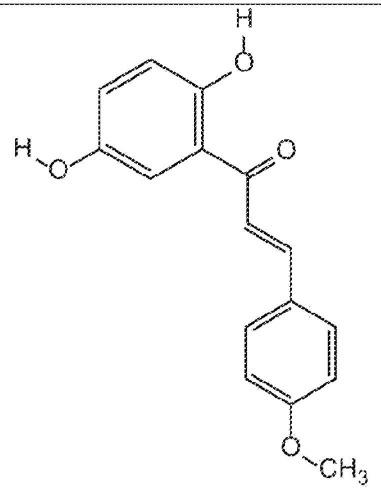
Figure 7:
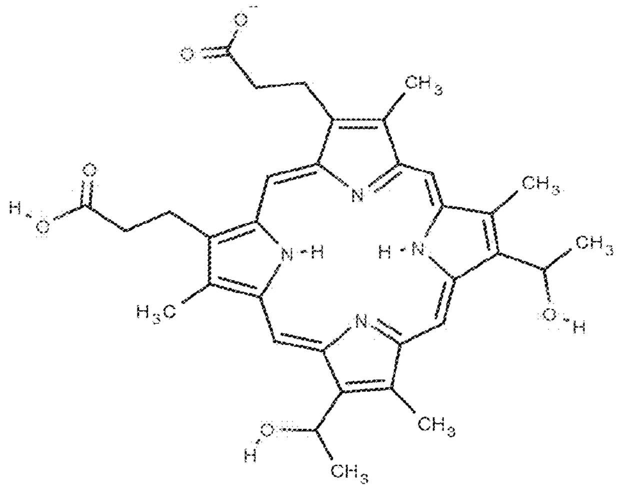
Figure 7:
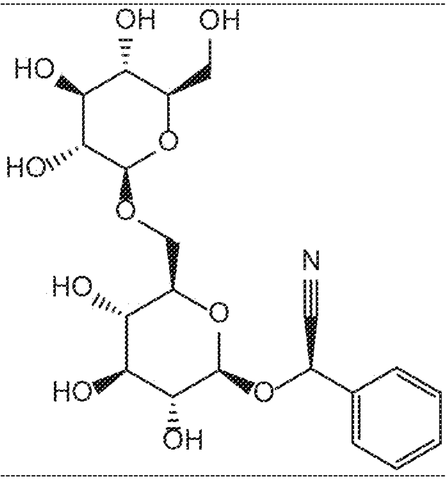
Figure 7:
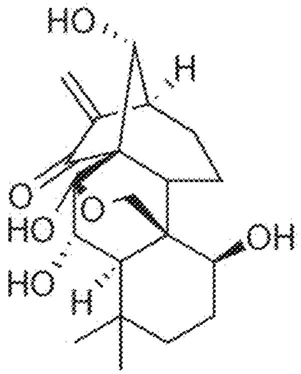
Figure 7:
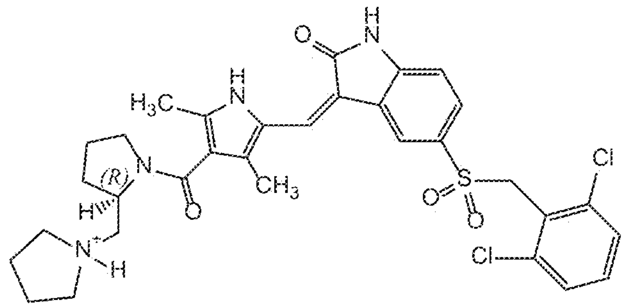
Figure 7:
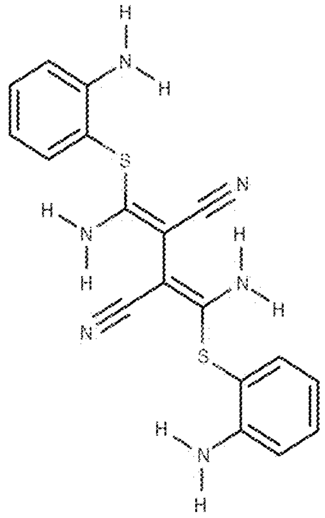
Figure 7:
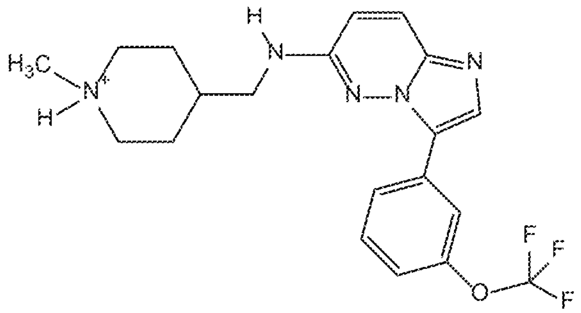
Figure 7:
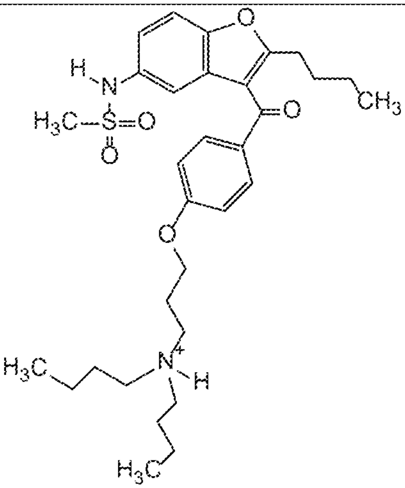
Figure 7:
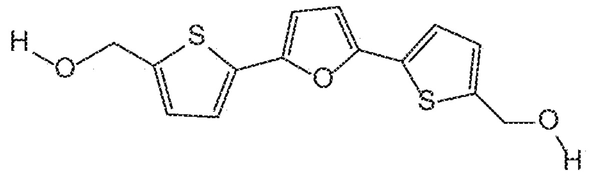
Figure 7:
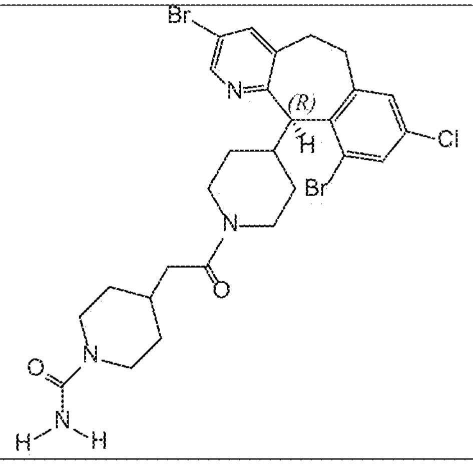
Figure 7:
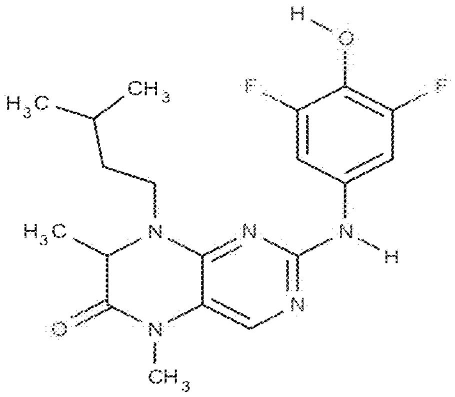
Figure 7:
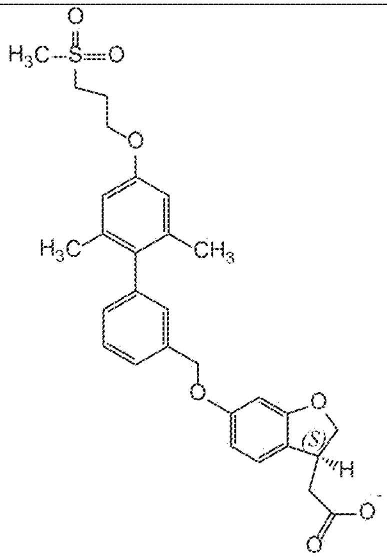
Figure 7:
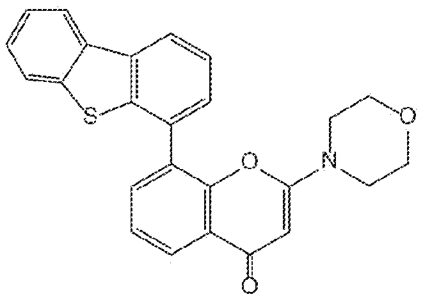
Figure 7:
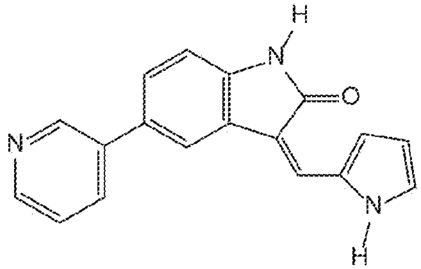
Figure 7:
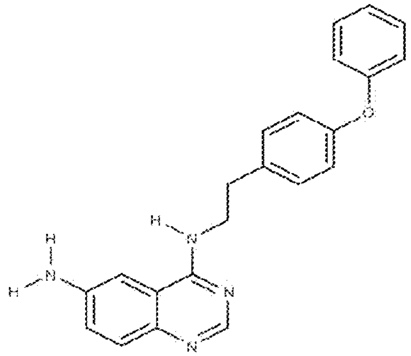
Figure 7:
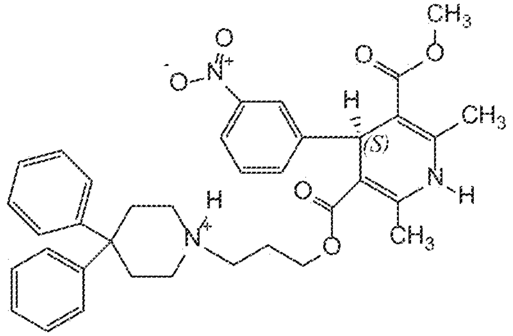
Figure 7:
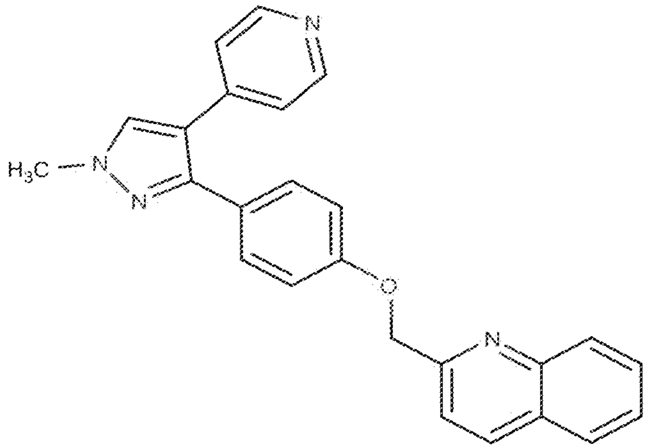
Figure 7:
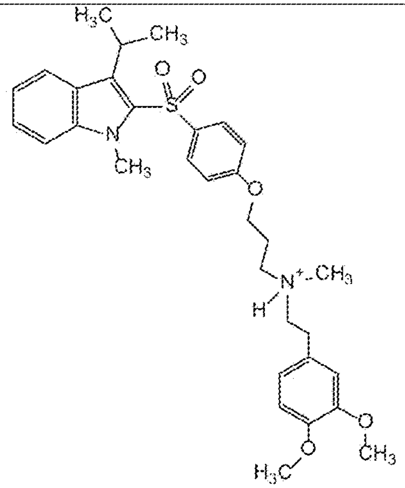
Figure 7:
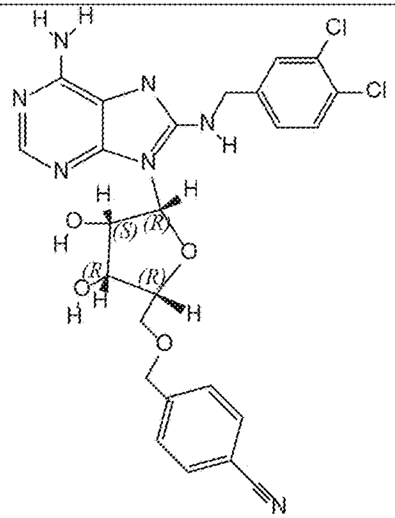

FIG. 7 Continued 42

| Molecule Name | Structure | Vendor | Cat no. | |
|---|---|---|---|---|
| PCM-0065029 | See FIG. 3 | SIGMA | #N/A | **SPI-29** |
| PCM-0081285 | See FIG. 3 | Enamine | Z56930679 | **SPI-85** |

SPI-31

SPI-4516K
Less reactive analog

SPT5 INHIBITORS AND USES THEREOF

RELATED APPLICATIONS

This application is a Continuation of PCT Patent Application No. PCT/IL2020/050171 having International filing date of Feb. 14, 2020, which claims the benefit of priority of Israel Patent Application No. 264854 filed on Feb. 14, 2019. The contents of the above applications are all incorporated by reference as if fully set forth herein in their entirety.

SEQUENCE LISTING STATEMENT

The ASCII file, entitled 88647SequenceListing.txt, created on Aug. 13, 2021, comprising 34,142 bytes, submitted concurrently with the filing of this application is incorporated herein by reference.

FIELD AND BACKGROUND OF THE INVENTION

The present invention, in some embodiments thereof, relates therapy, and, more specifically, but not exclusively, to compounds which are Spt5 inhibitors, and to uses thereof, for example, in treating nucleotide repeat disorders, inflammation, and cancer.

Spt5 is a transcription elongation factor that promotes proximal promoter pausing, promoter escape, elongation and mRNA processing. Spt5 is essential for cell viability and appears to be essential for life in e.g. bacteria, yeasts, *Drosophila*, Zebra fish and mammalian cells.

Spt5 is conserved in all three domains of life. Bacterial and archaeal Spt5 proteins contain an N-terminal domain (NGN) and a C-terminal Kyprides-Onzonis-Woese domain (KOW) separated by a flexible linker; Eukaryotic Spt5 contains NGN, several copies of the KOW domain and additional N- and C-terminal sequences that are absent in prokaryotic homologues (Werner, 2012).

Spt5 can function as a positive or a negative transcription elongation factor in collaboration with other protein factors. Spt5 binds a small zinc-binding protein, Spt4, to form a heterodimeric complex known as the DRB sensitivity-inducing factor (DSIF) complex. The DSIF complex with the negative elongation factor (NELF) participate in promoter-proximal pausing [i.e. stalling of RNA Polymerase II (Pol II) after transcribing ~30-120 nucleotides downstream of the transcription start site (TSS)]; wherein positive transcription elongation factor b (P-TEFb) facilitates release of DSIF and NELF inhibition of elongation (Diamant and Dikstein, 2013). During elongation, Spt5 has the ability to stabilize Pol II on the DNA template by interaction with upstream sequences and with RNA (e.g. Bernecky et al., 2016; Crickard et al., 2016; Hirtreiter et al., 2010). This activity was recently implicated in maintaining high transcriptional speed on long mRNAs (Fitz et al., 2018). Consistent with that, Spt5 was shown to accompany Pol II along the transcribed region until termination (Pavri et al., 2010; Rahl et al., 2010). Several studies showed that Spt5 plays specific roles in transcription of genes involved in cellular response to environmental signals, for example, inflammation and stress induced genes (e.g. Ainbinder et al., 2004; Amir-Zilberstein et al., 2007, Diamant et al., 2012, Diamant et al., 2016a); and tri-nucleotides expanded-repeat genes involved in inherited neurological pathologies including Huntington's disease (HD), amyotrophic lateral sclerosis (ALS) and frontotemporal dementia (FTD) (Cheng et al., 2015; Kramer et al., 2016; Liu et al., 2012).

To-date, no Spt5 inhibitor has been identified and most studies aiming to interfere with its activity used knockdown (KD) methods.

Additional Background Art uncludes WO 2008/124131; WO 2012/019113; WO 2018/236910; WO 2018/160356; CN 105481706; WO 2016/087936; JP 2018131429; WO 2016/200778; WO 2016/170163; WO 2007/12417; U.S. Patent Application Publication No. US 2013/281462; Wu, J. et al., Chem Biol. (24 Jun. 2011); 18(6), pages: 777-793, DOI:10.1016/j.chembiol.2011.04.012; Sandi, C. et al., Neurobiology of Disease (June 2011); 42(3), pages: 496-505; SIEBZEHNRÜBL, Florian A., et al., Proceedings of the National Academy of Sciences, 2018, 115.37: E8765-E8774; BEGLINGER, Leigh J., et al., Journal of clinical psychopharmacology, 2009, 29.5: 484, DOI: 10.1097/JCP.0b013e3181b2ac0a; and KARIYA, Shingo, et al., Neuroscience letters, 2006, 392.3: 213-215, DOI: 10.1016/j.neulet.2005.09.019.

SUMMARY OF THE INVENTION

According to an aspect of some embodiments of the present invention there is provided a method of treating a nucleotide repeat disorder in a subject in need thereof, the method comprising administering to the subject a therapeutically effective amount of a compound selected from:

a compound represented by Formula I:

Formula I

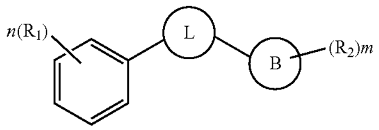

wherein:

n and m and w are each independently an integer of from 0 to 4;

$R_1$ and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate and thiocarboxylate;

B is a cyclic moiety selected from aryl, heteroaryl and heteroalicyclic;

L is a linking moiety, comprising from 2 to 12 atoms in length, and comprising a saturated or unsaturated, substituted or unsubstituted hydrocarbon chain, optionally interrupted by one or more of O, S, —S(═O)—, —S(═O)$_2$ and —NR$_4$—, wherein $R_4$ is hydrogen, alkyl, cycloalkyl or aryl, and a compound represented by Formula II:

Formula II

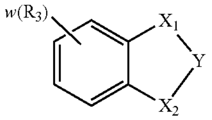

wherein:

w is an integer of from 0 to 4;

$R_3$ is a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate and thiocarboxylate;

$X_1$ and $X_2$ are each independently O, S or $NR_4$;

Y is —C(═$X_3$)— or —$CR_5R_6$—C(═$X_3$)—, wherein $X_3$ is O, S or $NR_4$, wherein $R_4$ is hydrogen, alkyl, cycloalkyl or aryl, and $R_5$ and $R_6$ are each independently selected from hydrogen, alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate and thiocarboxylate, or, alternatively, two or more of $R_4$, $R_5$ and $R_6$ from together a cyclic moiety, thereby treating the nucleotide repeat disorder in the subject. According to an aspect of some embodiments of the present invention there is provided a compound represented by Formula I or II as defined herein, for use in treating a nucleotide repeat disorder in a subject in need thereof.

According to an aspect of some embodiments of the present invention there is provided a compound represented by Formula Ia:

Formula Ia

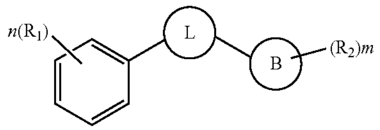

wherein:

n and m are each independently an integer of from 0 to 4;

$R_1$ and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate and thiocarboxylate;

B is a cyclic moiety selected from aryl, heteroaryl and heteroalicyclic;

L is a linking moiety, comprising from 2 to 12 atoms in length, and comprising a saturated or unsaturated, substituted or unsubstituted hydrocarbon chain, interrupted by or comprising one or more of S and —S(═O)$_2$, for use in treating a nucleotide repeat disorder in a subject in need thereof.

According to some of any of the embodiments described herein, the nucleotide repeat disorder is Huntington disease.

According to some of any of the embodiments described herein, $R_1$ is selected from hydroxy, alkoxy, thiohydroxy, thioalkoxy, aryloxy, amine and halo.

According to some of any of the embodiments described herein, B is a heteroaryl or a heteroalicyclic.

According to some of any of the embodiments described herein, L is a substituted, saturated hydrocarbon interrupted by at least one S, and optionally further interrupted by O. Exemplary such compounds are referred to herein as SPI-85, SPI-8690, SPI-0324, and SPI-8708.

According to some of any of the embodiments described herein, n is 1, and $R_1$ is amine, alkoxy, or thioalkoxy.

According to some of any of the embodiments described herein, m is 0, or wherein m is 1 and $R_2$ is halo.

According to some of any of the embodiments described herein, L is an unsaturated hydrocarbon which comprises and aryl and $SO_2$.

According to some of any of the embodiments described herein, L further comprises —$NR_4$—, wherein $R_4$ is hydrogen, alkyl, cycloalkyl or aryl. Exemplary such compounds are referred to herein as SPI-31, SPI-5726, SPI-0035, SPI-1477, SPI-3440 and SPI-4516K.

According to some of any of the embodiments described herein, n is 1 or 2 and wherein each $R_1$ is independently selected from alkyl, halo, alkoxy and thioalkoxy.

According to an aspect of some embodiments of the present invention there is provided a compound represented by Formula VII:

Formula VII

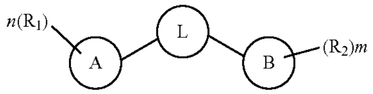

wherein:

n and m and w are each independently an integer of from 0 to 4;

$R_1$ and $R_2$ are each independently a substituent selected from alkyl, cycloalkyl, aryl, heteroaryl, heteroalicyclic, hydroxy, hydroxyalkyl, thiol, alkoxy, thioalkoxy, aryloxy, thioaryloxy, halo, alkyl, amine, amide, nitro, carboxylate and thiocarboxylate;

A and B are each independently a cyclic moiety selected from aryl, heteroaryl and heteroalicyclic;

L is a linking moiety, comprising from 2 to 12 atoms in length, and comprising a saturated or unsaturated, substituted or unsubstituted hydrocarbon chain, interrupted by or comprising one or more of O, S and —S(═O)$_2$, for use in treating a nucleotide repeat disorder in a subject in need thereof.

According to some of any of the embodiments described herein, the nucleotide repeat disorder is Huntington disease.

According to some of any of the embodiments described herein, L is an unsaturated, substituted hydrocarbon chain interrupted by O or S. An exemplary such compound is referred to herein as SPI-48.

According to some of any of the embodiments described herein, at least one of n and m is other than 0 and at least one of $R_1$ and $R_2$ if present is a hydroxyalkyl.

According to an aspect of some embodiments of the present invention there is provided a compound selected from the group of compounds presented in Tables 6, 7, 8 and 9, for use for use in treating a nucleotide repeat disorder in a subject in need thereof.

According to some of any of the embodiments described herein, the nucleotide repeat disorder is Huntington disease.

According to some of any of the embodiments of this aspect of the invention, the nucleotide repeat disorder is a Trinucleotide repeat disorder.

According to some of any of the embodiments of this aspect of the invention, the Trinucleotide repeat disorder is a Polyglutamine (PolyQ) disease.

According to some of any of the embodiments of this aspect of the invention, the Polyglutamine (PolyQ) disease is Huntington disease.

According to some of any of the embodiments of this aspect of the invention, the Trinucleotide repeat disorder is a Non-Polyglutamine disease.

According to some of any of the embodiments of this aspect of the invention, the compound is capable of down-regulating expression of a mutant huntingtin gene.

According to some of any of the embodiments of this aspect of the invention, the compound is represented by Formula II.

According to some of any of the embodiments of this aspect of the invention, Y is $C{=}X_3$.

According to some of any of the embodiments of this aspect of the invention, $X_3$ is O.

According to some of any of the embodiments of this aspect of the invention, $X_1$ and $X_2$ are each independently O or S.

According to some of any of the embodiments of this aspect of the invention, $X_1$ is O and $X_2$ is S.

According to some of any of the embodiments of this aspect of the invention, at least one of $R_3$ is hydroxy, alkoxy, thiohydroxy or thioalkoxy.

According to some of any of the embodiments of this aspect of the invention, at least one $R_3$ is hydroxy.

According to some of any of the embodiments of this aspect of the invention, w is 1.

According to some of any of the embodiments of this aspect of the invention, at least one of the $R_3$ is at the meta position with respect to $X_1$.

According to some of any of the embodiments of this aspect of the invention:

Y is C═O;

$X_1$ is O;

$X_2$ is S;

w is 1; and $R_3$ is hydroxy.

According to some of any of the embodiments of this aspect of the invention, the compound is represented by Formula I.

According to some of any of the embodiments of this aspect of the invention, n is 1 or 2.

According to some of any of the embodiments of this aspect of the invention, $R_1$ is selected from hydroxy, alkoxy, thiohydroxy, thioalkoxy, aryloxy, and halo.

According to some of any of the embodiments of this aspect of the invention, B is aryl.

According to some of any of the embodiments of this aspect of the invention, m is 1 or 2.

According to some of any of the embodiments of this aspect of the invention, $R_2$ is selected from hydroxy, alkoxy, carboxylate and halo.

According to some of any of the embodiments of this aspect of the invention, L is or comprises an unsaturated hydrocarbon chain substituted by one or more oxo (═O) groups.

According to some of any of the embodiments of this aspect of the invention:

n is 2;

each of $R_1$ is hydroxy;

B is aryl;

m is 1;

$R_2$ is alkoxy; and

L is an unsaturated hydrocarbon chain substituted by one or more oxo (═O) groups.

According to some of any of the embodiments of this aspect of the invention, B is a heteroaryl or a heteroalicyclic.

According to some of any of the embodiments of this aspect of the invention, L is a hydrocarbon interrupted by one or two —$NR_4$—, being optionally substituted and/or unsaturated.

According to some of any of the embodiments of this aspect of the invention, L is a saturated unsubstituted hydrocarbon interrupted by —$NR_4$—, and m is 1 (e.g., amine).

According to some of any of the embodiments of this aspect of the invention, m is 0.

According to some of any of the embodiments of this aspect of the invention, L is a substituted, saturated or unsaturated, hydrocarbon interrupted at least by S or $S({=}O)_2$.

According to some of any of the embodiments of this aspect of the invention:

B is a heteroalicyclic ring;

m is 0; and

L is a substituted, saturated hydrocarbon interrupted by O and S.

According to an aspect of some embodiments of the present invention there is provided a method of inducing suppression of appetite in a subject in need thereof, the method comprising administering to the subject an effective amount of a compound selected from a compound represented by Formula II, as defined herein, a compound represented by Formula III:

Formula III

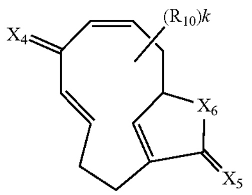

wherein:

k is an integer of from 0 to 8;

Each of $R_{10}$, if present, is selected from alkyl, cycloalkyl, halo, haloalkyl, hydroxy, alkoxy, thioalkoxy and thioaryloxy; and $X_4$, $X_5$ and $X_6$ are each independently selected from O, S and $NR_4$, wherein $R_4$ is hydrogen, alkyl, cycloalkyl or aryl, and a compound represented by Formula IV:

Formula IV

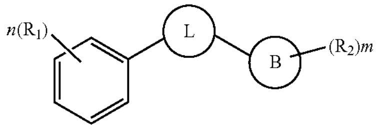

wherein:

n and m are each independently an integer of from 0 to 4;

$R_1$, and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, carboxylate, thiocarboxylate, nitro, cyano and haloalkyl;

B is a cyclic moiety selected from aryl, heteroaryl and heteroalicyclic;

L is a linking moiety, comprising from 2 to 12 atoms in length, and comprising a saturated or unsaturated, substituted or unsubstituted hydrocarbon chain, optionally interrupted by one or more of O, S, —S(═O)—, —$S({=}O)_2$, —N═ and —$NR_4$, thereby inducing suppression of appetite in the subject.

According to an aspect of some embodiments of the present invention there is provided a method of treating obesity in a subject in need thereof, the method comprising administering to the subject a therapeutically effective amount of a compound represented by Formula II, III or IV, as defined herein, thereby treating obesity in the subject.

According to an aspect of some embodiments of the present invention there is provided a compound represented by Formula II, III or IV, as defined herein, for use in treating obesity in a subject in need thereof.

According to an aspect of some embodiments of the present invention there is provided a method of treating a disease that can benefit from up-regulating growth and/or differentiation of cells, the method comprising administering to the subject a therapeutically effective amount of a compound represented by Formula II, III or IV, as defined herein, thereby treating the disease in the subject.

According to an aspect of some embodiments of the present invention there is provided a compound represented by Formula II, III or IV, as defined herein for use in treating a disease that can benefit from up-regulating growth and/or differentiation of cells in a subject in need thereof.

According to some of any of the embodiments of this aspect of the invention, the disease is an inflammatory disease, ischemia-reperfusion injury, tissue damage, cell/tissue transplantation and neurodegenerative disease.

According to some of any of the embodiments of this aspect of the invention, the inflammatory disease is selected from the group consisting of rheumatoid arthritis, atherosclerosis, Diabetes and sepsis.

According to some of any of the embodiments of this aspect of the invention, the compound is capable of up-regulating expression of a GDF15 gene.

According to an aspect of some embodiments of the present invention there is provided a method of treating a disease that can benefit from up-regulating expression of a heat-shock protein in a subject in need thereof, the method comprising administering to the subject a therapeutically effective amount of a compound represented by Formula II, III or IV, as defined herein, thereby treating the disease in the subject.

According to an aspect of some embodiments of the present invention there is provided a compound represented by Formula II, III or IV, as defined herein, for use in treating a disease that can benefit from up-regulating expression of a heat-shock protein in a subject in need thereof.

According to some of any of the embodiments of this aspect of the invention, the disease is an autoimmune disease or graft rejection.

According to some of any of the embodiments of this aspect of the invention, the autoimmune disease is rheumatoid arthritis or type I diabetes.

According to an aspect of some embodiments of the present invention there is provided a method of immunization a subject in need thereof, the method comprising administering to the subject a therapeutically effective amount of a compound represented by Formula II, III or IV, as defined herein, thereby immunizing the subject.

According to some of any of the embodiments of this aspect of the invention, the method comprising administering to the subject a therapeutically effective amount of a vaccine.

According to some of any of the embodiments of this aspect of the invention, the compound is capable of up-regulating expression of a heat-shock protein gene.

According to some of any of the embodiments of this aspect of the invention, the compound is represented by Formula IV.

According to some of any of the embodiments of this aspect of the invention:

n and m are each independently an integer of from 0 to 4;

$R_1$ and $R_2$ are each independently a substituent selected from alkyl, cycloalkyl, aryl, heteroaryl, heteroalicyclic, hydroxy, thiol, alkoxy, thioalkoxy, aryloxy, thioalryloxy, halo, alkyl, amine, amide, carboxylate, and thiocarboxylate;

B is a cyclic moiety selected from aryl, heteroaryl and heteroalicyclic; and

L is a linking moiety, comprising from 2 to 12 atoms in length, and comprising a saturated or unsaturated, substituted or unsubstituted hydrocarbon chain, optionally interrupted by one or more of O, S, —S(═O)—, —S(═O)$_2$, —N═ and —NR$_4$—.

According to some of any of the embodiments of this aspect of the invention, n is 1 or 2.

According to some of any of the embodiments of this aspect of the invention, $R_1$ is selected from hydroxy, alkoxy, thiohydroxy, thioalkoxy, aryloxy, halo and amine.

According to some of any of the embodiments of this aspect of the invention, B is aryl.

According to some of any of the embodiments of this aspect of the invention, m is 1.

According to some of any of the embodiments of this aspect of the invention, $R_2$ is selected from hydroxy and alkoxy.

According to some of any of the embodiments of this aspect of the invention, L is or comprises an unsaturated hydrocarbon chain substituted by one or more oxo (═O) groups.

According to some embodiments of this aspect of the invention:

n is 2;

each of $R_1$ is hydroxy;

B is aryl;

m is 1;

$R_2$ is alkoxy; and

L is an unsaturated hydrocarbon chain substituted by one or more oxo (═O) groups.

According to an aspect of some embodiments of the present invention there is provided method of treating a disease selected from the group consisting of infectious disease and cancer in a subject in need thereof, the method comprising administering to the subject a therapeutically effective amount of a compound represented by Formula V:

Formula V

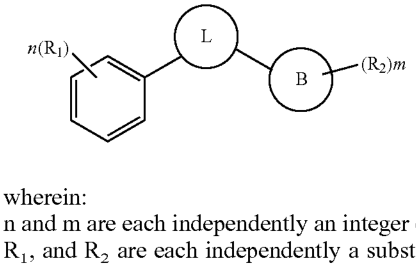

wherein:

n and m are each independently an integer of from 0 to 4;

$R_1$, and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate, thiocarboxylate, cyano and haloalkyl;

B is a cyclic moiety selected from aryl, heteroaryl and heteroalicyclic;

L is a linking moiety, comprising from 2 to 12 atoms in length, and comprising a saturated or unsaturated, substituted hydrocarbon chain, optionally interrupted by one or more of O, S, —S(═O)—, —S(═O)$_2$, —N= and —$NR_4$, wherein when the linker is saturated, $R_1$ is selected from hydroxy, alkoxy, aryloxy, and halo, thereby treating the disease in the subject.

According to an aspect of some embodiments of the present invention there is provided a compound represented by Formula V as defined herein, for use in treating a disease selected from the group consisting of infectious disease and cancer in a subject in need thereof.

According to some of any of the embodiments of this aspect of the invention, the subject immune system is not activated prior to the administering.

According to some of any of the embodiments of this aspect of the invention, the infectious disease is an HIV infection.

According to some of any of the embodiments of this aspect of the invention, the disease is in an immune privileged site.

According to some of any of the embodiments of this aspect of the invention, the compound is capable of up-regulating expression of a pro-inflammatory gene under basal conditions, wherein transcription of the pro-inflammatory gene is dependent on Spt5.

According to some of any of the embodiments of this aspect of the invention:

n and m are each independently an integer of from 0 to 4;

$R_1$ and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate, and thiocarboxylate;

B is a cyclic moiety selected from aryl, heteroaryl and heteroalicyclic; and

L is a linking moiety, comprising from 2 to 12 atoms in length, and comprising an unsaturated, substituted hydrocarbon chain, optionally interrupted by one or more of O, S, —S(=O)—, —S(=O)$_2$, —N= and —$NR_4$—.

According to some of any of the embodiments of this aspect of the invention, n is 1 or 2.

According to some of any of the embodiments of this aspect of the invention, B is aryl.

According to some of any of the embodiments of this aspect of the invention, m is 1.

According to some of any of the embodiments of this aspect of the invention, $R_2$ is selected from hydroxy and alkoxy.

According to some of any of the embodiments of this aspect of the invention, L is or comprises an unsaturated hydrocarbon chain substituted by one or more oxo (=O) groups.

According to some embodiments of the invention:

n is 2;

each of $R_1$ is hydroxy;

B is aryl;

m is 1;

$R_2$ is alkoxy; and

L is an unsaturated hydrocarbon chain substituted by one or more oxo groups.

According to an aspect of some embodiments of the present invention there is provided a method of treating an inflammatory disease in a subject in need thereof, the method comprising administering to the subject a therapeutically effective amount of a compound represented by Formula III, as defined herein, or a compound represented by Formula VI:

Formula VI

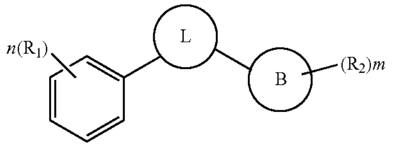

wherein:

n and m are each independently an integer of from 0 to 4;

$R_1$, and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate, thiocarboxylate, cyano and haloalkyl;

B is a cyclic moiety selected from aryl, heteroaryl and heteroalicyclic; and

L is a linking moiety, comprising from 2 to 12 atoms in length, and comprising a saturated or unsaturated, substituted or unsubstituted hydrocarbon chain, optionally interrupted by one or more of S, —S(=O)—, —S(=O)$_2$, —N= and —$NR_4$, wherein when the hydrocarbon chain is saturated, it is substituted by at least one =$X_7$ group, wherein $X_7$ is O, S, $NR_4$ or $CR_5R_6$, and/or it is interrupted by one or more of S, —S(=O)—, —S(=O)$_2$, —N= and —$NR_4$, thereby treating the inflammatory disease in the subject.

According to an aspect of some embodiments of the present invention there is provided a compound represented by Formula III as defined herein, or Formula VI as defined herein, for use in treating an inflammatory disease in a subject in need thereof.

According to some of any of the embodiments of this aspect of the invention, the inflammatory disease can benefit from down-regulating expression of a pro-inflammatory gene responsive to NFκB activation.

According to some of any of the embodiments of this aspect of the invention, the inflammatory disease is selected from the group consisting of an autoimmune disease, graft rejection disease and allergic disease.

According to some of any of the embodiments of this aspect of the invention, the compound is capable of down-regulating expression of a pro-inflammatory gene under TNFα-induced conditions, wherein transcription of the pro-inflammatory gene is dependent on Spt5.

According to an aspect of some embodiments of the present invention there is provided a method of down-regulating expression of a pro-inflammatory gene, the method comprising contacting a cell exposed to TNFα with a compound represented by Formula III as defined herein, or Formula VI as defined herein, wherein the cell expresses Spt5 and RNA Polymerase II and transcription of the pro-inflammatory gene is dependent on Spt5, thereby down-regulating expression of the pro-inflammatory gene.

According to some of any of the embodiments of this aspect of the invention, the method being effected in-vitro or ex-vivo.

According to some of any of the embodiments of this aspect of the invention, the method being effected in-vivo.

According to some of any of the embodiments of this aspect of the invention, the cell is a eukaryotic cell.

According to some of any of the embodiments of this aspect of the invention, the cell is a mammalian cell.

According to some of any of the embodiments of this aspect of the invention, the pro-inflammatory gene is responsive to NFκB activation.

According to some of any of the embodiments of this aspect of the invention, the pro-inflammatory gene responsive to NFκB activation is selected from the group consisting of A20, CCL20, IL6, IL8, CXCL2, JUNB and IEX1.

According to some of any of the embodiments of this aspect of the invention, the compound is represented by Formula VI.

According to some of any of the embodiments of this aspect of the invention:

n and m are each independently an integer of from 0 to 4;

$R_1$ and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate, and thiocarboxylate;

B is a cyclic moiety selected from aryl, heteroaryl and heteroalicyclic; and

L is the linking moiety.

According to some of any of the embodiments of this aspect of the invention, n is 1 or 2.

According to some of any of the embodiments of this aspect of the invention, $R_1$ is selected from hydroxy, alkoxy, thiohydroxy, thioalkoxy, aryloxy, halo and amine.

According to some of any of the embodiments of this aspect of the invention, B is aryl.

According to some of any of the embodiments of this aspect of the invention, m is 1.

According to some of any of the embodiments of this aspect of the invention, $R_2$ is selected from hydroxy and alkoxy.

According to some of any of the embodiments of this aspect of the invention, L is or comprises an unsaturated hydrocarbon chain substituted by one or more oxo (═O) groups.

According to some of any of the embodiments of this aspect of the invention:

n is 2;

each of $R_1$ is hydroxy;

B is aryl;

m is 1;

$R_2$ is alkoxy; and

L is an unsaturated hydrocarbon chain substituted by one or more oxo groups.

According to some of any of the embodiments of this aspect of the invention, B is heteroaryl.

According to some of any of the embodiments of this aspect of the invention, m is 0.

According to some of any of the embodiments of this aspect of the invention, L is a saturated hydrocarbon substituted by an oxo group and interrupted by S.

According to some of any of the embodiments of this aspect of the invention, n is 1 and $R_1$ is amine.

According to some of any of the embodiments of this aspect of the invention, the compound is represented by Formula III.

According to some of any of the embodiments of this aspect of the invention, $X_4$, $X_5$ and $X_6$ are each oxygen.

According to some of any of the embodiments of this aspect of the invention, k at least 2.

According to some of any of the embodiments of this aspect of the invention, $R_{10}$ is independently an alkyl.

According to an aspect of some embodiments of the present invention there is provided a method of inducing death of a cell, the method comprising contacting the cell with a toxic amount of a compound represented by Formula II as defined in claim of the present invention, Formula III, as defined herein, and Formula IV as defined herein, wherein the cell expresses Spt5 and RNA Polymerase II (Pol II), thereby inducing death of the cell.

According to some of any of the embodiments of this aspect of the invention, the cell is a diseased cell.

According to some of any of the embodiments of this aspect of the invention, the cell is a pathogenic cell (e.g. a pest, a bacteria, a virus, a fungi).

According to some of any of the embodiments of this aspect of the invention, the compound is represented by Formula IV.

According to some of any of the embodiments of this aspect of the invention:

n and m are each independently an integer of from 0 to 4;

$R_1$ and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate, and thiocarboxylate;

B is a cyclic moiety selected from aryl, heteroaryl and heteroalicyclic; and

L is the linking moiety.

According to some of any of the embodiments of this aspect of the invention, n is 1 or 2.

According to some of any of the embodiments of this aspect of the invention, $R_1$ is selected from hydroxy, alkoxy, thiohydroxy, thioalkoxy, aryloxy, and halo.

According to some of any of the embodiments of this aspect of the invention, B is aryl.

According to some of any of the embodiments of this aspect of the invention, m is 1 or 2.

According to some of any of the embodiments of this aspect of the invention, $R_2$ is selected from hydroxy, alkoxy, carboxylate and halo.

According to some of any of the embodiments of this aspect of the invention, L is or comprises an unsaturated hydrocarbon chain substituted by one or more oxo (═O) groups.

According to some of any of the embodiments of this aspect of the invention:

n is 2;

each of $R_1$ is hydroxy;

B is aryl;

m is 1;

$R_2$ is alkoxy; and

L is an unsaturated hydrocarbon chain substituted by one or more oxo (═O) groups.

According to some of any of the embodiments of this aspect of the invention, B is a heteroaryl or a heteroalicyclic.

According to some of any of the embodiments of this aspect of the invention, L is an unsaturated unsubstituted hydrocarbon interrupted by —$NR_4$— or by —S—.

According to some of any of the embodiments of the invention, the compound inhibits binding of Spt5 to Pol II or changes the conformation of a Spt5-Pol II complex.

According to some of any of the embodiments of the invention, the compound binds Spt5 or Pol II.

According to some of any of the embodiments of the invention, the Pol II comprises Rpb1.

According to some of any of the embodiments of the invention, the compound binds an NGN domain and/or a KOW domain of the Spt5, or a coiled-coil (CC) domain of the Rpb1.

According to an aspect of some embodiments of the present invention there is provided a method of identifying a Spt5 inhibitor, the method comprising determining binding of Spt5 to RNA Polymerase II (Pol II) in the presence of a test compound, wherein a decrease in binding of the Spt5 to the Pol II or a change in conformation of a Spt5-Pol II complex as compared to same in the absence of the test compound, indicates the test compound is a Spt5 inhibitor.

According to some of any of the embodiments of this aspect of the invention, the method is a cell free method.

According to some of any of the embodiments of this aspect of the invention, the method is effected in intact cells.

According to some of any of the embodiments of this aspect of the invention, the cells are immune activated.

According to some of any of the embodiments of this aspect of the invention, the method further comprising testing an effect of the test agent on a biological outcome of inhibition of the Spt5.

According to some of any of the embodiments of this aspect of the invention, the test agent is a small molecule.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1B:
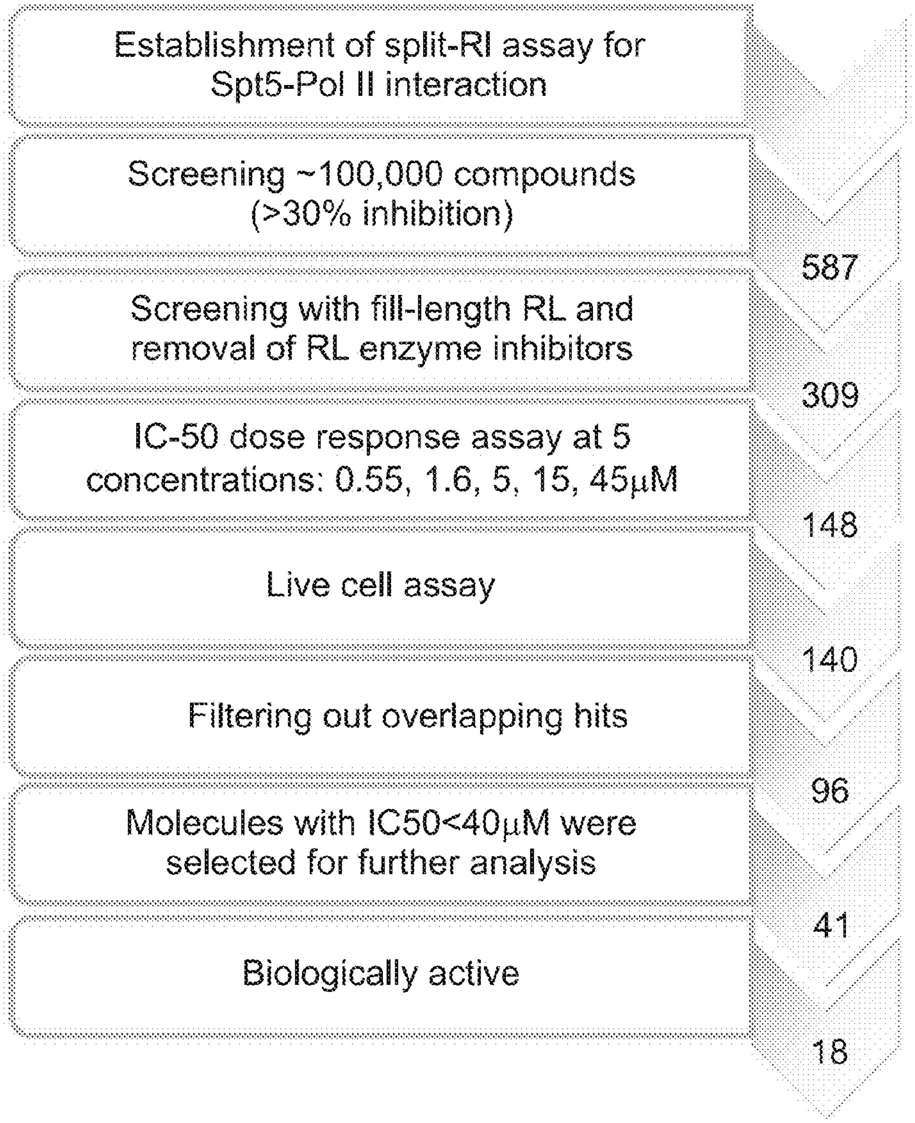
Figure 1C:
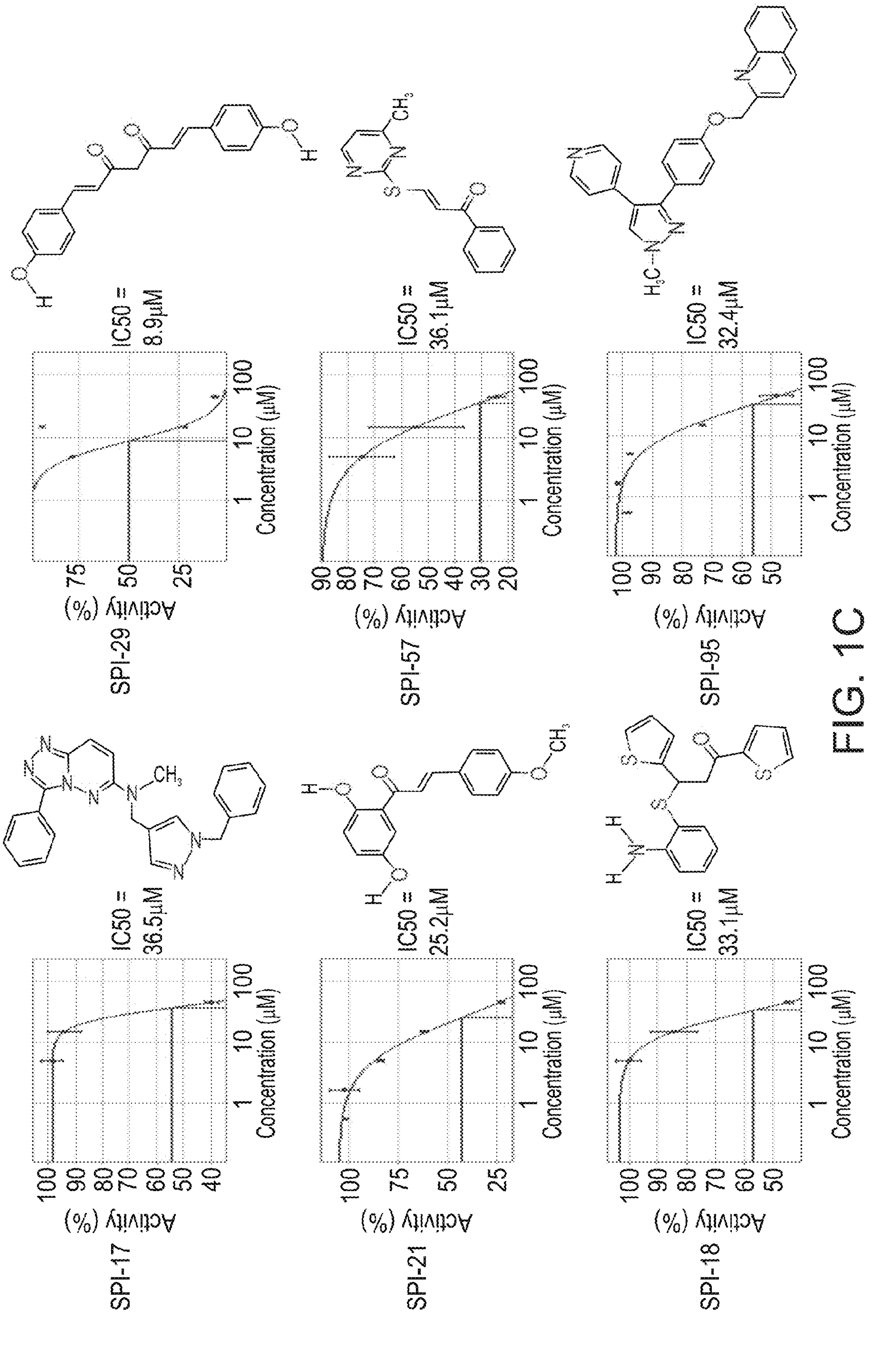
Figure 1C:
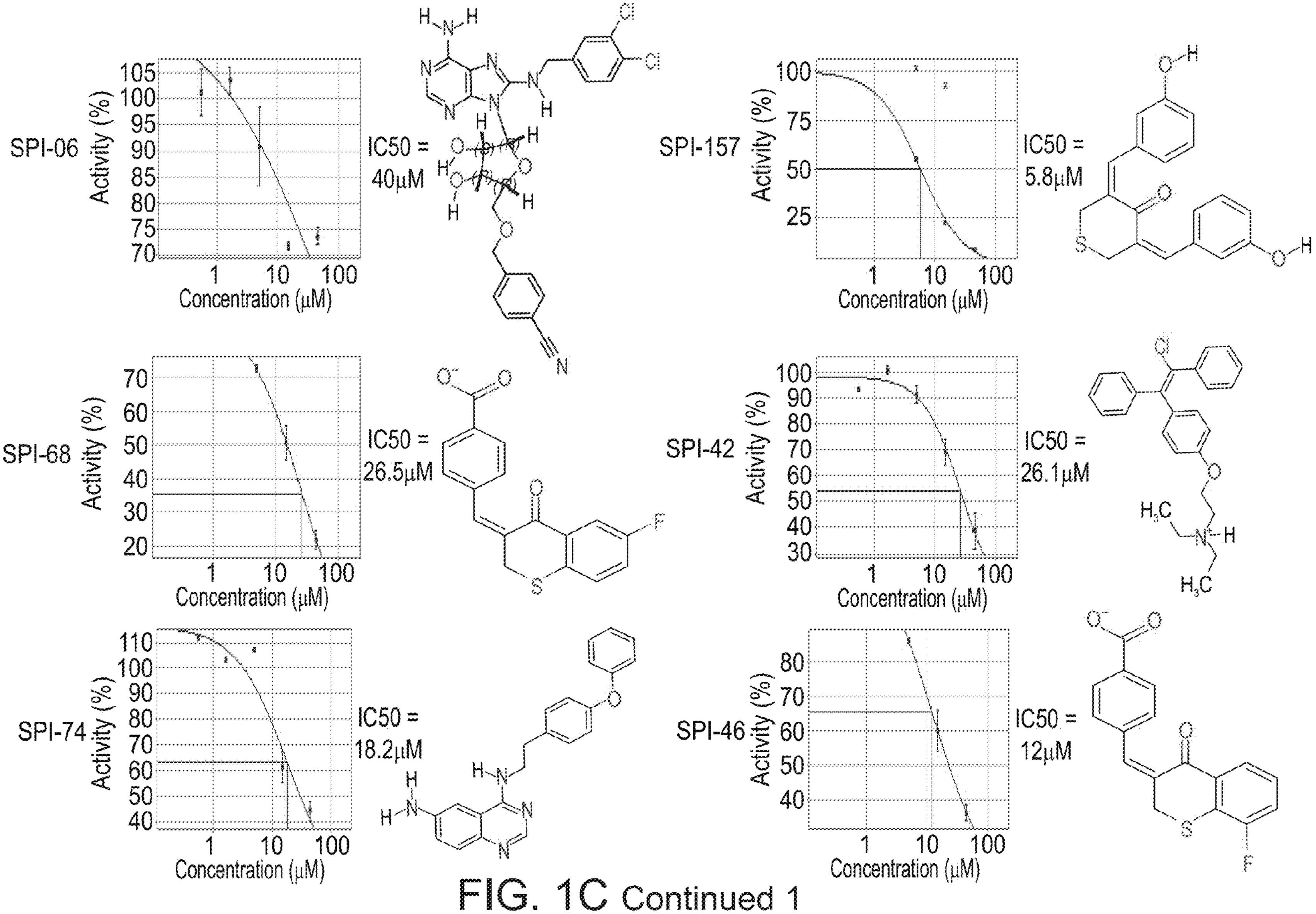
Figure 1C:
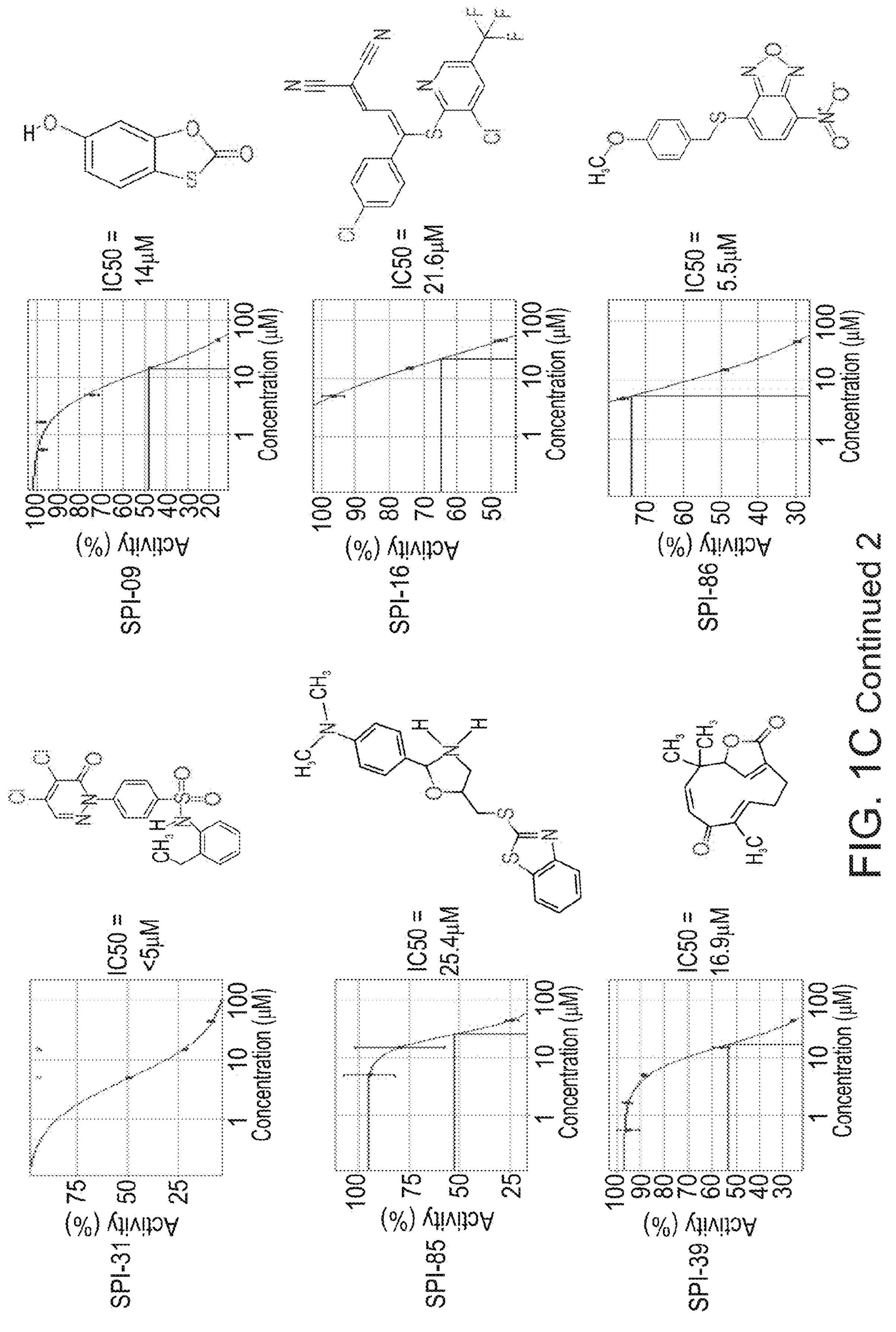
Figure 1D:
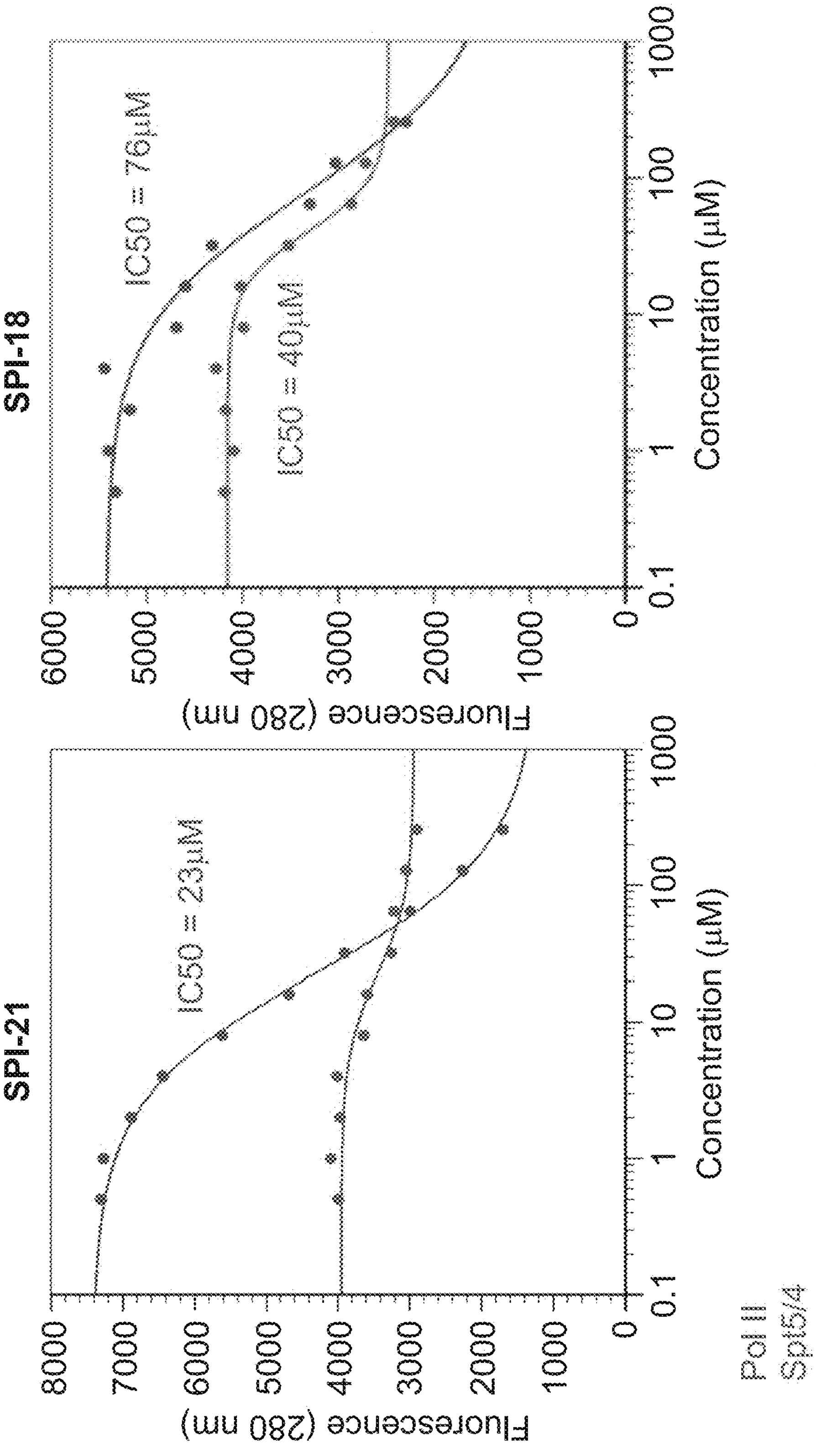
Figure 1E:
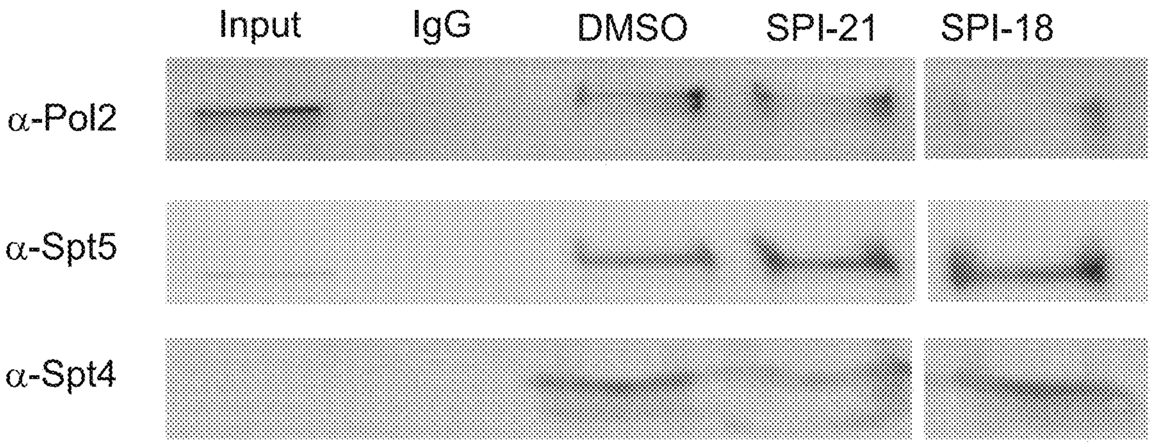
Figure 1F:
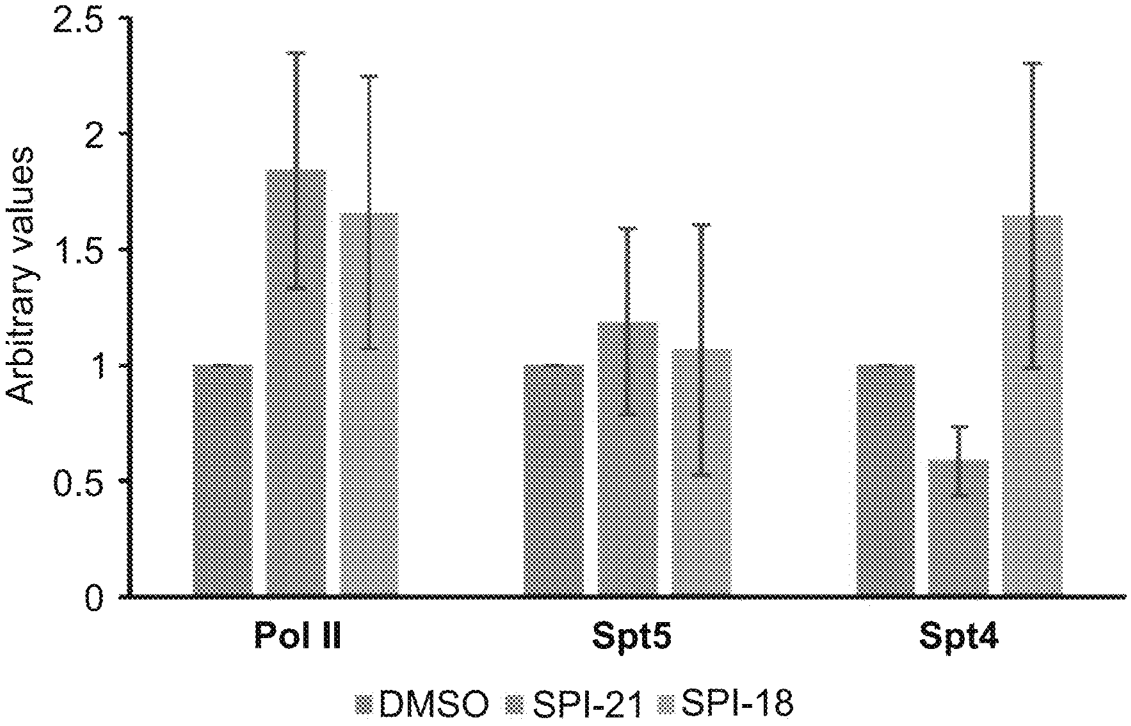

In the drawings:

FIGS. 1A-F demonstrate the high-throughput (HTS) drug screening assay and the identified Spt5 inhibitors (referred to herein as SPI). FIG. 1A is a schematic illustration of Spt5 and Pol II split-RL assay. FIG. 1B is a flow chart showing the steps used for the HTS. FIG. 1C demonstrates the chemical structure and the IC50 of 18 biologically active SPIs identified by the screen. FIGS. 1D and 1E demonstrate a direct interaction of the identified inhibitors SPI-21 or SPI-18 with Spt5 and/or Rpb1. FIG. 1D demonstrates intrinsic fluorescence levels of purified His-Spt5 or His-Rpb1 incubated with increasing concentrations of SPI-21 or SPI-18, as measured by a Cytation 5 instrument. The graph shows the changes in fluorescence intensities in response to the indicated concentration of SPIs and the calculated IC50. FIGS. 1E and 1F present a Western blot photograph and a bar graph, respectively, demonstrating co-immunoprecipitation of HeLa cells lysates pre-treated with either DMSO (vehicle control) or 50 μM SPI-21 or SPI18 using an anti-Spt5 antibody or rabbit IgG control. The immune-precipitated proteins were detected by Western blot using anti-Spt5, anti-Pol II and anti-Spt4 antibodies.

Figure 2A:
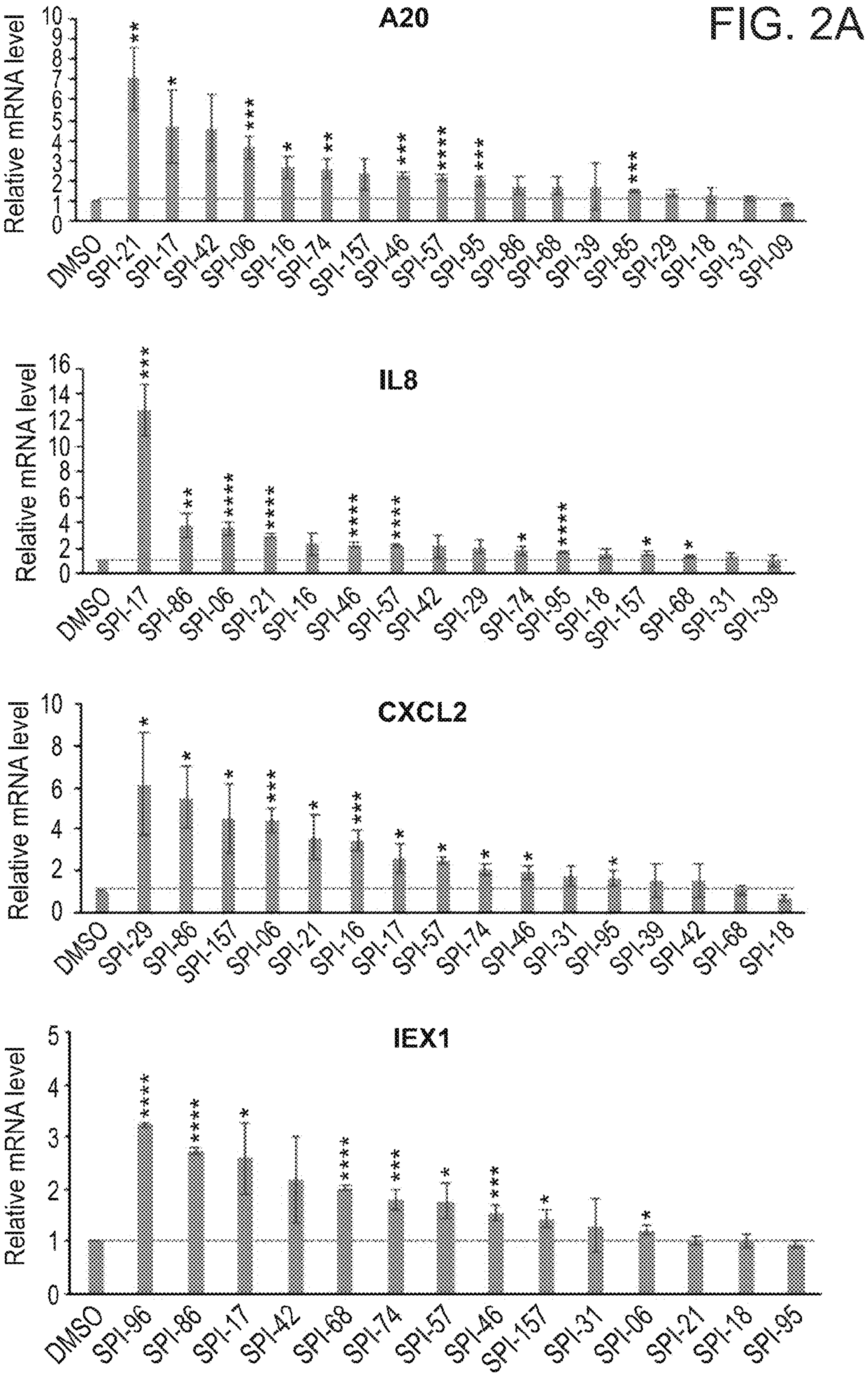
Figure 2A:
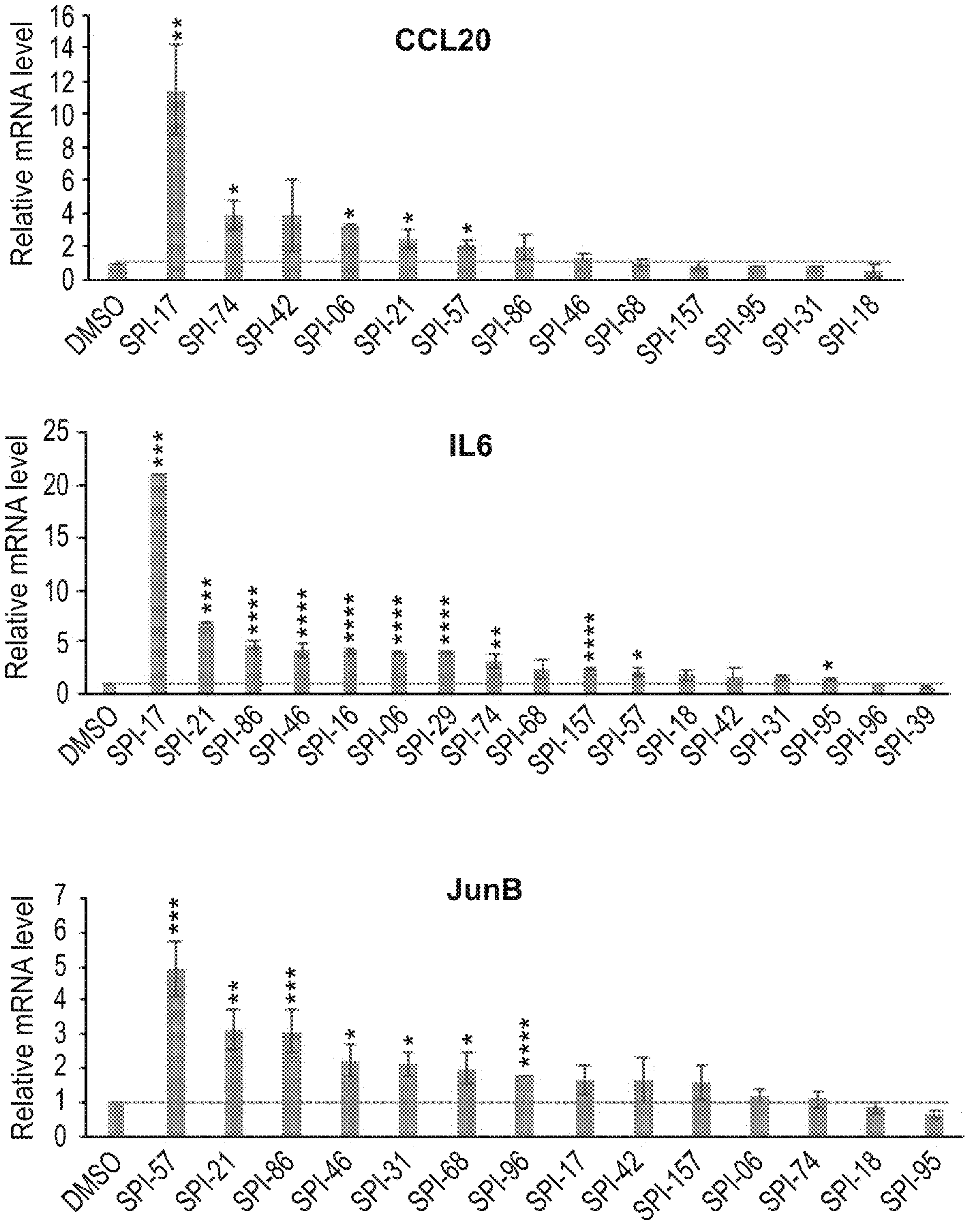
Figure 2B:
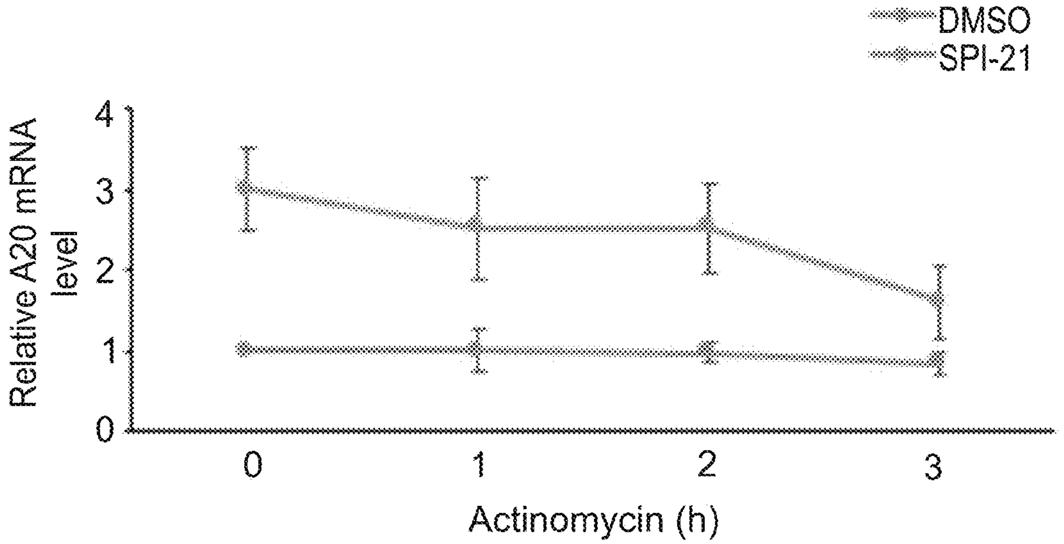
Figure 2C:
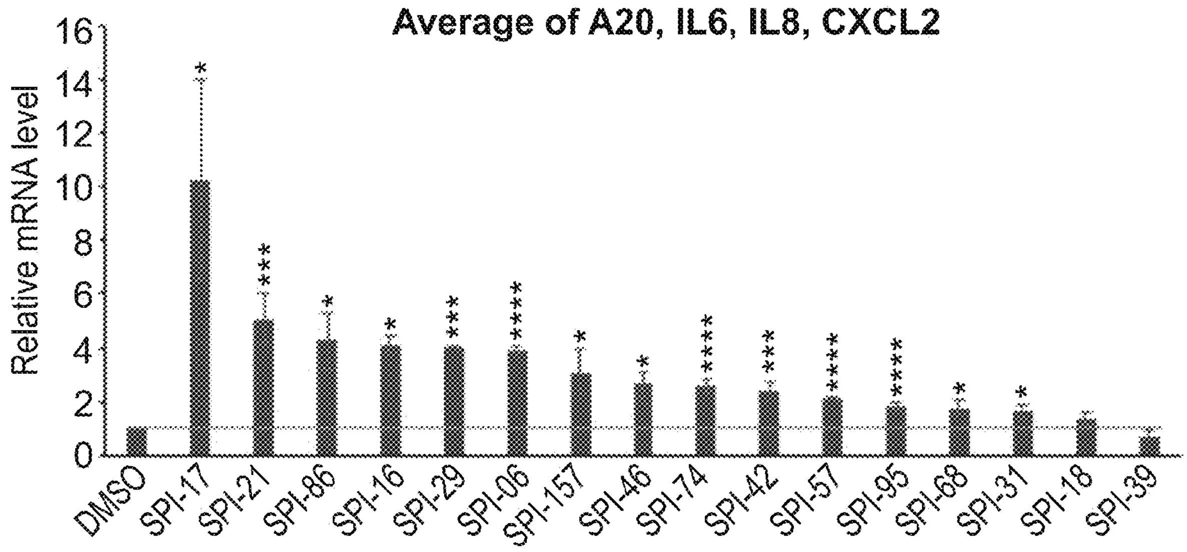
Figure 2D:
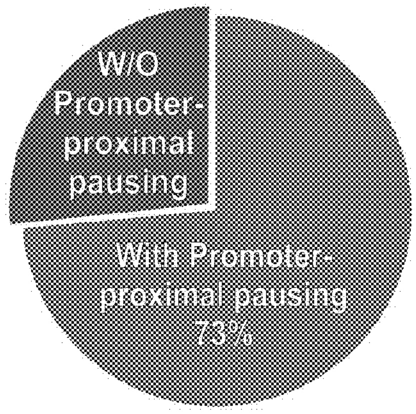
Figure 2E:
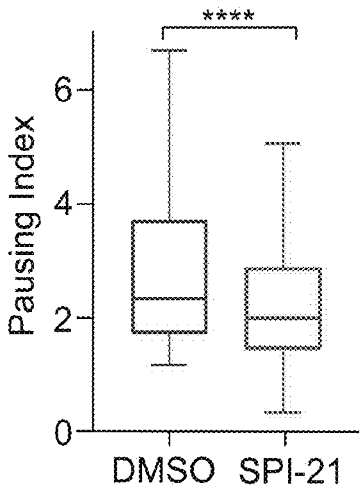

FIGS. 2A-F demonstrate the effect of the identified SPIs on the mRNA levels of pro-inflammatory genes, promoter-proximal pausing and Pol II recruitment, under basal conditions. FIG. 2A shows bar graphs of mRNA levels of the indicated genes (normalized to GAPDH) in HeLa cells treated for 2 hours with DMSO (vehicle control) or 50 μM of the indicated SPI, as determined by real-time qPCR. Bars represent the mean of at least 3±SEM independent experiments. The asterisks denote statistical significance differences relative to DMSO according to Student's t tests (typically one tailed, paired): *$p<0.05$; $p<0.01$; *$p<0.005$; **$p<0.001$. FIG. 2B is a graph demonstrating the effect of SPI-21 on the stability of mRNA under basal conditions. Shown are mRNA levels of A20 (normalized to GAPDH) in Hela cells treated with SPI-21 and incubated with actinomycin D for the indicated time points, as determined by real-time qPCR. The data points present the mean of 3±SEM independent experiments. FIG. 2C is a bar graph summarizing the average effect of the identified SPIs on the mRNA levels of the indicated genes under basal conditions, organized in descending order of potency. FIG. 2D is a pie chart demonstrating the percentage of SPI-21 upregulated genes that display promoter-proximal pausing (PI>1.2) in HeLa cells pretreated with SPI-21 for 90 minutes as compared to DMSO, as determined by GRO-seq analysis. The PI was calculated by dividing Pol II density (reads per 1,000 bp) around the TSS (−300 to +700 bp) by Pol II density in the gene body (+700 to +1,700). FIG. 2E is a boxplot presenting the change in the pausing index (PI) of the upregulated genes that display promoter-proximal pausing (PI>1.2 in DMSO) upon SPI-21 treatment. The significance of the difference in the median values between control and treatment was calculated by the Wilcoxon signed-rank test. FIG. 2**F shows several examples of GRO-seq reads aligned to the genome. DMSO and SPI-21 samples are presented in blue and red, respectively. The PIs, calculated for each gene, are shown on the right.

Figure 3A:
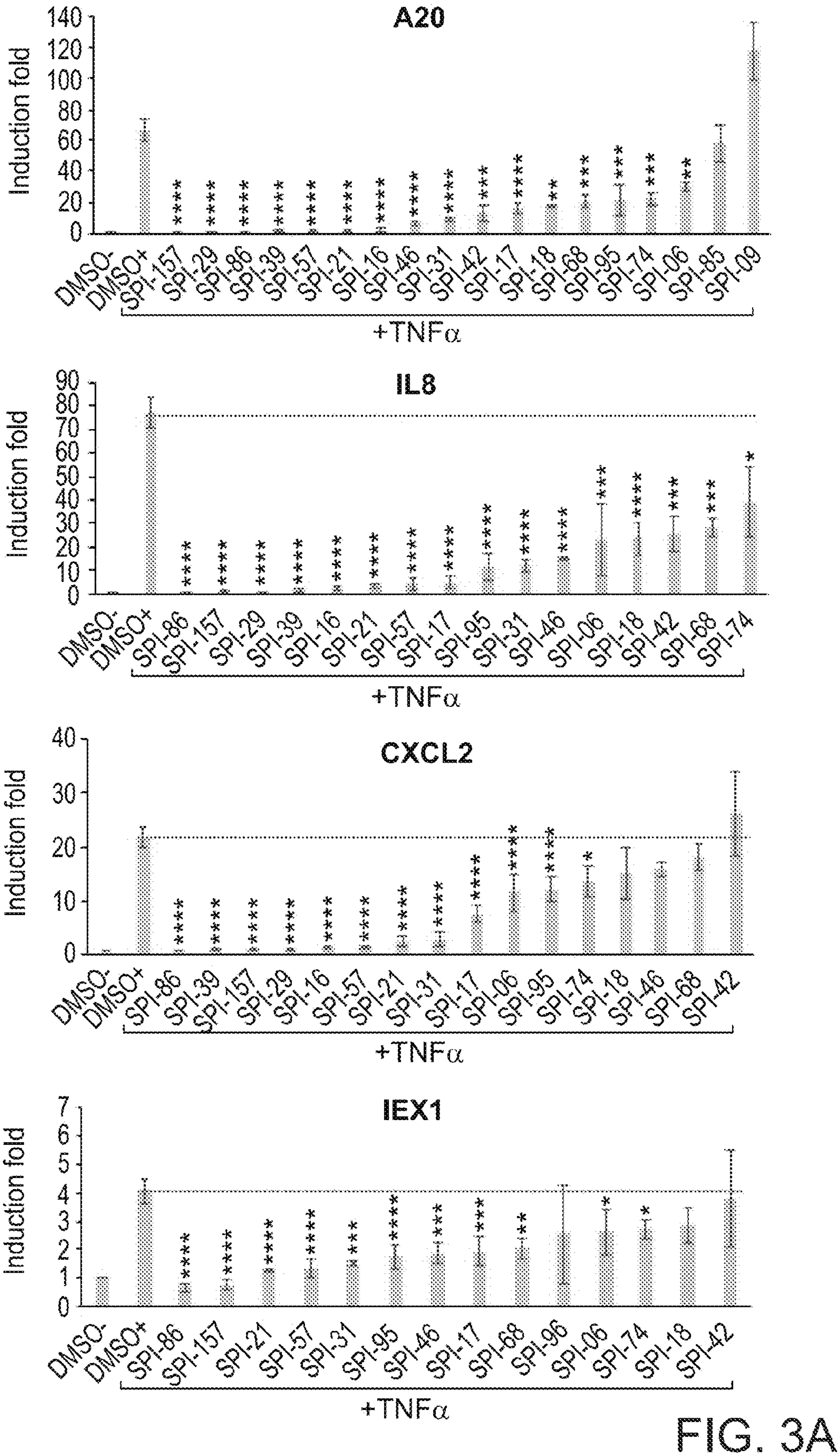
Figure 3A:
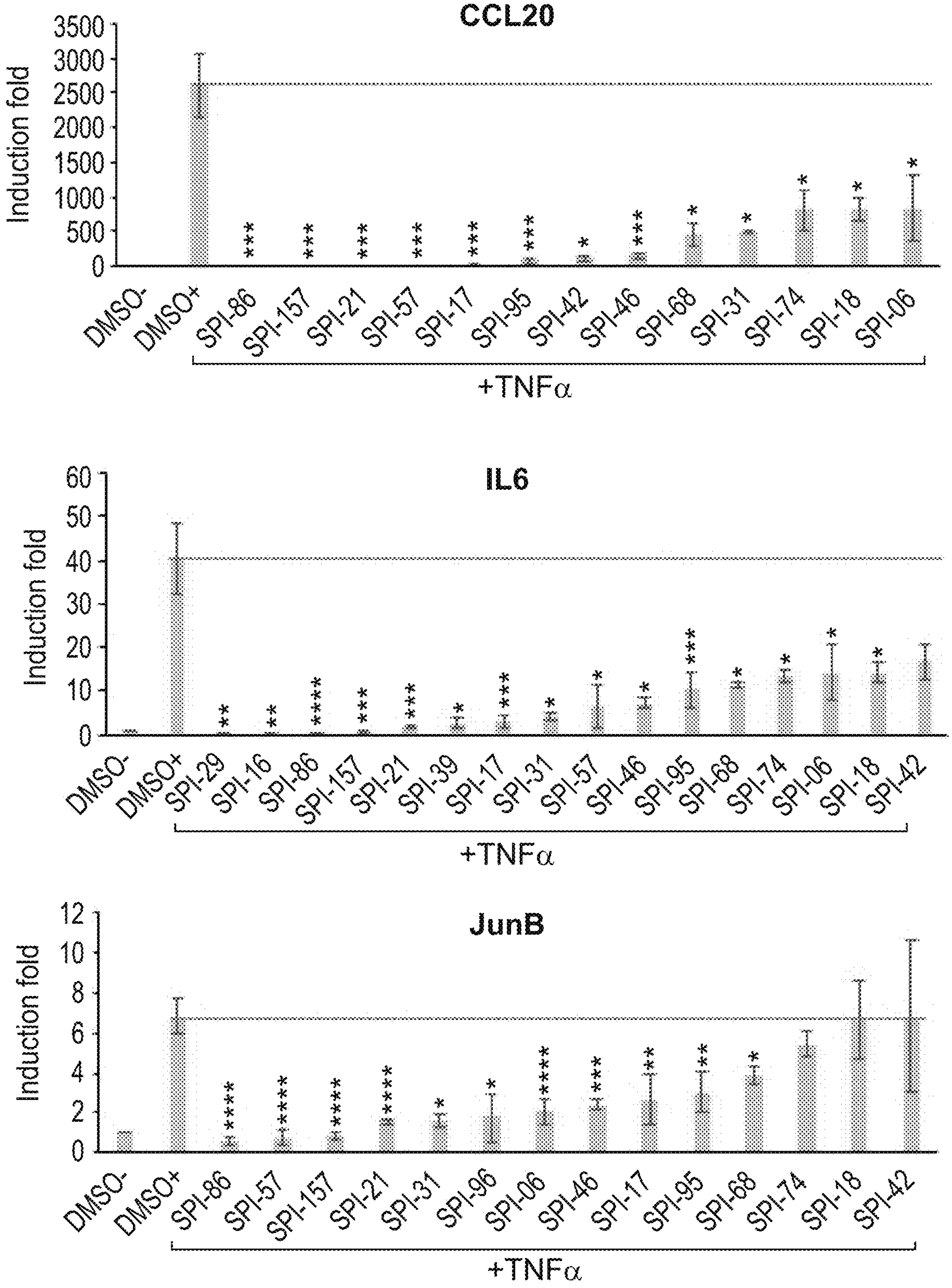
Figure 3B:
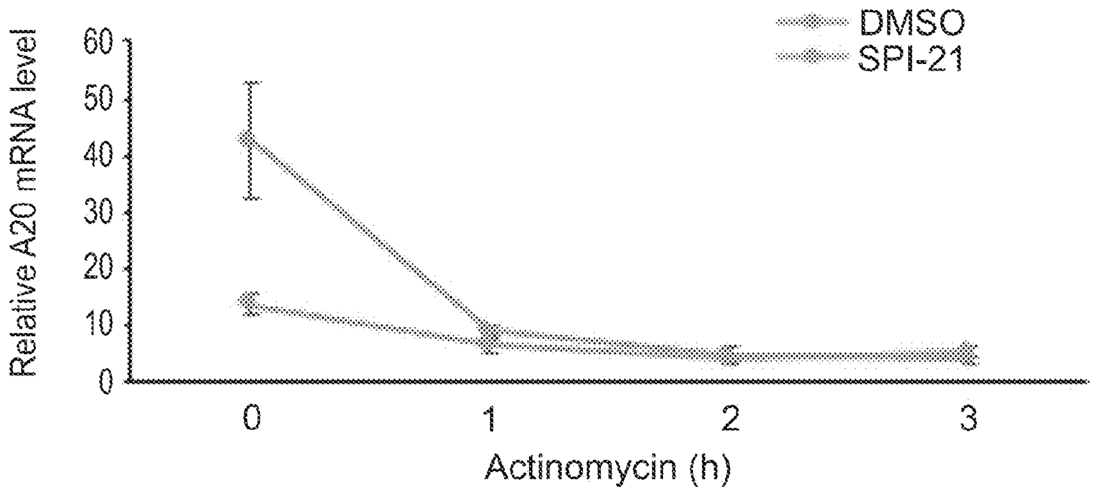
Figure 3C:
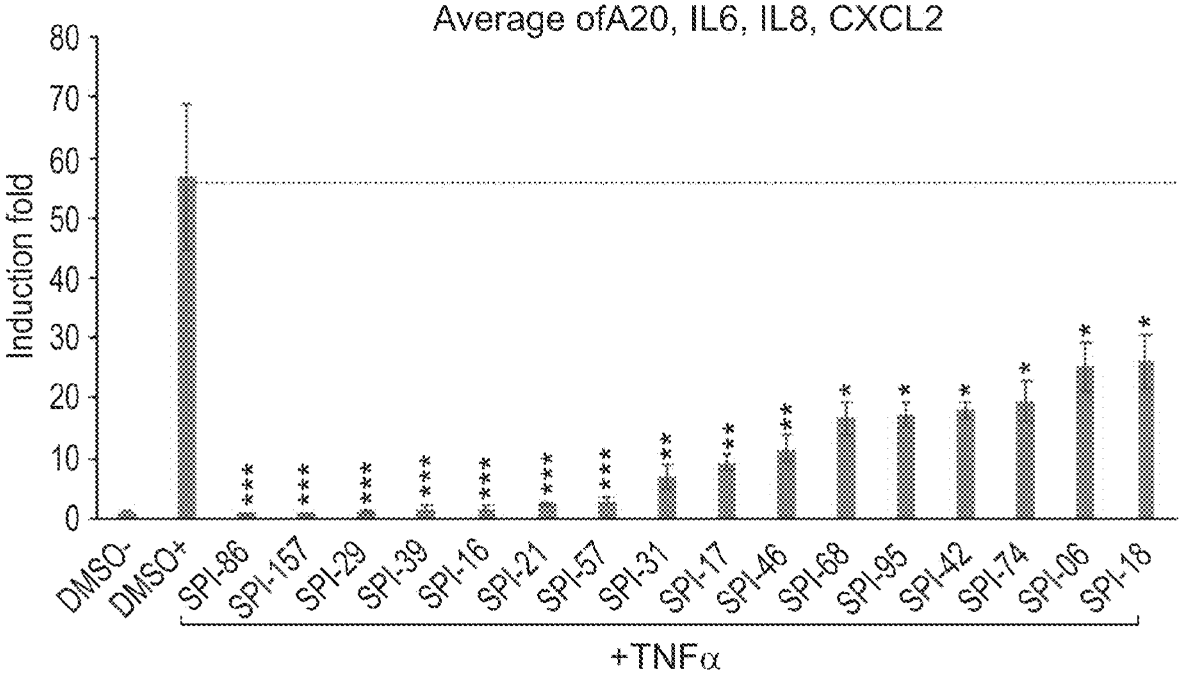
Figure 3D:
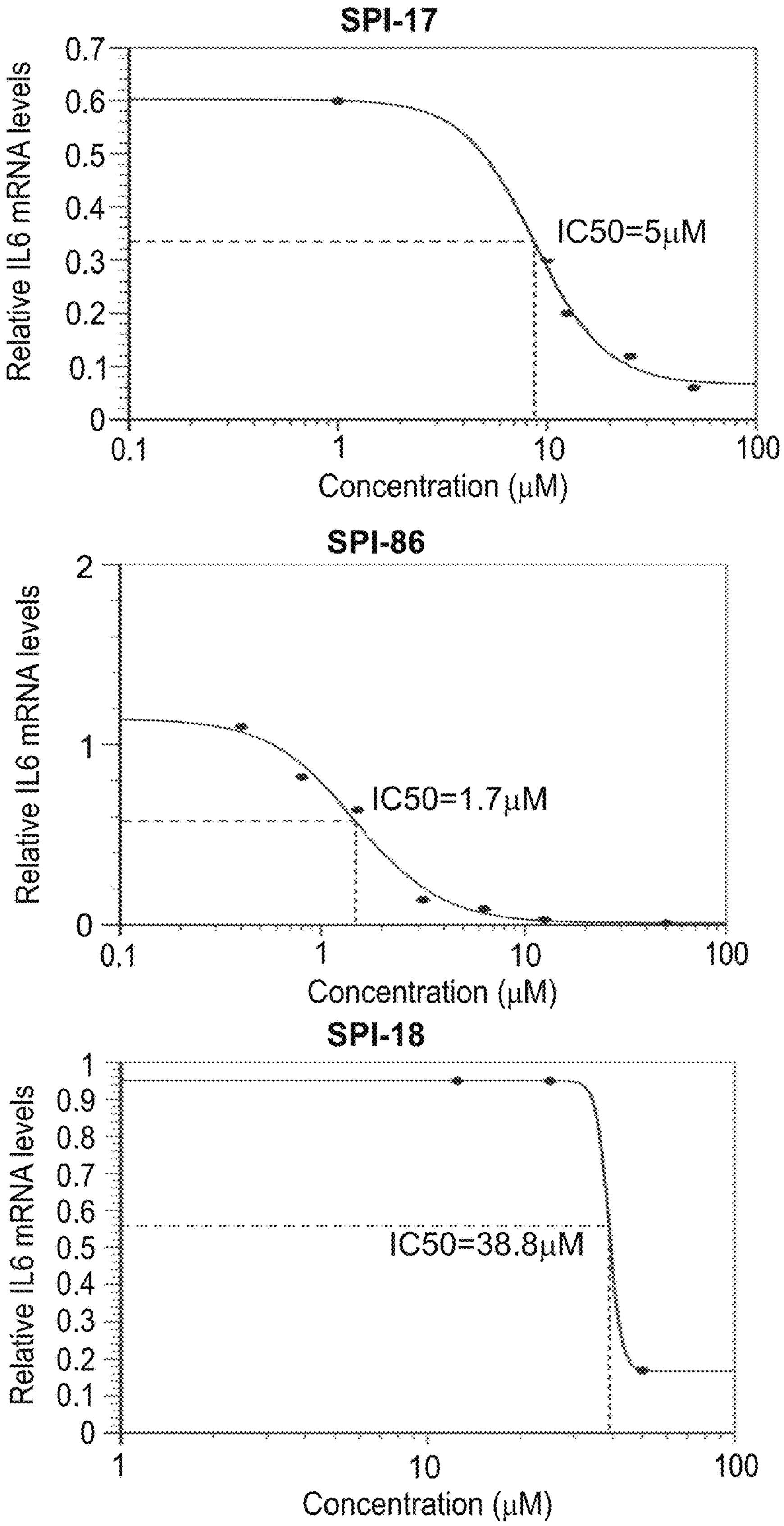
Figure 3D:
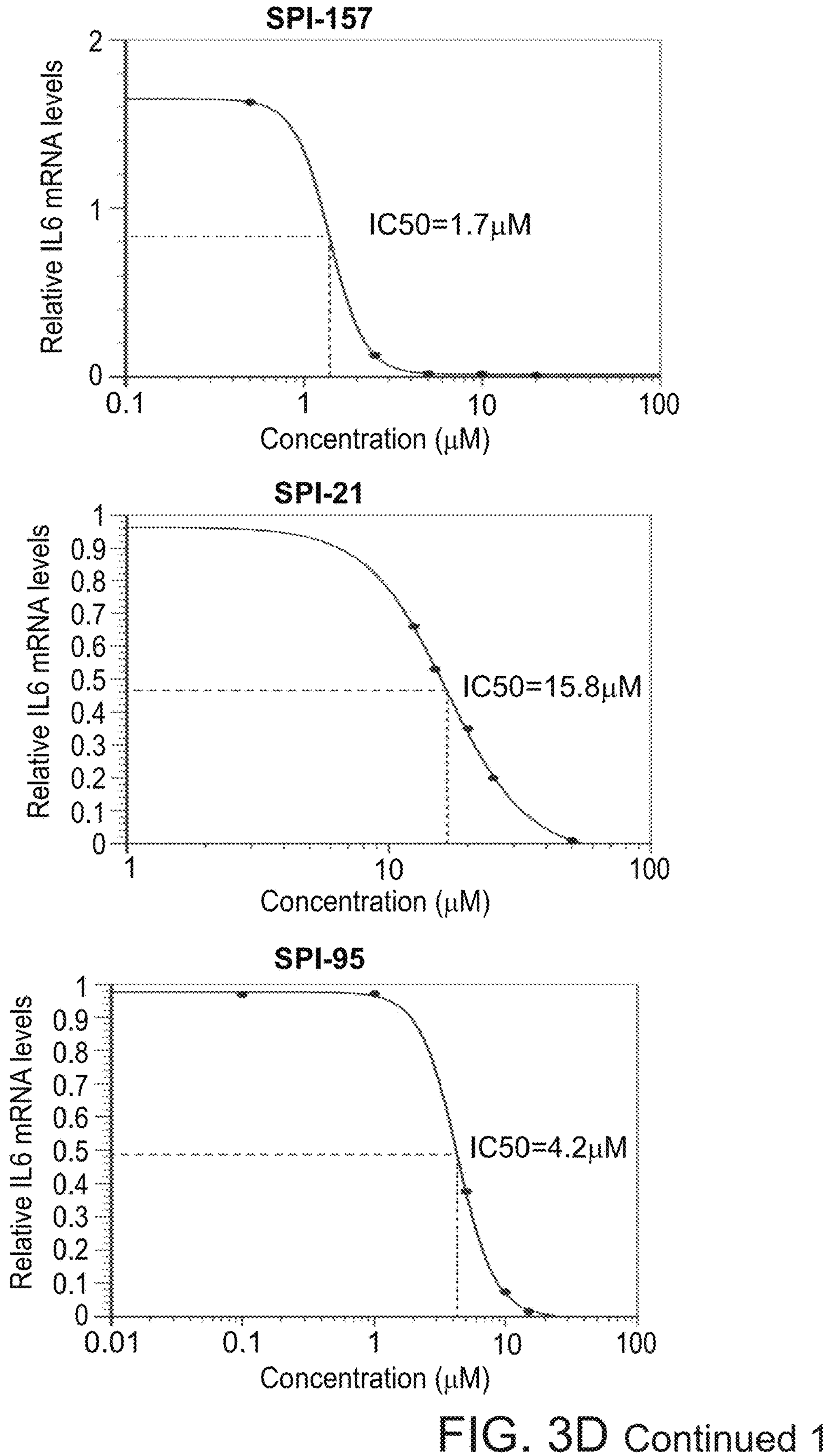
Figure 3D:
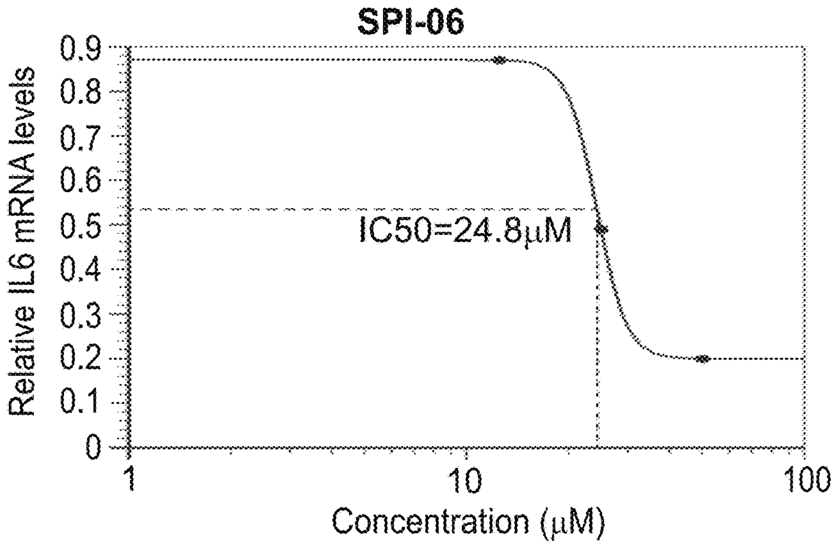
Figure 3D:
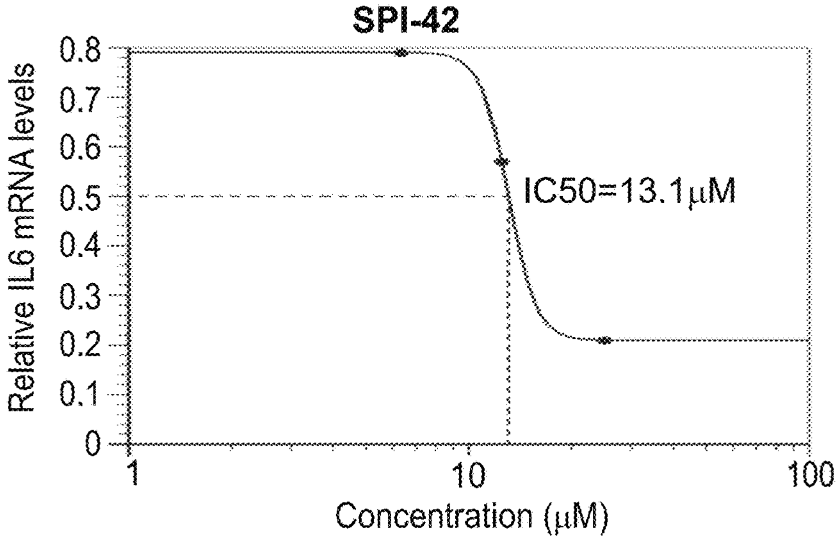
Figure 3D:
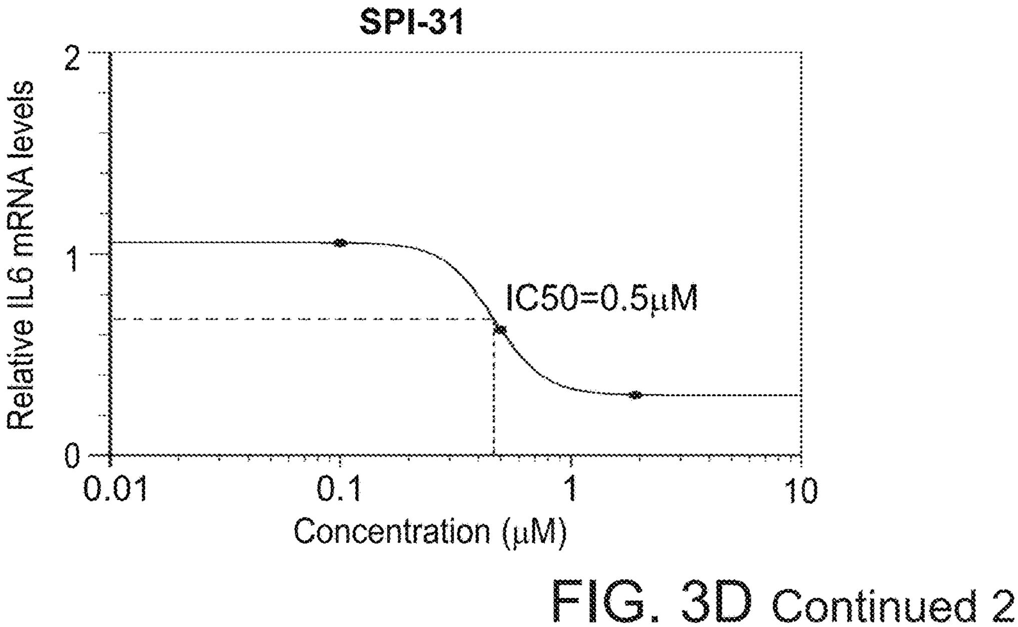
Figure 3E:
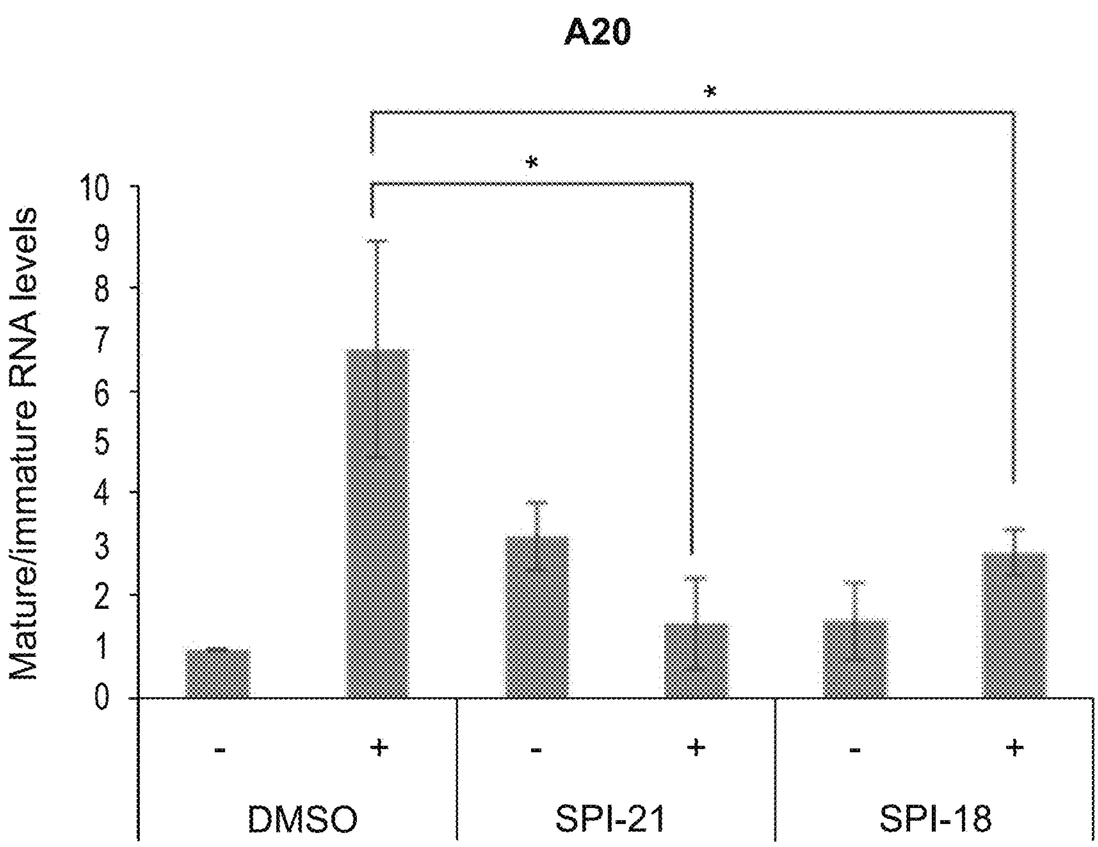
Figure 3F:
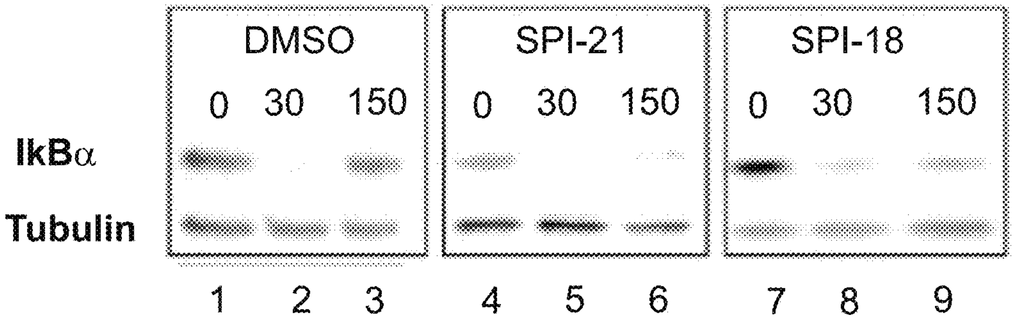
Figure 3G:
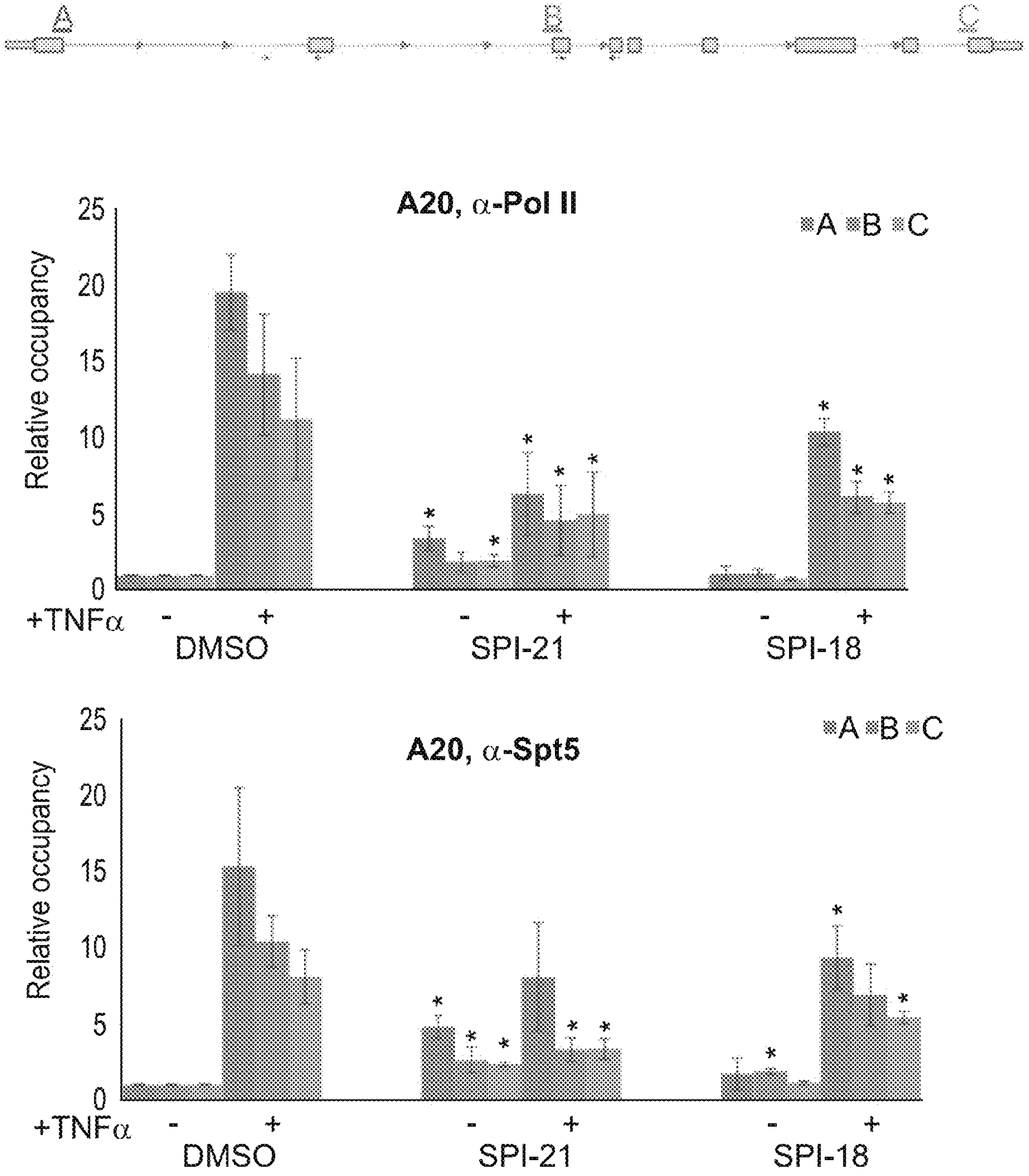
Figure 3H:
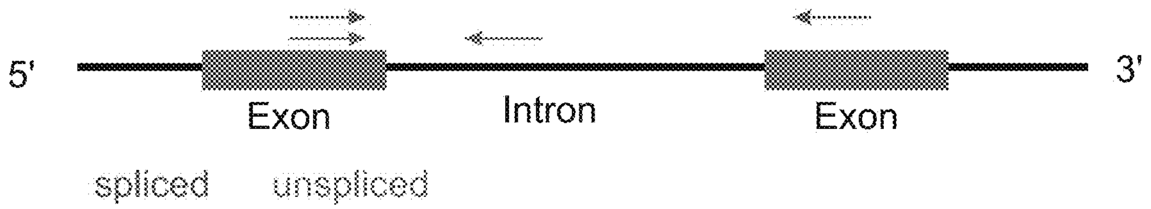
Figure 3H:
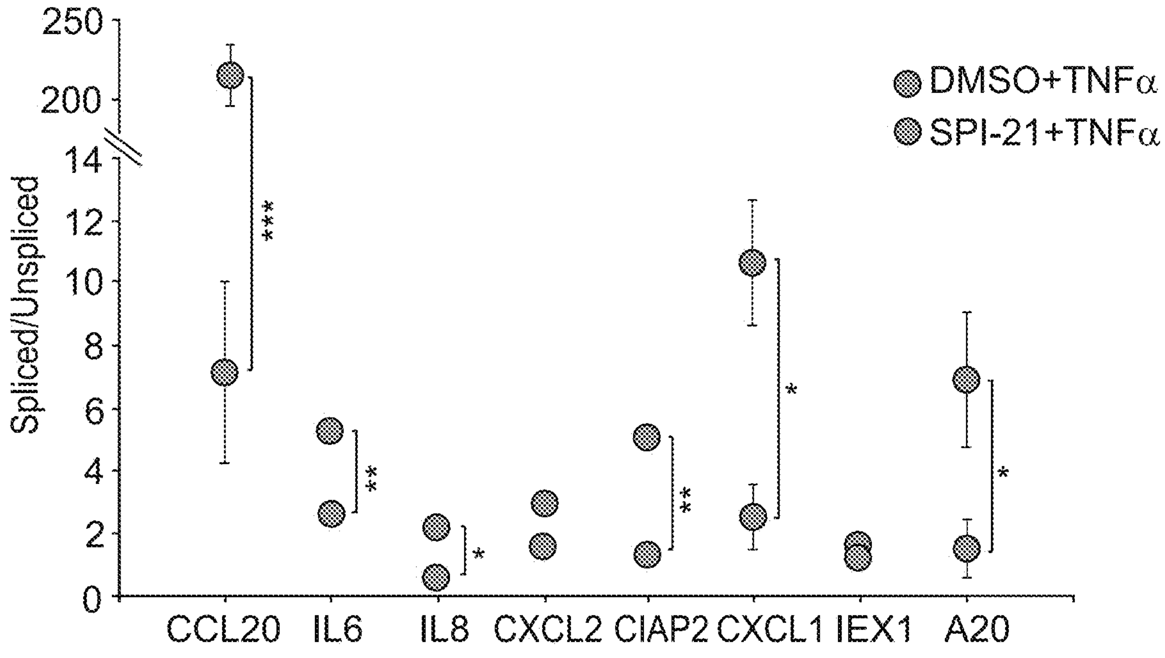

FIGS. 3A-H demonstrate the effect of the identified SPIs on the mRNA levels of pro-inflammatory genes under TNFα-induced conditions. FIG. 3A shows bar graphs of mRNA levels of the indicated genes (normalized to GAPDH) in HeLa cells treated for 1 hour with DMSO (vehicle control) or 50 μM of the indicated SPI, followed by treatment with TNFα (20 ng/ml) for an additional one hour, as determined by real-time qPCR. Bars represent the mean of at least 3±SEM independent experiments. The asterisks denote statistical significance differences relative to DMSO+TNFα control according to Student's t tests (typically one tailed, paired): *$p<0.05$; $p<0.01$; *$p<0.005$; **$p<0.001$. FIG. 3B is a graph demonstrating the effect of SPI-21 on the stability of mRNA under TNFα-induced conditions. Shown are mRNA levels of A20 (normalized to GAPDH) in Hela cells treated with SPI-21 and TNFα and incubated with actinomycin D for the indicated time points, as determined by real-time qPCR. The data points present the mean of 3±SEM independent experiments. FIG. 3C is a bar graph summarizing the average effect of the identified SPIs on the mRNA levels of the indicated genes under TNFα-induced conditions, organized in descending order of potency. FIG. 3D shows graphs demonstrating dose-response effects of the indicated SPIs on TNFα-induced IL6 mRNA levels and the calculated IC50 value. FIG. 3**E is a bar graph demonstrating the effect of SPI-21 and SPI-18 on splicing of the A20 gene. Shown are levels of mature and immature transcripts in cells incubated for 1 hour with DMSO (vehicle control) or 50 μM of SPI-21 or SPI-18 followed by treatment with TNFα for an additional one hour, as determined by real-time qPCR using primers spanning exons 3 and 4 (mature, black arrows shown in the scheme of G, SEQ ID NOs: 47 and 48) or intron 1 and exon 2 (immature, red arrows shown in the scheme of G, SEQ ID NOs: 49 and 50). The bars show the ratio between mature and immature transcripts in each sample. The data represent the mean of 3±SEM independent experiments; *=P<0.05 relative to DMSO+TNFα control. FIG. 3F demonstrates the effect of SPI-21 and SPI-18 on NF-κB signaling. DMSO (vehicle control), SPI-21 or SPI-18 treated cells were induced by TNFα for the indicated times and the levels of IκBα and β-Tubulin proteins were analyzed by western blot as indicated. FIG. 3G demonstrates the effect of SPI-21 and SPI-18 on Pol II and Spt5 occupancies of the A20 gene. Cells pre-treated with DMSO or SPI-21 and SPI-18 for one-hour were induced with TNFα for 30 minutes and then subjected to ChIP using anti-Rpb1 and anti-Spt5 antibodies. The occupancy of the A20 gene was analyzed by qPCR using primers from the first (A, SEQ ID NOs: 55 and 56), third (B, SEQ ID NOs: 57 and 58) and last (C, SEQ ID NOs: 59 and 60) exon-intron junctions. Bars present levels of Pol II and Spt5 relative to input, and are the mean±SEM of 3 independent experiments. * p<0.05 relative to the DMSO counterpart with or without TNFα. FIG. 3H is a dot plot presenting the effect of SPI-21 on the splicing efficiency of TNFα-induced genes. Shown are levels of mature and immature transcripts in cells incubated for 1 hour with DMSO (vehicle control) or 50 μM of SPI-21 or SPI-18 followed by treatment with TNFα for an additional one hour, as determined by real-time qPCR using different sets of primers (see scheme on top: red and green arrows for mature and immature transcripts, respectively). Each dot presents the ratio between mature and immature transcripts in each sample. The data represent the means±SEMs of 3 independent experiments, and the asterisks denote statistically significant differences relative to DMSO+TNFα.

Figure 3I:
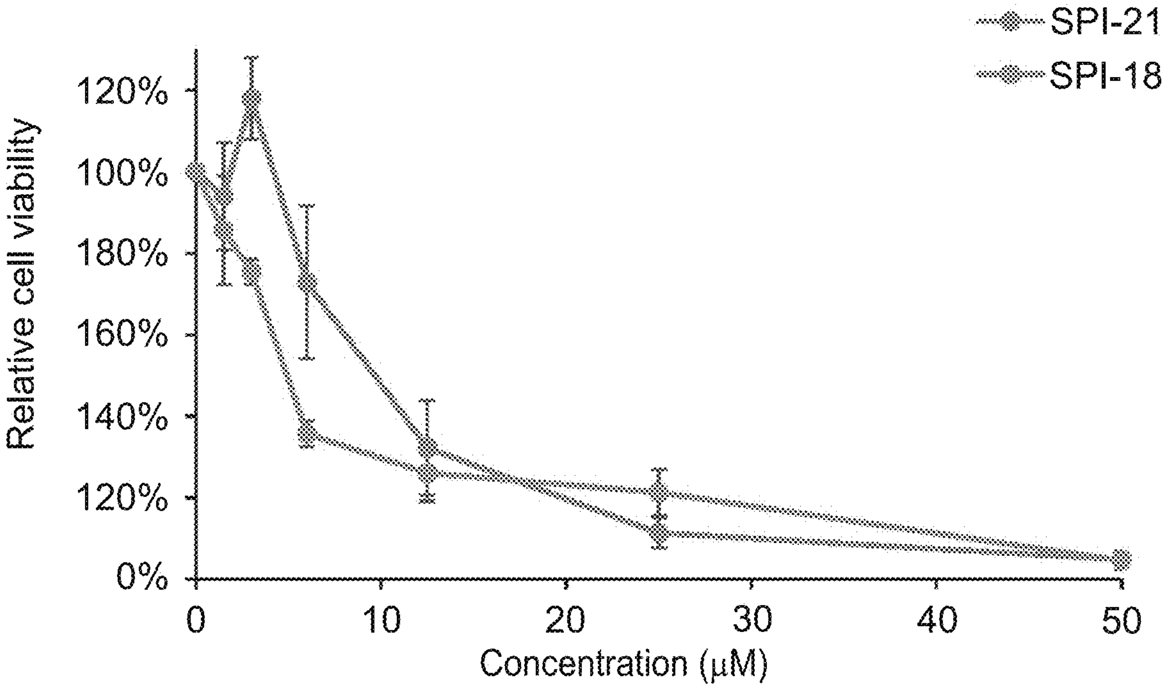

FIG. 3I presents comparative plots showing the effect of SPI-21 and SPI-18 on cell viability. Cells were treated with DMSO (control) or the indicated concentrations of the compounds for 48 h. Cell viability of control and treated cells was analyzed by Luminescent Cell Viability Assay. The data are shown as % of DMSO value and represent the mean±SEM of 3 independent experiments.

Figure 4A:
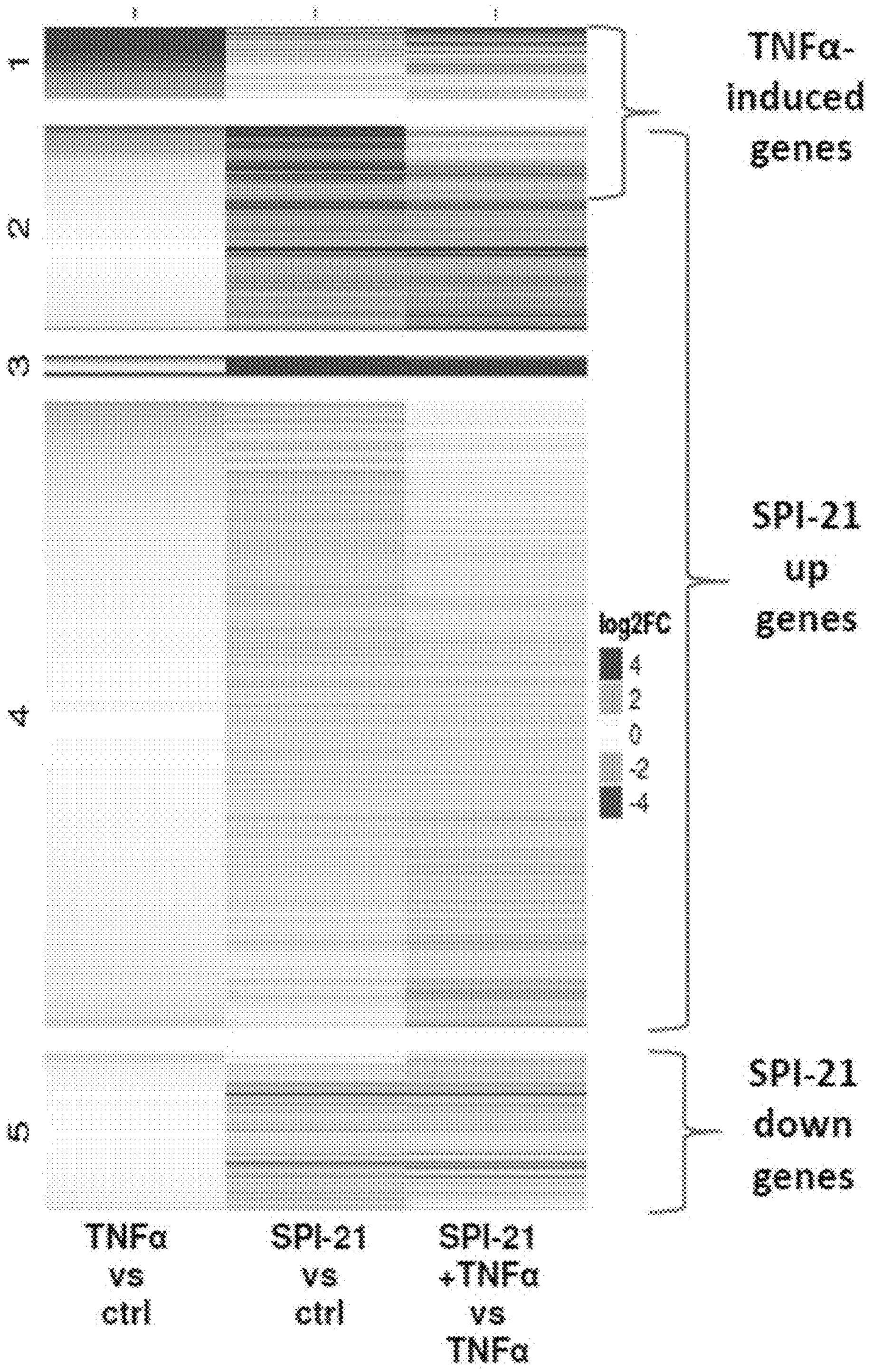
Figure 4B:
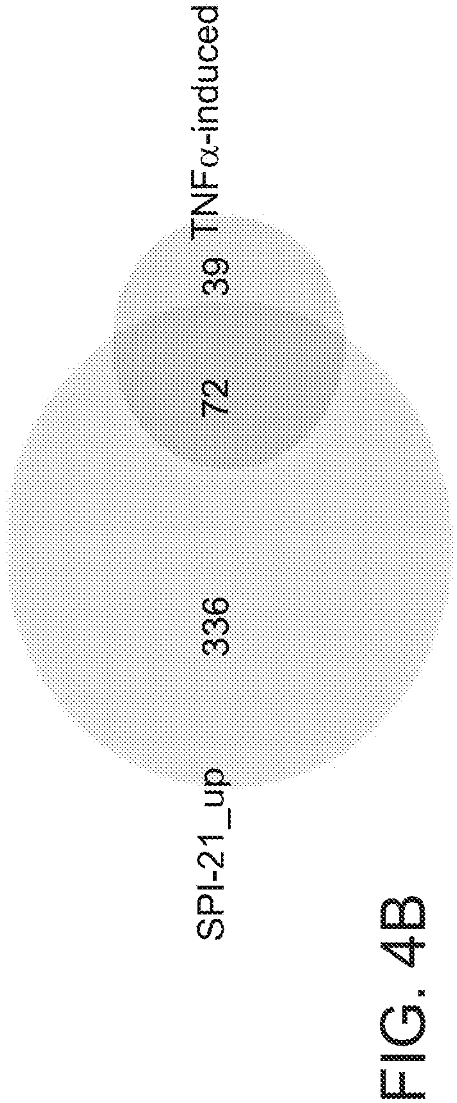
Figure 4C:
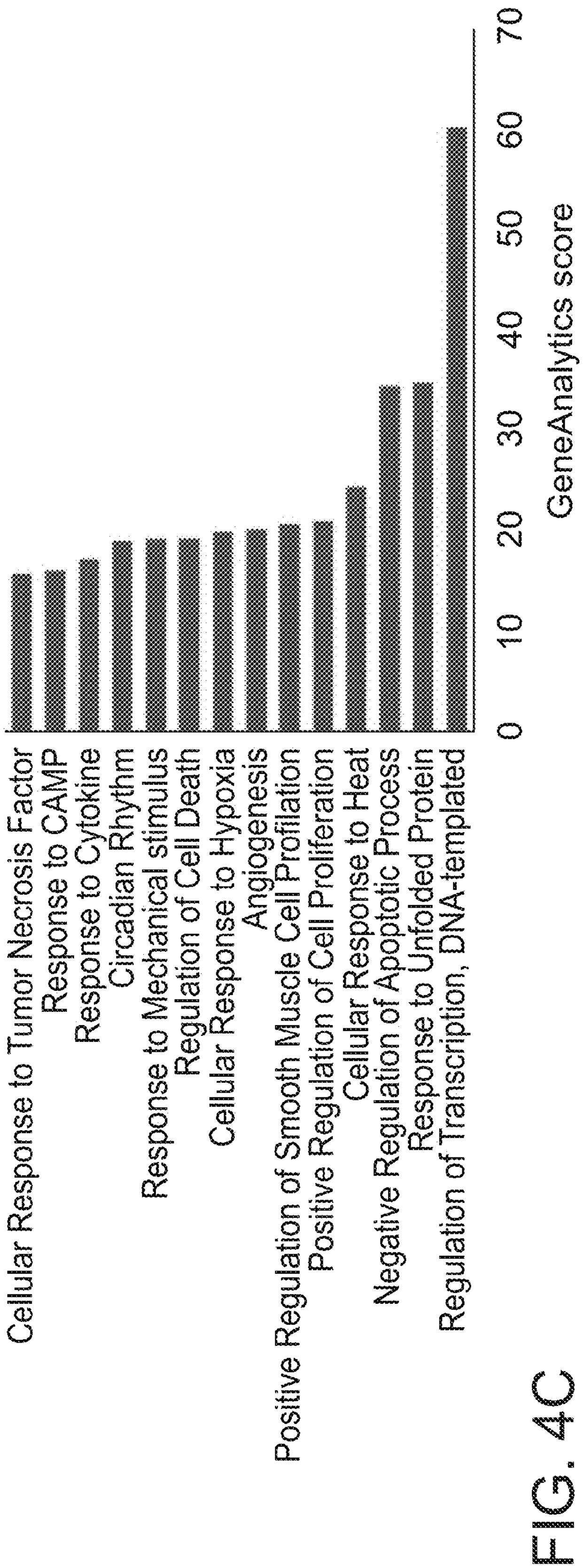
Figure 4D:
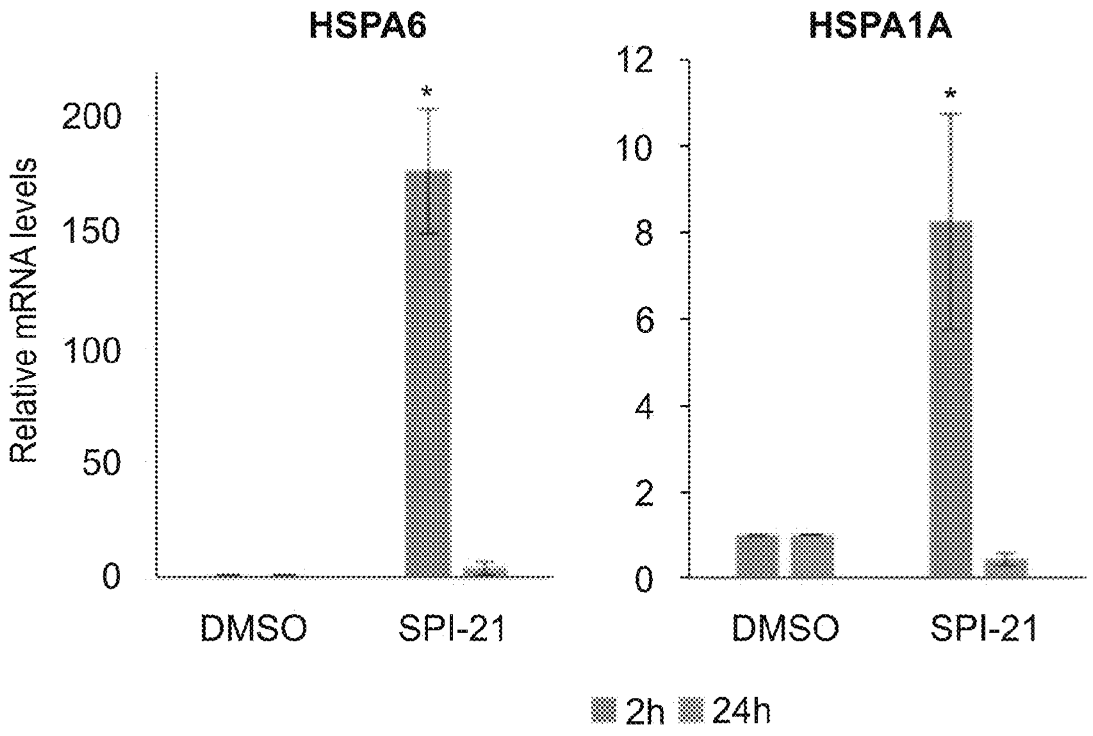
Figure 4E:
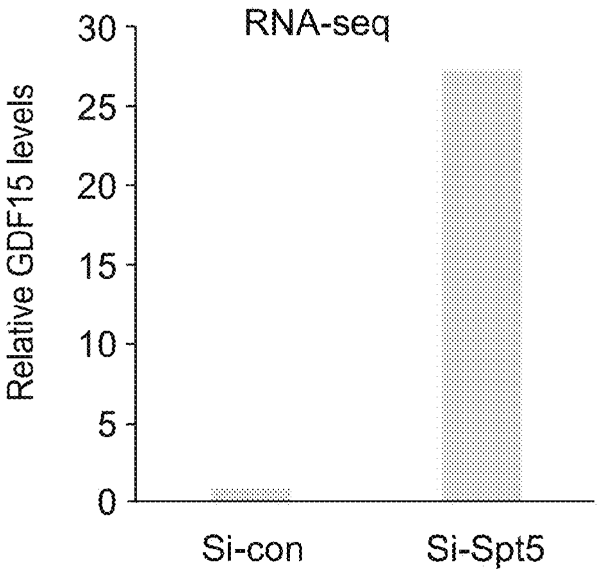
Figure 4F:
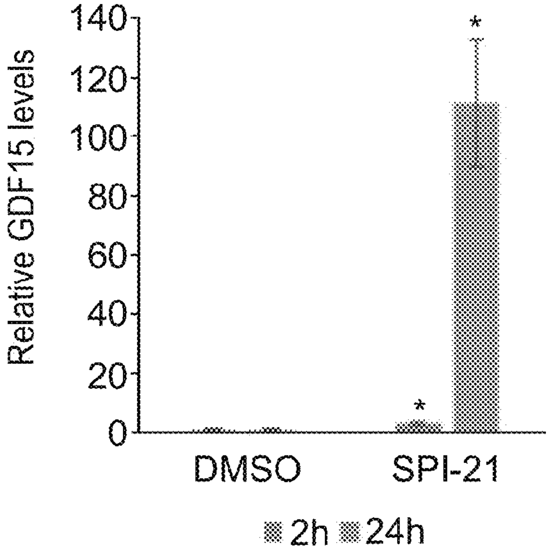
Figure 4G:
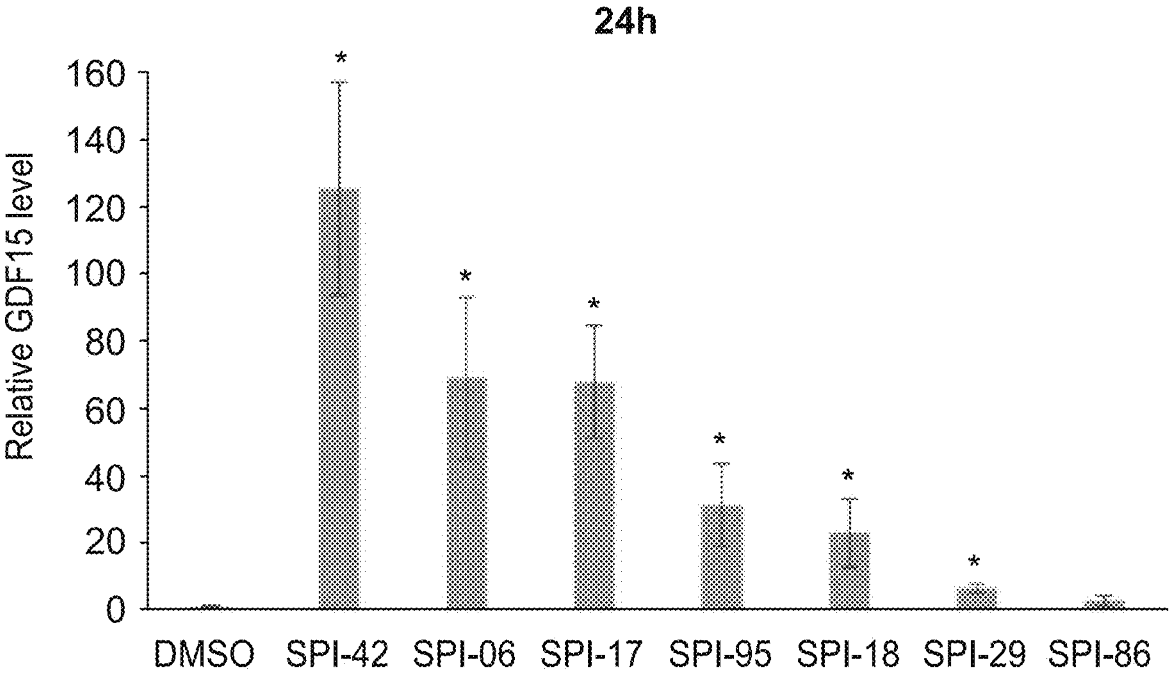
Figure 4H:
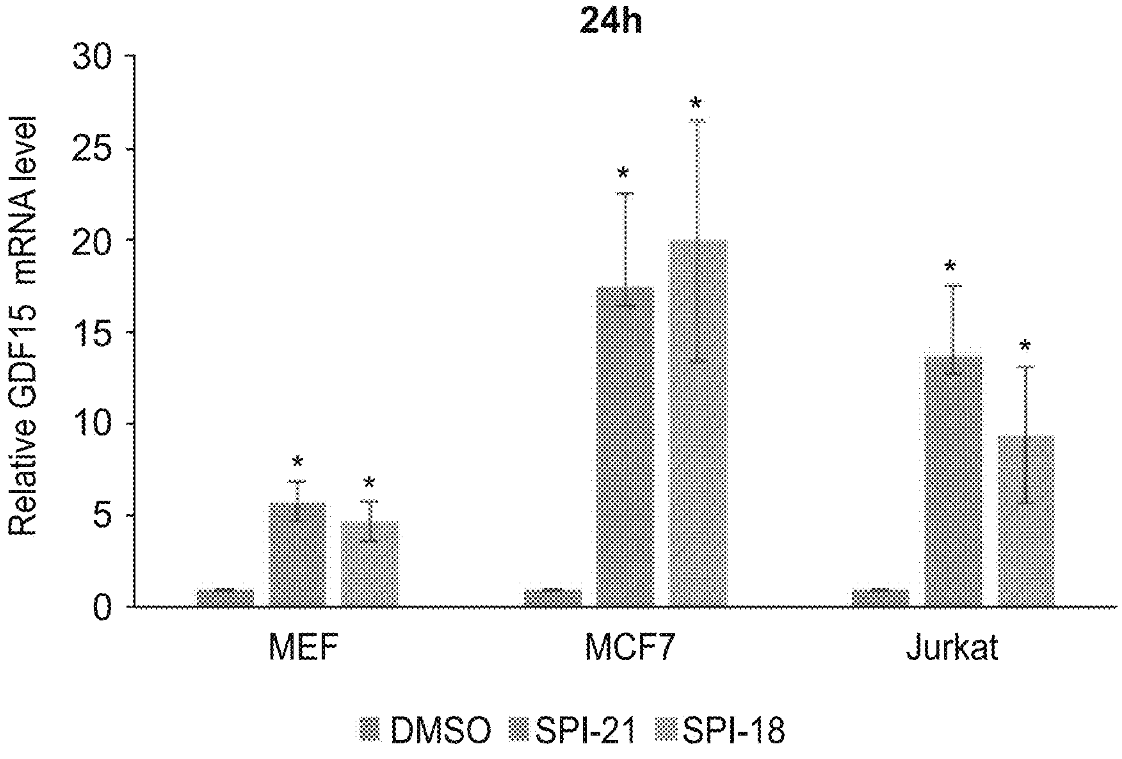
Figure 4I:
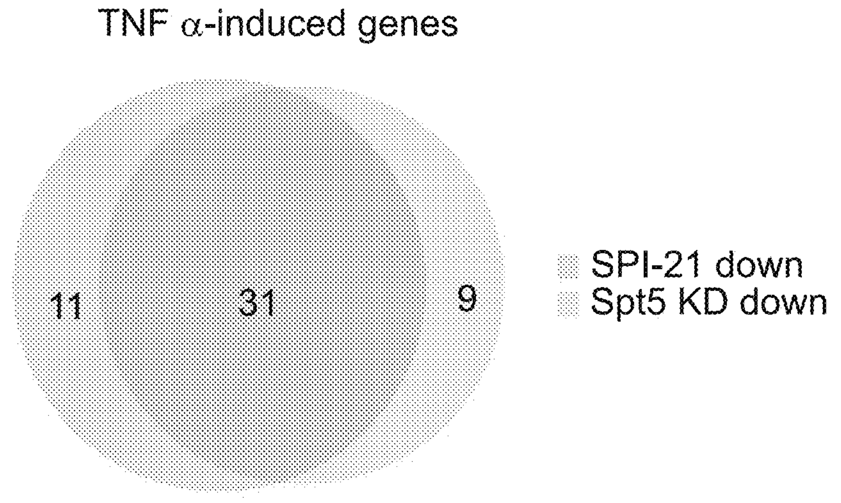
Figure 4J:
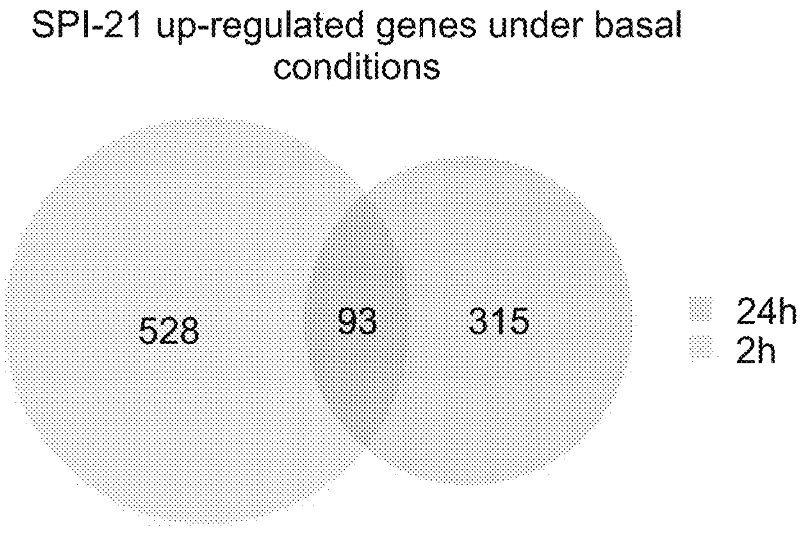

FIGS. 4A-J demonstrate identification of kinetically distinct Spt5 target genes and regulatory sequences. FIG. 4A demonstrates the global effect of SPI-21 and TNFα on mRNA levels. RNA samples (2 independent experiments) extracted from HeLa cells following 2 hours treatment with SPI-21 with or without one-hour TNFα were subjected to deep sequencing. Reads were aligned to the human genome and the ratios indicated at the bottom were calculated between the samples. The resulting gene list was clustered into 5 distinct groups and shown as a heat map of the log fold change of calculated ratios of differentially expressed genes. FIG. 4B is a Venn diagram showing the overlap between SPI-21 up-regulated genes under basal conditions and under TNFα-induced conditions. FIG. 4C demonstrate gene enrichment analysis of the biological processes associated with SPI-21 up-regulated genes. FIG. 4D shows bar graphs demonstrating the effects of short- and long-term treatments (2 and 24 hours, respectively) with SPI-21 on mRNA levels of the heat shock genes, HSPA6 and HSP1A1 (normalized to GAPDH) in HeLa cells, as determined by RT-qPCR. FIG. 4E is a bar graph demonstrating the change in GDF15 levels following 72 hours Spt5 KD. The data is a mean of two experiments and was retrieved from a previously published RNA-seq analysis (Diamant et al., 2016b). FIG. 4F is a bar graph demonstrating the effect of short- and long-term treatments (2 and 24 hours, respectively) with SPI-21 on mRNA levels of GDF15 (normalized to GAPDH) in HeLa cells, as determined by real-time qPCR. FIG. 4G is a bar graph demonstrating the effect of 24 hours treatment with the indicated SPIs on GDF15 mRNA levels (normalized to GAPDH) in HeLa cells, as determined by RT-qPCR. FIG. 4H is a bar graph demonstrating the effect of 24 hours treatment with SPI-21 or SPI-18 on GDF15 mRNA levels in mouse embryonic fibroblasts (MEFs), MCF7 and Jurkat cells. The graphs in FIGS. 4D and 4F-H represent the mean of at least 3±SEM independent experiments. * P<0.05 relative to DMSO (vehicle control). FIG. 4I is A Venn diagram showing the overlap between SPI-21 downregulated genes from the TNFα-induced set (presented in cluster 1) and the TNFα-induced genes that were downregulated upon Spt5 KD retrieved from the previously published RNA-seq data (clusters 2 and 3 in Diamant et al., 2016b). FIG. 4J shows comparison of the global effects of long- and short-term SPI-21 treatment. Cells were treated with SPI-21 (50 mM) or DMSO for 24 h and subjected to RNAseq. The extent of overlap between the upregulated gene sets (>2-fold change) from 2 h (described in FIG. 4A) and 24 h was determined using a Venn diagram.

Figure 4K:
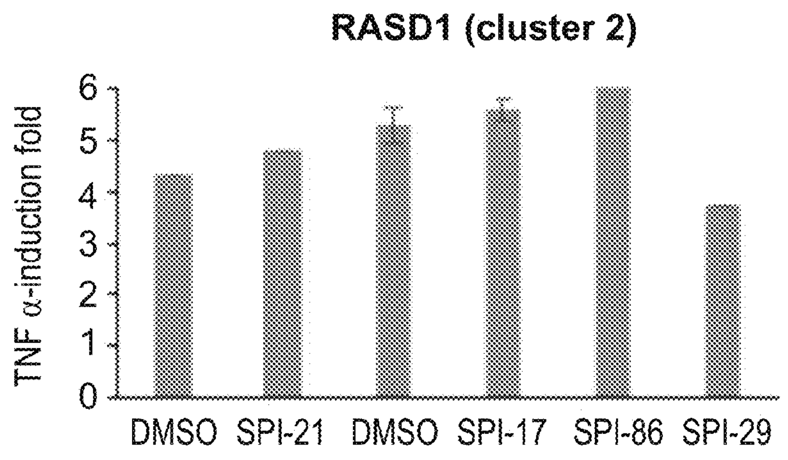
Figure 4L:
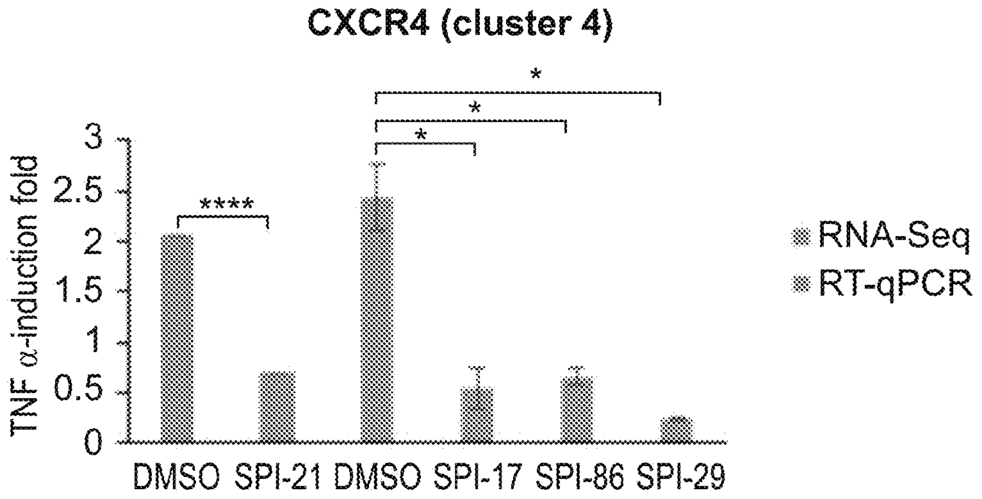
Figure 4M:
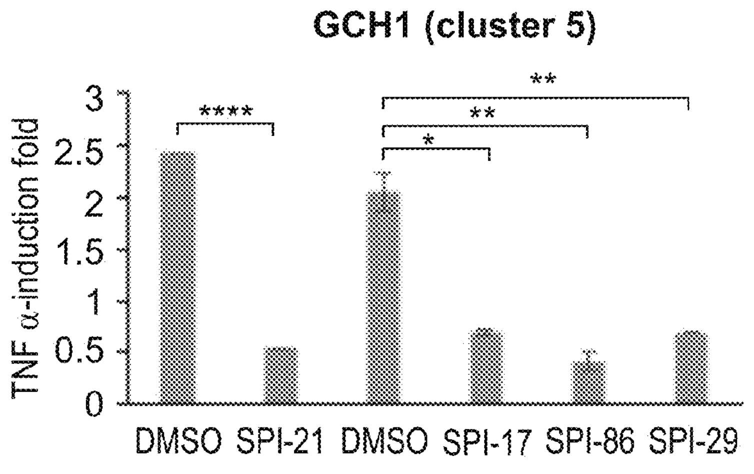

FIGS. 4K-M demonstrate the effect of SPIs on representative TNFα-induced genes. Genes were selected from different clusters of the RNA-Seq data of SPT-21-treated cells (2 hours) and analyzed by RT-qPCR. The graphs show the induction fold observed from the SPI-21 RNA-Seq data (orange) and RT-qPCR analysis of the indicated SPIs (blue). The presented data is the mean±SEM of 3 independent experiments. The asterisks denote statistically significant difference.

Figure 4N:
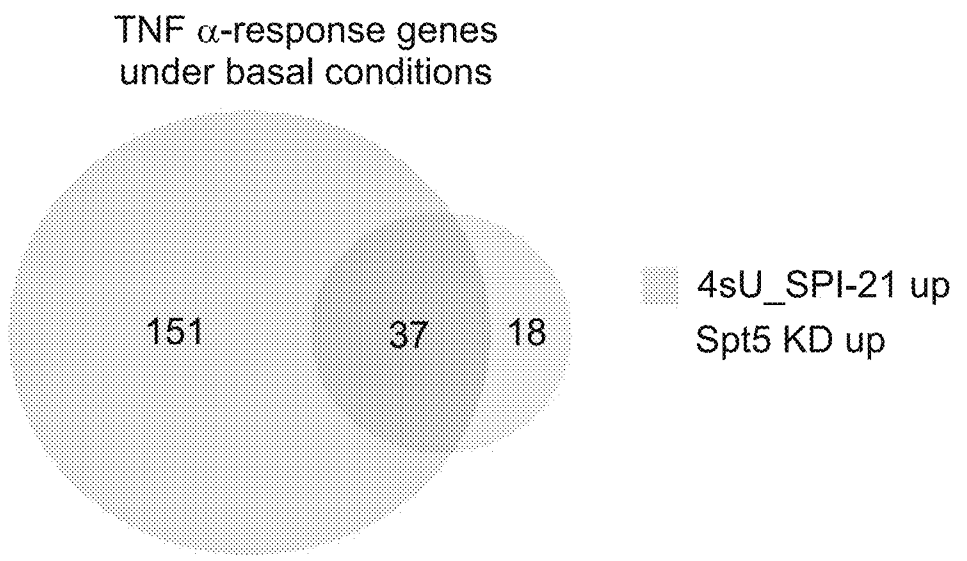
Figure 4O:
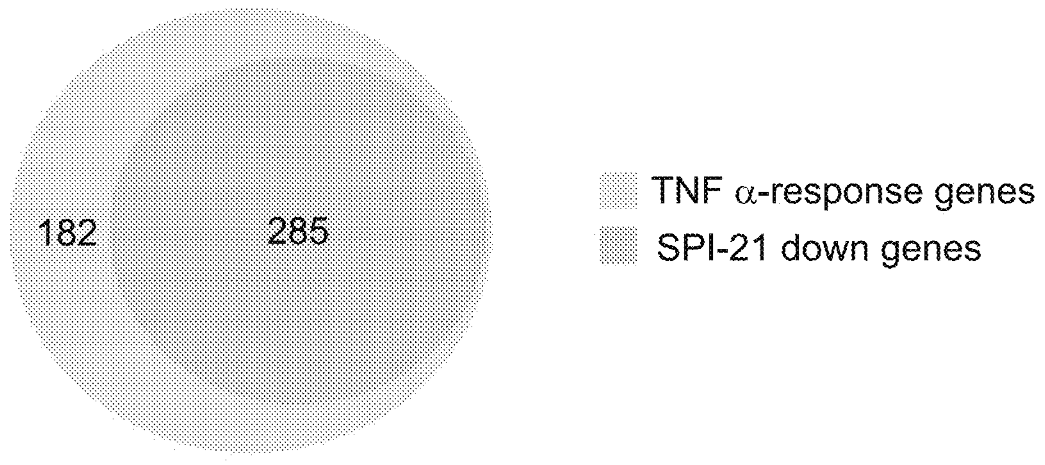

FIGS. 4N—O demonstrate the effect of SPIs on differentially expressed genes from RNA-Seq of 4sU metabolically labelled samples. Cells treated with DMSO or SPI-21 with or without TNFα were metabolically labeled with 5-thio-uridine and then RNA was extracted, biotinylated and the newly synthesized transcripts were isolated with streptavidin magnetic beads and subjected to RNA-Seq. Reads were mapped and differentially expressed genes were determined. FIG. 4N is a Venn diagram comparing upregulated genes (common to the two replicates, average) under basal conditions from SPI-21 treatment (4sU; ≥2 fold change) and Spt5 KD (retrieved from the RNA-Seq data reported in Diamant et al., 2016b; ≥1.2 fold change), filtered for the TNFα-response genes (≥2.5 fold change). FIG. 4O is a Venn diagram showing the fraction of TNFα-induced genes (≥2.5 fold change, common to the two replicates, average) that are downregulated by SPI-21 (≤0.5 fold change, common to the two replicates, average), both from the 4sU labeling experiment.

Figure 5A:
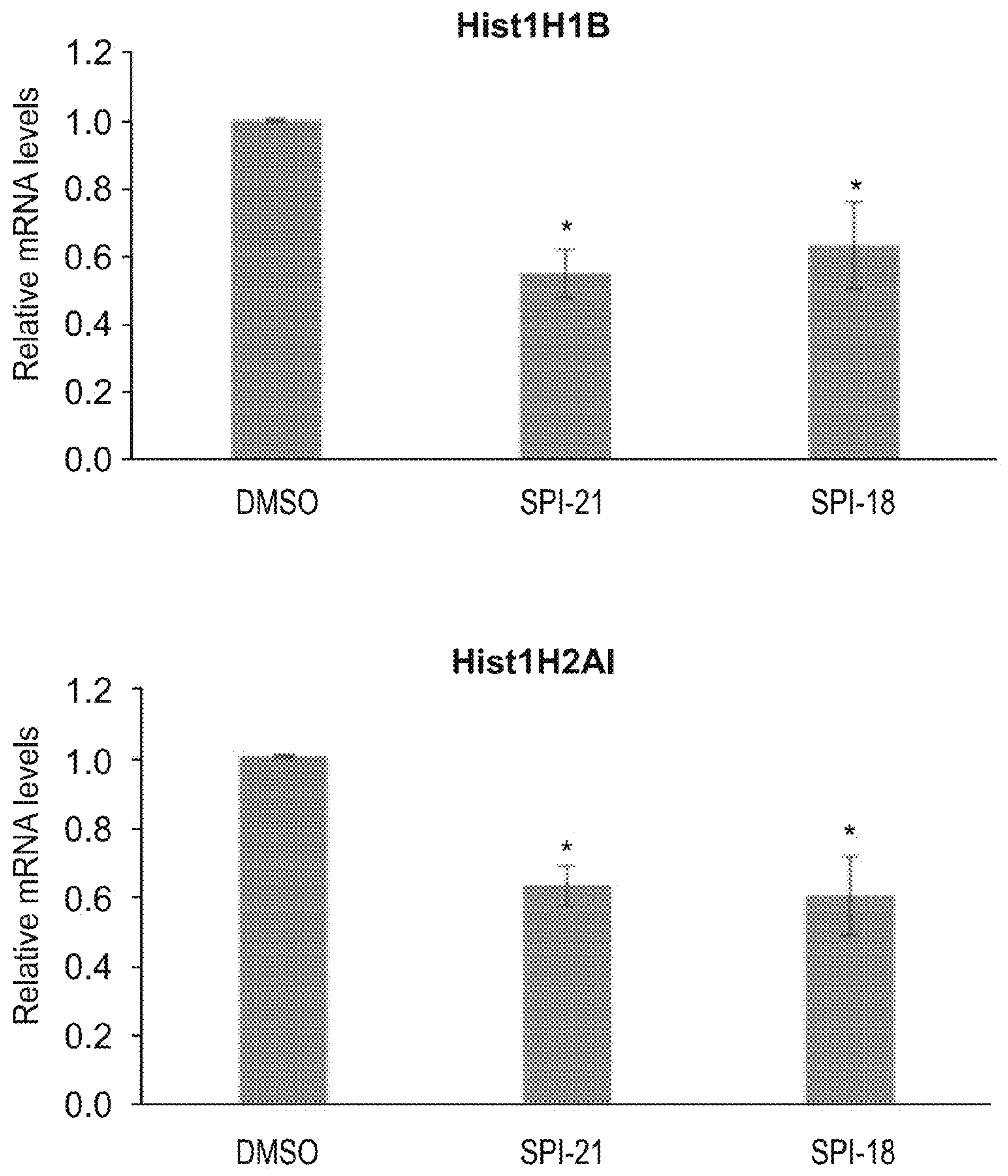
Figure 5A:
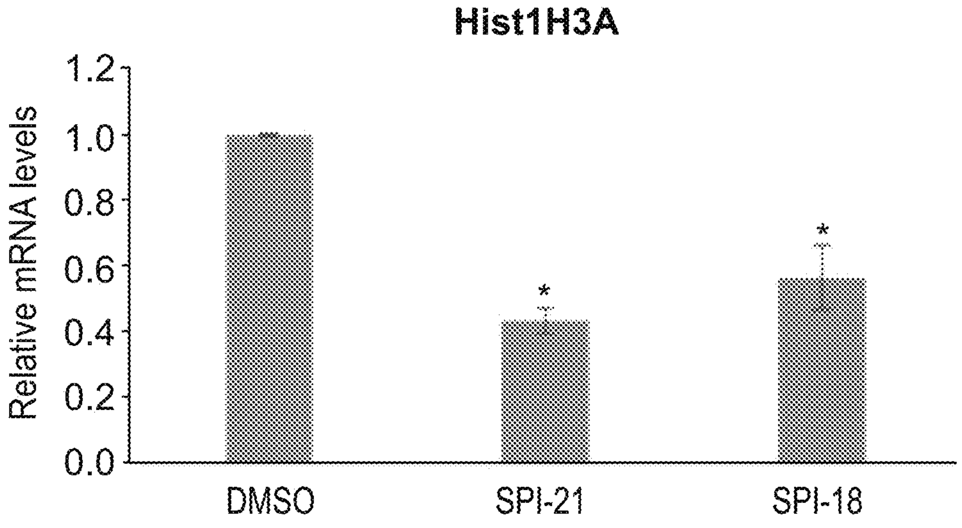
Figure 5A:
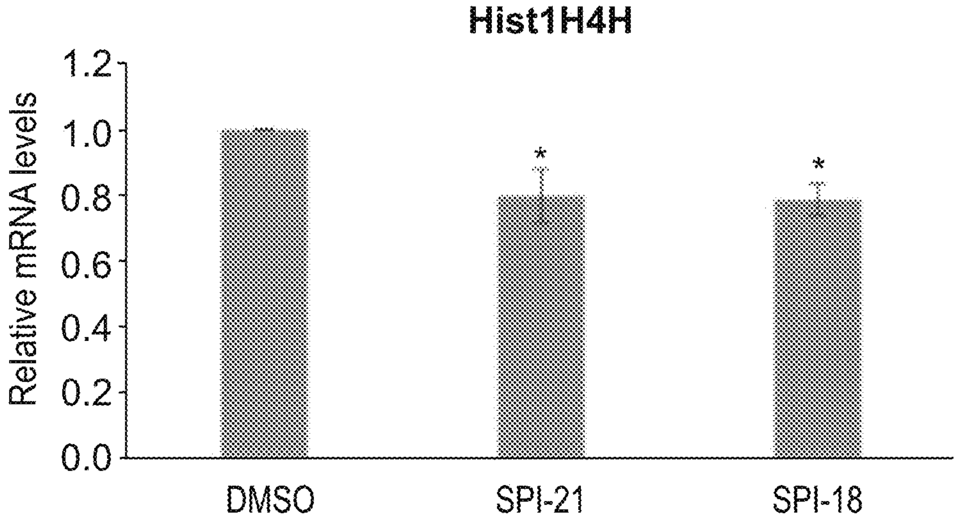
Figure 5B:
Figure 5B:
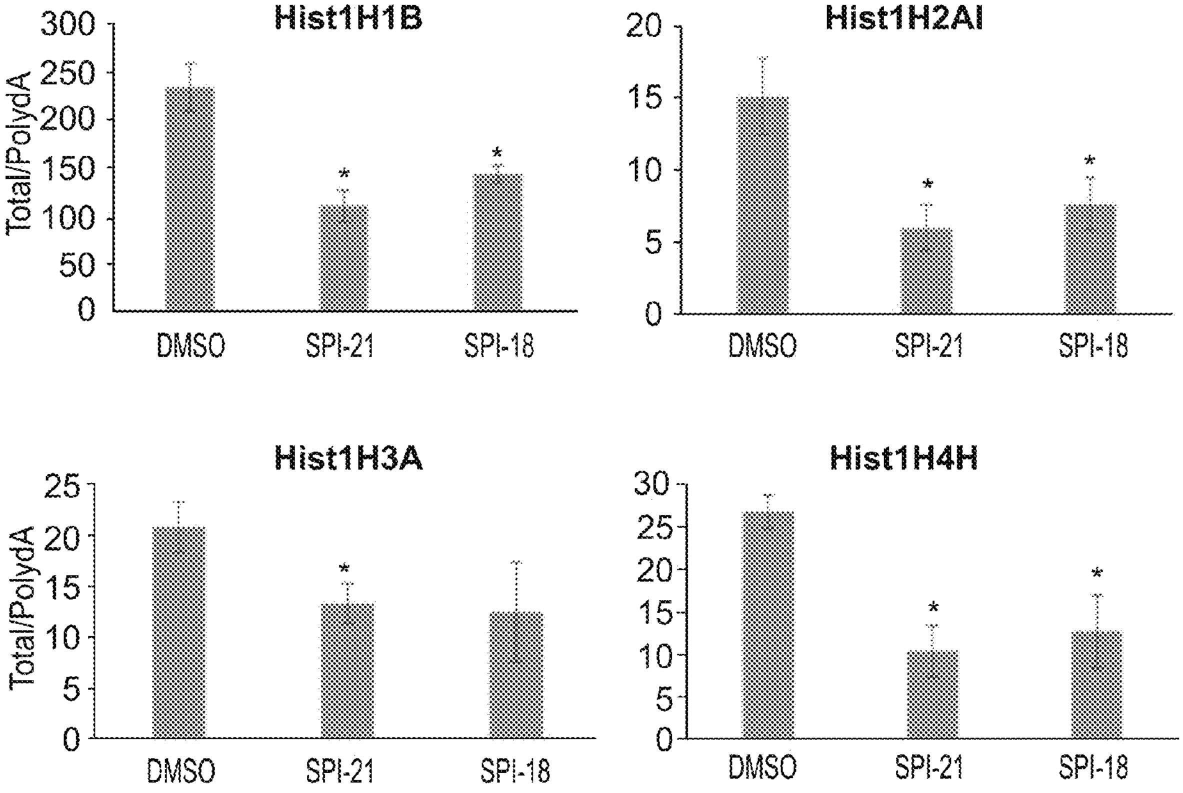
Figure 5C:
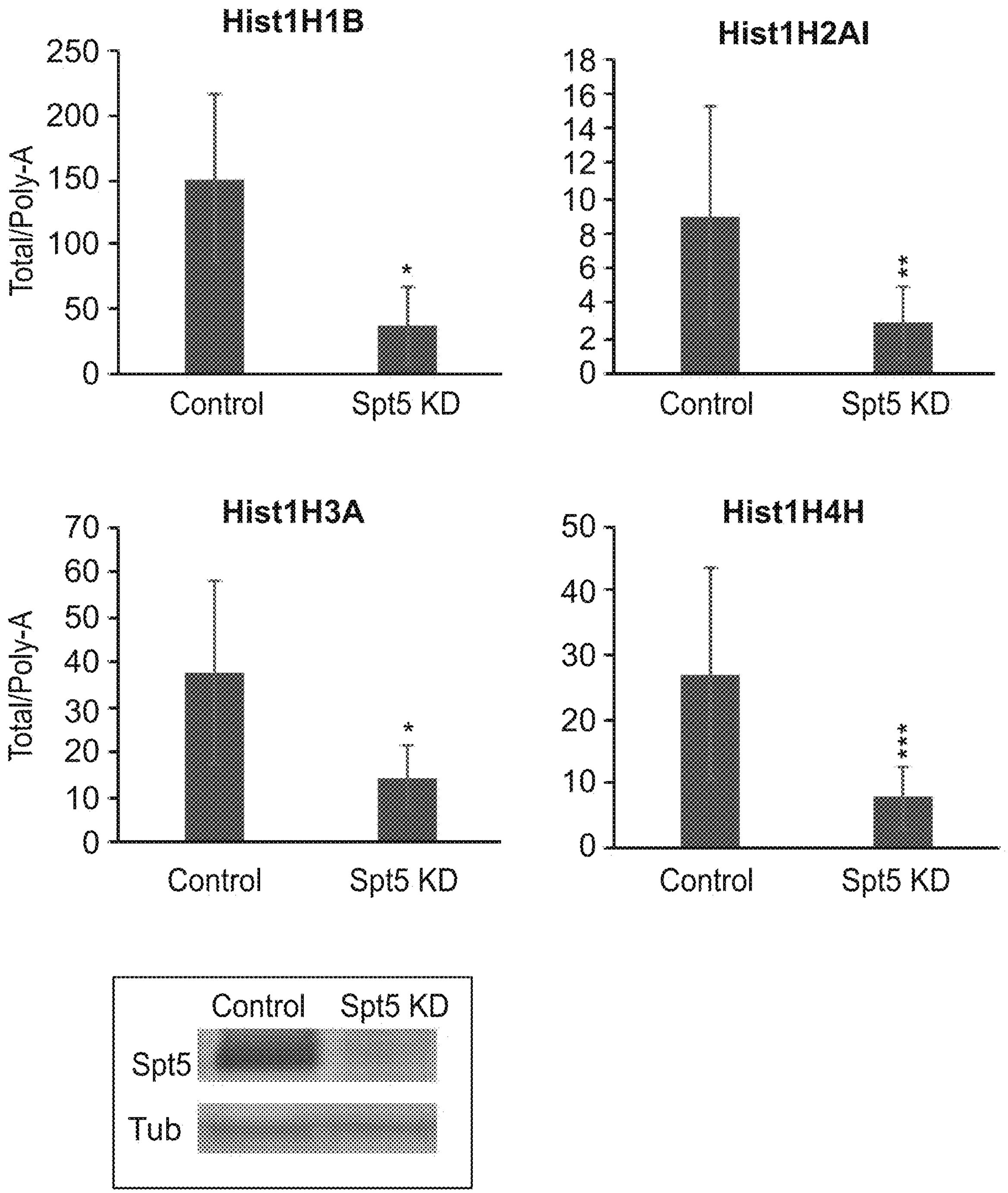

FIGS. 5A-C demonstrate regulation of histone genes by Spt5. FIG. 5A shows bar graphs demonstrating the effect of 24 hours treatment with SPI-21 or SPI-18 on selected replication-dependent histone genes, as determined by cDNA prepared with random hexamers. FIG. 5B demonstrates the ratio between total and Poly-A containing histone genes. A schematic illustration of a histone gene structure is shown on the top. For polyA+ RNA analysis, cDNA was prepared with a poly-dT oligonucleotide. In each analysis the levels were normalized to GAPDH; and the bars present the mean of 3±SEM independent experiments. * P<0.05 relative to DMSO (vehicle control). FIG. 5C shows an analysis that is similar to that in FIG. 5B using RNA from control and Spt5 KD cells. The bottom panel shows a western blot of control and Spt5 KD cells using the indicated antibodies. The data represent the means±SEMs of 3 independent experiments. The asterisks denote statistically significant differences relative to DMSO; according to Student's t tests (typically one-tailed, paired): *p<0.05; p<0.01; *p<0.005.

Figure 6A:
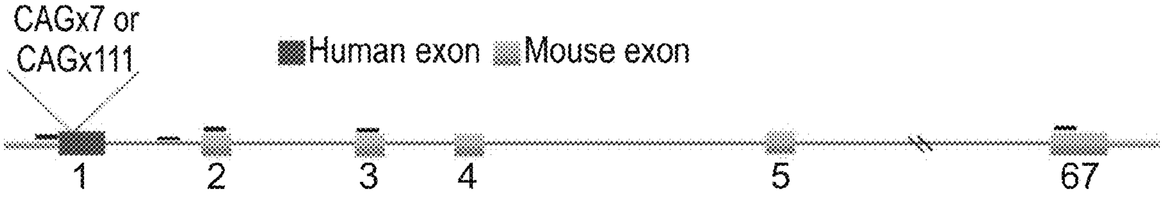
Figure 6B:
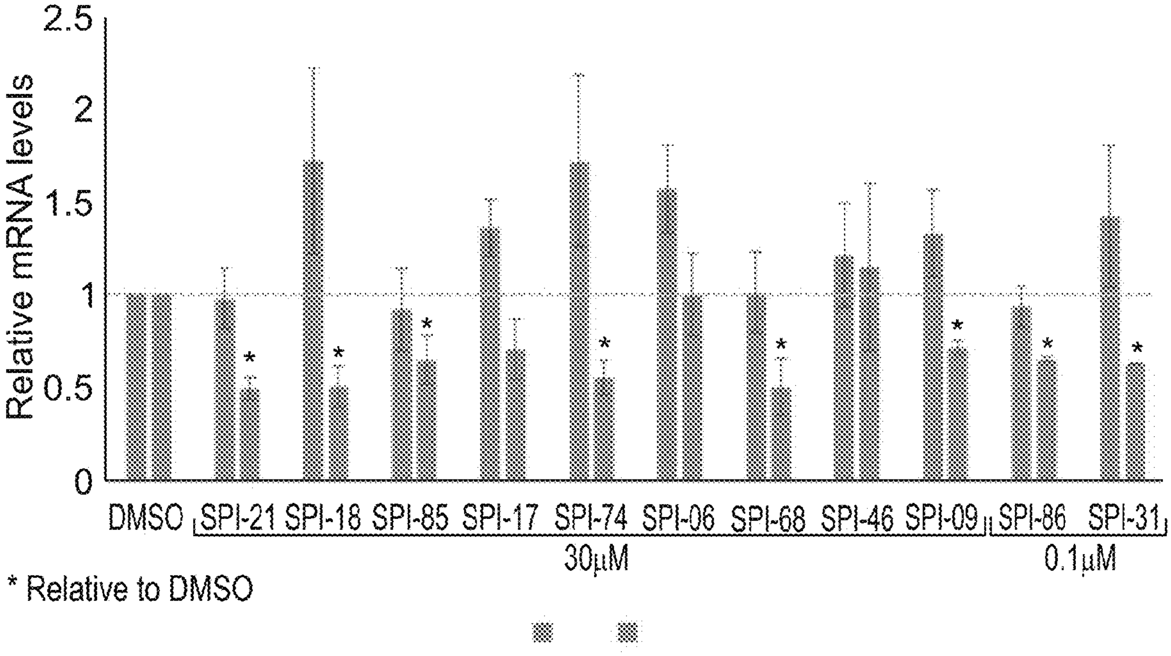
Figure 6C:
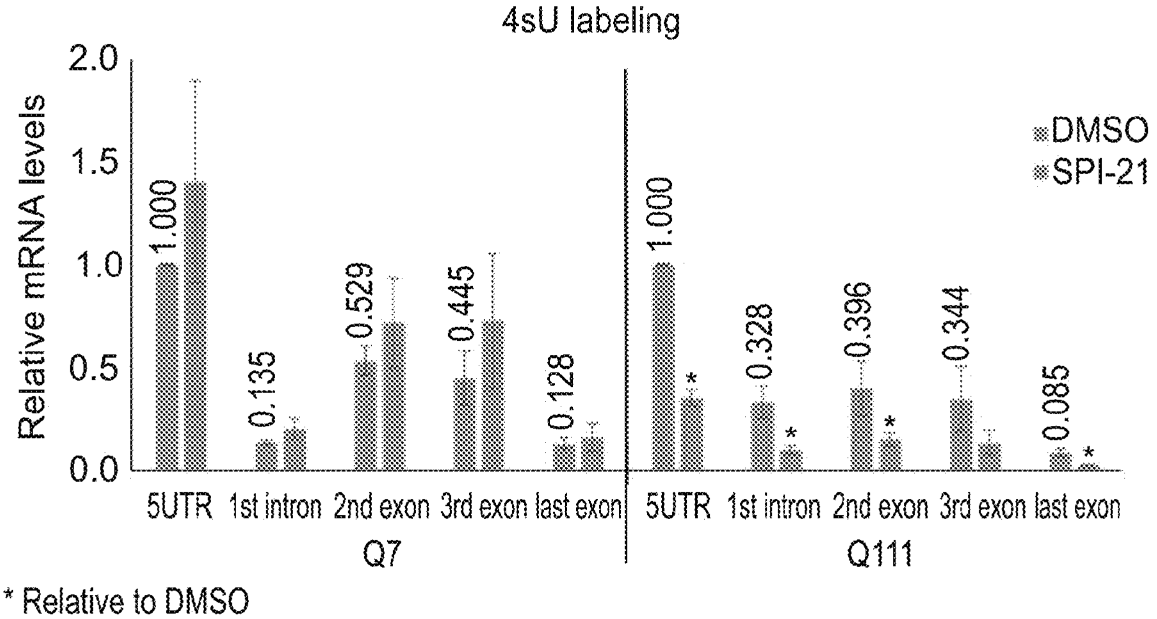
Figure 6D:
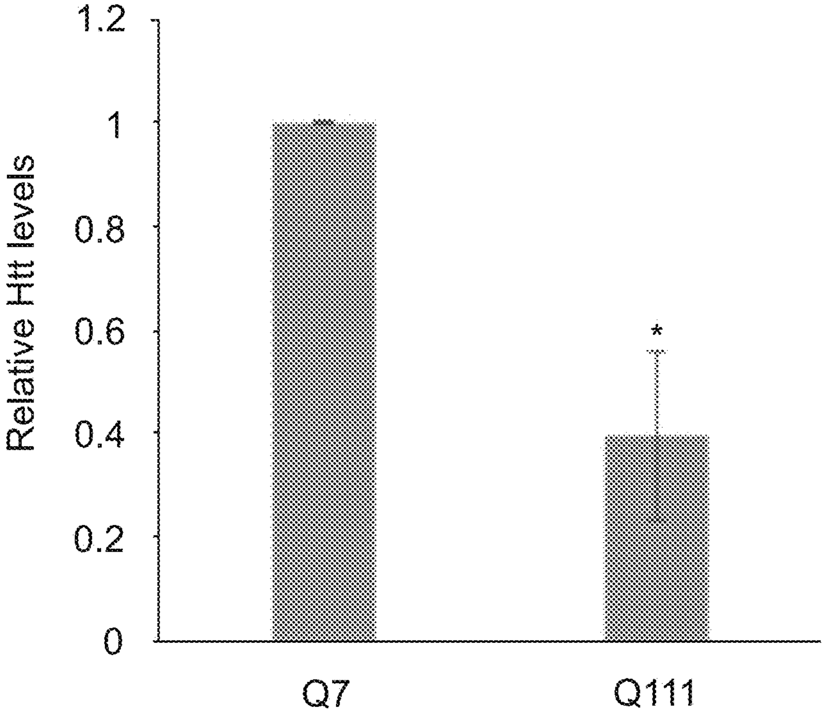

FIGS. 6A-D demonstrate that the identified SPIs selectively inhibit the transcription of mutant huntingtin (Htt) gene. FIG. 6A is a schematic representation of the structure of the wild type (Q7) and mutant (Q111) Htt gene of the transgenic striatal cell lines. FIG. 6B is a bar graph demonstrating Htt mRNA levels (normalization to β-actin) in Q7 and Q111 expressing cells treated for 48 hours with the indicated SPIs at the indicated concentrations, as determined by real-time qPCR. FIG. 6C is a bar graph demonstrating expression of newly synthesized Htt transcripts in Q7 and Q111 expressing cells that were metabolically labeled with 5-thio-uridine for 2 hours in the presence of DMSO (vehicle control) or SPI-21, as determined by real-time qPCR using primers from the indicated locations (SEQ ID NOs: 17-26). The bars in FIGS. 6B-C present the mean of at least 3±SEM independent experiments. * P<0.05 relative to DMSO. FIG. 6D is a bar graph demonstrating Htt levels in Q7 and Q111 cells normalized to β-actin. Levels of Q7 Htt was set to 1. *P<0.05 of Q111 relative to Q7.

FIG. 7 is a table presenting the identified Spt5 inhibitors and their chemical structures.

Figure 8A:
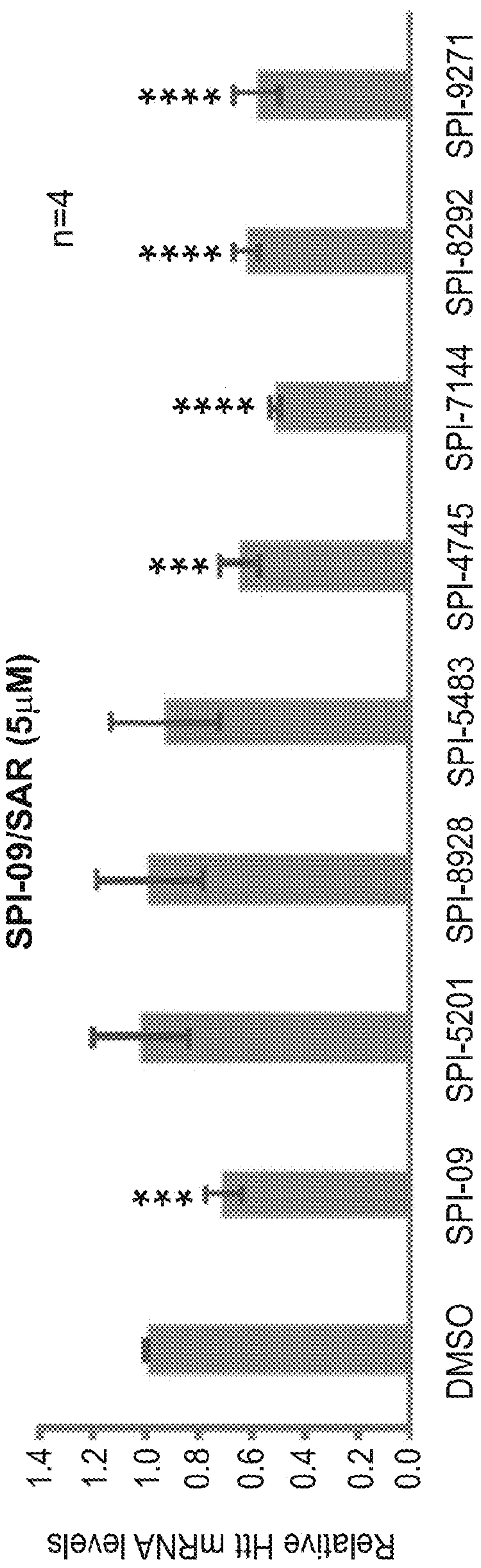
Figure 8B:
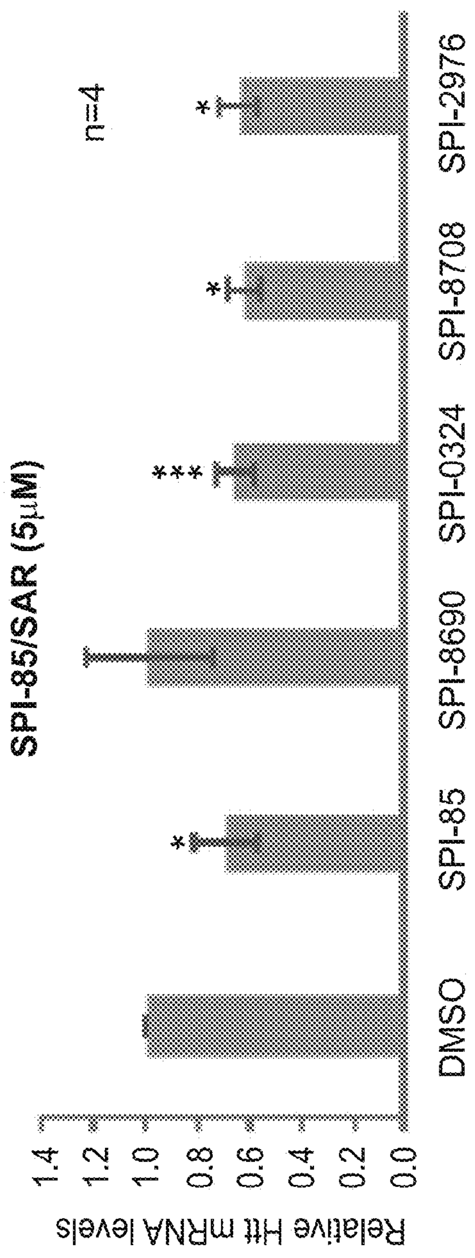
Figure 8C:
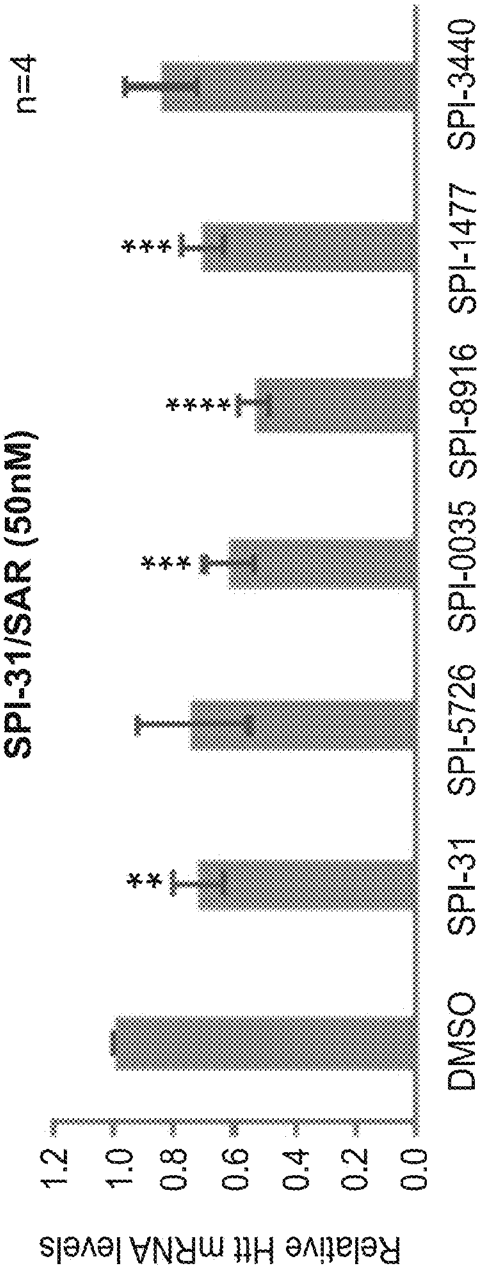
Figure 8D:
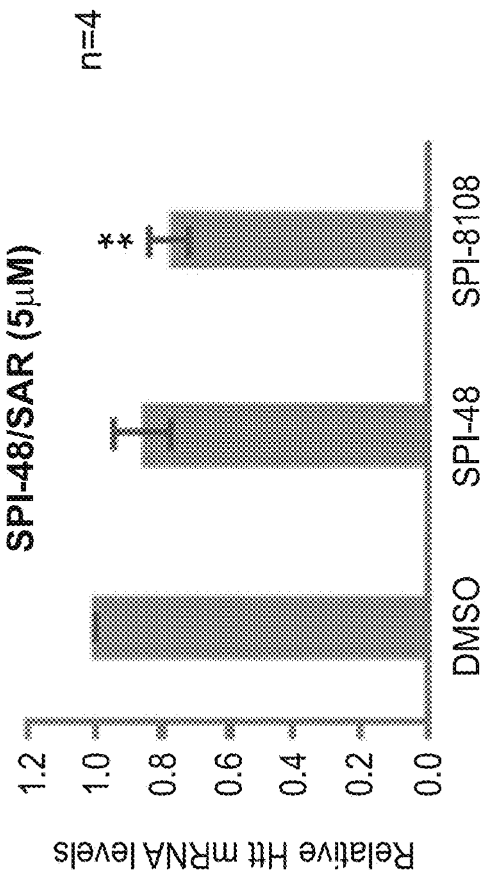

FIGS. 8A-D are bar graphs demonstrating Htt mRNA levels (normalized to β-actin) in Q111 expressing cells treated for 48 hours with the indicated SPIs at the indicated concentrations, as determined by real-time qPCR. FIG. 8A presents the data obtained for SPI-09 and structural analogs thereof as shown in Table 6. FIG. 8B presents the data obtained for SPI-85 and structural analogs thereof as shown in Table 7. FIG. 8C presents the data obtained for SPI-31 and structural analogs thereof as shown in Table 8. FIG. 8D presents the data obtained for SPI-48 and a structural analog thereof as shown in Table 9. The asterisks denote statistical significance differences according to Student's t tests (typically one tailed, paired): *p<0.05; p<0.01; *p<0.005; ****p<0.001.

Figure 9A:
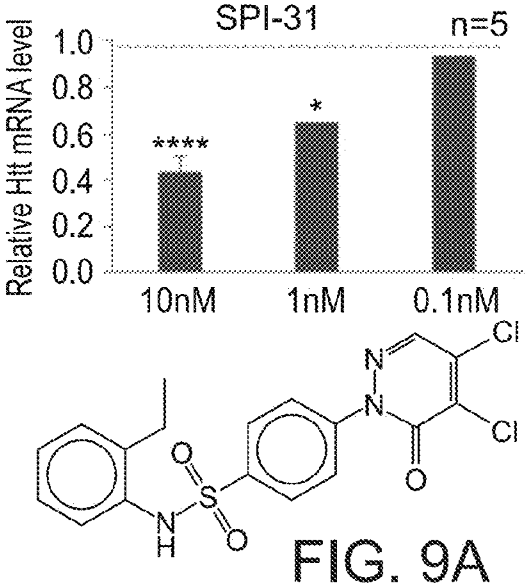
Figure 9B:
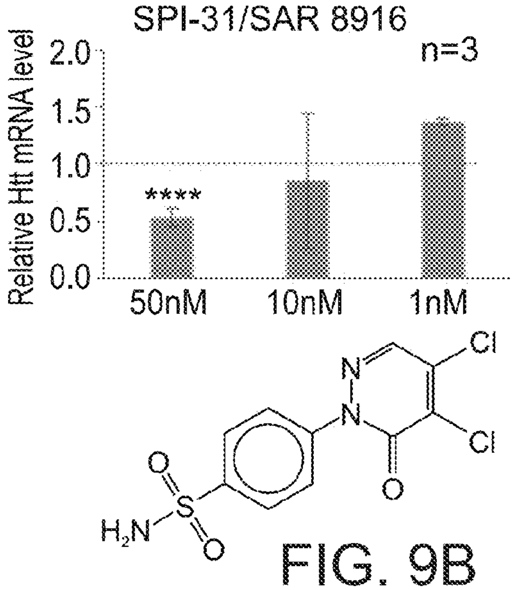
Figure 9C:
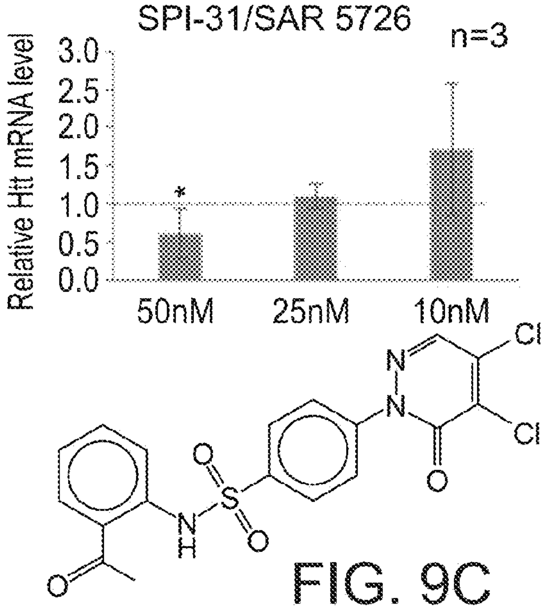
Figure 9D:
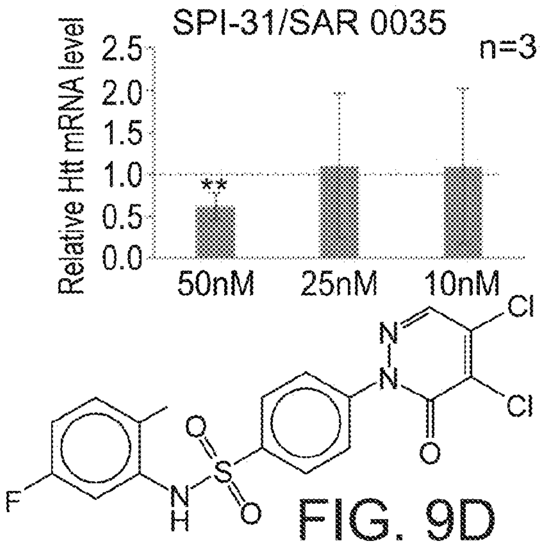
Figure 9E:
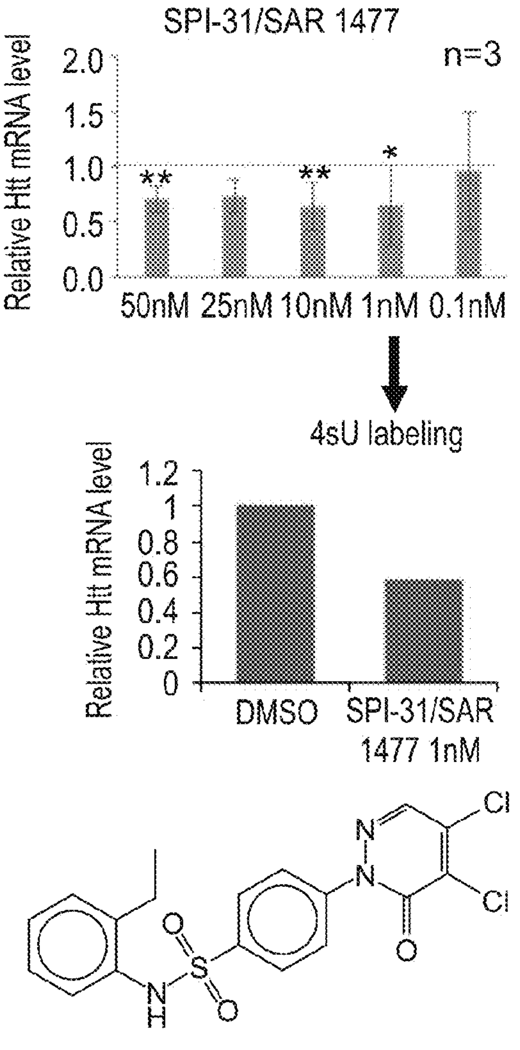
Figure 10A:
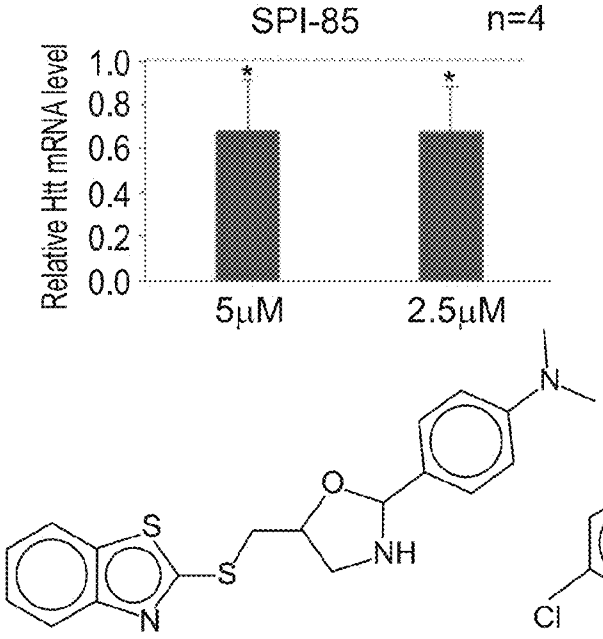
Figure 10B:
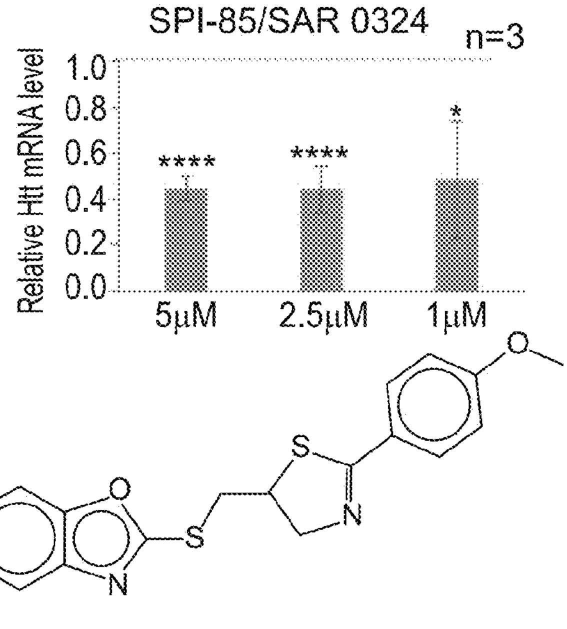
Figure 10C:
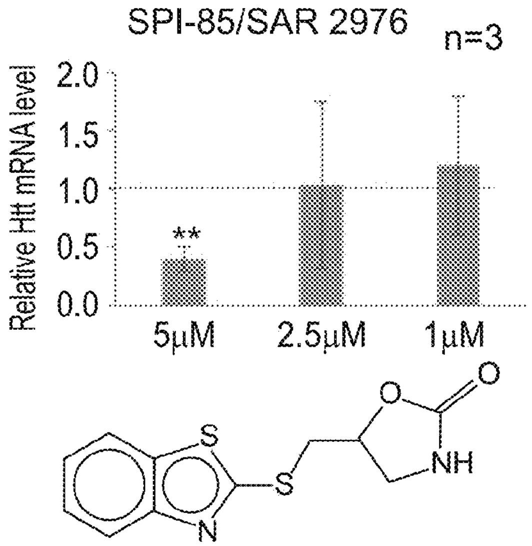
Figure 10D:
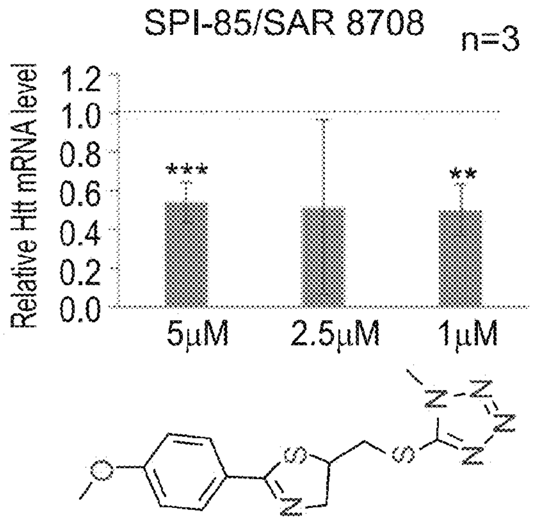

FIGS. 9A-E present bar graphs demonstrating Htt mRNA levels (normalized to β-actin) in Q111 expressing cells treated for 48 hours with varying doses of SPI-31 and structural analogs thereof, as determined by real-time qPCR (FIG. 9A-D) and a bar graph demonstrating expression of newly synthesized Htt transcripts in Q111 expressing cells that were metabolically labeled with 4-thio-uridine for 2 hours in the presence of DMSO (vehicle control) or SPI-1477, as determined by real-time qPCR using primers from the indicated locations (SEQ ID NOs: 17-26) (FIG. 9E). The asterisks denote statistical significance differences according to Student's t tests (typically one tailed, paired): *p<0.05; p<0.01; *p<0.005; ****p<0.001.

FIGS. 10A-D present bar graphs demonstrating Htt mRNA levels (normalized to β-actin) in Q111 expressing cells treated for 48 hours with varying doses of SPI-85 and structural analogs thereof, as determined by real-time qPCR. The asterisks denote statistical significance differences according to Student's t tests (typically one tailed, paired): *p<0.05; p<0.01; *p<0.005; ****p<0.001.

Figure 11A:
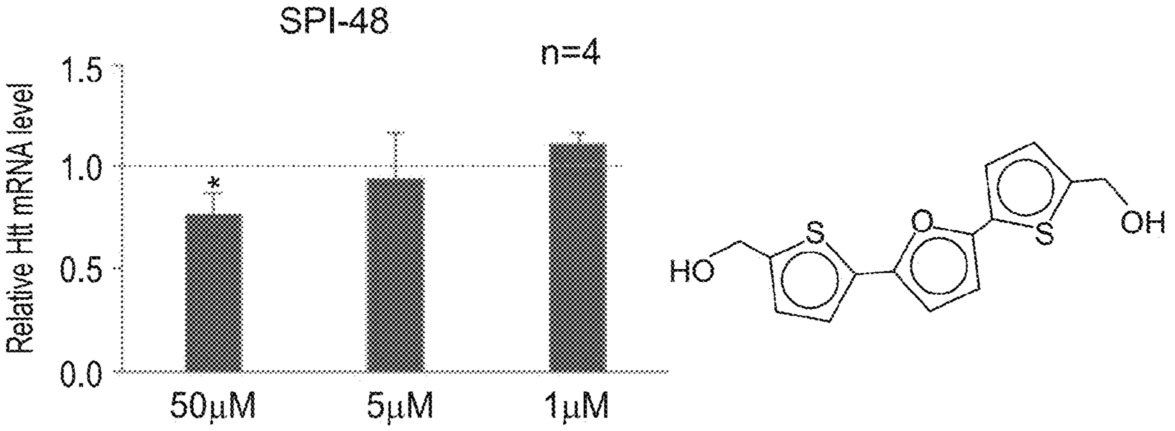
Figure 11B:
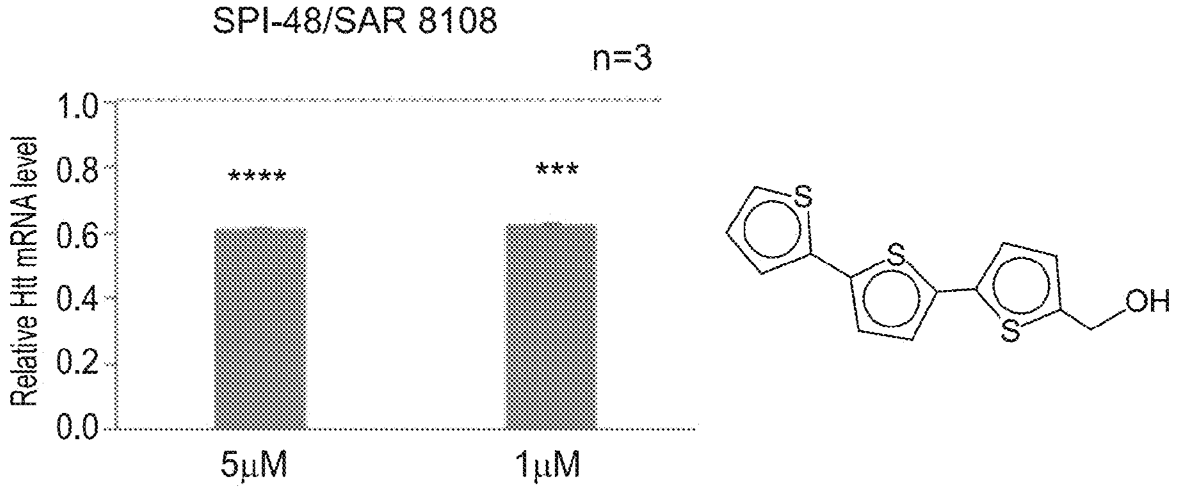

FIGS. 11A-B present bar graphs demonstrating Htt mRNA levels (normalized to β-actin) in Q111 expressing cells treated for 48 hours with varying doses of SPI-48 and a structural analog thereof, as determined by real-time qPCR. The asterisks denote statistical significance differences according to Student's t tests (typically one tailed, paired): *p<0.05; p<0.01; *p<0.005; ****p<0.001.

Figure 12A:
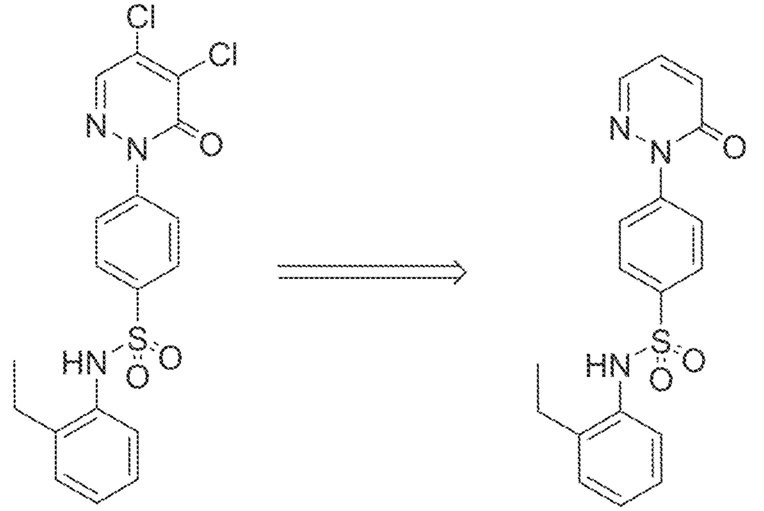
Figure 12B:
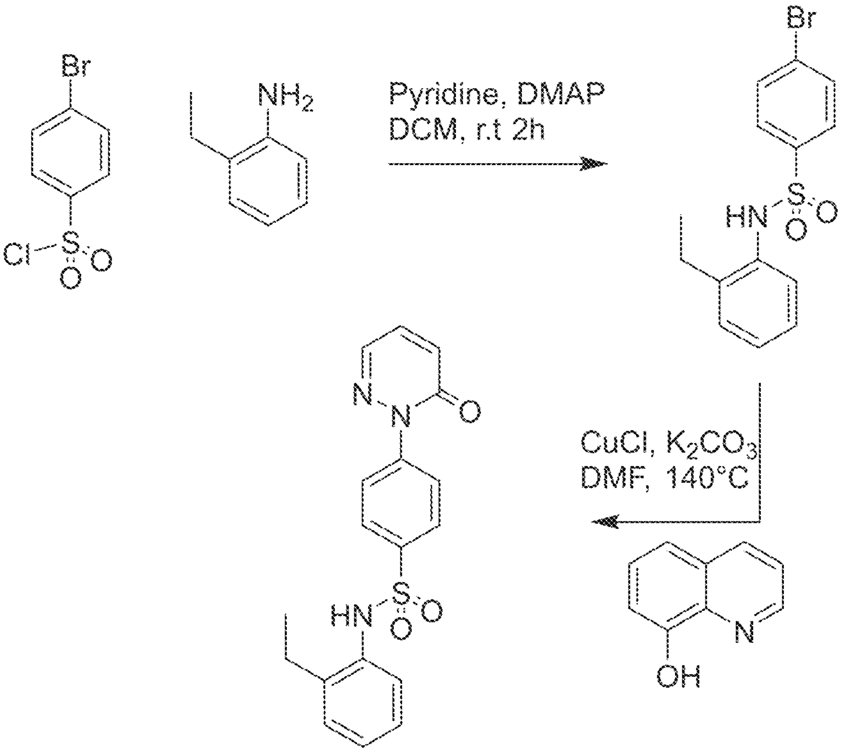
Figure 12C:
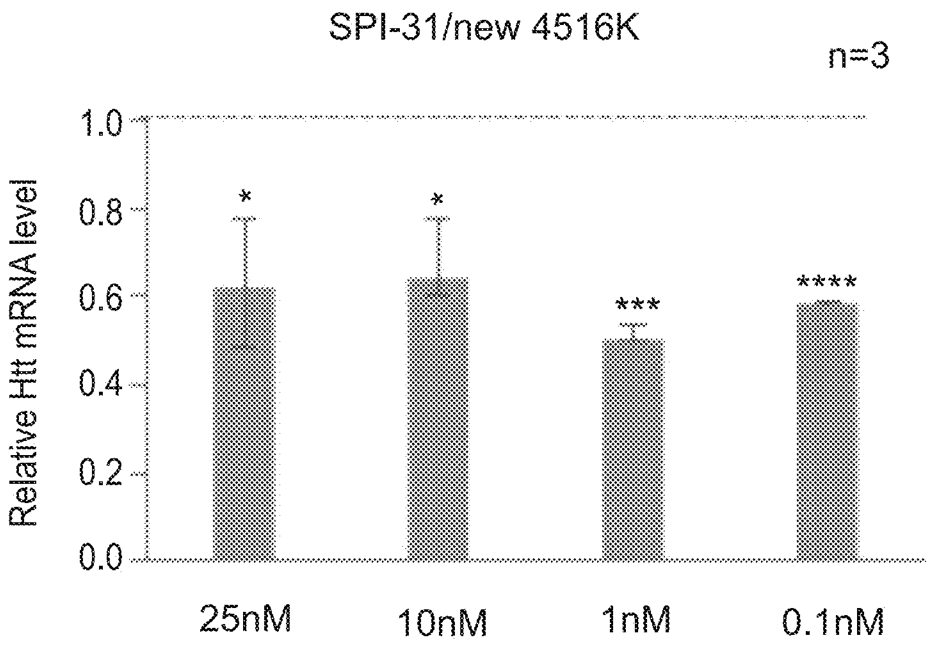
Figure 13A:
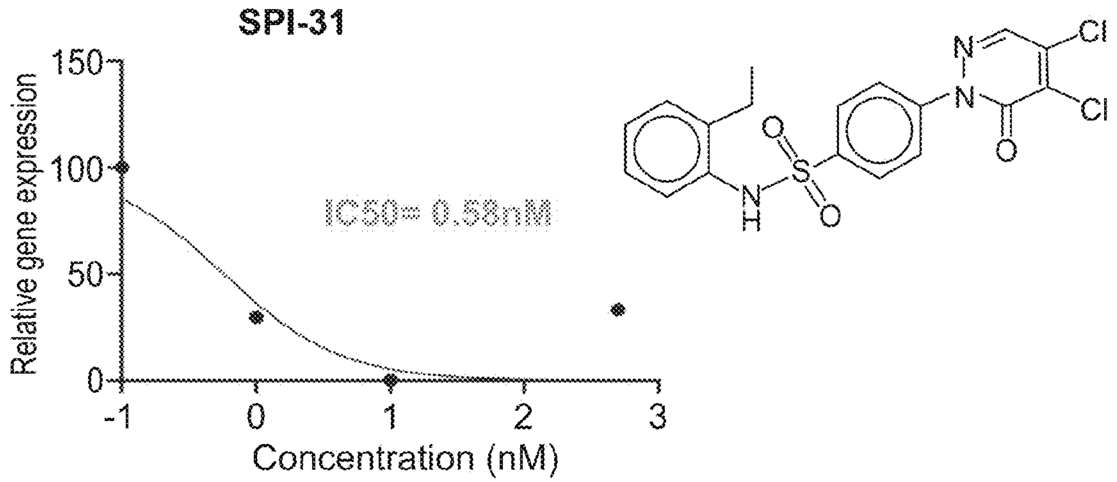
Figure 13B:
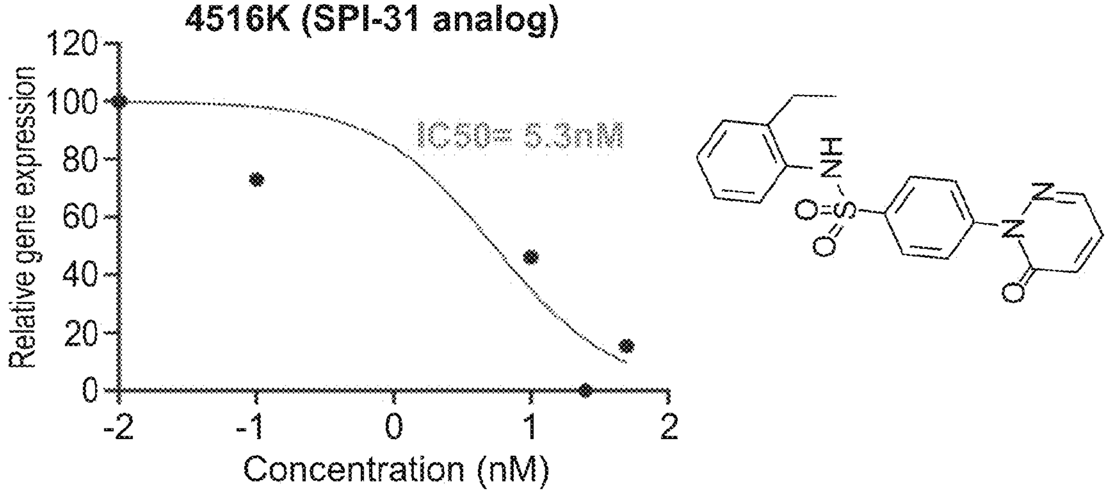
Figure 13C:
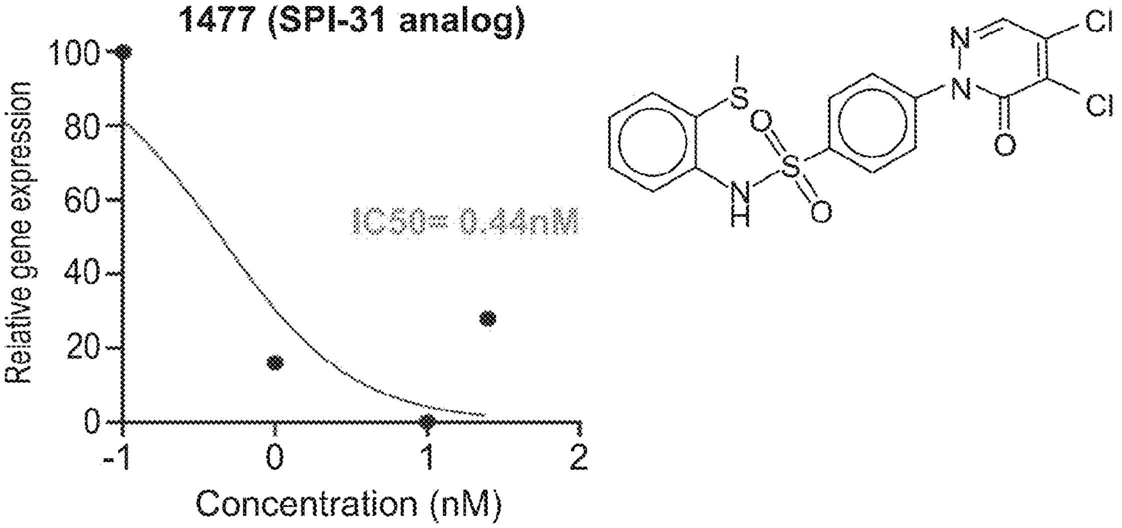
Figure 13D:
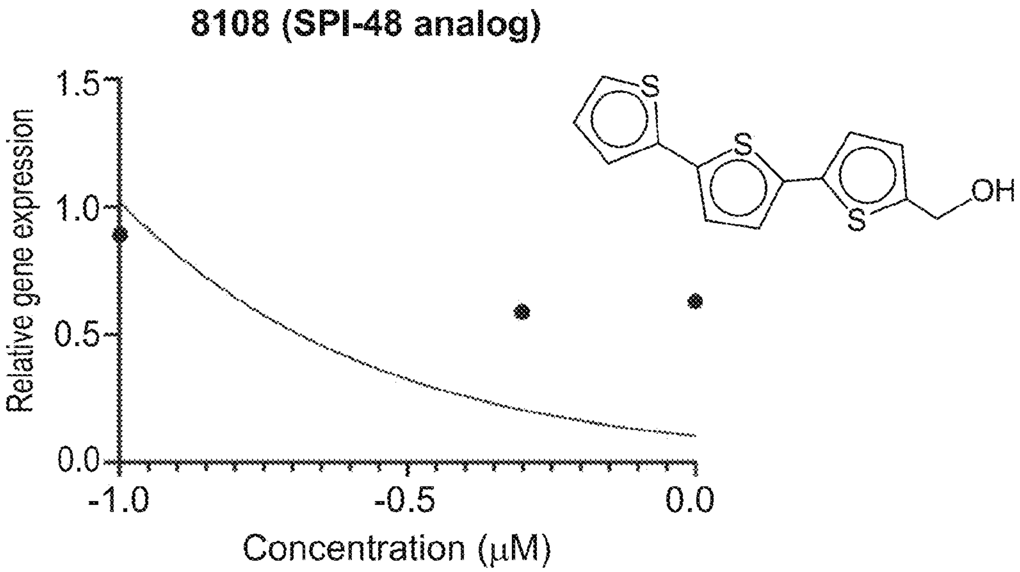
Figure 13E:
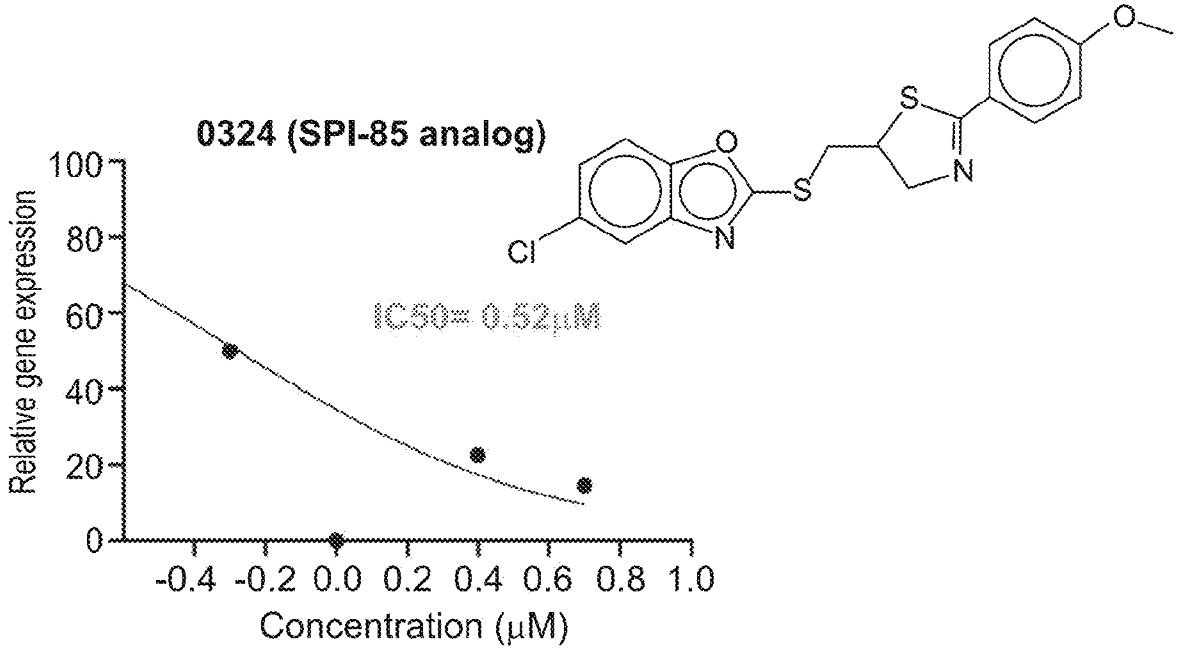

FIG. 12A-C present the chemical structure of the newly designed structural analog of SPI-31, denoted SPI-4516K (FIG. 12A), a scheme depicting its synthetic pathway (FIG. 12B) and a bar graph demonstrating Htt mRNA levels (normalization to β-actin) in Q111 expressing cells treated for 48 hours with varying doses of SPI-4516K, as determined by real-time qPCR (FIG. 12C). The asterisks denote statistical significance differences according to Student's t tests (typically one tailed, paired): *p<0.05; p<0.01; *p<0.005; ****p<0.001.

FIGS. 13A-E present plots demonstrating Htt mRNA levels (normalized to β-actin) in Q111 expressing cells treated for 48 hours with varying concentrations of the indicated SPI compound. The data was analysed using GraphPad Prism software and the calculated IC50 for each compound is indicated.

Figure 14A:
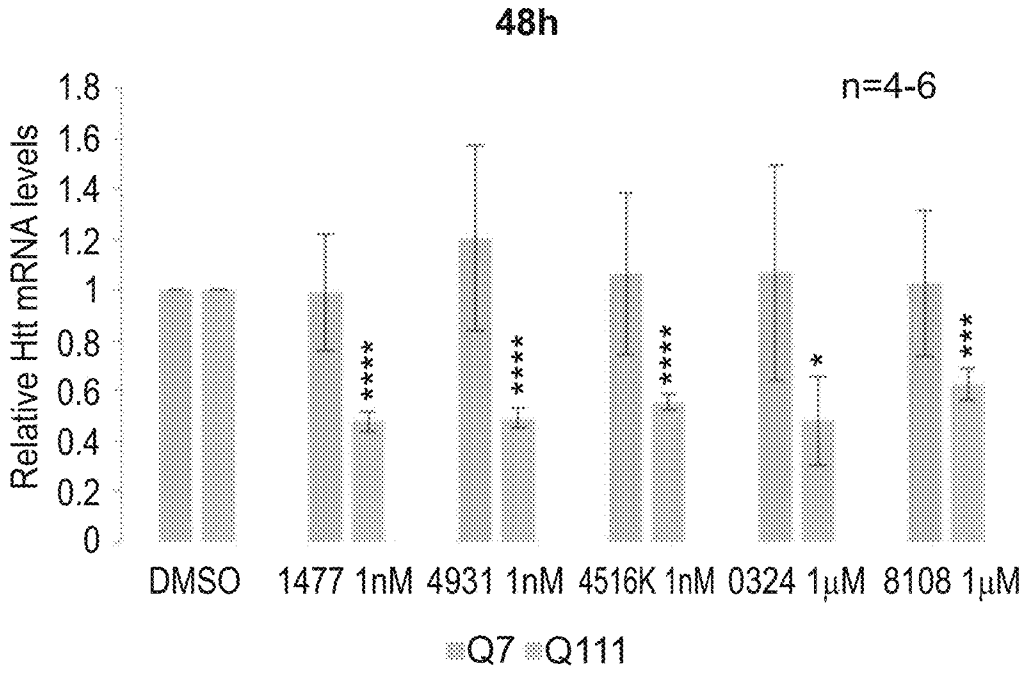

FIG. 14A presents a bar graph demonstrating Htt mRNA levels (normalized to β-actin) in Q7 and Q111 expressing stratial cells treated for 48 hours with the indicated concentration of the respective indicated SPI compound, as determined by real-time qPCR. The asterisks denote statistical significance differences according to Student's t tests (typically one tailed, paired): *p<0.05; p<0.01; *p<0.005; ****p<0.001.

Figure 14B:
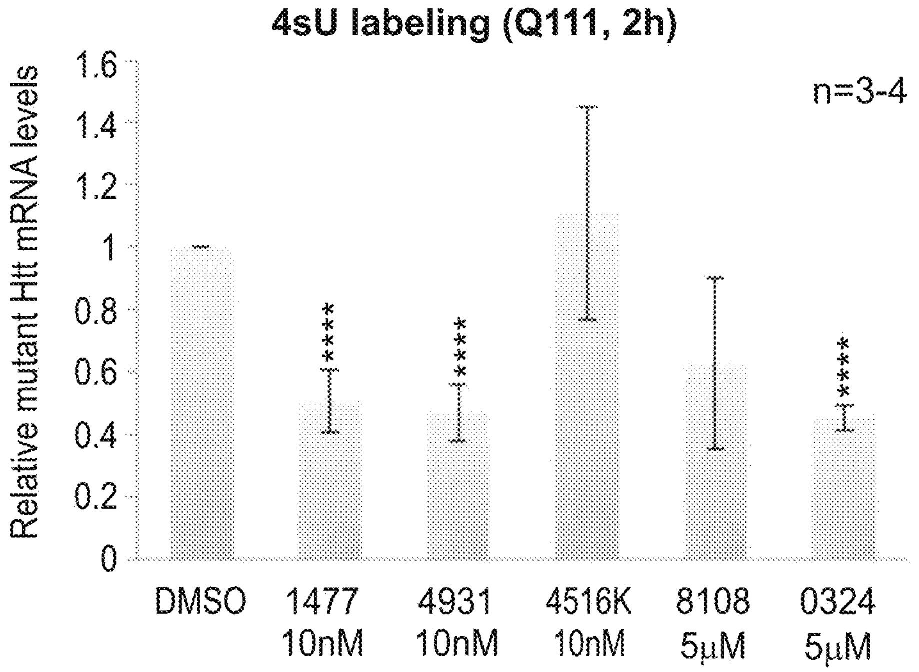

FIG. 14B presents a bar graph demonstrating expression of newly synthesized Htt transcripts in Q111 expressing Stratial cells that were metabolically labeled with 4-thio-uridine for 2 hours in the presence of DMSO (vehicle control) or the indicated SPI compound at the indicated respective concentration, as determined by real-time qPCR using primers from the indicated locations (SEQ ID NOs: 17-26). The asterisks denote statistical significance differences according to Student's t tests (typically one tailed, paired): *p<0.05; p<0.01; *p<0.005; ****p<0.001.

DESCRIPTION OF SPECIFIC EMBODIMENTS OF THE INVENTION

The present invention, in some embodiments thereof, relates therapy, and, more specifically, but not exclusively, to compounds which are Spt5 inhibitors, and to uses thereof, for example, in treating nucleotide repeat disorders, inflammation, obesity and cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Spt5 is a conserved and essential transcription elongation factor that promotes proximal promoter pausing, promoter escape, elongation and mRNA processing. To-date, no Spt5 inhibitor has been identified and most studies aiming to interfere with its activity used knockdown (KD) methods.

Whilst reducing the present invention to practice, the present inventors have now identified several compounds which inhibited several activities of Spt5.

As is illustrated hereinunder and in the examples section, which follows, the present inventors have developed a novel high throughput screening method to identify Spt1 inhibitors, referred to herein as SPIs, based on Spt5 interaction with polymerase II (Pol II) (Example 1, FIGS. 1A-E). Following, the present inventors have shown that several of the identified SPIs inhibited Spt5 proximal promoter pausing thereby increased mRNA expression of pro-inflammatory genes when applied on cells under basal conditions (i.e. not stimulated to induce activation of NF-κB) (Example 2, FIGS. 2A-C). The inventors further demonstrated that several of the identified SPIs diminished the positive activity of Spt5 towards expression of pro-inflammatory genes in response to NF-κB activation (i.e. following treatment with TNFα) (Example 2, FIG. 3A-F). Using SPIs the present inventors also demonstrated the requirement of Spt5 for proper 3'end processing of histone genes (Example 2, FIG. 3G). Moreover, several of the identified SPIs affected mRNA expression of genes involved in various pathways including an increase in expression of heat-shock proteins (HSP, e.g. HSPA6 and HSPA1A) and of GDF15, a food intake and body-weight inhibitor (Example 3, FIGS. 4A-H and 5A-B). In addition, several of the identified SPIs selectively inhibited transcription of long but not short expanded-repeat huntingtin gene in neuronal cells (Example 4, FIGS. 6A-D). Noteworthy, the identified SPIs mimicked the effect of Spt5 knock-down on the Spt5 aforementioned activities. The mechanism of action of the identified SPI compounds which exhibited selective inhibition of transcription of long but not short expanded-repeat huntingtin gene as the only biological activity was further tested by studying the activity of structural analogs thereof, and additional SPI compounds which exhibit such activity were uncovered (Example 6, FIGS. 8A-14B).

Consequently, specific embodiments of the present teachings suggest the use of the identified SPIs in the treatment of various diseases including, but not limited to, Trinucleotide repeat disorders, obesity, inflammatory diseases, infectious diseases and cancer.

As shown in the Examples section which follows, some of the identified SPI compounds and structural analogs thereof selectively inhibited transcription of mutant huntingtin gene in neuronal cells, and some were shown to exhibit this activity as the only activity that relates to Spt inhibition.

Thus, according to some aspects of the present invention, there is provided a method of treating a nucleotide repeat disorder in a subject in need thereof, the method comprising administering to the subject a therapeutically effective amount of a compound selected from a compound represented by Formula I as defined herein in any of the respective embodiments, a compound represented by Formula Ta as defined herein in any of the respective embodiments, a compound represented by Formula II as defined herein in any of the respective embodiments, a compound represented by Formula VII as defined herein in any of the respective embodiments, and the compounds presented in Tables 6-9 hereinunder, thereby treating the nucleotide repeat disorder in the subject.

According to some aspects of the present invention, there is provided a compound for use in treating a nucleotide repeat disorder in a subject in need thereof, the compound being selected from a compound represented by Formula I as defined herein in any of the respective embodiments, a compound represented by Formula Ia as defined herein in any of the respective embodiments, a compound represented by Formula II as defined herein in any of the respective embodiments, a compound represented by Formula VII as defined herein in any of the respective embodiments, and the compounds presented in Tables 6-9 hereinunder.

The term "treating" refers to inhibiting, preventing or arresting the development of a pathology (disease, disorder or condition, e.g. Trinucleotide repeat disorder, obesity, inflammatory disorder, infectious disease, cancer) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings, at any age and of any gender which suffer from the pathology. Alternatively, the subject is at a risk of developing such a pathology.

According to specific embodiments, the subject has an active immune system.

According to other specific embodiments, the subject is immunocompromised or treated with immunosuppressive agents.

According to specific embodiments, the subject immune system is activated above a predetermined baseline prior to said administering.

According to other specific embodiments, the subject immune system is not activated above a predetermined baseline prior to said administering.

According to specific embodiments, when administering a compound represented by Formula V, the subject immune system is not activated above predetermined baseline prior to said administering.

According to specific embodiments, when administering a compound represented by Formula V, the subject immune system is not activated above a predetermined baseline prior to said administering.

According to other specific embodiments, the subject immune system is activated above a predetermined baseline prior to said administering.

According to specific embodiments, when administering a compound represented by Formula III and/or when administering a compound represented by Formula IV, the subject immune system is activated above a predetermined baseline prior to said administering.

According to one embodiment, a predetermined baseline can be established by determining an immune state in a healthy subject.

Hence, according to specific embodiments, the method comprising determining an immune state of the subject prior to said administering.

According to specific embodiments, the determining is effected in-vitro or ex-vivo.

Methods of determining immune cells activation are well known in the art and include, but are not limited to, cytokine secretion assays such as intracellular cytokine staining ELISPOT and ELISA, proliferation assays such as BRDU and thymidine incorporation, cytotoxicity assays such as chromium release, expression of activation markers such as CD25, CD69 and CD69 using flow cytometry, and signaling of a stimulatory signals using e.g. binding assay using e.g. BiaCore, HPLC or flow cytometry, enzymatic activity assays such as kinase activity assays, and expression of molecules involved in the signaling cascade using e.g. PCR, Western blot, immunoprecipitation and immunohistochemistry. According to specific embodiments, immune cells activation is determined by production and/or secretion of cytokines such as TNFα in a biological sample of the subject or in a cell culture derived therefrom. Such biological samples include, but are not limited to, body fluids such as whole blood, serum, plasma, cerebrospinal fluid, urine, lymph fluids, and various external secretions of the respiratory, intestinal and genitourinary tracts, tears, saliva, milk as well as white blood cells, malignant tissues, amniotic fluid and chorionic villi.

According to specific embodiments, a level of TNFα in a biological sample of a subject (e.g. blood) of above 15 pg/ml, above 20 pg/ml, above 25 pg/ml, above 30 pg/ml or above 35 pg/ml is indicative of activation of the immune system in the subject.

According to specific embodiments, a level of TNFα in or in a cell culture derived from a biological sample of a subject of above 0.5 nl/ml, above 1 ng ml, above 5 ng/ml, above 10 ng/ml or above 15 ng/ml is indicative of activation of the immune system in the subject.

As used herein, the term "nucleotide repeat" refers to a segment of a nucleic acid sequence that consists of consecutive repeats of a particular nucleotide sequence. According to specific embodiments, the nucleotide repeat includes at least 5 consecutive nucleotide sequences. According to specific embodiments, the nucleotide repeat includes at least 10 consecutive nucleotide sequences. According to specific embodiments, the nucleotide repeat includes at least 20 consecutive nucleotide sequences. According to specific embodiments, the nucleotide repeat includes at least 40 consecutive nucleotide sequences. According to specific embodiments, the nucleotide repeat sequence is a trinucleotide repeat sequence. Exemplary trinucleotide sequences include, but are not limited to, CAG, CGG, GCC, GAA, CTG, and/or CGG. As used herein, the term "nucleotide repeat disorder", refers to a disease or disorder characterized by an expanded nucleotide repeat region located within a gene, the expanded nucleotide repeat region being causative of the disease or disorder. Non-limiting examples of nucleotide repeat disorder include Huntington disease, fragile X syndrome, mitotic dystrophy, spino-bulbar muscular atrophy (SBMA), Fragile XE mental retardation, Fragile X-associated tremor/ataxia syndrome, Jacobsen syndrome, Spinocerebellar ataxia (SCA) type 1, SCA 2, SCA3 (also known as Machado-Joseph disease), SCA6, SCAT, SCA 8, SCA7, SCA 10, SCA 12, SCA17, dentatorubral pallidoluysian atrophy, Friedreich ataxia, Huntington disease-like 2, oculopharyngeal muscular dystrophy, multiple epiphyseal dysplasia, cleidocranial dysplasia, synpolydactyly, Type-2 myotonic dystrophy (DM2), progressive myoclonus epilepsy (EPM1) and a non-folate sensitive fragile site, FRA16B.

According to specific embodiments, the nucleotide repeat disorder is characterized or caused by an expanded nucleotide repeat region at the 5' end of the coding region of a gene, the gene encoding a mutant protein which causes or is causative of the disease or disorder.

According to specific embodiments, the nucleotide repeat disorder is a Trinucleotide repeat disorder, also known as trinucleotide repeat expansion disorders (TRED), triplet repeat expansion disorders or codon reiteration disorders. Non-limiting Examples of Trinucleotide repeat disorders include Huntington disease, fragile X syndrome, Fragile XE mental retardation, Fragile X-associated tremor/ataxia syndrome, mitotic dystrophy type 1 (DM1), spino-bulbar muscular atrophy (SBMA), Jacobsen syndrome, Spinocerebellar ataxia (SCA) type 1, SCA 2, SCA3 (also known as Machado-Joseph disease), SCA6, SCAT, SCA 7, SCA 8 SCA 12, SCA 17, dentatorubral pallidoluysian atrophy, Friedreich ataxia, Huntington disease-like 2, oculopharyngeal muscular dystrophy, multiple epiphyseal dysplasia, cleidocranial dysplasia and synpolydactyly.

According to specific embodiments the Trinucleotide repeat disorder is a Polyglutamine (PolyQ) disease.

As used herein, the term "polyglutamine (PolyQ) disease", refers to any disease or disorder characterized by an expanded of a $(CAG)_n$ sequence repeats at the 5' end of the coding region (thus encoding an expanded polyglutamine region in the encoded protein). Non-limiting Examples of polyglutamine diseases include Huntington disease, spinobulbar muscular atrophy (SBMA), Spinocerebellar ataxia (SCA) type 1, SCA 2, SCA3 (also known as Machado-Joseph disease), SCA6, SCA7, SCA 17 and dentatorubral pallidoluysian atrophy.

According to specific embodiments, the PolyQ disease is Huntington disease.

According to specific embodiments, the Trinucleotide repeat disorder is a Non-Polyglutamine disease. Non-limiting Examples of Non-Polyglutamine disease include Fragile X syndrome, Fragile XE mental retardation, Fragile X-associated tremor/ataxia syndrome, mitotic dystrophy type 1 (DM1), Jacobsen syndrome, SCA 8, Friedreich ataxia, Huntington disease-like 2, oculopharyngeal muscular dystrophy, cleidocranial dysplasia and synpolydactyly.

According to specific embodiments, the compound is capable of down-regulating expression of a mutant huntingtin gene.

According to specific embodiments, the compound represented by the formula I or II is capable of down-regulating expression of a mutant huntingtin gene.

As used herein, the term "huntingtin gene" refers to the HTT gene (gene ID 3064) which encodes the protein huntingtin (Htt).

As used herein, the term "mutant huntingtin gene" refers to a huntingtin gene having at least 36 constitutive repeats of CAG nucleotide sequence in the Htt gene.

According to specific embodiments the compound is capable of down-regulating expression of a mutant huntingtin gene without affecting expression of a huntingtin gene having less than 36 constitutive repeats of CAG nucleotide sequence.

As used herein, the phrase "down-regulating expression" refers to the ability to decrease expression of a gene (e.g. mutant huntingtin gene). The decrease is of at least 5% in the gene in the presence of the compound as compared to same in the absence of the agent. According to a specific embodiment, the decrease is in at least 10%, 20%, 30%, 40% or even higher say, 50%, 60%, 70%, 80%, 90%, 99% or even 100%. According to specific embodiments the decrease is at least 1.5 fold, at least 2 fold, at least 3 fold, at least 5 fold, at least 10 fold, or at least 20 fold as compared to same in the absence of the compound.

Expression of a gene can be assessed on the RNA or protein level in multiple ways, including but not limited to, PCR, microarray, Northern blot, FISH, Western blot, immunohistochemistry and the like.

As shown in the Examples section which follows, few of the identified SPIs increased expression of GDF15. GDF15 is a TGFβ family member known to be a multifactorial protein involved in growth and differentiation of cells, having anti-inflammatory effects and also a food intake and body-weight inhibitor.

Thus according to an additional or an alternative aspect of the present invention, there is provided a method of inducing suppression of appetite in a subject in need thereof, the method comprising administering to the subject an effective amount of a compound represented by Formula II, Formula III or Formula IV, as defined herein, thereby inducing suppression of appetite in the subject.

According to an additional or an alternative aspect of the present invention, there is provided a method of treating obesity in a subject in need thereof, the method comprising administering to the subject a therapeutically effective amount of a compound represented by Formula II, III or IV, thereby treating obesity in the subject.

According to an additional or an alternative aspect of the present invention, there is provided a compound represented by Formula II, III or IV for use in treating obesity in a subject in need thereof.

According to an additional or an alternative aspect of the present invention, there is provided a method of treating a disease that can benefit from up-regulating growth and/or differentiation of cells, the method comprising administering to the subject a therapeutically effective amount of a compound represented by Formula II, III or IV, thereby treating the disease in the subject.

According to an additional or an alternative aspect of the present invention, there is provided a compound represented by Formula II, III or IV for use in treating a disease that can benefit from up-regulating growth and/or differentiation of cells in a subject in need thereof.

Suppression of appetite may be desirable under many circumstances. Thus, for example, suppression of appetite is effected in an obese subject, in a subject under fasting, as a weight control diet, and the like.

According to specific embodiments, the compound represented by Formula II, Formula III or Formula IV is included as a food additive in a dietary supplement.

As used herein, the term "obesity" refers to a whereby an otherwise healthy subject has a Body Mass Index (BMI)≥30 $kg/m^2$, or a condition whereby a subject with at least one co-morbidity has a BMI≥27 $kg/m^2$.

According to specific embodiments, the method and compounds of some embodiments of the present invention are used for the treatment of obesity and its related disorders e.g. diabetes, non-insulin dependent diabetes mellitus-type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

According to specific embodiments, the obesity is not in co-morbidity with other obesity related disorders e.g. diabetes, non-insulin dependent diabetes mellitus-type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

According to specific embodiments, the phrase "a disease that can benefit from up-regulating growth and/or differentiation of cells" refers to diseases or disorders (medical conditions in total) that can be ameliorated by up-regulating proliferation and/or differentiation of cells. Non-limiting examples of such diseases include, an inflammatory disease, ischemia-reperfusion injury, tissue damage (due to e.g. disease, trauma, physical injury, surgery, chemotherapy, radiotherapy, irritants or other exogenous substances), cell/tissue transplantation and neurodegenerative disease (e.g. but not limited to Alzheimer's disease, Parkinson's disease, Huntington, amyotrophic lateral sclerosis, prion disease).

Inflammatory diseases encompassed by some embodiments of the present invention are disclosed in details hereinbelow.

According to specific embodiments of this aspect of the present invention, the inflammatory disease is selected from the group consisting of rheumatoid arthritis, atherosclerosis, Diabetes and sepsis, each possibility represents a separate embodiment of the present invention.

According to specific embodiments, the compound is capable of up-regulating expression of a GDF15 gene.

According to specific embodiments, the compound represented by Formula II, III or IV is capable of up-regulating expression of a GDF15 gene.

As used herein, the term "GDF15" refers to the growth/differentiation factor 15 gene (gene ID 9518).

As used herein, the phrase "up-regulating expression" refers to the ability to increase expression of a gene (e.g. GDF15 gene). The increase is of at least 5% in the gene in the presence of the compound as compared to same in the absence of the agent. According to a specific embodiment, the increase is in at least 10%, 20%, 30%, 40% or even higher say, 50%, 60%, 70%, 80%, 90%, 99%, 100%. According to specific embodiments the increase is at least 1.5 fold, at least 2 fold, at least 3 fold, at least 5 fold, at least 10 fold, or at least 20 fold as compared to same in the absence of the compound.

Expression of a gene can be assessed on the RNA or protein level in multiple ways, including but not limited to, PCR, microarray, Northern blot, FISH, Western blot, immunohistochemistry and the like.

As further shown in the Examples section which follows, few of the identified SPIs increased expression of the heat-shock proteins HSP70 member 6 (encoded by the HSPA6 gene) and HSP72 (encoded by the HSPA1A gene).

HSPs are a family of proteins produced by cells in response to stress such as, but not limited to, a rise in temperature, glucose deprivation, exposure to cold, exposure to UV light, and during wound healing or tissue remodeling. Their use have been suggested as e.g. vaccine adjuvants; and also for e.g. inducing immune tolerance and treating autoimmune diseases.

Thus, according to an additional or an alternative aspect of the present invention, there is provided a method of immunization a subject in need thereof, the method comprising administering to the subject a therapeutically effective amount of a compound represented by Formula II, III or IV, thereby immunizing the subject.

According to specific embodiments of this aspect of the present invention, the compound represented by Formula II, III or IV is used as an adjuvant.

Thus, according to specific embodiments, the method comprising administering to said subject a therapeutically effective amount of a vaccine.

According to specific embodiments, the compound is administered prior to the vaccine.

According to specific embodiments, the vaccine is administered prior to the compound.

According to specific embodiments, the compound and the vaccine are administered concomitantly.

Thus, according to an aspect of the present invention there is provided an article of manufacture comprising a packaging material packaging a compound represented by Formula II, III or IV; and a vaccine.

According to specific embodiments, the article of manufacture is identified for immunization or vaccination.

According to specific embodiments, the compound and the vaccine are in a co-formulation.

According to other specific embodiments, the compound and the vaccine are in separate containers.

According to an additional or an alternative aspect of the present invention, there is provided a method of treating a disease that can benefit from up-regulating expression of a heat-shock protein in a subject in need thereof, the method comprising administering to the subject a therapeutically effective amount of a compound represented by Formula II, III or IV, thereby treating the disease in the subject.

According to an aspect of the present invention, there is provided a compound represented by Formula II, III or IV for use in treating a disease that can benefit from up-regulating expression of a heat-shock protein in a subject in need thereof.

As used herein, the phrase "a disease that can benefit from up-regulating expression of a heat-shock protein" refers to diseases or disorders (medical conditions in total) that can be ameliorated by up-regulating expression of a heat-shock protein. Non-limiting Examples of HSPs include HSP10, HSP40, HSP60, Hsp27, HSPB6, HspBl, HSP71, HSP70, HSP70 member 6, HSP72, Grp78 (BiP), Hsx70, hsp65, hsp90, Grp94, hsp100, hsp10-12, hsp20-30, Hsp104 and Hsp110.

According to specific embodiments, the HSP is HSP70 member 6 and/or HSP72. Non-limiting examples of such diseases include an autoimmune disease or graft rejection.

Non-limiting Examples of autoimmune diseases and graft rejection diseases encompassed by some embodiments of the present invention are disclosed in details hereinbelow.

According to specific embodiments of this aspect of the present invention, the autoimmune disease is rheumatoid arthritis or type I diabetes.

According to specific embodiments, the compound is capable of up-regulating expression of a heat-shock protein gene.

According to specific embodiments, the compound represented by II, III or IV is capable of up-regulating expression of a heat-shock protein gene.

As shown in the Examples section which follows, several of the identified SPIs increased mRNA expression of pro-inflammatory genes when applied on cells under basal conditions.

Thus, according to an additional or an alternative aspect of the present invention, there is provided a method of treating a disease selected from the group consisting of infectious disease and cancer in a subject in need thereof, the method comprising administering to the subject a therapeutically effective amount of a compound represented by Formula V as defined herein, thereby treating the disease in the subject.

According to another aspect of the present invention there is provided a compound represented by Formula V for use in treating a disease selected from the group consisting of infectious disease and cancer in a subject in need thereof.

Examples of infectious diseases include, but are not limited to, chronic infectious diseases, subacute infectious diseases, acute infectious diseases, viral diseases, bacterial diseases, protozoan diseases, parasitic diseases, fungal diseases, *mycoplasma* diseases and prion diseases.

Non-limiting examples of viral diseases include human immunodeficiency virus (HIV), polio, hepatitis A, rubella, dengue, encephalitis, yellow fever, rabies, ebola, parainfluenza, mumps, measles, influenza, hemorrhagic fever viruses, rotaviruses, Hepatitis B, papilloma, polyoma, herpes simplex virus (HSV) 1 and 2, varicella zoster, cytomegalovirus (CMV), herpes, variola, vaccinia, pox, African swine fever, Hepatitis C.

According to specific embodiments, the infectious disease is an HIV infection.

Bacterial diseases include diseases caused by gram negative and gram positive bacteria such as, but not limited to, *Helicobacter pyloris, Borelia burgdorferi, Legionella* pneumophilia, Mycobacteria sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelii.*

Non-limiting Examples of infectious fungi include *Cryptococcus neoformans, Histoplasma capsulatum, Coccidioides immitis, Blastomyces dermatitidis, Chlamydia trachomatis, Candida albicans.*

Non-limiting examples of other infectious organisms (i.e., protists) include *Plasmodium* spp. such as *Plasmodium falciparum, Plasmodium malariae, Plasmodium ovale*, and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii.*

Other medically relevant microorganisms have been described extensively in the literature, e.g., see C. G. A Thomas, *Medical Microbiology*, Bailliere Tindall, Great Britain 1983, the entire contents of which is hereby incorporated by reference.

As used herein, the term "cancer" has its general meaning in the art and includes, but is not limited to, solid tumors and blood-borne tumors. The term cancer includes diseases of the skin, tissues, organs, bone, cartilage, blood and vessels. The term "cancer" further encompasses both primary and metastatic cancers. Examples of cancers that may be treated by methods and compositions of the invention include, but are not limited to, cancer cells from the bladder, blood, bone, bone marrow, brain, breast, colon, esophagus, gastrointestinal tract, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignanthistiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In some embodiments, the method of the present invention is particularly suitable for the treatment of metastatic cancer to bone, wherein the metastatic cancer is breast, lung, renal, multiple myeloma, thyroid, prostate, adenocarcinoma, blood cell malignancies, including leukemia and lymphoma; head and neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, and cervical cancer; bladder cancer; brain cancer, including neuroblastoma; sarcoma, osteosarcoma; and skin cancer, including malignant melanoma or squamous cell cancer.

According to specific embodiments, the infectious disease or the cancer is in an immune privileged site (e.g. central nervous system, eye, testis).

According to specific embodiments, the compound is capable of up-regulating expression of a pro-inflammatory gene under basal conditions, wherein transcription of said pro-inflammatory gene is dependent on Spt5.

According to specific embodiments, the compound represented by Formula V is capable of up-regulating expression of a pro-inflammatory gene under basal conditions, wherein transcription of said pro-inflammatory gene is dependent on Spt5.

Further, as shown in the Examples section which follows, several of the identified SPIs inhibited mRNA expression pro-inflammatory genes in response to NF-κB activation.

Thus, according to an additional or an alternative aspect of the present invention, there is provided a method of treating an inflammatory disease in a subject in need thereof, the method comprising administering to the subject a therapeutically effective amount of a compound represented by Formula III or VI as defined herein, thereby treating the inflammatory disease in the subject.

According to another aspect of the present invention, there is provided a compound represented by Formula III or VI as defined herein for use in treating an inflammatory disease in a subject in need thereof.

Inflammatory diseases include, but are not limited to, chronic inflammatory diseases and acute inflammatory diseases. Below are non-limiting examples of inflammatory diseases.

Inflammatory diseases associated with hypersensitivity—Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec.

15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus *foliaceus*.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune diseases—Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus *foliaceus.*

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

According to specific embodiments, the autoimmune disease is rheumatoid arthritis or type I diabetes.

Graft rejection diseases—Examples of diseases associated with transplantation of a graft include, but are not limited to, graft rejection, chronic graft rejection, subacute graft rejection, hyperacute graft rejection, acute graft rejection and graft versus host disease.

Allergic diseases—Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to specific embodiments, the inflammatory disease is selected from the group consisting of rheumatoid arthritis, atherosclerosis, Diabetes and sepsis, each possibility represents a separate embodiment of the present invention.

According to specific embodiments, the inflammatory disease is selected from the group consisting of an autoimmune disease, graft rejection disease and allergic disease.

According to specific embodiments, the inflammatory disease can benefit from down-regulating expression of a pro-inflammatory gene.

As used herein, the phrase "an inflammatory disease that can benefit from down-regulating expression of a pro-inflammatory gene" refers to refers to diseases or disorders (medical conditions in total) that can be ameliorated by down-regulating expression of a pro-inflammatory gene.

Pro-inflammatory genes are well known in the art and include, but not limited to A20, CCL20, IL6, IL8, CXCL2, JUNB, IEX1, BIRC3, TNFRSF9, TRAF1, BCL3, PTGS2, CXCL2, ICAM1, NFκBIA, NCOA7, SOD2, CD83, IL1A, CCL20, TNFAIP3, PLAU, TNFAIP6, SDC4, EREG, IRF1, IL1B, BMP2, IL6, IER3, TIFA, PLK2, NFκBIE, NUAK2, PTX3, CXCL3, CXCL1, TMEM52B, RRAD, EFNA1, CXCL10, CXCL8, JUNB, OLR1, C8orf4, CSF1, TNFAIP2, TNF, CFB.

According to specific embodiments, the pro-inflammatory gene is responsive to NFκB activation.

Thus, According to specific embodiments, the inflammatory disease can benefit from down-regulating expression of a pro-inflammatory gene responsive to NFκB activation.

Methods of activating NFκB are well known in the art and include exposure to cytokines such as TNFα, IL6, IL8.

Pro-inflammatory genes responsive to NFκB activation are known in the art and include, but not limited to A20, CCL20, IL6, IL8, CXCL2, JUNB, IEX1, BIRC3, TNFRSF9, TRAF1, BCL3, PTGS2, CXCL2, ICAM1, NFκBIA, NCOA7, SOD2, CD83, IL1A, CCL20, TNFAIP3, PLAU, TNFAIP6, SDC4, EREG, IRF1, IL1B, BMP2, IL6, IER3, TIFA, PLK2, NFκBIE, NUAK2, PTX3, CXCL3, CXCL1, TMEM52B, RRAD, EFNA1, CXCL10, CXCL8, JUNB, OLR1, C8orf4, CSF1, TNFAIP2, TNF, CFB.

According to specific embodiments, the transcription of the pro-inflammatory gene is dependent on Spt5.

Thus, according to specific embodiments, the inflammatory disease can benefit from down-regulating expression of a pro-inflammatory gene, wherein transcription of said pro-inflammatory gene is dependent on Spt5.

As used herein, the term "Spt5" refers to the transcription elongation factor encoded by the SUPT5H (Gene ID 6829) or a homolog or ortholog thereof. According to a specific embodiment, the Spt5 refers to the human Spt5, such as provided in the following Accession Numbers: NP_001104490, NP_001124296, NP_001124297, NP_001306919, NP_001306920. According to a specific embodiment, the Spt5 refers to the mouse Spt5, such as provided in Accession Number NP_038704.

Pro-inflammatory genes which transcription is dependent on Spt5 are known in the art and include, but not limited to A20, CCL20, IL6, IL8, CXCL2, JUNB, IEX1, TNFRSF9, TRAF1, BCL3, PTGS2, CXCL2, ICAM1, NFκBIA, NCOA7, SOD2, CD83, IL1A, CCL20, TNFAIP3, PLAU, TNFAIP6, SDC4, EREG, IRF1, IL1B, BMP2, IL6, IER3, TIFA, PLK2, NFκBIE, NUAK2, PTX3, CXCL3, CXCL1, TMEM52B, RRAD, EFNA1, CXCL10, CXCL8, JUNB, OLR1, C8orf4, CSF1, TNFAIP2, TNF, CFB.

According to specific embodiments the pro-inflammatory gene is selected from the group consisting of A20, CCL20, IL6, IL8, CXCL2, JUNB and IEX1, each possibility represents a separate embodiments of the present invention.

According to specific embodiments, the compound is capable of down-regulating expression of a pro-inflammatory gene under TNFα-induced conditions, wherein transcription of said pro-inflammatory gene is dependent on Spt5.

According to specific embodiments, the compound represented by Formula III or VI is capable of down-regulating expression of a pro-inflammatory gene under TNFα-induced conditions, wherein transcription of said pro-inflammatory gene is dependent on Spt5.

As the compounds of Formula III and Formula VI inhibited mRNA expression pro-inflammatory genes in response to NF-κB activation, according to an additional or an alternative aspect of the present invention, there is provided a method of down-regulating expression of a pro-inflammatory gene, the method comprising contacting a cell exposed to TNFα with a compound represented by Formula III or VI, as defined herein, wherein said cell expresses Spt5 and RNA Polymerase II and transcription of said pro-inflammatory gene is dependent on Spt5, thereby down-regulating expression of the pro-inflammatory gene.

As used herein "RNA Polymerase II (Pol II)" refers to a DNA-directed RNA polymerase E.C. number 2.7.7.6.

According to specific embodiments, Pol II comprises Rpb1.

As used herein the term "Rpb1" refers to the expression product of the POLR2A gene (Gene ID 5430) or a homolog or ortholog thereof. According to a specific embodiment, the Rpb1 refers to the human Rpb1, such as provided in the following Accession Numbers: NP_000928. According to a specific embodiment, the Rpb1 refers to the mouse Rpb1, such as provided in Accession Number NP_001277997.

According to specific embodiments, the method (e.g. the contacting) is effected in-vitro or ex-vivo.

According to specific embodiments, the method (e.g. the contacting) is effected in-vivo.

The cell may be of any origin including eukaryotes and prokaryotes.

According to specific embodiments, the cell is a eukaryotic cell.

According to specific embodiments the cell is a bacterial cell, yeast, *Drosophila* cell, Zebra fish cells or a mammalian cell.

According to specific embodiments, the cell is a mammalian cell.

According to specific embodiments, the cell is a murine cell.

According to specific embodiments, the cell is a human cell.

The cell of some embodiments of the present invention is exposed to TNFα. According to specific embodiments, the cell is exposed to a level of at least 0.1 ng/ml, at least 0.5 ng/ml, at least 1 ng/ml, at least 10 ng/ml, at least 20 ng/ml of TNFα.

According to specific embodiments the cell is exposed to a level of at least 0.5 ng/ml of TNFα.

As Spt5 is essential for cell viability and appears to be essential for life, according to an additional or an alternative aspect of the present invention, there is provided a method of inducing death of a cell, the method comprising contacting the cell with a toxic amount of a compound represented by Formula II, III or IV, as defined herein, wherein said cell expresses Spt5 and RNA Polymerase II (Pol II), thereby inducing death of the cell.

According to specific embodiments, the cell is a diseased cell.

According to specific embodiments, the cell is a pathogenic cell (e.g. a pest, a bacteria, a virus, a fungi).

According to specific embodiments, the method is effected in-vitro or ex-vivo.

According to specific embodiments, the method is effected in-vivo.

Methods of determining cell death are well known in the art and include, but not limited to, light and electron microscopy, flow cytometry, vital dyes, nuclear stains, DNA laddering, lactate dehydrogenase enzyme release, MTT/XTT enzyme activity.

The compounds of some embodiments of the invention can be administered to a subject in combination with other established (e.g. gold standard) or experimental therapeutic regimen to treat a disease (e.g. Trinucleotide repeat disorder, obesity, inflammatory disorder, infectious disease, cancer) including, but not limited to analgesics, chemotherapeutic agents, radiotherapeutic agents, cytotoxic therapies (conditioning), hormonal therapy, antibodies, antibiotics, anti-inflammatory drugs and other treatment regimens (e.g., surgery) which are well known in the art.

The compounds of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compound accountable for the biological effect.

According to specific embodiments, the "active ingredient" is an adjuvant (e.g. elicits an immune response in a subject to enhance the efficacy of e.g. a vaccine).

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide.

In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients effective to prevent, alleviate or ameliorate symptoms of a disorder or prolong the survival of the subject being treated. According to specific embodiments, the effective amount is a toxic amount effective to kill a cell.

Determination of a therapeutically effective amount or a toxic amount is well within the capability of those skilled in the art, especially in light of the detailed disclosure provided herein.

For any preparation used in the methods of the invention, the therapeutically effective amount or toxic amount or dose can be estimated initially from in vitro and cell culture assays.

For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Herein throughout, and according to any of the respective embodiments, compounds represented by Formula II include compounds collectively represented by Formula II below:

Formula II

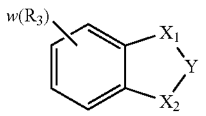

wherein:

w is an integer of from 0 to 4 (i.e., 0, 1, 2, 3 or 4);

$R_3$ is a substituent selected from alkyl, cycloalkyl, aryl, heteroaryl, heteroalicyclic, hydroxy, thiol, alkoxy, thioalkoxy, aryloxy, thioalryloxy, halo, alkyl, amine, amide, carboxylate and thiocarboxylate, or, alternativelty or in addition, w is greater than 1 and two or more $R_3$ substituents from together a cyclic moiety fused to the phenyl;

$X_1$ and $X_2$ are each independently O, S or $NR_4$;

Y is —C(=$X_3$)— or —$CR_5R_6$—C(=$X_3$)—, wherein $X_3$ is O, S or $NR_4$, wherein $R_4$ is hydrogen, alkyl, cycloalkyl or aryl, such that $X_1$—Y—$X_2$ form a heteroalicylic 5- or 6-membered ring fused to the phenyl and substituted by an oxo, thiooxo or imine, and $R_5$ and $R_6$ are each independently selected from hydrogen, alkyl, cycloalkyl, aryl, heteroaryl, heteroalicyclic, hydroxy, thiol, alkoxy, thioalkoxy, aryloxy, thioalryloxy, halo, alkyl, amine, amide, carboxylate and thiocarboxylate, or, alternatively, two or more of $R_4$, $R_5$ and $R_6$ from together a cyclic moiety.

According to some of any of the embodiments of Formula II, Y is C=$X_3$, such that $X_1$—Y—$X_2$ form a heteroalicylic 5-membered ring fused to the phenyl and substituted by an oxo, thiooxo or imine.

According to some of any of the embodiments of Formula II, $X_3$ is O, such that $X_1$—Y—$X_2$ form a heteroalicylic 5- or 6-membered ring fused to the phenyl and substituted by an oxo group.

According to some of any of the embodiments of Formula II, Y is C=$X_3$ and $X_3$ is O, such that $X_1$—Y—$X_2$ form a heteroalicylic 5-membered ring fused to the phenyl and substituted by an oxo group.

According to some of any of the embodiments of Formula II, $X_1$ and $X_2$ are each independently O or S.

According to some of any of the embodiments of Formula II, $X_1$ is O and $X_2$ is S.

According to some of any of the embodiments of Formula II, the one or more of substituents on the phenyl, $R_3$, if present, is halo, alkyl, hydroxy, alkoxy, thiohydroxy and/or thioalkoxy.

According to some of any of the embodiments of Formula II, at least one of substituents on the phenyl, $R_3$, if present, is hydroxy.

According to some of any of the embodiments of Formula II, w is 1.

According to some of any of the embodiments of Formula II, w is 1 and $R_3$ is selected from halo, alkyl, hydroxy, alkoxy, thiohydroxy and/or thioalkoxy.

According to some of any of the embodiments of Formula II, w is 1 and $R_3$ is hydroxy.

According to some of any of the embodiments of Formula II, at least one of the substituents on the phenyl, $R_3$ is at the meta position with respect to $X_1$. According to some of these embodiments, w is 1 and $R_3$ is hydroxy.

According to exemplary embodiments of Formula II, Y is C=O; $X_1$ is O; and $X_2$ is S.

According to exemplary embodiments of Formula II, Y is C=O; $X_1$ is O; $X_2$ is S; w is 1 and $R_3$ is at the meta position with respect to $X_1$.

According to exemplary embodiments of Formula II, Y is C=O; $X_1$ is O; $X_2$ is S; w is 1 and $R_3$ is hydroxy. $R_3$ can be at the meta, ortho or para position with respect to $X_1$.

According to exemplary embodiments of Formula II, Y is C=O; $X_1$ is O; $X_2$ is S; w is 1 and $R_3$ is hydroxy and is at the meta position with respect to $X_1$. Such a compound is referred to herein as SPI-09 (see, FIG. 1C).

According to some of any of the embodiments of Formula II, w is 2.

According to some of any of the embodiments of Formula II, w is 2 and each of the $R_3$ substituents is independently selected from halo, alkyl, hydroxy, alkoxy, thiohydroxy and/or thioalkoxy.

According to some of any of the embodiments of Formula II, w is 2 and each $R_3$ is hydroxy, or one of $R_3$ is hydroxy and the other is chloro.

According to some of these embodiments of Formula II, at least one of the substituents on the phenyl, $R_3$, is at the meta position with respect to $X_1$. According to some of these embodiments, a hydroxy substituent is at the meta position.

According to exemplary embodiments of Formula II, Y is C=O; $X_1$ is O; $X_2$ is S; w is 1 and $R_3$ is at the ortho position with respect to $X_1$. In some of these embodiments, $R_3$ is hydroxy.

According to exemplary embodiments of Formula II, Y is C=O; $X_1$ is O; $X_2$ is S; w is 2 and the $R_3$ substituents are each hydroxy, or are hydroxy and chloro, or are hydroxy and alkyl (e.g., methyl).

According to exemplary embodiments of Formula II, Y is C=O; $X_1$ is O; $X_2$ is S; w is 3, two of the $R_3$ substituents form together a phenyl ring fused to the phenyl (to thereby provide a naphthyl) and the other $R_3$ is a carboxylate, optionally substituted by a phenyl which can be substituted or not.

Exemplary compounds of Formula II are presented in Table 6 hereinunder.

According to some embodiments of the present invention, compounds of Formula I, Ia, VII and/or II as described herein are for use in treating a nucleotide repeat disorder in a subject in need thereof, as described herein in any of the respective embodiments.

According to some embodiments of the present invention, compound SPI-21 is for use in treating a nucleotide repeat disorder in a subject in need thereof, as described herein in any of the respective embodiments.

According to some embodiments of the present invention, compounds of Formula I, Ia, VII and/or II as described herein are capable of down-regulating expression of a mutant huntingtin gene.

According to some embodiments of the present invention, compound SPI-85 is for use in treating a nucleotide repeat disorder in a subject in need thereof, as described herein in any of the respective embodiments.

According to some embodiments of the present invention, compound SPI-09 is for use in treating a nucleotide repeat disorder in a subject in need thereof, as described herein in any of the respective embodiments.

According to some embodiments of the present invention, compound SPI-31 is for use in treating a nucleotide repeat disorder in a subject in need thereof, as described herein in any of the respective embodiments.

According to some embodiments of the present invention, compound SPI-48 is for use in treating a nucleotide repeat disorder in a subject in need thereof, as described herein in any of the respective embodiments.

According to some embodiments of the present invention, a compound as presented in Tables 6, 7, 8 and 9 is for use in treating a nucleotide repeat disorder in a subject in need thereof, as described herein in any of the respective embodiments.

Herein throughout, and according to any of the respective embodiments, compounds represented by Formula III include compounds collectively represented by Formula III below:

Formula III

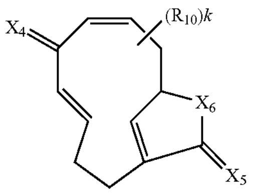

wherein:

k is an integer of from 0 to 8;

Each of $R_{10}$, if present, is selected from alkyl, cycloalkyl, halo, haloalkyl, hydroxy, alkoxy, thioalkoxy and thioaryloxy; and $X_4$, $X_5$ and $X_6$ are each independently selected from O, S and $NR_4$, wherein $R_4$ is hydrogen, alkyl, cycloalkyl or aryl.

According to some of any of the embodiments of compounds of Formula III, at least one, at least two or each of $X_4$, $X_5$ and $X_6$ is oxygen (O).

According to some of any of the embodiments of compounds of Formula III, each of $X_4$, $X_5$ and $X_6$ is oxygen (O).

According to some of any of the embodiments of compounds of Formula III, k is at least 2, such that there are at least two $R_{10}$ substituents on the heteroalicyclic ring.

According to some of any of the embodiments of compounds of Formula III, at least one of the $R_{10}$ substituents is an alkyl.

According to some of any of the embodiments of compounds of Formula III, each of the $R_{10}$ substituents is independently an alkyl.

According to some of any of the embodiments of compounds of Formula III, k is at least 2, and at least one of the $R_{10}$ substituents is an alkyl.

According to some of any of the embodiments of compounds of Formula III, k is at least 2, and each of the $R_{10}$ substituents is independently alkyl.

According to some of any of the embodiments of compounds of Formula III, k at least 2, and each of the $R_{10}$ substituents is independently alkyl.

According to some of any of the embodiments of compounds of Formula III, which $R_{10}$ is alkyl, the alkyl is a lower alkyl (e.g., methyl).

An exemplary compound of Formula III is SPI-39 (see, FIG. 1C).

According to some embodiments of the present invention, compounds of Formula III as described herein are capable of down-regulating transcription of pro-inflammatory genes under TNFα induced conditions.

According to some embodiments of the present invention, a compound of Formula III (e.g., SPI-39) is usable for, or is for use in, treating an inflammatory disease in a subject in need thereof, as described herein in any of the respective embodiments.

Herein throughout, and according to any of the respective embodiments, compounds represented by Formula IV include compounds collectively represented by Formula IV below:

Formula IV

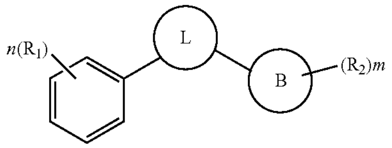

wherein:

n and m are each independently an integer of from 0 to 4 (e.g., 0, 1, 2, 3 or 4);

$R_1$, and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, carboxylate, thiocarboxylate, cyano and haloalkyl;

B is a cyclic moiety selected from aryl, heteroaryl and heteroalicyclic; and

L is a linking moiety, comprising from 2 to 20, or from 2 to 12 atoms in length, and comprising a saturated or unsaturated, substituted or unsubstituted hydrocarbon chain, optionally interrupted by one or more of O, S, —S(═O)—, —S(═O)$_2$, ═N—, and —$NR_4$.

According to some of any of the embodiments of compounds of Formula IV:

n and m are each independently an integer of from 0 to 4;

$R_1$ and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, carboxylate, and thiocarboxylate;

B is a cyclic moiety selected from aryl, heteroaryl and heteroalicyclic; and

L is a linking moiety, comprising from 2 to 12 atoms in length, and comprising a saturated or unsaturated, substituted or unsubstituted hydrocarbon chain, optionally interrupted by one or more of O, S, —S(═O)—, —S(═O)$_2$, ═N— and —$NR_4$—.

According to some of any of the embodiments of compounds of Formula IV, $R_1$ is an electron donating moiety (e.g., hydroxy, alkoxy, aryloxy, cyano, amine) at the ortho or para position of the phenyl and/or an electron withdrawing group (e.g., halo such as fluoro or chloro) at the meta position of the phenyl, as described hereinafter for Formula I.

According to some of any of the embodiments of compounds of Formula IV, n is 1 or 2.

According to some of any of the embodiments of compounds of Formula IV, B is aryl, for example, phenyl.

According to some of any of the embodiments of compounds of Formula IV, m is 1 or 2.

According to some of any of the embodiments of compounds of Formula IV, m is 1.

According to some of any of the embodiments of compounds of Formula IV, $R_2$ is an electron donating group such as alkyl, amine, hydroxy and/or alkoxy. In some embodiments, $R_2$ is as described hereinafter for Formula I.

According to some of any of the embodiments of compounds of Formula IV, the L linking moiety can be any of the linking moieties described hereinafter in the context of compounds of Formula I, V or VI, and can alternatively or in addition include any other saturated and unsaturated hydrocarbon moieties, optionally interrupted by one or more of $NR_4$, —N═, S, O, S═O, and $S(═O)_2$, and further optionally substituted by one or more $═R_7$ groups as described herein.

The L linking moiety can be attached to B via one or two attachment points, for example, be attached to one or two carbon atoms of B.

In some of any of the embodiments of compounds of Formula IV, L is or comprises a saturated or unsaturated hydrocarbon chain substituted by one or more $═X_7$ group, wherein $X_7$ is O, S, $NR_4$ or $CR_5R_6$.

$R_4$, $R_5$ and $R_6$ can each independently be hydrogen, alkyl, cycloalkyl, alkaryl, halo and like substituents.

In some of any of the embodiments of compounds of Formula IV, L is or comprises an unsaturated hydrocarbon chain substituted by one or more oxo (═O) groups (such that $R_7$ is O). In some of these embodiments, B is aryl. Alternatively, B is a heteroaryl.

For example, L is or comprises one or more moieties represented by Formula A:

—C(═O)—CR'═CR"— Formula A wherein R' and R" can each independently be hydrogen, alkyl, cycloalkyl, alkoxy, hydroxy, thiol, thioalkoxy and any other substituent as described herein, or, R' and R" can form a 5-, 6-, or 7-membered ring, optionally together with one or more atoms of B.

In some of these embodiments, R' and R" are each independently hydrogen and/or alkyl, and in some embodiments, both R' and R" are hydrogen.

In some of these embodiments, the linking moiety L can further comprise other moieties linked to the moiety presented in Formula A, including, for example, saturated or unsaturated hydrocarbon of 1 to 10 carbon atoms, optionally interrupted by one or more heteroatoms, or a heteroatom per se, or otherwise a biradical alkyl, alkenyl, alkynyl, aryl, heteroalicyclic, heteroaryl, ether, thioether, and like biradical groups of any of the substituents described herein.

A linking moiety which comprises an unsaturated hydrocarbon chain substituted by one or more oxo (═O) groups can alternatively or in addition include an unsaturated hydrocarbon (e.g., a hydrocarbon that comprises one or more of alkenyl, alkynyl and aryl groups) which further comprises one or more heteroatoms that is substituted by oxo groups. An example includes an unsaturated hydrocarbon that is interrupted or terminates by a group such as —S(═O) and/or $S(═O)_2$.

Exemplary L linking moieties include —C(═O)—CH═CH—; —CH═CH—C(═O)—$CH_2$—C(═O)—CH═CH—; —C(═O)—C($CH_2$S—)═CH— (connected to B via two attachment points), —CH═CR'—C(═O)—CR"═CH—, wherein R' and R" form a cyclic ring (e.g., S-containing heteroalicyclic ring); —C(═O)—CH═CH—S—; and like moieties.

According to some of any of the embodiments of compounds of Formula IV, L is or comprises a saturated hydrocarbon substituted by one or more of $═NR_{10}$ and $═CR_{11}R_{12}$. Exemplary such compounds include SPI-95, SPI-16 and SPI-42 (see, FIG. 1C).

According to some of any of the embodiments of compounds of Formula IV, L is or comprises a saturated or unsaturated hydrocarbon interrupted or terminating by one or more heteroatoms. In some of these embodiments, the hydrocarbon is interrupted or terminating by one or more of S, —S(═O)—, —$S(═O)_2$ and —$NR_4$.

In some of these embodiments, the heteroatom is —S— or —$NR_4$—. The hydrocarbon can be substituted or unsubstituted, and, when substituted, the one or more substituents can include an oxo substituent and/or other substituents.

In some of these embodiments, the hydrocarbon is a saturated hydrocarbon.

Exemplary linking moieties according to these embodiments include or consist of, but are not limited to, one or more of the following moieties: —(Rx)a-S—(Ry)b, wherein Rx and Ry are each independently a substituted or unsubstituted alkylene of 1 to 6 carbon atoms in length and a and b are each independently 0 or 1, provided that one of a and b is 1; —(Rx)a-$NR_4$—(Ry)b, wherein a, b, Rx and Ry are as defined herein; —(Rx)a-S—(Ry)b-$NR_4$—(Rw)c-, wherein a, b, Rx and Ry are as defined herein, c is 0 or 1, and Rw is as defined for Rx and Ry; —(Rx)a-S(═O)d-(Ry)b-$NR_4$—(Rw)c-, wherein a, b, c, Rx, Ry and Rw are as defined herein, and d is 1 or 2; —(Rx)a-S—(Ry)b-C(═O)-(Rw)c-, wherein a, b, Rx and Ry are as defined herein, c is 0 or 1, and Rw is as defined for Rx and Ry; —(Rx)a-S—(Ry)b-O—(Rw)c-, wherein a, b, Rx and Ry are as defined herein, c is 0 or 1, and Rw is as defined for Rx and Ry, and wherein optionally, Ry and Rw form together a heteroalicyclic ring that comprises said 0 and optionally an additional heteroatom (e.g., —$NR_5$—, wherein $R_5$ is as defined for $R_4$). Each of the above exemplary linking moieties can be attached to B in any order, and is preferably attached to B via one attachment point. In some of these embodiments, B is a heteroaryl. Alternatively, B is aryl.

In some of any of the embodiments of compounds of Formula IV, L is or comprises a heterocylic moiety, which can be a heteroalicyclic or a heteroaryl moiety, and in which the heteroatom can form a part of the hydrocarbon chain or of a substituent thereof.

Additional exemplary L linking moieties according to some embodiments of compounds of Formula IV include a moiety such as:

(Rx)a-N-N=(Ry)b-N-(Rw)c=N—N—, wherein Rx, Ry, Rw, a, b and c are as defined herein.

According to some of any of the embodiments of compounds of Formula IV, n is 2; each of $R_1$ is hydroxy; B is aryl; m is 1; $R_2$ is alkoxy; and L is an unsaturated hydrocarbon chain substituted by one or more oxo (═O) groups as described herein in any of the respective embodiments.

According to some of any of the embodiments of compounds of Formula IV, the compound is SPI-21.

According to some of any of the embodiments of compounds of Formula IV, the compound is SPI-21, SPI-86, SPI-74, SPI-29, SPI-68, SPI-31, SPI-18, SPI-85, SPI-17, SPI-157, SPI-57, SPI-46, SPI-42, SPI-95, SPI-06 and/or SPI-16, as these compounds are depicted in FIG. 1C.

According to some of the embodiments of compounds of Formula IV, the compound is a structural analog of SPI-31 or of SPI-85, and is collectively represented by Formula Ia.

According to some of any of the embodiments of compounds of Formula IV, the compound has Formula I as described hereinafter in any of the respective embodiments and any combination thereof.

According to some of any of the embodiments of compounds of Formula IV, the compound has Formula V as described hereinafter in any of the respective embodiments and any combination thereof.

According to some of any of the embodiments of compounds of Formula IV, the compound has Formula VI as described hereinafter in any of the respective embodiments and any combination thereof.

Herein throughout, and according to any of the respective embodiments, compounds represented by Formula VI include compounds collectively represented by Formula VI below:

Formula VI

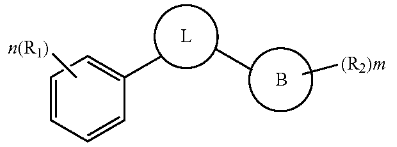

wherein:

n and m are each independently an integer of from 0 to 4 (0, 1, 2, 3 or 4);

$R_1$, and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, carboxylate, thiocarboxylate, cyano and haloalkyl;

B is a cyclic moiety selected from aryl, heteroaryl and heteroalicyclic; and

L is a linking moiety, comprising from 2 to 20, or from 2 to 16, or from 2 to 12 atoms in length, and comprising a saturated or unsaturated, substituted or unsubstituted hydrocarbon chain, optionally interrupted by one or more of S, —S(═O)—, —S(═O)$_2$, ═N— and —NR$_4$.

According to some of any of the embodiments described herein for Formula VI, n, m, $R_1$, $R_2$ and B are as described herein for any of the respective embodiments of Formula IV or Formula I.

According to some of any of the embodiments described herein for Formula VI, the L linking moiety is as described herein for compounds of Formula IV, when a hydrocarbon is an unsaturated hydrocarbon.

According to some of any of the embodiments described herein for Formula VI, the L linking moiety comprises a saturated hydrocarbon chain, and the saturated hydrocarbon is substituted by one or more ═X$_7$ groups, wherein $X_7$ is O, S, NR$_4$ or CR$_5$R$_6$, as described herein in respective embodiments of compounds of Formula IV.

According to some of any of the embodiments described herein for Formula VI, the L linking moiety comprises a saturated hydrocarbon chain, and the saturated hydrocarbon is interrupted by one or more of S, —S(═O)—, —S(═O)$_2$, —N═, and —NR$_4$.

According to some of any of the embodiments described herein for Formula VI, the L linking moiety comprises a hydrocarbon chain interrupted as described herein, yet the hydrocarbon is not interrupted by both —S— and —O—.

According to some of any of the embodiments described herein for Formula VI, the compound is SPI-21, SPI-86, SPI-74, SPI-29, SPI-68, SPI-31, SPI-18, SPI-17, SPI-157, SPI-57, SPI-46, SPI-42, SPI-95, SPI-06 and/or SPI-16, as these compounds are depicted in FIG. 1C.

According to some of any of the embodiments described herein for Formula VI, the compound is SPI-21, SPI-86, SPI-74, SPI-29, SPI-68, SPI-31, SPI-18, SPI-17, SPI-157, SPI-57, SPI-46, SPI-42, SPI-95, and/or SPI-16, as these compounds are depicted in FIG. 1C.

According to some of any of the embodiments described herein for Formula VI, n and m are each independently an integer of from 0 to 4; $R_1$ and $R_2$ are each independently a substituent selected from alkyl, cycloalkyl, aryl, heteroaryl, heteroalicyclic, hydroxy, thiol, alkoxy, thioalkoxy, aryloxy, thioalryloxy, halo, alkyl, amine, amide, carboxylate, nitro and thiocarboxylate; B is a cyclic moiety selected from aryl, heteroaryl and heteroalicyclic; and L is a linking moiety as described herein in any of the respective embodiments.

According to some of any of the embodiments described herein for Formula VI, n is 1 or 2.

According to some of any of the embodiments described herein for Formula VI, $R_1$ is selected from hydroxy, alkoxy, thiohydroxy, thioalkoxy, aryloxy, halo and amine.

According to some of any of the embodiments described herein for Formula VI, $R_1$ is an electron donating group as described herein, and in some of these embodiments, $R_1$ is at the ortho and/or para positions of the phenyl. According to some of any of the embodiments described herein for Formula VI, $R_1$ is an electron withdrawing group as described herein, and in some of these embodiments, $R_1$ is at a meta position of the phenyl.

According to some of any of the embodiments described herein for Formula VI, B is aryl.

According to some of any of the embodiments described herein for Formula VI, m is 1.

According to some of any of the embodiments described herein for Formula VI, B is aryl and m is 1.

According to some of any of the embodiments described herein for Formula VI, $R_2$ is hydroxy and/or alkoxy.

According to some of any of the embodiments described herein for Formula VI, B is aryl, and $R_2$ is hydroxy and/or alkoxy. In some of these embodiments, m is 1.

According to some of any of the embodiments described herein for Formula VI, L is or comprises an unsaturated hydrocarbon chain substituted by one or more oxo (═O) groups, as described herein in any of the respective embodiments.

According to some of any of the embodiments described herein for Formula VI, n is 2; each of $R_1$ is hydroxy; B is aryl; m is 1; $R_2$ is alkoxy; and L is an unsaturated hydrocarbon chain substituted by one or more oxo groups.

According to some of any of the embodiments described herein for Formula VI, a compound of Formula VI is SPI-21 (see, FIG. 1C).

According to some of any of the embodiments described herein for Formula VI, B is heteroaryl.

According to some of any of the embodiments described herein for Formula VI, m is 0.

According to some of any of the embodiments described herein for Formula VI, B is heteroaryl which is unsubstituted, such that m is 0.

According to some of these embodiments, L is a saturated hydrocarbon.

According to some of these embodiments, the hydrocarbon is substituted by an oxo group and/or is interrupted by a heteroatom as described herein. According to some of these embodiments, the hydrocarbon is substituted by an oxo group and is interrupted by S.

According to some of these embodiments, the hydrocarbon is substituted, and in some of these embodiments, the hydrocarbon is substituted by a cyclic group, for example, cycloalkyl, heteroalicyclic or heteroaryl. In some embodiments, the hydrocarbon is substituted by a heteroaryl.

According to some of any of the embodiments described herein for Formula VI, n is 1 and $R_1$ is amine.

According to some of any of the embodiments described herein for Formula VI, n is 1; $R_1$ is amine; B is a heteroaryl, m is 0 and L is a or comprises a saturated hydrocarbon interrupted by a heteroatom, as described herein.

According to some of any of the embodiments described herein for Formula VI, n is 1; $R_1$ is amine; B is a heteroaryl, m is 0 and L is a or comprises a saturated hydrocarbon interrupted by —S—.

According to some of any of the embodiments described herein for Formula VI, n is 1; $R_1$ is amine; B is a heteroaryl, m is 0 and L is a or comprises a saturated hydrocarbon substituted by an oxo group.

According to some of any of the embodiments described herein for Formula VI, n is 1; $R_1$ is amine; B is a heteroaryl, m is 0 and L is a or comprises a saturated hydrocarbon interrupted by —S— and substituted by an oxo group.

According to some of any of the embodiments described herein for Formula VI, the compound is SPI-18 (see, FIG. 1C).

According to some embodiments of the present invention, compounds of Formula VI as described herein are capable of down-regulating transcription of pro-inflammatory genes under TNFα induced conditions.

According to some embodiments of the present invention, a compound of Formula VI is usable for, or is for use in, treating an inflammatory disease in a subject in need thereof, as described herein in any of the respective embodiments.

Herein throughout, and according to any of the respective embodiments, compounds represented by Formula V include compounds collectively represented by Formula V below:

Formula V

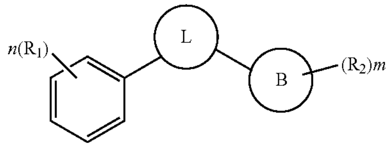

wherein:

n and m are each independently an integer of from 0 to 4;

$R_1$, and $R_2$ are each independently a substituent selected from alkyl, cycloalkyl, aryl, heteroaryl, heteroalicyclic, hydroxy, thiol, alkoxy, thioalkoxy, aryloxy, thioalryloxy, halo, alkyl, amine, amide, carboxylate, thiocarboxylate, cyano and haloalkyl;

B is a cyclic moiety selected from aryl, heteroaryl and heteroalicyclic;

L is a linking moiety, comprising from 2 to 12 atoms in length, and comprising a saturated or unsaturated, substituted or unsubstituted hydrocarbon chain, optionally interrupted by one or more of O, S, —S(═O)—, —S(═O)$_2$—, —N═ and —NR$_4$—, as described herein in any of the respective embodiments of compounds of Formula IV or VI.

In some of any of the embodiments described herein for compounds of Formula V, the linking moiety L is or comprises an unsaturated hydrocarbon, which can be substituted or unsubstituted, preferably substituted, as described herein for compounds of Formula IV or VI.

In some of any of the embodiments described herein for compounds of Formula V, the linking moiety L is or comprises a saturated hydrocarbon, and in these embodiments, $R_1$ is not amine or alkyl. In some of these embodiments, $R_1$ is hydroxy, alkoxy, aryloxy, and/or halo, as described herein in any of the respective embodiments of Formula IV, VI and I.

In some of any of the embodiments described herein for compounds of Formula V, n and m are each independently an integer of from 0 to 4; $R_1$ and $R_2$ are each independently a substituent selected from alkyl, cycloalkyl, aryl, heteroaryl, heteroalicyclic, hydroxy, thiol, alkoxy, thioalkoxy, aryloxy, thioalryloxy, halo, alkyl, amine, amide, carboxylate, nitro and thiocarboxylate; B is a cyclic moiety selected from aryl, heteroaryl and heteroalicyclic; and L is a linking moiety, comprising from 2 to 12 atoms in length, and comprising an unsaturated, substituted hydrocarbon chain, optionally interrupted by one or more of O, S, —S(═O)—, —S(═O)$_2$—, —N═ and —NR$_4$—.

In some of any of the embodiments described herein for compounds of Formula V, n is 1 or 2.

In some of any of the embodiments described herein for compounds of Formula V, B is aryl.

In some of any of the embodiments described herein for compounds of Formula V, m is 1.

In some of any of the embodiments described herein for compounds of Formula V, B is aryl and m is 1.

In some of any of the embodiments described herein for compounds of Formula V, $R_2$ is hydroxy and/or alkoxy.

In some of any of the embodiments described herein for compounds of Formula V, L is or comprises an unsaturated hydrocarbon chain substituted by one or more oxo (═O) groups, as described herein in any of the respective embodiments.

In some of any of the embodiments described herein for compounds of Formula V, n is 2; each of $R_1$ is hydroxy; B is aryl; m is 1; $R_2$ is alkoxy; and L is an unsaturated hydrocarbon chain substituted by one or more oxo groups.

In some of any of the embodiments described herein for compounds of Formula V, the compound is SPI-21 (see, FIG. 1C).

In some of any of the embodiments described herein for compounds of Formula V, the compound is SPI-21, SPI-86, SPI-74, SPI-29, SPI-68, SPI-17, SPI-157, SPI-57, SPI-46, SPI-42, SPI-95, SPI-06 and/or SPI-16, as these compounds are depicted in FIG. 1C.

In some of any of the embodiments described herein for compounds of Formula V, the compound is SPI-21, SPI-86, SPI-74, SPI-29, SPI-68, SPI-17, SPI-157, SPI-57, SPI-46, SPI-42, SPI-95, and/or SPI-16, as these compounds are depicted in FIG. 1C.

According to some embodiments of the present invention, compounds of Formula V as described herein are capable of up-regulation of pro-inflammatory genes under basal conditions.

According to some embodiments of the present invention, a compound of Formula V is usable for, or is for use in, treating an infectious disease or cancer in a subject in need thereof, as described herein in any of the respective embodiments.

Herein throughout, and according to any of the respective embodiments, compounds represented by Formula I include compounds collectively represented by Formula I below:

Formula I

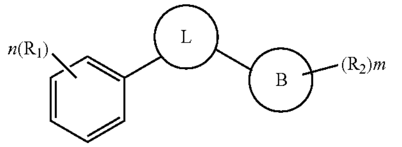

wherein:

n and m are each independently an integer of from 0 to 4;

$R_1$ and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, carboxylate and thiocarboxylate;

B is a cyclic moiety selected from aryl, heteroaryl and heteroalicyclic;

L is a linking moiety being from 2 to 20, or from 2 to 12 atoms in length, and comprising a saturated or unsaturated, substituted or unsubstituted hydrocarbon chain, optionally interrupted by one or more of O, S, —S(═O)—, —S(═O)$_2$ and —NR$_4$—, wherein $R_4$ is hydrogen, alkyl, cycloalkyl or aryl.

In some of any of the embodiments of Formula I, L has a chain of 2 to 10, or 2 to 8, atoms (typically carbon atoms and optionally heteroatoms) in length.

According to some of any of the embodiments related to Formula I, n, which represents the number of substituents on the phenyl shown in Formula I, is positive, that is, is 1, 2, 3, or 4, and is some embodiments, n is 1 or 2. The substituent(s) can be as defined for $R_1$.

According to some of any of the embodiments related to Formula I, $R_1$ is selected from hydroxy, alkoxy, thiohydroxy, thioalkoxy, aryloxy, and halo.

According to some of any of the embodiments related to Formula I, n is 1 or 2, and $R_1$ is an electron donating group (e.g., alkyl, hydroxy, alkoxy, aryloxy, amine, etc.). In some of these embodiments, $R_1$ is at the ortho and/or para positions of the phenyl.

According to some of any of the embodiments related to Formula I, n is 1 or 2, and $R_1$ is an electron withdrawing group (e.g., halo, for example, fluoro or chloro). In some of these embodiments, $R_1$ is at a meta position of the phenyl.

According to some of any of the embodiments related to Formula I, B is aryl, e.g., phenyl.

According to some of these embodiments, the aryl (e.g., phenyl) is substituted such that m is 1, 2, 3 or 4. In some of these embodiments, m is 1 or 2.

The substituent(s) on the aryl ring can be as defined herein for $R_2$.

In some embodiments, one or more, or each, of $R_2$ is hydroxy, alkoxy, carboxylate or halo.

In some embodiments, one or more, or each, of $R_2$ is hydroxy, alkoxy, or carboxylate.

In some of any of the embodiments of Formula I in which B is aryl (e.g., phenyl), L is or comprises an unsaturated hydrocarbon chain substituted by one or more oxo (═O) groups.

For example, L is or comprises one or more moieties represented by Formula A:

—C(═O)—CR'═CR"— Formula A wherein R' and R" can each independently be hydrogen, alkyl, cycloalkyl, alkoxy, hydroxy, thiol, thioalkoxy and any other substituent as described herein, or, R' and R" can for a 5-6-, or 7-membered ring, optionally together with 1 or more atoms of B.

In some of these embodiments, R' and R" are each independently hydrogen and/or alkyl, and in some embodiments, both R' and R" are hydrogen.

In some of these embodiments, the linking moiety L can further comprise other moieties linked to the moiety presented in Formula A, including, for example, saturated or unsaturated hydrocarbon of 1 to 10 carbon atoms, optionally interrupted by one or more heteroatoms, or a heteroatom per se, or otherwise a biradical alkyl, alkenyl, alkynyl, aryl, heteroalicyclic, heteroaryl, ether, thioether, and like biradical groups of any of the substituents described herein.

A linking moiety which comprises an unsaturated hydrocarbon chain substituted by one or more oxo (═O) groups can alternatively include an unsaturated hydrocarbon (e.g., a hydrocarbon that comprises one or more of alkenyl, alkynyl and aryl groups) which further comprises one or more heteroatoms that is substituted by oxo groups. An example includes an unsaturated hydrocarbon that is interrupted or terminates by a group such as —S(═O) and/or S(═O)$_2$.

The L linking moiety can be attached to B (e.g., phenyl) via one or two attachment points, that is, be attached to one or two carbon atoms of the aryl ring (e.g., the phenyl).

Exemplary L linking moieties include —C(═O)—CH═CH—; —CH═CH—C(═O)—CH$_2$—C(═O)—CH═CH—; —C(═O)—C(CH$_2$S—)═CH— (the latter being connected to B via two attachment points).

In some of any of the embodiments described herein n is 1 or 2, each of $R_1$ is an electron donating moiety such as alkyl, hydroxy, alkoxy or aryloxy, preferably at the ortho and/or para positions, B is aryl, and L is a linking moiety that comprises a moiety of Formula A as described herein. In some of these embodiments, m and $R_2$ are as defined herein. Exemplary such compounds include those referred to herein as SPI-21, SPI-29 and SPI-68 (see, FIG. 1C).

In some of any of the embodiments described herein n is 1 or 2, each of $R_1$ is an electron donating moiety such as alkyl, hydroxy, alkoxy or aryloxy, preferably at the ortho and/or para positions, or an electron withdrawing group preferably at the meta position, and L is a linking moiety that comprises an unsaturated hydrocarbon chain substituted by one or more oxo (═O) groups. In some of these embodiments, B, m and $R_2$ are as defined herein in any of the respective embodiments. Exemplary such compounds include the compounds referred to herein as SPI-21, SPI-29, SP-31, SPI-68 and SPI-18 (see, FIG. 1C).

In exemplary embodiments of Formula I, n is 2; each of $R_1$ is hydroxy; B is aryl; m is 1; $R_2$ is alkoxy; and L is an unsaturated hydrocarbon chain substituted by one or more oxo (═O) groups, e.g., is or comprises a moiety of Formula A as described herein. In exemplary embodiments, the compound of Formula I is SPI-21 (see, FIG. 1C).

In some of any of the embodiments described herein for Formula I, B is a heteroaryl or a heteroalicyclic, as defined herein. The heteroaryl or heteroalicyclic preferably includes 1 or 2 rings (e.g., 2 fused rings), and one or more heteroatoms such as nitrogen, oxygen and/or sulfur. The heteroaryl or heteroalicyclic can be substituted (e.g., m is 1, 2, 3 or 4, preferably 1 or 2), or unsubstituted (m is 0). The substituent ($R_2$) can be any of the substituents described herein. Non-limiting examples of $R_2$ include halo, amine, nitro and oxo.

In some of the embodiments of Formula I wherein B is a heteroaryl or heteroalicyclic, n is 1 or 2, and $R_1$ is an electron donating group preferably at the ortho and/or para positions, as described hereinabove. In exemplary embodiments, each $R_1$ is independently alkyl, halo, alkoxy, thioalkoxy or amine.

In some of any of the embodiments of Formula I wherein B is a heteroaryl or heteroalicyclic, L is a saturated or unsaturated hydrocarbon interrupted by one or more heteroatoms such as O, S, and/or $NR_4$. In some of these embodiments, the heteroatom is S or —$NR_4$—. The hydrocarbon can be substituted or unsubstituted, and, when substituted, the one or more substituents can include an oxo substituent or other substituents.

Exemplary linking moieties according to these embodiments include or consist of, but are not limited to, one or more of the following moieties: —(Rx)a-S—(Ry)b, wherein Rx and Ry are each independently a substituted or unsubstituted alkylene of 1 to 6 carbon atoms in length and a and b are each independently 0 or 1, provided that one of and b is 1; —(Rx)a-$NR_4$—(Ry)b, wherein a, b, Rx and Ry are as defined herein; —(Rx)a-S—(Ry)b-$NR_4$—(Rw)c-, wherein a, b, Rx and Ry are as defined herein, c is 0 or 1, and Rw is as defined for Rx and Ry; —(Rx)a-S(═O)d-(Ry)b-$NR_4$—(Rw)c-, wherein a, b, c, Rx, Ry and Rw are as defined herein, and d is 1 or 2; —(Rx)a-S—(Ry)b-C(═O)-(Rw)c-, wherein a, b, Rx and Ry are as defined herein, c is 0 or 1, and Rw is as defined for Rx and Ry; —(Rx)a-S—(Ry)b-O—(Rw)c-, wherein a, b, Rx and Ry are as defined herein, c is 0 or 1, and Rw is as defined for Rx and Ry, and wherein optionally, Ry and Rw form together a heteroalicyclic ring that comprises said O and optionally an additional heteroatom (e.g., —$NR_5$—, wherein $R_5$ is as defined for $R_4$. Each of the above exemplary linking moieties can be attached to B in any order, and is preferably attached to B via one attachment point.

Exemplary compounds according to these embodiments include SPI-86, SPI-31, SPI-18, SPI-74 and SPI-85 (see, FIG. 1C).

In some of any of the embodiments of Formula I wherein B is a heteroaryl or heteroalicyclic, L is a hydrocarbon interrupted by one or two —$NR_4$—, being optionally substituted and/or unsaturated.

In some of any of the embodiments of Formula I wherein B is a heteroaryl or heteroalicyclic, L is a saturated unsubstituted hydrocarbon interrupted by —$NR_4$—, and m is 1 (e.g., amine). An exemplary such compound is SPI-74 (see, FIG. 1C) In some of any of the embodiments of Formula I wherein B is a heteroaryl or heteroalicyclic, m is 0.

In some of any of the embodiments of Formula I wherein B is a heteroaryl or heteroalicyclic, and L is a substituted, saturated or unsaturated hydrocarbon which comprises or is interrupted at least by S or $S(═O)_2$. In some of these embodiments, m is 0. Exemplary such compounds are SPI-86, SPI-31, SPI-18 and SPI-85 (see, FIG. 1C).

In exemplary embodiments, n is 1 or 2; $R_1$ is an amine at the ortho and/or para positions; B is a heteroalicyclic ring; m is 0; and L is a substituted, saturated hydrocarbon interrupted by 0 and S. An exemplary such compound is SPI-85 (see, FIG. 1C).

Herein throughout, whenever a linking moiety or a hydrocarbon chain is described as being "interrupted by" one or more heteroatoms, it is to be understood that the one or more heteroatom can each independently be either between two carbon atoms of the linking moiety or be attached to one carbon atom and to another heteroatom or to the phenyl, A or B moieties to which the linking moiety is attached. The phrase "interrupted by" is used herein interchangeably with the term "comprises" or "comprising", and means that the linking moiety comprises, in addition to a hydrocarbon chain, one or more heteroatoms or heteroatom-containing moiety, which are linked to two carbon atoms of the hydrocarbon chain or to one carbon atom, as described hereinabove.

According to some embodiments of the present invention, compounds of Formula I as described herein are capable of down-regulating expression of a mutant huntingtin gene.

According to some embodiments of the present invention, compounds of Formula I as described herein is usable for, or is for use in, treating a nucleotide repeat disorder in a subject in need thereof, as described herein in any of the respective embodiments.

According to some of any of the embodiments related to compounds of Formula I or II, the compound is selected from SPI-21, SPI-29, SPI-86, SPI-74, SPI-68, SPI-31, SPI-18, SPI-85 and SPI-09, as shown in FIG. 1C, and the respective compounds presented in Tables 6, 7 and 8 as structural analogs of SPI-09, SPI-85 and SPI-31, respectively.

According to some of the embodiments related to compounds of Formula I, the compounds are collectively represented by Formula Ia:

Formula Ia

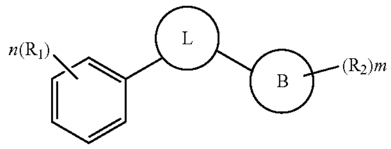

wherein:

n and m are each independently an integer of from 0 to 4;

$R_1$ and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate and thiocarboxylate, as described herein in any of the respective embodiments of Formula I;

B is a cyclic moiety selected from aryl, heteroaryl and heteroalicyclic, as described herein in any of the respective embodiments of Formula I;

L is a linking moiety, comprising from 2 to 12 atoms in length, and comprising a saturated or unsaturated, substituted or unsubstituted hydrocarbon chain, interrupted by or comprising one or more of S and —$S(═O)_2$, as described herein in any of the respective embodiments.

In some of any of the embodiments described herein for compounds of Formula Ia, $R_1$ is selected from hydroxy, alkoxy, thiohydroxy, thioalkoxy, aryloxy, amine and halo.

In some of any of the embodiments described herein for compounds of Formula Ia, B is a heterocyclic moiety, for example, a heteroaryl or a heteroalicyclic.

In exemplary embodiments of Formula Ia, B is a heteroaryl.

In exemplary embodiments of Formula Ia, B is a heteroaryl which comprises one or more nitrogen heteroatoms.

In exemplary embodiments of Formula Ia, B is a thiazole, for example, a benzothiazole.

In exemplary embodiments of Formula Ia, B is an oxazole, for example, a benzoxazole.

In exemplary embodiments of Formula Ia, B is a terazole.

In exemplary embodiments, B is a pyridazine, for example, a pyridazinone.

In some of any of the embodiments described herein for Formula Ia, L is a substituted, saturated hydrocarbon interrupted by at least one S, and optionally further interrupted by 0 and/or $NR_4$ and/or C═O.

Exemplary linking moieties according to these embodiments include or consist of, but are not limited to, one or more of the following moieties: —(Rx)a-S—(Ry)b, wherein Rx and Ry are each independently a substituted or unsubstituted alkylene of 1 to 6 carbon atoms in length and a and b are each independently 0 or 1, provided that one of a and b is 1; —(Rx)a-S—(Ry)b-$NR_4$—(Rw)c-, wherein a, b, Rx and Ry are as defined herein, c is 0 or 1, and Rw is as defined for Rx and Ry; —(Rx)a-S—(Ry)b-C(═O)-(Rw)c-, wherein a, b, Rx and Ry are as defined herein, c is 0 or 1, and Rw is as defined for Rx and Ry; —(Rx)a-S—(Ry)b-O—(Rw)c-, wherein a, b, Rx and Ry are as defined herein, c is 0 or 1, and Rw is as defined for Rx and Ry; —(Rx)a-S—(Ry)b-S—(Rw)c-, wherein a, b, Rx and Ry are as defined herein, c is 0 or 1, and Rw is as defined for Rx and Ry, and wherein optionally, for each of the above, two or Rx, Ry and Rw form together a heteroalicyclic ring that comprises said $NR_4$, said C(═O), said S or said 0 and optionally an additional heteroatom (e.g., —$NR_5$—, wherein $R_5$ is as defined for $R_4$, or —N═). Each of the above exemplary linking moieties can be attached to B in any order, and is preferably attached to B via one attachment point.

In some of any of the embodiments described herein for Formula Ia, L is a substituted, saturated hydrocarbon interrupted by at least one S, and optionally further interrupted by O.

In exemplary embodiments, L is —(Rx)a-S—(Ry)b-O—(Rw)c-, or —(Rx)a-S—(Ry)b-S—(Rw)c-, wherein a is 0, b and c is 1, Ry and Rw are each a substituted alkylene, and from together with 0 or S a heteroalicyclic ring. In some of these embodiments, the heteroalicyclic ring comprises —$NR_5$—, wherein $R_5$ is as defined for $R_4$ or —N═. In some of these embodiments, the S heteroatom is linked to B and Rw is linked to A.

In exemplary embodiments, B is thiazole, oxazole, or tetrazole and L is —(Rx)a-S—(Ry)b-O—(Rw)c-, or —(Rx) a-S—(Ry)b-S—(Rw)c-, wherein a is 0, b and c is 1, Ry and Rw are each a substituted alkylene, and from together with 0 or S a heteroalicyclic ring, as described herein in any of the respective embodiments. In some of these embodiments, the heteroalicyclic ring comprises —$NR_5$—, wherein $R_5$ is as defined for $R_4$ or —N═. Exemplary such compounds are referred to herein as SPI-85, SPI-8690, SPI-0324, and SPI-8708.

In some of these embodiments, m and n are each 0.

In some other embodiments, n is 1 and $R_1$ is an electron-donating group as described herein, for example, amine, thioalkoxy or alkoxy. In some of these embodiments, m is 0.

In some other embodiments, m is 1 and $R_2$ is, for example, halo (e.g., chloro). In some of these embodiments, n is 0. In some of these embodiments, N is 1 and $R_1$ is, for example, alkoxy.

In some of any of the embodiments described herein for Formula Ia, L is a substituted, unsaturated hydrocarbon interrupted by at least one $SO_2$, and optionally further interrupted by 0 and/or $NR_4$.

Exemplary linking moieties according to these embodiments include or consist of, but are not limited to, one or more of the following moieties: —(Rx)a-(Ry)b=(Rw)c-(Rq)d-S(═O)$_2$—(Rz)e-, —(Rx)a-(Ry)b=(Rw)c-(Rq)d-S(═O)$_2$—(Rz)e-($NR_4$)—, —(Rx)a-(Ry)b=(Rw)c-(Rq)d-S(═O)$_2$—(Rz)e-O-, —(Rx)a-O—(Ry)b=(Rw)c-(Rq)d-S(═O)$_2$—(Rz)e-, —(Rx)a-$NR_4$—(Ry)b=(Rw)c-(Rq)d-S(═O)$_2$—(Rz)e-, and similar linking moieties, wherein optionally, for each of the above, two or Rx, Ry, Rq, Rz and Rw may form together a cyclic ring, which, depending on the atoms that form it, can be saturated or unsaturated (e.g., aromatic) all-carbon ring, or saturated or unsaturated heterocyclic ring. For example, in any of the above exemplary linking moieties, Ry and Rw can form an aromatic ring (e.g., phenyl). Each of the above exemplary linking moieties can be attached to B in any order, and is preferably attached to B via one attachment point.

In exemplary embodiments, the hydrocarbon chain comprises or consists of an aromatic ring (e.g., phenyl), as described herein.

In exemplary embodiments, L comprises or consists of an aromatic ring, $SO_2$ and optionally $NR_4$, as defined herein.

In exemplary embodiments, L is —(Rx)a-(Ry)b=(Rw)c-(Rq)d-S(═O)$_2$—(Rz)e-($NR_4$)—, wherein a is 0, Ry and Rw form a phenyl, and e is 0, such that L is an unsaturated hydrocarbon which comprises and aryl and $SO_2$. In some of these embodiments, Ry is linked to B and $NR_4$ is linked to A.

In exemplary embodiments of Formula Ia, B is a pyridazin-3-one, optionally substituted, and L is —(Rx)a-(Ry)b=(Rw)c-(Rq)d-S(═O)$_2$—(Rz)e-($NR_4$)—, wherein a is 0, Ry and Rw form a phenyl, and e is 0, as described herein in any of the respective embodiments.

Exemplary such compounds include SPI-31, SPI-5726, SPI-0035, SPI-1477, SPI-3440 and SPI-4516.

In some of these embodiments, n is 1 or 2 and $R_1$ is as described herein for Formula I.

In some of these embodiments, m is 2, and each $R_2$ is halo (e.g., chloro). In other embodiments, m is 0.

According to an aspect of some embodiments of the present invention, there is provided a compound represented by Formula VII as described herein, which is usable for, or is for use in, treating a nucleotide repeat disorder in a subject in need thereof, as described herein in any of the respective embodiments.

According to an aspect of some embodiments of the present invention, there is provided a method of treating a nucleotide repeat disorder in a subject in need thereof, as described herein in any of the respective embodiments, which comprises administering to a subject in need thereof, as described herein in any of the respective embodiments, a therapeutically effective amount of a compound represented by Formula VII, as described herein in any of the respective embodiments.

Herein throughout, and according to any of the respective embodiments, compounds represented by Formula VII include compounds collectively represented by Formula VII below:

Formula VII

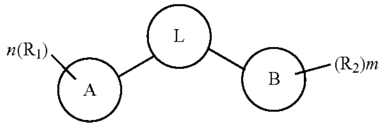

wherein:

n and m are each independently an integer of from 0 to 4;

$R_1$ and $R_2$ are each independently a substituent selected from alkyl, cycloalkyl, aryl, heteroaryl, heteroalicyclic, hydroxy, hydroxyalkyl, thiol, alkoxy, thioalkoxy, aryloxy, thioaryloxy, halo, alkyl, amine, amide, nitro, carboxylate and thiocarboxylate;

A and B are each independently a cyclic moiety selected from aryl, heteroaryl and heteroalicyclic;

L is a linking moiety, comprising from 2 to 12 atoms in length, and comprising a saturated or unsaturated, substituted or unsubstituted hydrocarbon chain, interrupted by or comprising one or more of O, S and —S(═O)$_2$, for use in treating a nucleotide repeat disorder in a subject in need thereof.

In some of any of the embodiments of Formula VII, A is aryl, L is a linking moiety, comprising from 2 to 12 atoms in length, and comprising a saturated or unsaturated, substituted or unsubstituted hydrocarbon chain, interrupted by or comprising one or more of S and —S(═O)$_2$, and the compound can be represented by Formula Ia as described herein.

In some of any of the embodiments of Formula VII, A is a heteroaryl, B is a cyclic moiety as described herein for, for example, Formula I, and $R_1$, $R_2$, m, n and L are as described herein for Formula I or Ia, in any of the respective embodiments and any combination thereof.

In some of any of the embodiments of Formula VII, A is aryl, and the compound can be represented by respective embodiments and any combination thereof as described herein for Formula I.

In some of any of the embodiments of Formula VII, L is an unsaturated, substituted hydrocarbon chain interrupted by 0 or S.

Exemplary such linking moieties include, but are not limited to, linking moieties that comprise, or consist of one or more unsaturated heterocylic ring(s) in which the heteroatom form a part of the hydrocarbon chain, for example, furan or thiophene, wherein the carbon atoms adjacent to the heteroatom are linked to A and B, or to other portions of the linking moiety.

In some of any of the embodiment of Formula VII, at least one of n and m is other than 0 and at least one of $R_1$ and $R_2$ if present is hydroxy, thiol, hydroxyalkyl, thioalkyl, alkoxy or thioalkoxy.

In some of any of the embodiment of Formula VII, at least one of n and m is other than 0 and at least one of $R_1$ and $R_2$ if present is hydroxyalkyl.

In some of any of the embodiments of Formula VII, L is an unsaturated, substituted hydrocarbon chain interrupted by O or S, as described herein in any of the respective embodiments, and A and B are each a heteroaryl (e.g., furan or thiophene). In some of any of the embodiment of Formula VII, at least one of n and m is other than 0 and at least one of $R_1$ and $R_2$ if present is hydroxyalkyl.

Exemplary such compounds include SPI-48 and SPI-8108.

According to an aspect of some embodiments of the present invention, there is provided a compound selected from the compounds presented in Tables 6, 7, 8 and 9, which is usable for, or is for use in, treating a nucleotide repeat disorder in a subject in need thereof, as described herein in any of the respective embodiments.

According to an aspect of some embodiments of the present invention, there is provided a method of treating a nucleotide repeat disorder in a subject in need thereof, as described herein in any of the respective embodiments, which comprises administering to a subject in need thereof, as described herein in any of the respective embodiments, a therapeutically effective amount of a compound selected from the compounds presented in Tables 6, 7, 8 and 9.

According to some embodiments of these aspects, the compound is SPI-85.

According to some embodiments of these aspects, the compound is SPI-0324.

According to some embodiments of these aspects, the compound is SPI-31.

According to some embodiments of these aspects, the compound is SPI-4516K.

According to some embodiments of these aspects, the compound is SPI-1477.

According to some embodiments of these aspects, the compound is SPI-48.

According to some embodiments of these aspects, the compound is SPI-8108.

According to an aspect of some embodiments of the present invention there is provided the compound denoted herein as SPI-4516K or SPI-4516 (see, FIG. 12A).

The compounds represented by Formulas I-VII defined herein inhibit binding of Spt5 to Pol II or change the conformation of a Spt5-Pol II complex.

As used herein the term "inhibit binding" refers to the ability to decrease binding of Spt5 to Pol II. According to specific embodiments, the decrease is a significant decrease. According to specific embodiments, the decrease is of at least 2% in the gene in the presence of the compound as compared to same in the absence of the compound. According to a specific embodiment, the decrease is in at least 5% at least 10%, 20%, 30%, 40% or even higher say, 50%, 60%, 70%, 80%, 90%, 99% or even 100%. According to specific embodiments the decrease is at least 1.5 fold, at least 2 fold, at least 3 fold, at least 5 fold, at least 10 fold, or at least 20 fold as compared to same in the absence of the compound.

Determining binding of Spt5 to Pol II may be effected by any method known in the art including, but not limited to, immunopercipitation, BiaCore, HPLC or flow cytometry. An exemplary method of determining binding of Spt5 to Pol II is based on a split-*Renilla* luciferase (RL) complementation assay that is described e.g. in Ashkenazi et al., 2016; Ashkenazi et al., 2017, the contents of which are fully incorporated herein by reference.

Determining conformation may be effected by any method known in the art including, but not limited to fluorescence intensity measurements, Fluorescence resonance energy transfer (FRET), Limited proteolysis followed by analysis on SDS-PAGE gels, immunochemical analysis using Conformation-sensitive antibodies, chemical foot printing, chemical crosslinking, spectroscopy or microscopy.

According to specific embodiments, the compound directly binds Spt5 or Pol II.

According to specific embodiments, the compound binds Spt5.

According to specific embodiments, the compound binds an NGN domain and/or a KOW domain of Spt5.

According to specific embodiments, the compound directly binds Pol II.

According to specific embodiments, the compound binds the Rpb1 subunit of Pol II.

According to specific embodiments, the compound binds a coiled-coil (CC) domain of Rpb1.

In addition, as shown in the Examples section which follows, the present inventors have developed a novel screening method. Hence, the present teachings are directed to the identification of SPIs according to the following aspect.

According to an aspect of the present invention there is provided a method of identifying a Spt5 inhibitor, the method comprising determining binding of Spt5 to RNA Polymerase II (Pol II) in the presence of a test compound, wherein a decrease in binding of said Spt5 to said Pol II or a change in conformation of a Spt5-Pol II complex as compared to same in the absence of said test compound, indicates said test compound is a Spt5 inhibitor.

According to specific embodiments, the test agent is a small molecule.

According to specific embodiments, the method is effected in-vitro or ex-vivo.

According to specific embodiments of this aspect of the present invention, the method is a cell free method.

According to specific embodiments of this aspect of the present invention, the method is effected in intact cells.

According to specific embodiments of this aspect of the present invention, the cells are immune activated (e.g. by exposure to TNFα).

Determining binding of Spt5 to Pol II may be effected by any method known in the art including, as further described hereinabove.

Determining conformation may be effected by any method known in the art including, as further described hereinabove.

According to specific embodiments, the decrease is a significant decrease.

According to specific embodiments, a decrease of at least 2%, at least 5%, at least 10%, at least 20%, at least 30%, at least 40%, at least 50%, at least 60%, at least 70%, at least 80%, at least 90%, or at least 99% e in binding of said Spt5 to said Pol II or a change in conformation of a Spt5-Pol II complex as compared to same in the absence of said test compound, indicates said test compound is a Spt5 inhibitor.

A non-limiting example of a screening method is described in Example 1 in the Examples section which follows, which serve as an integral part of the specification of the present invention.

According to specific embodiments of this aspect of the present invention, the method further comprising testing an effect of said test agent on a biological outcome of inhibition of said Spt5.

Such biological activities include, but are not limited to, down-regulation of expression of a mutant huntingtin gene; up-regulation of expression of a GDF15 gene; inhibition of proximal promoter pausing which may be determined by e.g. up-regulation of expression of a pro-inflammatory gene under basal conditions, wherein transcription of said pro-inflammatory gene is dependent on Spt5; down-regulation expression of a pro-inflammatory gene under TNFα-induced conditions; as further disclosed in details in the Examples section which follows.

As used herein the term “about” refers to ±10% The terms “comprises”, “comprising”, “includes”, “including”, “having” and their conjugates mean “including but not limited to”.

The term “consisting of” means “including and limited to”.

The term “consisting essentially of” means that the composition, method or structure may include additional ingredients, steps and/or parts, but only if the additional ingredients, steps and/or parts do not materially alter the basic and novel characteristics of the claimed composition, method or structure.

As used herein, the singular form “a”, “an” and “the” include plural references unless the context clearly dictates otherwise. For example, the term “a compound” or “at least one compound” may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases “ranging/ranges between” a first indicate number and a second indicate number and “ranging/ranges from” a first indicate number “to” a second indicate number are used herein interchangeably and are meant to include the first and second indicated numbers and all the fractional and integral numerals therebetween.

As used herein the term “method” refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

The present embodiments encompass any enantiomers, diastereomers, prodrugs, solvates, hydrates and/or pharmaceutically acceptable salts of the compounds described herein.

As used herein, the term “enantiomer” refers to a stereoisomer of a compound that is superposable with respect to its counterpart only by a complete inversion/reflection (mirror image) of each other. Enantiomers are said to have “handedness” since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term “diastereomers”, as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereoconfiguration, namely any diastereomer.

The term “prodrug” refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the “prodrug”). Such a prodrug is hydrolyzed in vivo, to thereby provide the free compound (the parent drug). The selected ester may affect both the solubility characteristics and the hydrolysis rate of the prodrug.

The term “solvate” refers to a complex of variable stoichiometry (e.g., di-, tri-, tetra-, penta-20, hexa-, and so on), which is formed by a solute (the compound of the present invention) and a solvent, whereby the solvent does not interfere with the biological activity of the solute. Suitable solvents include, for example, ethanol, acetic acid and the like.

The term “hydrate” refers to a solvate, as defined hereinabove, where the solvent is water.

The phrase “pharmaceutically acceptable salt” refers to a charged species of the parent compound and its counter ion, which is typically used to modify the solubility characteristics of the parent compound and/or to reduce any significant irritation to an organism by the parent compound, while not abrogating the biological activity and properties of the administered compound. In the context of the present embodiments, a pharmaceutically acceptable salt can be, for example, an ammonium ion of a nitrogen-containing compound and an acid addition salt thereof, or a carboxylate ion of a carboxylate-containing compound and a counter ion such as sodium, potassium, and like.

Herein throughout, the phrase “linking moiety” or “linking group” describes a group that connects two or more moieties or groups in a compound. A linking moiety is typically derived from a bi- or tri-functional compound, and can be regarded as a bi- or tri-radical moiety, which is connected to two or three other moieties, via two or three atoms thereof, respectively.

Exemplary linking moieties include a hydrocarbon moiety or chain, optionally interrupted by one or more heteroatoms, as defined herein, and/or any of the chemical groups listed below, when defined as linking groups.

When a chemical group is referred to herein as “end group” it is to be interpreted as a substituent, which is connected to another group via one atom thereof.

Herein, the term “hydrocarbon” describes an organic moiety that includes, as its basic skeleton, a chain of carbon atoms, also referred to herein as a backbone chain, substituted mainly by hydrogen atoms. The hydrocarbon can be saturated or unsaturated, be comprised of aliphatic, alicyclic and/or aromatic moieties, and can optionally be substituted by one or more substituents (other than hydrogen).

A substituted hydrocarbon may have one or more substituents, whereby each substituent can independently be, for example, alkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, carbamate, oxo, amide, and hydrazine, and any other substituents as described herein (for example, as defined herein for $R_1$ and $R_2$).

The hydrocarbon moiety can optionally be interrupted by one or more heteroatoms, including, without limitation, one or more oxygen, nitrogen (substituted or unsubstituted, as defined herein for —NR'—) and/or sulfur atoms.

In some embodiments of any of the embodiments described herein relating to a hydrocarbon chain, the hydrocarbon can be or comprise an alkylene chain, or be comprised of alkyls, cycloalkyls, aryls, alkaryls, aralkyls, alkenes and/or alkynes, as defined herein, covalently attached to one another in any order.

An “electron-withdrawing group” refers to a chemical group which, by virtue of its greater electronegativity inductively draws electron density away from nearby groups and toward itself, leaving the less electronegative group with a partial positive charge. This partial positive charge, in turn, can stabilize a negative charge on an adjacent group thus facilitating any reaction, which involves a negative charge, either formal or in a transition state, on the adjacent group.

As used herein, the term “amine” describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term “amine” is used herein to describe a —NR'R" group in cases where the amine is an end group, as defined hereinunder, and is used herein to describe a —NR'— group in cases where the amine is a linking group or is or part of a linking moiety.

The term “alkyl” describes a saturated aliphatic hydrocarbon including straight chain and branched chain groups. Preferably, the alkyl group has 1 to 30, or 1 to 20 carbon atoms. Whenever a numerical range; e.g., “1-20”, is stated herein, it implies that the group, in this case the alkyl group, may contain 1 carbon atom, 2 carbon atoms, 3 carbon atoms, etc., up to and including 20 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, 0-thiocarbamate, urea, thiourea, N-carbamate, 0-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

Herein, a C(1-4) alkyl, substituted by a hydrophilic group, as defined herein, is included under the phrase "hydrophilic group" herein.

Alkene and Alkyne, as used herein, are an alkyl, as defined herein, which contains one or more double bond or triple bond, respectively.

The term "cycloalkyl" describes an all-carbon monocyclic ring or fused rings (i.e., rings which share an adjacent pair of carbon atoms) group where one or more of the rings does not have a completely conjugated pi-electron system. Examples include, without limitation, cyclohexane, adamantine, norbornyl, isobornyl, and the like. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

Cycloalkyls of 1-6 carbon atoms, substituted by two or more hydrophilic groups, as defined herein, is included under the phrase "hydrophilic group" herein.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system.

Representative examples are piperidine, piperazine, tetrahydrofurane, tetrahydropyrane, morpholino, oxalidine, and the like.

The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system.

Examples, without limitation, of heteroaryl groups include pyrrole, furan, thiophene, imidazole, oxazole, tetrazole, thiazole, pyrazole, pyrazine, pyrazide, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "halide" and "halo" describes fluorine, chlorine, bromine or iodine.

The term "haloalkyl" describes an alkyl group as defined above, further substituted by one or more halide.

The term "imine" describes a CR"R'═N- or —CR'═NR" end group, or a —CR'═N=linking group, as these phrases are defined herein, where R' and R" are as defined herein.

The term "sulfate" describes a —O—S(═O)$_2$—OR' end group, as this term is defined hereinabove, or an —O—S(═O)$_2$—O— linking group, as these phrases are defined hereinabove, where R' is as defined hereinabove.

The term "thiosulfate" describes a —O—S(═S)(═O)—OR' end group or a —O—S(═S)(═O)—O— linking group, as these phrases are defined hereinabove, where R' is as defined hereinabove.

The term "sulfite" describes an —O—S(═O)—O—R' end group or a —O—S(═O)—O— group linking group, as these phrases are defined hereinabove, where R' is as defined hereinabove.

The term "thiosulfite" describes a —O—S(═S)—O—R' end group or an —O—S(═S)—O— group linking group, as these phrases are defined hereinabove, where R' is as defined hereinabove.

The term "sulfinate" describes a —S(═O)—OR' end group or an —S(═O)—O— group linking group, as these phrases are defined hereinabove, where R' is as defined hereinabove.

The term "sulfoxide" or "sulfinyl" describes a —S(═O)R' end group or an —S(═O)— linking group, as these phrases are defined hereinabove, where R' is as defined hereinabove.

The term "sulfonate" describes a —S(═O)$_2$—R' end group or an —S(═O)$_2$— linking group, as these phrases are defined hereinabove, where R' is as defined herein.

The term "S-sulfonamide" describes a —S(═O)$_2$—NR'R" end group or a —S(═O)$_2$—NR'— linking group, as these phrases are defined hereinabove, with R' and R" as defined herein.

The term "N-sulfonamide" describes an R'S(═O)$_2$—NR"— end group or a —S(═O)$_2$—NR'— linking group, as these phrases are defined hereinabove, where R' and R" are as defined herein.

The term "disulfide" refers to a —S—SR' end group or a —S-S— linking group, as these phrases are defined hereinabove, where R' is as defined herein.

The term "phosphonate" describes a —P(═O)(OR')(OR") end group or a —P(═O)(OR')(O)— linking group, as these phrases are defined hereinabove, with R' and R" as defined herein.

The term "thiophosphonate" describes a —P(═S)(OR')(OR") end group or a —P(═S)(OR')(O)— linking group, as these phrases are defined hereinabove, with R' and R" as defined herein.

The term "phosphinyl" describes a —PR'R" end group or a —PR'— linking group, as these phrases are defined hereinabove, with R' and R" as defined hereinabove.

The term "phosphine oxide" describes a —P(═O)(R')(R") end group or a —P(═O)(R')— linking group, as these phrases are defined hereinabove, with R' and R" as defined herein.

The term "phosphine sulfide" describes a —P(═S)(R')(R") end group or a —P(═S)(R')— linking group, as these phrases are defined hereinabove, with R' and R" as defined herein.

The term "phosphite" describes an —O-PR'(═O)(OR") end group or an —O—PH(═O)(O)— linking group, as these phrases are defined hereinabove, with R' and R" as defined herein.

The term "carbonyl" or "carbonate" as used herein, describes a —C(═O)—R' end group or a —C(═O)— linking group, as these phrases are defined hereinabove, with R' as defined herein.

The term "thiocarbonyl" as used herein, describes a —C(═S)—R' end group or a —C(═S)— linking group, as these phrases are defined hereinabove, with R' as defined herein.

The term "oxo" as used herein, describes a (═O) group, wherein an oxygen atom is linked by a double bond to the atom (e.g., carbon atom) at the indicated position.

The term "thiooxo" as used herein, describes a (═S) group, wherein a sulfur atom is linked by a double bond to the atom (e.g., carbon atom) at the indicated position.

The term "oxime" describes a ═N—OH end group or a ═N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The "hydroxyalkyl" is also referred to herein as "alcohol", and describes an alkyl, as defined herein, substituted by a hydroxy group.

The term "cyano" describes a —C≡N group.

The term "isocyanate" describes an —N═C═O group.

The term "isothiocyanate" describes an —N═C═S group.

The term "nitro" describes an —NO$_2$ group.

The term "acyl halide" describes a —(C═O)R"" group wherein R"" is halide, as defined hereinabove.

The term "azo" or "diazo" describes an —N═NR' end group or an —N═N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "carboxylate" as used herein encompasses C-carboxylate and O-carboxylate.

The term "C-carboxylate" describes a —C(═O)—OR' end group or a —C(═O)—O— linking group, as these phrases are defined hereinabove, where R' is as defined herein.

The term "O-carboxylate" describes a —OC(═O)R' end group or a —OC(═O)— linking group, as these phrases are defined hereinabove, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(═S)—OR' end group or a —C(═S)—O— linking group, as these phrases are defined hereinabove, where R' is as defined herein.

The term "O-thiocarboxylate" describes a —OC(═S)R' end group or a —OC(═S)— linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone.

Alternatively, R' and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an R"OC(═O)—NR'— end group or a —OC(═O)—NR'— linking group, as these phrases are defined hereinabove, with R' and R" as defined herein.

The term "O-carbamate" describes an —OC(═O)—NR'R" end group or an —OC(═O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(═S)—NR'R" end group or a —OC(═S)—NR'— linking group, as these phrases are defined hereinabove, with R' and R" as defined herein.

The term "N-thiocarbamate" describes an R"OC(═S)NR'— end group or a —OC(═S)NR'— linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(═S)—NR'R" end group or a —SC(═S)NR'— linking group, as these phrases are defined hereinabove, with R' and R" as defined herein.

The term "N-dithiocarbamate" describes an R"SC(═S)NR'— end group or a —SC(═S)NR'— linking group, as these phrases are defined hereinabove, with R' and R" as defined herein.

The term "urea", which is also referred to herein as "ureido", describes a —NR'C(═O)—NR"R'" end group or a —NR'C(═O)—NR"— linking group, as these phrases are defined hereinabove, where R' and R" are as defined herein and R'" is as defined herein for R' and R".

The term "thiourea", which is also referred to herein as "thioureido", describes a —NR'—C(═S)—NR"R'" end group or a —NR'—C(═S)—NR"— linking group, with R', R" and R'" as defined herein.

The term "amide" as used herein encompasses C-amide and N-amide.

The term "C-amide" describes a —C(═O)—NR'R" end group or a —C(═O)—NR'— linking group, as these phrases are defined hereinabove, where R' and R" are as defined herein.

The term "N-amide" describes a R'C(═O)—NR"— end group or a R'C(═O)—N— linking group, as these phrases are defined hereinabove, where R' and R" are as defined herein.

An amide can be linear or cyclic. When cyclic, R' and the carbon atom are linked together to form a ring, in C-amide, and this group is also referred to as lactam. Cyclic amides can function as a linking group, for example, when an atom in the formed ring is linked to another group.

The term "guanyl" describes a R'R"NC(═N)— end group or a —R'NC(═N)— linking group, as these phrases are defined hereinabove, where R' and R" are as defined herein.

The term "guanidine" describes a —R'NC(═N)—NR"R'" end group or a —R'NC(═N)—NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

As used herein, the term "hydrazide" describes a —C(═O)—NR'—NR"R'" end group or a —C(═O)—NR'—NR"— linking group, as these phrases are defined hereinabove, where R', R" and R'" are as defined herein.

As used herein, the term "thiohydrazide" describes a —C(═S)—NR'—NR"R'" end group or a —C(═S)—NR'—NR"— linking group, as these phrases are defined hereinabove, where R', R" and R'" are as defined herein.

As used herein throughout the term "about" refers to ±10% or ±5%.

It is appreciated that certain features of the invention, which are, for clarity, described in the context of separate embodiments, may also be provided in combination in a single embodiment.

Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Cell culture—HEK293T, HeLa, MCF7, Jurkat and mouse embryonic fibroblasts (MEFs) cells were grown and maintained in Dulbecco's modified Eagle's medium supplemented with 10% fetal calf serum (Gibco) and 1% penicillin-streptomycin. To avoid NF-κB activity, HeLa cells were kept from reaching confluence and re-plated no more than 10 times following initial thawing. To induce NF-κB activity, cells were treated with 20 ng/μl recombinant human TNF-α (Peprotech) for the indicated times. STHdh Q111 and STHdh Q7 striatal cell lines (Coriell Institute for Medical Research) were grown in Dulbecco's modified Eagle's medium supplemented with 10% fetal calf serum (Gibco), 1% penicillin-streptomycin and 0.4 mg/ml G418 at 33° C. The cells were re-plated no more than 5-6 times, as recommended.

Manipulations in cultured cells—_Spt5 knockdown (KD) was carried out as previously described (Diamant, 2012). Briefly, 1,250,000 cells were plated in 10 cm dish and transfected 24 hours later using ICAFectin®441 (In-Cell-Art) and 12 g or either pSUPER or a mix of two distinct pSUPER-spt5-RNAi, together with 0.5 g CMV-GFP-Puro plasmid. Transfected cells were selected for 24 hours with puromycin (1 μg/ml).

Plasmid construction—The mammalian expression plasmids RSV-AC/AN *Renilla* luciferase (pRL-AC/AN), encoding the N-terminal amino acid residues 1-229 or the C-terminus 230-311 of the *Renilla* luciferase (RL) were previously described in Ashkenazi et al., 2016; and Ashkenazi et al., 2017. The split-*Renilla* luciferase fusion plasmids were constructed by two-step PCR using the pRL-AC or pRL-AN as backbones and plasmids encoding the region spanning NGN and KOW 1&2 of human Spt5 (SEQ ID NOs: 1-3) or the coiled-coil (CC) domain of human Rpb1 (SEQ ID NOs: 4-6), respectively, as insert sources. For bacterial expression of the split-RL fusion proteins the double expression plasmid pRSFDuet was used. All constructs were verified by sequencing. All primers used are listed in Table 2 hereinbelow.

High-throughput drug screening (HTS)—About 100,000 compounds [from MEGxp library: Pure natural compounds from plants (see Table 1 hereinbelow) were screened for their effect on Spt5-Pol II interaction (a schematic representation of the assay is shown in FIG. 1B). The HTS of was carried out in a 1536 wells plate format as previously described (Ashkenazi et al., 2017), with the following modifications: the final concentration of each drug was 15 μM and incubation time with the CTZ RL substrate was 30 minutes at RT. Compounds that diminished the luminescence activity by >30% were subjected for an additional screen with a bacterial lysate expressing recombinant full-length RL (diluted 1: 500 in phosphate buffer) that served as a control for false-positive compounds that inhibit the RL enzymatic activity itself (Ashkenazi et al., 2017). Compounds that did not affect RL activity were further analyzed for their IC50 dose using a dose-response assay (concentrations of 0.55 μM, 1.6 μM, 5 μM, 15 μM and 45 μM in duplicates). The selected compounds were further subjected to a live-cell split-RL assay as described in Ashkenazi et al., 2017. The analysis of the luminescence data for all the above described assays was performed using GeneData software (Basel, Switzerland).

TABLE 1

Compounds Libraries used form the HTS

| Supplier | Library Name | Library Size | Comment-rational |
|---|---|---|---|
| Analyticon | MEGxp: Pure natural compounds from plants | 3540 | Old Collection |
| ChemBridge | DIVERSet ™-CL | 50000 | Compounds represented in the DIVERSet ™ libraries are carefully selected to provide the broadest pharmacophore space coverage possible within a 50,000 compound set of diverse structures. Stringent druglike and desirable chemical group filters coupled with a 3D conformer analysis, are used in selecting a premium set of diverse, druglike compounds for each set with maximum pharmacophore coverage. |
| Enamine | Drug-Like Set (DLS) | 20160 | PRE-PLATED REPRESENTATIVE SETS-drug-like compounds selected using diversity sorting from the combined file of HTS and Historical collections. All compounds within the set strictly conform to rules of Lipinski and Veber, and do not bear undesired reactive functional groups. |
| LOPAC/ SIGMA | Navigator $LOPAC^{1280}$ | 1280 | Library of Pharmacologically Active Compounds |
| MayBridge | HitFinder ™ Collection | 14400 | The pre- plated HitFinder ™ Collection consists of 14,400 Maybridge Screening Compounds, selected to represent the diversity of the Maybridge Screening Collection using a clustering algorithm based on standard Daylight Fingerprints and Tanimoto similarity, and is |

TABLE 1-continued

Compounds Libraries used form the HTS

| Supplier | Library Name | Library Size | Comment-rational |
|---|---|---|---|
| | | | conveniently supplied as dry films in Matrix 96 shallow well plates or 384 well microplates. |
| MicroSource | Spectrum Collection-Known Drugs (66%), Natural Products (26%) and Other Bioactive Components (8%) | 2400 | The Spectrum Collection includes Amlexanox (Berta's request) |
| Prestwick | Prestwick Chemical Library ®-approved drugs | 1200 | 100% approved drugs (FDA, EMEA and other agencies) |
| Selleck Chemicals | Bioactive Screening Libraries | 1682 | All of their unique bioactive compounds. |

Cells extract and Western blotting—Whole-cell extracts of HeLa cells were prepared with a commercial Reporter lysis buffer (E4030, Promega). Following, samples were separated by SDS-PAGE and subjected to Western blot analysis using an anti-IκBα antibody (BD-transductions) as described in Burnette W N. Analytical Biochemistry. (1981) 112 (2): 195-203.

RNA analysis—Total RNA was extracted using Tri-reagent (Bio-Lab Chemicals) and Direct-Zol™ RNA Mini-Prep kit (Zymo Research). Following, cDNA was synthesized from 0.5-1 ag of total RNA using a High-Capacity cDNA Reverse Transcription Kit (ABI, Thermo Fisher Scientific). cDNA samples were analyzed by quantitative PCR (qPCR) in a ViiA 7 Real-Time PCR System using Fast qPCRBIO SYBR Green Mix (PCR Biosystems). The primers used are shown in Table 2 hereinbelow.

TABLE 2

List of primers

| SEQ ID NO | Gene | Primer Sequence (5'-3') | Remarks |
|---|---|---|---|
| 7 | HSPA1A_F | TAACCCCATCATCAGCGGAC | For RNA-seq vali-dation |
| 8 | HSPA1A_R | AGCTCCAAAACAAAAACAGCAA | |
| 9 | HSPA6_F | CAGAGGAACGCCACTATCCC | |
| 10 | HSPA6_R | ACTGAGTTCAAAACGCCCCA | |
| 11 | mActb F | GGAGGGGGTTGAGGTGTT | 3'-UTR |
| 12 | mActb R | GTGTGCACTTTTATTGGTCTCAA | |
| 13 | GDF15_F | CCATGTCGCTTGTGTCCTTTC | ex-ex NM_ 004864.3 |
| 14 | GDF15_R | CTTGCAAGGCTGAGCTGACG | |
| 15 | mGDF15_F | CCTCCATCTTCTATCTGAGCCTG | ex-ex NM_ 001330687.1 |
| 16 | mGDF15_R | CCATGTCGCTTGTGTCCTTTC | |
| 17 | mHtt_last exon_F | CTCAGTCTAGTCGGGCAGGT | Exon 67 |
| 18 | mHtt_last exon_R | CCACAGGCAGGATTCTCACA | |
| 19 | mHtt_ intron1_F | TCTGACTCTGACTTTGTGCCA | |
| 20 | mHtt_ intron1_R | TTCTCTCCAGTCACAAGCAGC | |
| 21 | mHTT_ exon2_F | GAAGGAACTCTCAGCCACCA | |
| 22 | mHTT_ exon2_R | AGACTGTGCCACAATGTTTTCAC | |
| 23 | mHtt_ exon3_F | CAGAAACTCTTGGGCATCGC | |
| 24 | mHtt_ exon3_R | TTGATGACTTTGTTGAGGCACT | |
| 25 | mHtt 5UTR exon_F | GGGCCCAAGATGGCTGAG | |
| 26 | mHtt 5UTR exon_R | ACCCTGAAGACTTGGAGCCT | |
| 27 | IL6_ Promoter_F | CAAATGTGGGATTTTCCCATGAGT | ChIP. human |
| 28 | IL6_ Promoter_R | CAGGGCTAAGGATTTCCTGC | |
| 29 | IL6_mid_F | GTACCTCCAGAACAGATTTGAGAGT | |
| 30 | IL6_mid_R | GCAGGAACTGGATCAGGACT | |
| 31 | IL6_end_F | AATGGAAAGTGGCTATGCAGT | |
| 32 | IL6_end_R | TAGCCATTTATTTGAGGTAAGCCT | |
| 33 | A20_ Promoter_F | ACTTCGCAGCCCGACC | |
| 34 | A20_ Promoter_R | CTGGGGGTGTGATCTCTCTTG | |
| 35 | HIST1H1B_F | GTGGCGAAGAGCCCTAAGAA | |
| 36 | HIST1H1B_R | TGGCCTTTGCAGCTTTAGGT | |
| 37 | HIST1H3A F | TGCTCGGAAGTCTACTGGTG | |
| 38 | HIST1H3A_R | CCAGGCGCTGGAAAGGTAG | |
| 39 | HIST1H2AI_F | TGGCCATCCGCAACGATGA | |
| 40 | HIST1H2AI_R | CTTCTACTTGCCCTTCGCCTTGT | |
| 41 | HIST1H4H_F | GGTGTTCTGAAGGTGTTCCTG | |

TABLE 2-continued

List of primers

| SEQ ID NO | Gene | Primer Sequence (5'-3') | Remarks |
|---|---|---|---|
| 42 | HIST1H4H_R | TTAGCCACCGAAGCCGTAAA | |
| 43 | IEX1_F | CTCGAGTGGTCCGGCG | |
| 44 | IEX1_F | ACGATGGTGAGCAGCAGAAA | |
| 45 | GAPDH_F | CTGAGCTGAACGGGAAGCTC | |
| 46 | GAPDH_R | CACCTGGTGCTCAGTGTAGC | |
| 47 | A20_Exon3_F | GCTGGCAACTGGAGTCTCTC | mature |
| 48 | A20_Exon4_R | TTGTCCCATTCATCATTCCA | |
| 49 | A20_ intron1_F | TCCTTTTCAGGTGTTGGAGAGC | im-mature |
| 50 | A20_Exon2_R | CCGTATCTTCACAGCTTTCCG | |
| 51 | JunB_F | ACAAACTCCTGAAACCGAGC | |
| 52 | JunB_R | AAGAGGCGAGCTTGAGAGAC | |
| 53 | CXCL2_F | CATCCAAAGTGTGAAGGTGAAG | |
| 54 | CXCL2_R | GCTTTCTGCCCATTCTTGAG | |
| 55 | A20 Exon #1_F | ACCAGGACTTGGGACTTTGC | "A"; ChIP |
| 56 | A20 Intron #1_R | AGGAGCGCTGCAAAACCAAC | |
| 57 | A20 Intron #2_F | TCTTCTCCTCCTTTCTGTCC | "B"; ChIP |
| 58 | A20 Exon #3_R | TGAGATTTGAGAGACTCCAG | |
| 59 | A20 intron #8_F | CTGGCTCATAGACTGCAATG | "C"; ChIP |
| 60 | A20 Exon #9_R | TGAGGTGCTTTGTGTGGTTC | |
| 61 | IL8_F | GCTCTGTGTGAAGGTGCAGT | |
| 62 | IL8_R | TCTGTGTTGGCGCAGTGT | |
| 63 | IL6_F | CATGTGTGAAAGCAGCAAAGA | |
| 64 | IL6_R | CCTCAAACTCCAAAAGACCAGT | |
| 65 | CCL20_F | GAGTTTGCTCCTGGCTGCT | |
| 66 | CCL20_R | GTTGCTTGCTGCTTCTGATTC | |
| 67 | dC-RL-spt5_F | AGCGGTGGCGGAGGGAGCaaggatcccaatctgtggac | Cloning |
| 68 | dC-RL-spt5_R | GAAGCGGCCGCTCTAGAATTAcaccttcacgtggtcccccatc | |
| 69 | Pol2-dN-RL_F | CTCACTATAGGCTAGCCACCatggagcgagtgcatgagatcttc | |
| 70 | Pol2-dN-RL_R | CACCGCTCCCTCCGCCACCgtcgggggtgatgacagtac | |
| 71 | dC-Spt5 in pRSF duet_F | CATCACCATCATCACCACAGCCAGGATCCGATGACTTCGAAAGTTTATGATC | |
| 72 | dC-Spt5 in pRSF duet_R | TCGACTTAAGCATTATGCGGCCGCAAGCTTCTAGGTCTTTATAGCTGTGTC | |
| 73 | Pol2-dN in pRSF duet_F | ATTAGTTAAGTATAAGAAGGAGATATACATATGtcgggggacagcgcatgcccgc | |
| 74 | Pol2-dN in pRSF duet_R | CGCAGCAGCGGTTTCTTTACCAGACTCGAGTTATTGTTCATTTTTGAGAAC | |

TABLE 2-continued

List of primers

| SEQ ID NO | Gene | Primer Sequence (5'-3') | Remarks |
|---|---|---|---|
| 75 | Fused Spt5-Spt4(pRL)_F | gatgggggaccacgtgaaggtgGGTGGCGGAGGGAGCGGTG | Cloning |
| 76 | Fused Spt5-Spt4(pRL)_R | GAAGCGGCCGCTCTAGAActaggtctttatagctgtgtc | |
| 77 | Fused Spt5-Spt4 in pRSF duet_F | catcaccacagccaggatccgATGAAGGATCCCAATCTGTGGAC | |
| 78 | Fused Spt5-Spt4 in pRSF duet_R | TCGACTTAAGCATTATGCGGCCGCAAGCTTctaggtctttatagctgtgtc | |
| 79 | Pol2 in pRSF duet_F | ATTAGTTAAGTATAAGAAGGAGATATACATATGtcgggggacagcgcatgcccgc | |
| 80 | Pol2 in pRSF duet_R | gcagcggtttctttaccagactcgagTTAGTCGGGGGTGATGACAGTACG | |

High-throughput sequencing of RNA transcripts (RNA-Seq)—HeLa cells with basal NF-κB activity or HeLa cells with induced NF-κB activity (treated with TNF-α for 60 minutes) were treated for 2 hours with DMSO (vehicle control) or with the tested SPI compound (e.g., SPJ-21). Following, the cells were subjected to high-throughput sequencing as described in Diamant et al., 2016b.

Metabolic labeling of newly synthesized RNA with 4-thiouridine (4sU)—STHdh Q111 and STHdh Q7 cells (collected from 10 cm dishes) were treated for 30 minutes with DMSO (vehicle control) or the tested SPI compound (e.g., SPJ-21). Following, 4-thiouridine (4sU, 150 μM final concentration) was added for additional 2 hours. The labeling was terminated by removing the 4sU-containing medium and washing the cells 3 times with phosphate-buffered saline (PBS). Total RNA was extracted as described above. 10 μg of RNA were biotinylated using biotin-HPDP (1:5; A8008, APExBIO) for 1.5 hours at room temperature and the biotinylated RNA was purified using chloroform and isopropanol extraction and dissolved in DEPC water. Following, the biotinylated RNA was captured by incubation with Streptavidin-coated magnetic beads (NEB, S1420S) for 30 minutes at room temperature in constant rotation. Bound RNA was eluted with 100 μl of 0.1 M fresh DTT. RNA isolation was performed using an RNA Clean & Concentrator kit (Zymo Research); and cDNA preparation and qPCR were effected as described above.

Chromatin immunoprecipitation (ChIP)—HeLa cells were treated with DMSO (vehicle control) or the indicated compound (50 μM; 60 minutes), followed by TNF-α induction (30 minutes) in 100-mm plates. Following, the cells were cross-linked with 1% formaldehyde for 10 minutes at room temperature, and fixation was terminated by adding 1/20 volume of 2.5 M glycine.

Chromatin extraction and immunoprecipitation were carried out as previously described in Diamant et al., 2012. For immunoprecipitation (IP), 3 μg of anti-RNA polymerase II (ab817, Abcam) anti-Spt5 [previously described in Amir-Zilberstein et al., 2007] or control IgG (SC-2025, Santa Cruz Biotechnology) was added to 1 ml of the soluble chromatin DNA. IP and input samples were analyzed by qPCR as described above.

Co-immunoprecipitation (CO-IP)—HeLa cells were detached from a 10 cm dish with ice-cold PBS and a cell scraper, centrifuged for 5 minutes at 2,000 rpm and re-suspended in 200 μl lysis buffer (20 mM Tris-HCl pH 8, 400 mM NaCl, 2 mM EDTA, 0.5% NP-40, 10% glycerol) to which a protease inhibitor cocktail (1:100) and PMSF (200 μM) were freshly added. The lysates were rotated for 10 minutes at 4° C.; and centrifuged for 15 minutes at 13,000 rpm. Following, the supernatants were diluted with lysis buffer without NaCl to reach a final concentration of 100 mM NaCl. Cell lysates were then incubated at 4° C. overnight with an anti-Spt5 antibody (Tadashi Wada et al., 1998 Genes and Development. PMID: 9450929) or rabbit IgG (SC-2025, Santa Cruz Biotechnology), followed by 2 hours incubation at 4° C. with Protein A/G Sepharose beads (GE Healthcare). Following, the samples were washed 3 times and incubated for 2 hours at 4° C. with DMSO (vehicle control) or the indicated compound. The immune-precipitated proteins were detected by SDS-PAGE followed by western blot using an anti-Spt5, anti-Pol II (ab817, Abcam) or anti-Spt4 (Kim D K. et al, Genes to cells 2003 PMID: 12653964).

Binding assay—In order to measure binding of the indicated compound to Spt5 and/or Pol II; Spt5-Spt4 or Rpb1 fused to a histidine (His) tag were expressed in *E. coli* (SEQ ID Nos: 2-3, 5-6 and 81) and purified on nickel agarose beads as described in Ashkenazi et al. 2016. The proteins were incubated for 10 minutes with increasing concentrations of the indicated compound in a black 384 wells microplate in a total volume of 20 μl. Binding was assessed by measuring the changes in the intrinsic fluorescence (280 nm) using Cytation™ 5 (BioTek).

Global Run-On experiment—HeLa cells (15 cm plate×3) were treated with the tested SPI compound (e.g., SPI-21) (50 μM) for 1.5 hours, washed 3 times with cold PBS, collected and pelleted at 1000×g for 5 minutes at 4° C. Cells were swollen by resuspension in 2 ml swelling buffer [10 mM Tris-Cl pH 7.5, 10% glycerol, 3 mM $CaCl_2$), 3 mM $MgCl_2$, protease inhibitor cocktail (EDTA free), and 4 units/ml of RNase inhibitor], incubated at 4° C. for 20 minutes and pelleted again at 1000×g for 5 minutes at 4° C. Cells were resuspended in 1 ml of ice-cold lysis buffer (10 mM Tris-Cl pH7.5, 300 mM sucrose, 10 mM NaCl, 3 mM $CaCl_2$), 2 mM $MgCl_2$, 0.5% Igepal, 0.5 mM DTT, protease inhibitors and RNase inhibitor) and then homogenized and lysed by transferring them 5 times through 27 G needle. Nuclei were pelleted at 1000×g for 5 minutes at 4° C., washed once with 10 ml of lysis buffer and once with 1 ml storage buffer (50 mM Tris-Cl pH 8.0, 25% glycerol, 5 mM $MgCl_2$, 0.1 mM EDTA, 5 mM DTT). For the Run-on reaction nuclei were resuspended at $5\times10^6$ nuclei/100 μl of storage buffer and mixed with equal volume of reaction buffer (10 mM Tris-Cl pH 8.0, 5 mM $MgCl_2$, 1 mM DTT, 300 mM KCl, 20 units of RNase Inhibitor, 1% sarkosyl, 500 μM ATP, GTP, CTP and Br-UTP). The reaction was allowed to proceed for 5 minutes at 30° C., followed by the addition of 1 ml Trizol. RNA was further extracted with Direct-Zol™ RNA Mini-Prep kit and DNase I treatment was performed. Fragmentation of NRO-RNA was performed using fragmentation reagents (AM8740) for 10 minutes at +70° C. and then terminated by addition of stop solution (1:1). The fragments were purified by Micro Bio-Spin® Columns with Bio-Gel® P-30 (BioRad) according to the manufacturer's instructions. BrU-labeled RNA was purified with pre-blocked anti-BrdU beads and eluted 4 times (10 min each) with elution buffer (20 mM DTT, 300 mM NaCl, 5 mM Tris-cl pH 7.5, 1 mM EDTA, and 0.1% SDS) at +42° C. while shaking. Eluted RNA was extracted using Trizol and Direct-zol RNA Mini-Prep.

High-throughput sequencing of the total, labeled and Run-On transcripts (RNA-Seq and Gro-seq)—_The RNA-Seq libraries were prepared by the Genomics unit in The Nancy and Stephen Grand Israel National Center for Personalized Medicine (G-INCPM, Weizmann Institute of Science). Samples from 2-hour SPI treatment were prepared using in-house mRNA Seq protocol and polyA capturing and those from 24-hpur and 4sU treatments were prepared using the same protocol w/o PolyA capture (with random hexamers), and sequenced using an Illumina HiSeq 2500 system yielding about 30M SE reads of 61 bases. The GRO-seq RNA samples were reverse transcribed and amplified (15 cycles) using in-house mRNA Seq protocol w/o PolyA capture (with random hexamers) and sequenced in one lane using an Illumina HiSeq High Output (480 million reads, yielding more than 100M SE reads of 47 bases per sample). Each RNA-Seq analysis was carried out using two independent replicates.

RNA-Seq and GRO-seq Bioinformatics analysis—_For the analysis of the 24 h, 4sU and GRO-seq data, we used the RNA-Seq pipeline of UTAP (Kohen et al. 2019) to determine the differentially expressed genes. For the 2-hour data, reads were mapped to the *H. sapiens* GRCh38 reference genome using STAR (Dobin et al., 2013) and expression levels for each gene were quantified using htseq-count (Anders et al., 2015). Differentially expressed genes were identified using DESeq2 (Love et al., 2014). The pausing index (PI) analysis was determined for the upregulated genes from the GRO-seq experiment with at least 50 reads in the DMSO sample. The reads coverage was calculated using bed files containing the desired genomic regions and orientation (awk command) and the bedtools coverage tool (Quinlan et al., 2010).

Cells viability assay—_HeLa cells were plated in an opaque-walled 96 well plate (50,000 cells per well) and treated with increasing concentrations of the tested SPI compounds (e.g., SPI-21 or SPI-18) for 48 hours. After equilibrating the plate and its contents at room temperature for 30 minutes, 100 1 (1:1) of CellTiter-Glo® Reagent (G7571, Promega) was added to each well and shook for 2 minutes to induce cell lysis. Following 10 minutes incubation at room temperature, the luminescent signal was detected using the Cytation 5 instrument.

Quantification and statistical analysis—_To calculate p-values, student's t-tests (typically one-tail, paired) were performed. The significance of the difference in the median values was calculated by the Wilcoxon Signed Rank test. Significance symbols in all experiments are: *=$p<0.05$; =$p<0.01$; *=$p<0.005$; ****=$p<0.001$.

Data and code availability—_The RNA-Seq datasets have been deposited in NCBI's Gene Expression Omnibus (Edgar et al., 2002) and are accessible through GEO Series accession number GSE136026.

Example 1

Identification of Spt5 Inhibitors

The present inventors developed a high throughput screening assay for identification of Spt5 inhibitors based on Spt5 interaction with polymerase II (Pol II). Spt5 is an essential transcription elongation factor and its activities are critically dependent on its ability to bind Pol II (see for example Diamant 2012, 2016). Thus, the present inventors envisaged that inhibiting formation of the Spt5-Pol II complex will inhibit Spt5 activity.

Specifically, a split-*Renilla* luciferase (RL) complementation assay was used to detect Spt5 interaction with Pol II (Ashkenazi et al., 2016; Ashkenazi et al., 2017). In this assay, RL is split into two inactive N- and C-terminal fragments and fused to target proteins. Interaction of the target proteins brings the N- and C-termini in close proximity thereby restoring the RL enzymatic activity. In this system the spatial arrangement of the two RL parts is critical for enzymatic activity; therefore it is sensitive not only to direct interference with the interacting proteins but also to conformation/allosteric effects on the fused proteins (Haimov 2018). Mammalian Spt5 is a large protein having several conserved functional domains (Werner, 2012) including: NusG N-terminal homology domain (NGN) that mediates the interaction with Pol II; four KOW domains which are also involved in interaction with Pol II; a repetitive heptapeptide motif in the C-terminal region called CTR implicated in the positive elongation activity of Spt5 (Chen et al., 2009; Ivanov et al., 2000; Yamada et al., 2006); and a C-terminal domain with an unknown function. For the RL complementation assay the region spanning NGN and KOW 1&2 of Spt5 and the coiled-coil (CC) domain of Rpb1, the large subunit of Pol II, were fused to N-RL and C-RL, respectively (FIG. 1A) and co-expressed in *E. coli* from a single plasmid. Following, bacterial cell lysates were used in a 1536-wells plate format to screen a library of about 100,000 small molecules with diverse chemical nature (FIG. 1B). 587 of the tested compounds inhibited the RL activity and these were further tested with a full-length RL enzyme to eliminate compounds which inhibit activity of the RL enzyme itself. The remaining 309 compounds were further validated in a dose-response assay using the N-RL-Spt5 and Pol II-C-RL pair as well as the full-length RL. About half of the compounds inhibited also the full-length RL reporter at the high concentration, leaving 148 compounds that specifically inhibited the activity of the N-RL-Spt5 and Pol II-C-RL pair. To select for compounds that can enter mammalian cells, the identified compounds were further tested in a live-cell Split-RL assay, of which 140 retained their inhibitory activity. 44 were filtered out as potentially non-specific compounds as they also appeared in other screens. The chemical structures of the remaining 96 compounds are presented in FIG. 7. Finally, 41 compounds which displayed a IC-50≤40 μM [referred to herein as Spt5-Pol II inhibitors (SPI)] were selected for further analysis. Thus far, 18 compounds were found to exert at least one biological effect, as further described in details hereinbelow. The chemical structures and the IC50 measurements of these biologically active compounds are shown in FIGS. 1C and 7. Notably, several of these compounds appear to be chemically related. For example, one class includes SPI-21, SPI-29 and SPI-57 and the other SPI-68, SPI-46 and SPI-157.

Two identified compounds, SPI-21 and SPI-18, were further validated for their direct interaction with either Spt5 or Rpb1 CC domain. To this end, His-Rpb1 and His-Spt5 (fused to Spt4 to increase its stability) were each expressed in *E. coli* and purified by nickel agarose beads. Using the purified proteins, fluorescence intensity measurements were performed in the presence of increasing concentrations of SPI-21 or SPI-18. This method analyzes binding by monitoring the changes in the intrinsic fluorescence of the proteins as a consequence of conformational changes. Both Spt5 and Rpb1 displayed significant intrinsic fluorescence as expected from the presence of aromatic residues in both. SPI-21 decreased the intrinsic fluorescence of Rpb1 in a dose dependent manner with an IC50 of 23 μM while it had no significant effect on Spt5 (FIG. 1D). This IC50 is comparable to the 25 μM IC50 value seen in the split-RL assay with SP-21 (FIG. 1D) and suggests that SPI-21 primarily binds the Rpb1 CC domain. SP-18 on the other hand, seemed to affect the fluorescence of both proteins and the measured IC50 was 40 μM for Spt5 and 76 μM for Pol II. The Spt5 IC50 is close to the values obtained with the split-RL (33 μM, FIG. 1D) and inflammatory gene inhibition (39 μM, FIG. 3D). These findings are consistent with direct interaction of the identified compounds with Spt5 and Rbpl.

In the next step, co-immunoprecipitation in the presence of SPI-21 or SPI-18 was performed to test their effect of endogenous Spt4/Spt5-Pol II complex. As shown in FIGS. 1E and 1F, these compounds did not disrupt Spt5-Pol II binding. These findings suggest that binding of SP-21 or SP-18 to Spt5 and/or Rpb1 is likely to induce conformational changes that diminish Spt5-Pol II function. Alternatively or additionally, as binding of Spt5 to the multi-subunit Pol II involves multiple domains, several subunits and many contact points, interference with one domain may not be sufficient to detach Spt5 from Pol II.

Direct interaction with either the Spt5 or the Rpb1 CC domain of SPI-21 and SPI-18 was further validated. His-Rpb1 and His-Spt5 (fused to Spt4 to increase its stability) and His-eIF4E, used as a negative control, were each expressed in *E. coli* and purified by nickel agarose beads. Using the purified proteins, fluorescence intensity measurements were performed in the presence of increasing concentrations of SPI-21 and SPI-18. This method analyzes binding by monitoring the changes in the intrinsic fluorescence of the proteins as a consequence of conformational changes. Spt5, Rpb1, and eIF4E display significant intrinsic fluorescence, as expected from the presence of aromatic residues in all of them. SPI-21 decreased the intrinsic fluorescence of Rpb1 in a dose-dependent manner with an IC50 of 23 mM, while it had no significant effect on Spt5 and eIF4E (FIG. 1D, left). This IC50 is comparable to the 25 mM IC50 value seen in the split-RL assay with SP-21 (FIG. 1C) and suggests that SPI-21 primarily binds the Rpb1 CC domain. SPI-18, however, seems to affect the fluorescence of both Spt5 and Rpb1, and the measured IC50 is 40 mM for Spt5 and 76 mM for Rpb1 (FIG. 1D, right). The IC50 of Spt5 binding by SPI-18 is close to the values obtained with the split-RL (33 mM; FIG. 1C) and with the inhibition of inflammatory genes (39 mM; FIG. 3D). These findings are consistent with the direct interaction of the identified SPI compounds with the Spt5 and Rpb1 proteins.

FIG. 7 presents the 96 identified Spt5 inhibitors and their chemical structures.

Example 2

The Effect of the Identified Spt5 Inhibitors on Expression of Pro-Inflammatory Genes In-vitro transcription assays along with Spt5 knock-down (KD) studies established the NF-κB-responsive A20 gene as a target for proximal promoter pausing by Spt5 under basal conditions (i.e. not stimulated to induce activation of NF-κB) (Ainbinder et al., 2004; Amir-Zilberstein and Dikstein, 2008). Following NF-κB activation by TNFα, Spt5 turns into a positive regulatory factor and facilitates promoter escape and mRNA splicing (Diamant et al., 2012; Diamant et al., 2016a). Genome-wide analysis of cytosolic and chromatin-associated transcripts from Spt5 KD cells identified other Spt5 regulated genes under basal and TNFα-induced conditions (Diamant et al., 2016b).

Thus, a subset of Spt5-responsive pro-inflammatory genes from the aforementioned studies and from others (Aida et al., 2006; Fujita et al., 2009), namely A20, CCL20, IL6, IL8, CXCL2, JUNB and IEX1, were selected and the effect of the identified SPIs on their expression under basal conditions and in response to NF-κB activation was tested (FIGS. 2A-C and 3A-C). Specifically, for analyzing expression under basal conditions, Hela cells were treated with vehicle (DMSO) or SPI for 2 hours and following RNA was extracted and analyzed by RT-qPCR. As shown in FIG. 2A, under basal conditions most of the tested SPIs increased mRNA expression of the selected pro-inflammatory genes (FIG. 2A), akin to the effect previously shown with Spt5 KD. To determine whether the observed effect is linked to activated transcription or increased mRNA stability, Hela cells were treated with actinomycin D in the presence or absence of one selected compound, namely SPI-21, and mRNA levels of A20 were measured at different time points following treatment. As shown in FIG. 2B, mRNA stability was not enhanced but in fact moderately reduced in the SPI-21-treated samples; indicating that the observed elevation in the mRNA levels of the tested genes following a short-term treatment with the tested SPIs is at the transcription level and consistent with a relieve of proximal promoter pausing.

Figure 2F:
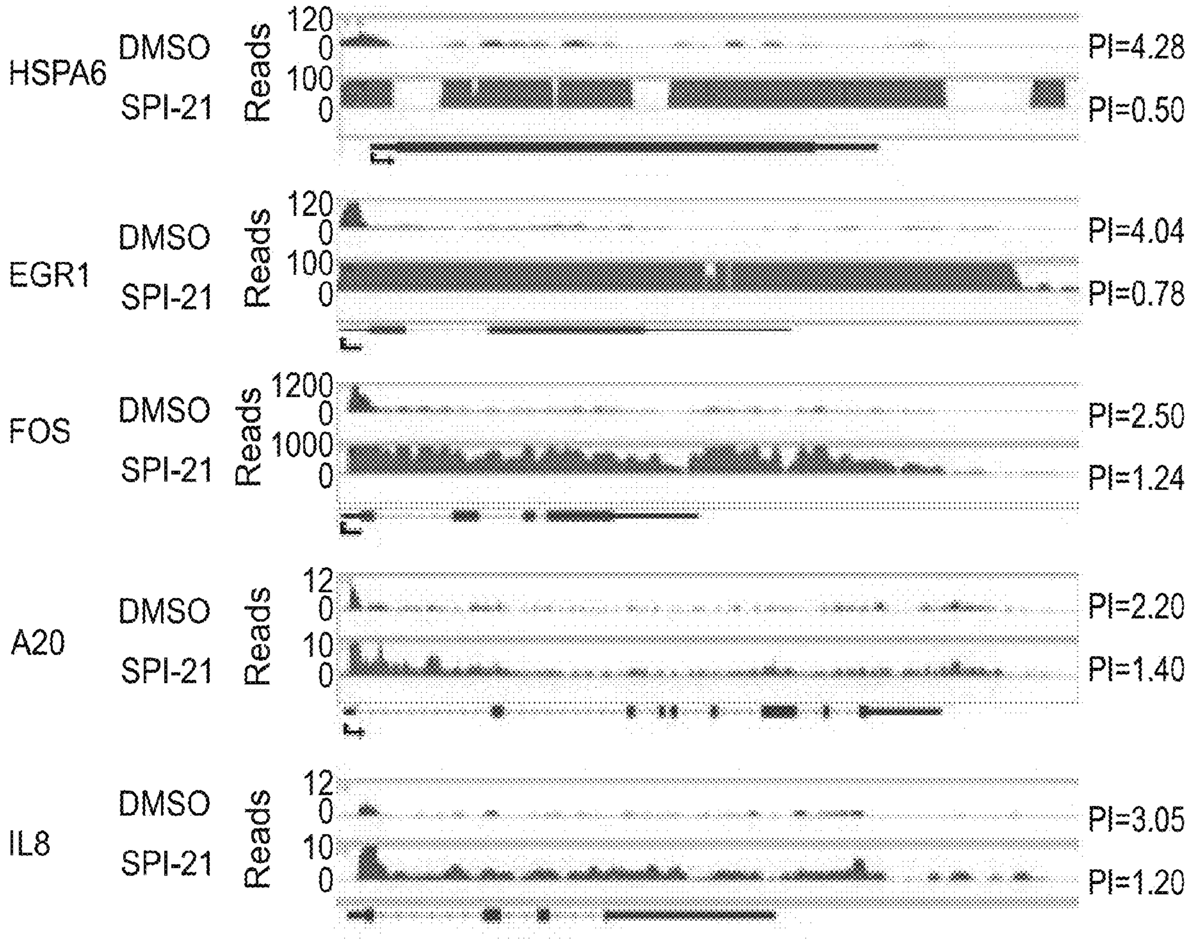

To obtain a genome-wide view of the impact of SPIs on transcription, Global run-on sequencing (GRO-seq) was performed using the nuclei of HeLa cells treated with either DMSO (control) or SPI-21. The GRO-seq experiment measures the distribution of transcriptionally active Pol II along the length of the gene (Core et al., 2008). This analysis revealed that short-term SPI-21 treatment caused a transcription upregulation (≥2-fold) of 1,371 genes, among them A20 (TNFAIP3), IL-6, IL-8 (CXCL8), and CCL20 (analyzed above), while CXCL2, IEX1 (IER3), and JUNB were unchanged. The reduction of promoter-proximal pausing is expected to release the paused Pol II into the gene body, and thus upregulate transcription. Hence, the ratio between Pol II density around the TSS and the gene body (pausing index [PI]) of the SPI-21 upregulated gene set was calculated and indicated that the majority display promoter-proximal pausing (PI>1.2) (FIG. 2D). Furthermore, treatment with SPI-21 resulted in a general reduction in their PI (FIG. 2E). The sequencing tracks of a few examples of upregulated genes with reduced PI values following SPI-21 treatment are shown in FIG. 2F. These findings together confirmed that elevated mRNA levels following short-term SPI treatment are, at least in part, a consequence of promoter-proximal pausing relief, which is consistent with a known function of Spt5.

In the next step, the effect of the identified SPIs on expression of the selected genes following NF-κB activation was analyzed. Specifically, Hela cells were pre-incubated with DMSO or SPI (50 μM or less) for 1 hour followed by treatment with TNFα for an additional 1 hour. As shown in FIG. 3A, the selected genes were either moderately (CXCL2, JUNB, IEX1) or strongly (A20, CCL20, IL6, IL8) activated by TNFα. The induced levels of all these genes were diminished to a variable degree by all the tested SPIs, similarly to the effect previously seen with Spt5 KD (Diamant et al., 2016a; Diamant and Dikstein, 2013). Interestingly, the potent inhibitors decreased the induction rate of all the analyzed genes while the weaker inhibitors such as SPI-68, SPI-74, SPI-95, SPI-42 and SPI-06, affected mainly the genes that were strongly induced by the TNFα treatment [A20, CCL20, IL6, IL8 vs. CXCL2, JUNB, IEX1 (FIG. 3A)]. This effect of the weak inhibitors is remarkably similar to the effect seen with Spt5 depletion which primarily diminished the induction of strongly induced genes (Diamant et al., 2016b). Treatment with actinomycin D in the presence or absence of SPI-21, indicated that the reduced mRNA levels was not a consequence of diminished mRNA stability (FIG. 3B). In fact, the half-life of the TNFα-induced A20 mRNA levels in control samples was shorter than the half-life in the SPI-21 treated cells; indicating that the observed reduction in the mRNA levels of the tested genes under TNFα-induced conditions is a consequence of diminished transcription. Following, it was confirmed that the observed effects were not a consequence of changes in Rpb1 and Spt5 protein levels caused by SPI-21 (data not shown). In addition, no significant alterations was found in the occupancy of the NF-kB protein p65 of its target genes upon SPI-21 treatment under basal and TNF-α conditions (data not shown). The IC50 of some of the SPIs on TNFα-induced transcription was further determined and found to be mostly at the low μM range (FIG. 3D).

Summing up the effect of the tested compounds on all selected genes a ranking of their potency in inhibiting the negative and positive regulatory activities of Spt5 was obtained (FIGS. 2C and 3C). This analysis revealed that several compounds, including SPI-68, SPI-31, SPI-18 and SPI-39 inhibited mainly the positive activity of Spt5 with little or no effect on proximal promoter pausing while SPI-06 predominantly affected proximal promoter pausing, suggesting that the positive and negative activities can be uncoupled.

As Spt5 KD was also shown to reduce the splicing efficiency of the TNFα-induced A20 mRNA (Diamant et al., 2012), the effect of SPI-21 and SPI-18 on splicing was examined by determining the ratio between mature and immature mRNA under basal and TNFα-induced conditions. The results revealed a clear decrease in mature/immature ratio following treatment with SPI-21 or SPI-18 following TNFα induction (FIGS. 3E and 3H) consistent with the effect seen previously with Spt5 depletion by KD (Diamant et al., 2012; Diamant et al., 2016b).

IκBα, the major inhibitor of NF-1B, is also a primary target gene of NF-1B itself, forming a negative feedback loop. Spt5 was shown to be central in maintaining this regulatory circuit (Diamant et al., 2012; Diamant et al., 2016b). Hence, the effect of SPI-21 and SPI-18 on IκBα protein was examined. In control cells the initial levels of IκBα were diminished 30 minutes following TNFα induction as a consequence of its degradation and recovered 150 minutes following TNFα treatment due to its induction by NF-1B (FIG. 3F, lanes 1-3). Upon SPI-21 or SPI-18 treatment, the recovery of IκBα at 150 minutes following TNFα induction was markedly reduced (FIG. 3F, lanes 6 and 9) in accordance with the effect of Spt5 KD (Diamant et al., 2012; Diamant et al., 2016a).

To further examine the impact of the identified SPIs on chromatin occupancy of Spt5 and Pol II, chromatin immunoprecipitation (ChIP) in the presence of DMSO, SPI-21 or SP-18 followed by 30 minutes TNFα treatment was performed. Analysis of 3 loci of the A20 gene under basal conditions (TNFα-) revealed a moderate but significant enhancement of Spt5 and Pol II occupancy at the 3 loci by SPI-21 while their levels were unchanged with SPI-18 (FIG. 3G). This finding is consistent with the increase in transcription under basal conditions exerted by SPI-21 but not by SPI-18 (FIG. 2A). Upon TNFα induction the levels of Pol II and Spt5 were dramatically elevated and this induction was diminished by both SPI-21 and SPI-18 at all the analyzed loci (FIG. 3G, TNFα+). This finding is consistent with the decrease in transcription under TNFα-induced conditions of both SPI-21 and SIP-18 (FIG. 3A).

Taken together, the effects of the identified SPIs on the expression of NF-κB target genes under basal and TNFα- induced conditions are in full agreement with the previously reported negative and positive effects of Spt5 on transcription of pro-inflammatory genes as revealed by the KD approach.

Spt5 was reported to be essential for cell growth and survival in mammalian cells (Komori et al., 2009). Thus, the effect of increasing concentrations of SPI-21 and SPI-18 on cell growth was examined and found that both compounds dramatically diminish cellular viability in a dose-dependent manner (FIG. 3I).

Example 3

The Identified Spt5 Inhibitors Affect Expression of Genes Involved in Several Signaling Pathways A major limitation of KD and KO studies is the prolonged deficiency of the target protein. Small molecule inhibitors on the other hand, inactivate their target shortly following their application. To examine the global effect of a short-term Spt5 inhibition, cells were treated for 2 hours with SPI-21 for 2 hours or for 1 hour SPI-21 and additional 1 hour with TNFα and then subjected to RNA-seq. Reads were aligned to the human genome and normalized expression of each gene was determined. Subsequently, the following ratios were calculated: TNFα vs. control, which describes the response to TNFα; SPI-21 vs. control, which describes the effect of SPI-21 on gene expression under basal conditions; and SPI-21+TNFα vs. TNFα, which describes the effect of SPI-21 under TNFα-induced conditions. A total of 506 genes displayed a statistically significant fold change in at least one of the ratios, and these were grouped into 5 distinct clusters (FIG. 4A). The vast majority of SPI-21 affected genes were up-regulated, as also seen with the GRO-seq, and similarly to the global effect seen upon Spt5 KD in human (Diamant et al., 2016b) and mouse (Fitz et al., 2018) cells. Clusters 1-4 contain genes that are up-regulated by SPI-21 under basal conditions and cluster 5 contain SPI-21 down-regulated genes. Cluster 1 also contains TNFα-induced genes that are sensitive to Spt5 inhibition while the TNFα-induced genes in cluster 2 are not. Several genes from the different clusters were selected to examine the effect of a few other SPIs on their expression by qRT-PCR (excluding cluster 1, which is represented in FIGS. 2A and 3A). The changes in their levels are highly similar to those of SPI-21 (FIGS. 4K, 4L and 4M). Further analysis of this data provided several insights: There is a substantial overlap between genes that are prone to be induced by TNFα and those that are up-regulated by SPI-21 under basal conditions, suggesting that proximal promoter pausing is central to this signaling pathway (FIG. 4B). Comparing the effect of SPI-21 with that of Spt5 KD (Diamant et al., 2016b) on the TNF-α-induced genes, indicated that most of the downregulated genes are common to the two treatments (FIG. 4T). In addition, biological pathway analysis of the SPT-21 up-regulated genes revealed remarkable enrichment of inducible genes in response to a variety of extracellular signals apart from TNFα, including unfolded protein response, heat, hypoxia, cAMP and mechanical stimulus (FIG. 4C). Of particular interest are heat shock genes which were very strongly up-regulated. While heat shock genes were previously reported as Spt5 targets for proximal promoter pausing in *Drosophila* (Missra and Gilmour, 2010; Wu et al., 2003), these genes were not identified by Spt5 KD studies in mammalian cells (Diamant et al., 2016b). Activation of these genes is also apparent in the GRO-seq data (see FIG. 2F and Table 3). Hence, it was hypothesized that the effect of Spt5 inhibition on heat shock genes might be transient and therefore is not detected by the prolonged KD approach. To test this possibility, cells were treated with SPI-21 for 2 and 24 hours and the levels of the heat shock genes HSPA6 and HSPA1A were determined by RT-qPCR. As shown in FIG. 4D, both genes were strongly up-regulated following 2 hours treatment; however, following 24 hours treatment the extent of their activation was substantially smaller (FIG. 4D). These results indicate that the effect of Spt5 depletion on HSP gene expression is temporary and explain the absence of these genes from the Spt5 KD study. To further test the idea of kinetically distinct Spt5 target genes, the global effect of long-term SPI-21 treatment (24 hours) was determined by RNA-seq and the affected genes between the short and long-term treatments were compared. 80% of the affected genes differed between the short- and long-term treatments (FIG. 4J).

Further analysis of the RNA-seq data of Spt5 KD cells (Diamant et al., 2016b) revealed GDF15 as the top up-regulated gene, elevated by 27-fold (FIG. 4E). GDF15 is a member of the TGF-β superfamily and is associated with regulation of body-weight and food intake in humans and rodents (Emmerson et al., 2017; Hsu et al., 2017; Mullican et al., 2017; Tsai et al., 2018; Yang et al., 2017). Although GDF15 was among the SPI-21 up-regulated genes in the RNA-seq data, it did not pass the threshold of fold change and significance. Hence, it was suggested that the strong up-regulation of GDF15 seen upon Spt5 KD is associated with the prolonged downregulation of Spt5 by the KD approach. To test this possibility, GDF15 expression was analyzed following 2 and 24 hours treatment with SPI-21. As shown in FIG. 4F, GDF15 was up-regulated about 100-fold following 24 hours treatment while only moderately up-regulated following 2 hours of SPI-21 treatment. These findings support the idea that the strong up-regulation of GDF15 requires persistent Spt5 inhibition and suggest that this effect may be partially indirect. The dramatic elevation of GDF15 was also seen by other identified SPIs (FIG. 4G) and was not limited to HeLa cells but was also detected in other human and mouse cell lines (FIG. 4H). Thus, the utilization of SPIs enables distinguishing between temporary and constitutive Spt5-regulated genes and unveiled a previously unknown but significant role of Spt5 in the control of an important mammalian metabolic pathway via GDF15.

To validate that the effects of SPIs are at the transcriptional level, cellular RNA was metabolically labeled with 4-thiouridine (4sU) for 2 hours in the presence of DMSO or SPI-21 in the presence or absence of TNFα. Newly synthesized labeled RNA was then purified and subjected to RNA-seq. The overlap between the SPI-21 and Spt5 KD upregulated genes of the TNF-α-responsive set were determined, and found that 37% of Spt5 KD upregulated genes are common to the newly synthesized SPI-21 upregulated genes from this set (FIG. 4N). Analysis of the effect of TNFα induction in these data showed a remarkably high number of TNF-α-induced genes (467) compared to the conventional RNA-seq (<100; see FIG. 4A and Diamant et al., 2016b). A substantial fraction of these genes (285 genes, 61%) was downregulated by SPI-21 (FIG. 4O), while only 301 of 13,890 expressed genes (2.2%) were downregulated under basal conditions. Thus, the observed reduction in TNFα activation by SPI-21 is highly specific and is a consequence of diminished transcription.

The SPI-21 upregulated genes from the GROseq data were further evaluated for the enrichment of regulatory elements in their control regions (−2,000 to +2,000 around the TSS) using a gene set enrichment analysis (GSEA) database and software (Subramanian et al., 2005). One of the highest-scoring motifs identified has a CAGGTG/CACGTG (SEQ ID NO: 82) sequence (Table 3 hereinbelow) that is remarkably similar to the E-box motif of the A20 promoter CACGTG (SEQ ID NO: 83), which was found to control promoter-proximal pausing through Spt5 (Ainbinder et al., 2004; Amir-Zilberstein and Dikstein, 2008). Another enriched motif is the binding site of heat shock factor 1 (HSF1), a transcription activator of heat shock genes, which was found to be regulated by Spt5 via promoter-proximal pausing in mammalian cells (see FIGS. 2F and 4D).

TABLE 3

Enrichment of regulatory sequences in SPI-21 upregulated genes (≥2-fold change). Shown are the top 11 output sequences, along with their enrichment score and statistical significance.

| Motif sequence | Motif name | Enrichment fold | No. of genes | P value | FDR q-value |
|---|---|---|---|---|---|
| GGG(C/A)GGR | SP1/MAZ | 3.1 | 411 | 4.5E-69 | 2.8E-66 |
| TTGTTT | FOXO4 | 3.5 | 182 | 2.7E-50 | 8.2E-48 |
| TGGAAA | NFAT | 3.5 | 168 | 1.7E-46 | 3.5E-44 |
| AACTTT | UNKNOWN | 3.5 | 164 | 3.5E-44 | 5.4E-42 |
| GATTGGY | NFY | 3.9 | 113 | 6.9E-35 | 8.5E-33 |
| CA(G/C)GTG | E12/MYC | 3.0 | 265 | 8.8E-35 | 9.1E-33 |
| CTTTGT | LEF1 | 2.9 | 144 | 1.4E-30 | 1.1E-28 |
| RGAANNTTC | HSF1 | 5.7 | 64 | 2.1E-29 | 1.4E-27 |
| TTCYRGAA | UNKNOWN | 6.7 | 55 | 4.7E-29 | 2.9E-27 |
| GTGACGY | E4F1 | 4.6 | 76 | 2.2E-28 | 1.2E-26 |
| TGACGTCA | CREB | 7.1 | 47 | 3.9E-26 | 2.0E-24 |

Previous Spt5 KD studies indicated a relatively small number of down-regulated genes (43 genes), of which 20 are replication-dependent histone genes (Table 4, Diamant et al., 2016b), suggesting that it plays an important role in their expression. Histone genes are coordinately synthesized with DNA during S-phase and do not end with a polyA tail but end with a conserved stem-loop structure. Since the RNA-seq following treatment with SPI-21 detects only polyadenylated transcripts and the treatment was effected for 2 hours, during which only a fraction of cells is in S-phase, an effect on histone genes was not found. Thus, to investigate further the regulation of histone genes by Spt5 using the identified SPIs, cells were treated for 24 hours with SPI-21 or SPI-18, to allow all cells to pass S-phase at least once. Following, mRNA was extracted and cDNA was prepared using random hexamers and the levels of 4 histone genes were determined. Similarly to Spt5 KD, both SPI-21 and SPI-18 diminished expression of the selected histone genes (FIG. 5A and Table 4). Spt5 requirement for expression of histone genes cannot be explained by a positive effect on elongation or mRNA processing since histone genes are very short and are intron-less. Moreover, analysis of the RNA-seq data of the 4sU metabolic labeling experiment actually revealed a moderate increase in histone gene transcription upon SPI-21 treatment (Table 4), suggesting that their synthesis during S phase is not affected. To resolve the discrepancy between the effect of Spt5 inhibition on steady-state levels and synthesis rate, the possibility that Spt5 is required for the processing of histone mRNAs was considered. In addition to the conserved stem-loop, histone genes have a canonical polyadenylation signal downstream of the stem-loop structure (FIG. 5B). It was therefore considered that Spt5 controls the choice between 3' end processing via the stem-loop pathway or the polyadenylation pathway of histone pre-mRNAs. To this end, cDNA prepared by random hexamer and Poly-T the ratio between total and poly-A tailed histone genes was determined. As shown in FIG. 5B, relative to control cells, this ratio was significantly reduced, consistent with an increase in the relative amount of Poly-A tailed histone genes upon Spt5 inhibition (FIG. 5B). A similar analysis with RNA extracted from Spt5 KD cells shows the same effect (FIG. 5C). Thus, the reduction in the histone gene expression upon Spt5 inhibition may be associated, at least in part, to a defect in 3' end processing.

TABLE 4

The levels of 20 replication-dependent histone genes following 72-h Spt5 KD, 24-h SPI-21 treatment, and 4sU metabolic labeling.

| | RNA-seq | | |
|---|---|---|---|
| | Spt5 KD | SPI-21 24 h | 4sU labelling |
| HIST1H1B | 0.3 | 0.4 | 1.3 |
| HIST1H1E | 0.4 | 0.5 | 1.3 |
| HIST1H2AG | 0.4 | 0.4 | 1.3 |
| HIST1H2AH | 0.4 | 0.5 | 1.4 |
| HIST1H2AI | 0.3 | 0.5 | 1.4 |
| HIST1H2AK | 0.3 | 0.6 | 1.1 |
| HIST1H2AL | 0.6 | 0.5 | 1.1 |
| HIST1H2BF | 0.4 | 0.5 | 1.3 |
| HIST1H3A | 0.4 | 0.4 | 1.2 |
| HIST1H3B | 0.5 | 0.5 | 1.4 |
| HIST1H3D | 0.4 | 0.4 | 1.4 |
| HIST1H3F | 0.5 | 0.5 | 1.3 |
| HIST1H3G | 0.3 | 0.5 | 1.4 |
| HIST1H4A | 0.4 | 0.5 | 1.7 |
| HIST1H4B | 0.3 | 0.5 | 1.4 |
| HIST1H4C | 0.4 | 0.7 | 1.5 |
| HIST1H4D | 0.3 | 0.5 | 1.6 |
| HIST1H4H | 0.4 | 0.7 | 1.3 |
| HIST2H2AC | 0.6 | 0.5 | 1.3 |
| HIST2H3D | 0.4 | 0.3 | 1.4 |

*Data is a mean of two experiments and was retrieved from a previously published RNA-seq data of which cDNA was generated with random hexamers (Diamant et al., 2016b).

Example 4

The Identified Spt5 Inhibitors Selectively Inhibit Transcription of Mutant Huntingtin Gene Huntington's disease (HD) is an inherited genetic disorder caused by expansion trinucleotide CAG repeats (36 and higher) encoding glutamine (Q) in the huntingtin (Htt) gene. Expression of the mutant gene in neurons of the striatum and the frontal cortex leads to degeneration of neuronal cells that control body movements, emotions and intellect. Previous studies identified Spt4 and Spt5 as important players in promoting the transcription of mutant huntingtin gene (Htt) containing long CAG repeats, but has little effect on short CAG stretches (Cheng et al., 2015; Liu et al., 2012). To examine the potential effect of SPIs in this context, striatal cell lines established from wild type (Q7) or from mutant (Q111) Htt knock-in mice were used. In these cell lines the coding region of the first exon of the mouse Htt gene was replaced with the same region of human wild type (Q7) or mutant (Q111) Htt, as schematically shown in FIG. 6A. The two cell lines were treated for 48 hours with the identified SPIs and following the levels of Htt mRNA were determined. The results revealed that none of the tested SPI decreased the wild type (Q7) mRNA levels; however several SPIs selectively diminished the mutant (Q111) Htt mRNA levels. Notably the effective concentration of SPI-86 and SPI-31 was about 15 fold lower than the concentration needed for these drugs to inhibit expression of the pro-inflammatory genes (FIGS. 3A-D). To examine whether the selective effect on mutant Htt is at the transcription level, metabolic labeling of cellular RNA with 4-thio-uridine (4sU) for 2 hours in the presence of DMSO (vehicle control) or SPI-21 was performed. Analysis of the RNA levels using primers from different regions of the Htt gene (shown in FIG. 6A) revealed that the levels of the newly synthesized Q111 but not Q7 Htt were diminished by SPI-21 and the extent of inhibition was greater compared to SPI-21 effect on steady state levels (FIG. 6C). These results indicate that SPI-21 indeed acts at the level of mRNA transcription. In addition, in control cells the relative levels of the first intron were much lower in Q7 as compared to Q111, suggesting that the splicing efficiency of the longer repeats is lower. Moreover, the levels measured from the second exon relative to the first were fairly higher in Q7 compared to Q111 and this small difference was kept all along the gene. This finding is consistent with a modest reduction in transcription elongation. The reduction in transcription elongation rate and in splicing are also associated with reduced expression levels of the Q111 Htt mRNA as compared to the Q7 (FIG. 6D), and may be the underlying basis for the sensitivity of Q111 to Spt5 inactivation.

Example 5

Intermediate Concluding Remarks

The influence of the different SPIs on various biological activities of Spt5, described in Examples 1-4 hereinabove, is summarized in Table 5 below. From this combined data it is apparent that SPIs can be classified according to their effect on the various Spt5 activities. The first class that includes SPI-21, SPI-86, SPI-29, SPI-74 and SPI-68, affect all the tested Spt5 activities and can be considered as general inhibitors. The second class affects a single activity e.g. SPI-85 and SPI-09 diminished mutant Htt expression but had little or no effect on basal and induced pro-inflammatory gene expression; SPI-39 inhibited only the induced inflammatory gene transcription while SPI-06 predominantly affected proximal promoter pausing. The largest class which includes SPI-17, SPI-157, SPI-46, SPI-57, SPI-16, SPI-42, SPI-06 and SPI-95, did not affect mutant Htt expression but affected the basal and the TNFα-induced pro-inflammatory gene transcription (Table 5). Data obtained for an additional commercially available compound, SPI-48, shown below, is also presented in Table 5.

SPI-48

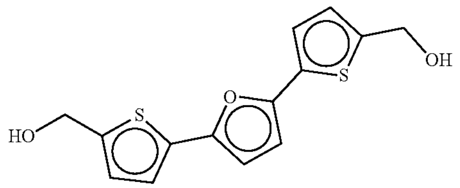

TABLE 5

Summary of the effects of the indicated SPIs

| SPI | Up-regulation of pro-inflammatory genes under basal conditions (i.e. inhibiting proximal promoter pausing of pro-inflammatory genes induced by Spt5)* | Down-regulating transcription of pro-inflammatory genes under TNFα induced conditions (i.e. inhibiting transcription elongation of pro-inflammatory genes induced by Spt5)** | Down-regulating transcription of Mutant Htt (i.e. inhibiting transcription elongation of mutant Htt gene induced by Spt5)*** |
|---|---|---|---|
| SPI-21 | ++ | +++ | + |
| SPI-86 | ++ | +++ | + |
| SPI-29 | ++ | +++ | + |
| SPI-74 | + | ++ | + |
| SPI-68 | + | ++ | + |
| SPI-31 | — | +++ | + |
| SPI-18 | — | + | + |
| SPI-85 | — | — | + |
| SPI-09 | — | — | + |
| SPI-48 | — | — | + |
| SPI-17 | +++ | +++ | — |
| SPI-157 | ++ | +++ | — |
| SPI-16 | ++ | +++ | n.d |
| SPI-46 | + | +++ | — |
| SPI-57 | + | +++ | — |
| SPI-42 | + | ++ | — |
| SPI-06 | ++ | + | — |
| SPI-95 | + | ++ | — |
| SPI-39 | — | +++ | — |

*+++ represent effect >10; ++ >3 and + >1.6.
**+++ represent >80% inhibition; ++ >65% and + >50%.
***+ represent a statistically significant effect.

Example 6

Structural Analogs of Spt5 Inhibitors that Selectively Inhibit Transcription of Mutant Huntingtin Gene In a search for additional selective SPI inhibitors, the present inventors have tested the activity of structural analogs of SPI-31, SPJ-09, SPJ-85 and SPJ-48, which, as shown in Table 5, exhibit a single activity as SPI inhibitors towards inhibiting transcription of Htt gene.

The compounds were tested as described in Example 4 hereinabove. In brief, Q111 (or Q7, where indicated) expressing Striatal cells were treated with the tested compound at the indicated concentrations for 48 hours. Then, RNA was extracted and levels of Htt mRNA were determined by qRT-PCR and normalized to β-actin. The data was analysed using GraphPad Prism software.

In assays conducted for showing that the selective effect on mutant Htt is at the transcription level, the cells were metabolically labeled with 4-thio-uridine (4sU) for 2 hours in the presence of DMSO of the indicated SPI analogs. Then RNA was extracted, biotinylated and the newly synthesized transcripts were isolated with streptavidin magnetic beads. Newly synthesized Htt transcript levels were determined by RT-qPCR.

Table 6 below presents the chemical structures of SPI-09 and of the tested structural analogs thereof. The obtained activity data is shown in FIG. 8A.

TABLE 6

| | |
|---|---|
| SPI-09 | 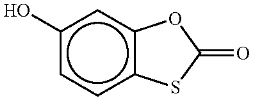 |
| SPI-5201 | 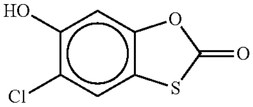 |
| SPI-8928 | 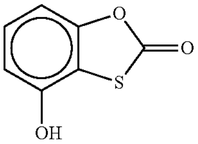 |
| SPI-5483 | 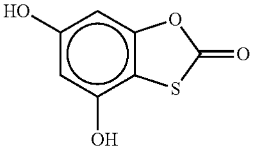 |
| SPI-4745 | 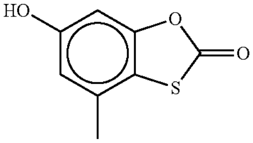 |
| SPI-7144 | 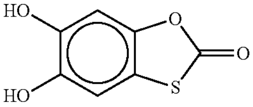 |
| SPI-8292 | 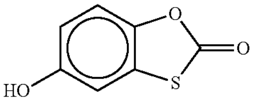 |
| SPI-9271 | 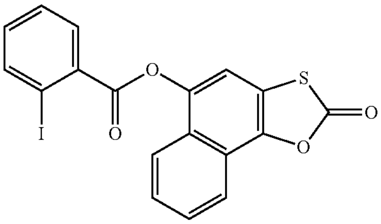 [SMILES: O=C(Oc1cc2sc(=O)oc2c2ccccc12)c1ccccc1I] |

Table 7 below presents the chemical structures of SPI-85 and of the tested structural analogs thereof. The obtained activity data is shown in FIGS. 8B and 9A-D.

TABLE 7

| | |
|---|---|
| SPI-85 | 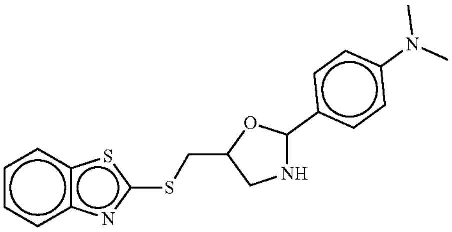 |

TABLE 7-continued

| | |
|---|---|
| SPI-8690 | 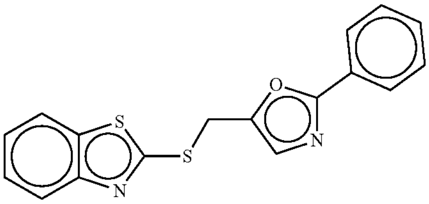 |
| SPI-0324 | 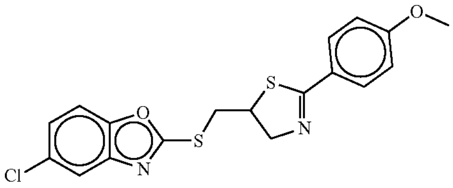 |
| SPI-8708 | 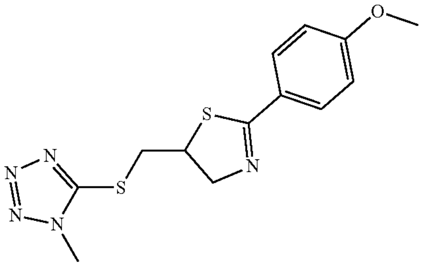 [SMILES: COc1ccc(C2=NCC(CSc3nnnn3C)S2)cc1] |
| SPI-2976 | 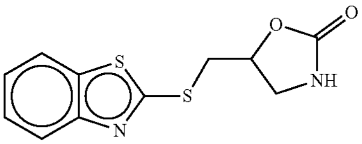 |

Table 8 below presents the chemical structures of SPI-31 and of the tested structural analogs thereof. The obtained activity data is shown in FIGS. 8C and 10A-E.

TABLE 8

| | |
|---|---|
| SPI-31 | 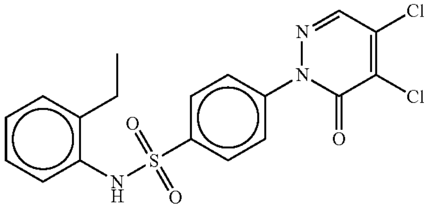 |
| SPI-5726 | 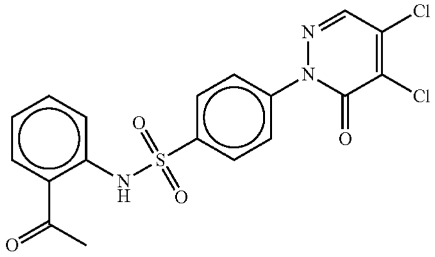 |

TABLE 8-continued

| | |
|---|---|
| SPI-0035 | 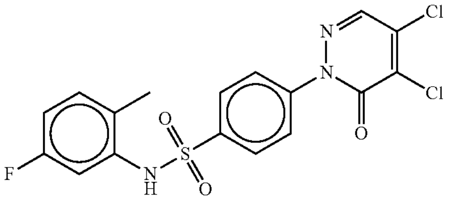 |
| SPI-8916 | 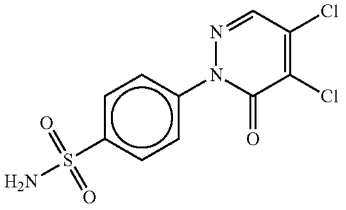 |
| SPI-1477 | 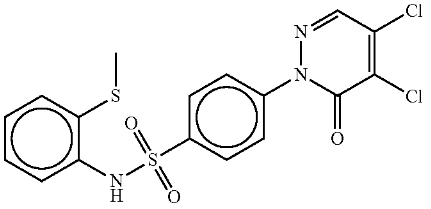 |
| SPI-3440 | 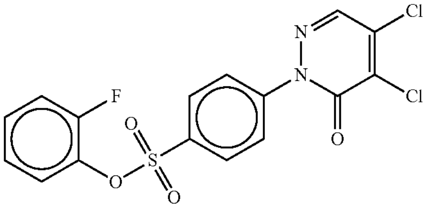 |
| SPI-4516K | 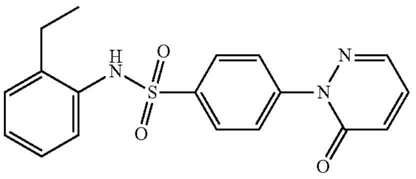 [SMILES: CCc1ccccc1NS(=O)(=O)c1ccc(-n2ncccc2=O)cc1] |

SPI-4516 is a newly designed analog. FIGS. 12A-C present its synthetic scheme, chemical structure and activity.

SPI-4516 was synthesized in two steps as described in FIG. 12B. The first step is a coupling reaction. The second step was performed as follows:

In a micro wave vial was added 4-bromo-N-(2-ethylphenyl) benzenesulfonamide (58 mg, 0.17 mmol), pyridazin-3 (2H)-one (25 mg, 0.26 mmol), $K_2CO_3$ (36.6 mg, 0.27 mmol), quinolin-8-ol (2.4 m, 17 umol) CuCl (1.7 mg, 17 umol) and DMF (2 mL). Then the vial was capped with a crimp cap flushed 3 times with argon and heated in the micro wave reactor (Biotage Initiator) at 140° C. for 14 hours. The reaction mixture was then poured into water (10 mL) and extracted 3 times with EtOAc, the combined organic layers where washed with water and brine then dried on $Na_2SO_4$. The reaction mixture was then concentrated under vacuum and chromatographed using the CombiFlash EZ Prep system, DCM to EtOAc 16 minutes gradient, N-(2-ethylphenyl)-4-(6-oxopyridazin-1(6H)-yl)benzenesulfonamide eluted in 50% EtOAc which was concentrated to give a white solid.

MS (ES): m/z calc ([M+H]=356.1); found (356.3).

$^1$H-NMR (500 MHz, $(CD_3)_2SO$): 9.71 (s, 1H), 8.11 (dd, J=5, 2 Hz, 1H), 7.82-7.78 (m, 4H), 7.52 (dd, J=9, 4 Hz, 1H), 7.24-7.19 (m, 1H), 7.18-7.15 (m, 1H), 7.12-7.07 (m, 2H), 6.91 (dd, J=9, 2 Hz, 1H), 2.52-2.49 (m, 2H1), 0.98 (t, J=8 Hz, 3H).

Table 9 below presents the chemical structures of SPI-48 and of the tested structural analogs thereof. The obtained activity data is shown in FIGS. 8D and 11A-B.

TABLE 9

| | |
|---|---|
| SPI-48 | 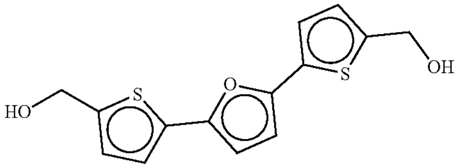 |
| SPI-8108 | 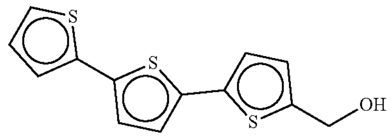 |

FIGS. 13A-E and 14A-B present the data obtained for the selected compounds SPI-31 (also referred to herein interchangeably as SPI-4931), SPI-4516, SPI-8108, SPI-0324 and SPI-1477, demonstrating their efficacy in selectively inhibiting transcription of Htt gene.

Example 7

Effect of SPI Compounds on the Toxicity Driven by polyQ Mutant Htt Protein

The effect of SPI-85, SPI-31, SPI-48 and the structural analogs thereof as described herein in Example 6 is tested using PC-12 stable cell lines bearing inducible Q23-RFP and Q145-RFP, purchased from Coriell Institute for Medical Research.

The cells are incubated for 72 hours with Ponasterone A (25 µM final concentration; ALX-370-014-M001 from ENZO life sciences) together with the different SPIs and their analogs, or DMSO as control (the final concentration of SPI-31 and SPI-1477 is 1 nM, the final concentration of SPI-85, SPI-0324, SPI-48 and SPI-8108 is 0.5 µM). The media that contains the Ponasterone A and the SPIs is refreshed every 24 hours. The effect of the tested compound on the viability of the cells is determined using the CellTiter-Glo® Reagent (G7571, Promega) as indicated in the materials and methods section.

Expression of Q145-RFP but not Q23 should lead to cell death. SPIs rescue, at least partially, the toxic effect of the mutant Htt.

Example 8

In Vivo Studies

The effect of lead SPI compounds in animal models of HD (the full-length 97Q-mHtt transgenic BACHD mouse and matched control is tested in accordance with the protocol described in Aharony I. et al, Human Mol. Gen., 2015.

(i) Determining the Preventive Potential of SPIs.

Healthy and Htt mutant mice (before the disease onset—at the age of 5 weeks) are injected with vehicle or SPIs and mice are monitored for the appearance of disease symptoms (motor performance, depressive-like behavior, basal locomotor activity, Exploratory activity and anxiety-related behavior).

(ii) Determining the Therapeutic Potential of SPIs.

HD mice that started to show symptoms (at the age of 30-36 weeks) are injected with vehicle or SPI. The disease progression is monitored as mentioned above and the ability of SPIs to relieve the symptoms is examined.

(iii) Brain Samples from the Treated Mice are Collected and the Level of Htt mRNA is Determined.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Other References are Cited Throughout the Application

Aida, M., Chen, Y., Nakajima, K., Yamaguchi, Y., Wada, T., and Handa, H. (2006). Transcriptional pausing caused by NELF plays a dual role in regulating immediate-early expression of the junB gene. Mol Cell Biol 26, 6094-6104.

Ainbinder, E., Amir-Zilberstein, L., Yamaguchi, Y., Handa, H., and Dikstein, R. (2004). Elongation inhibition by DRB sensitivity-inducing factor is regulated by the A20 promoter via a novel negative element and NF-kappaB. Mol Cell Biol 24, 2444-2454.

Ainbinder, E., Revach, M., Wolstein, O., Moshonov, S., Diamant, N., and Dikstein, R. (2002). Mechanism of rapid transcriptional induction of tumor necrosis factor alpha-responsive genes by NF-kappaB. Mol Cell Biol 22, 6354-6362.

Amir-Zilberstein, L., Ainbinder, E., Toube, L., Yamaguchi, Y., Handa, H., and Dikstein, R. (2007). Differential regulation of NF-kappaB by elongation factors is determined by core promoter type. Mol Cell Biol 27, 5246-5259.

Amir-Zilberstein, L., and Dikstein, R. (2008). Interplay between E-box and NF-kappaB in regulation of A20 gene by DRB sensitivity-inducing factor (DSIF). The Journal of biological chemistry 283, 1317-1323.

Ashkenazi, S., Plotnikov, A., Bahat, A., Ben-Zeev, E., Warszawski, S., and Dikstein, R. (2016). A Novel Allosteric Mechanism of NF-kappaB Dimerization and DNA Binding Targeted by an Anti-Inflammatory Drug. Mol Cell Biol 36, 1237-1247.

Ashkenazi, S., Plotnikov, A., Bahat, A., and Dikstein, R. (2017). Effective cell-free drug screening protocol for protein-protein interaction. Anal Biochem 532, 53-59.

Bernecky, C., Herzog, F., Baumeister, W., Plitzko, J. M., and Cramer, P. (2016). Structure of transcribing mammalian RNA polymerase II. Nature 529, 551-554.

Blythe, A. J., Yazar-Klosinski, B., Webster, M. W., Chen, E., Vandevenne, M., Bendak, K., Mackay, J. P., Hartzog, G. A., and Vrielink, A. (2016). The yeast transcription elongation factor Spt4/5 is a sequence-specific RNA binding protein. Protein science: a publication of the Protein Society 25, 1710-1721.

Boehm, A. K., Saunders, A., Werner, J., and Lis, J. T. (2003). Transcription factor and polymerase recruitment, modification, and movement on dhsp70 in vivo in the minutes following heat shock. Mol Cell Biol 23, 7628-7637.

Chen, H., Contreras, X., Yamaguchi, Y., Handa, H., Peterlin, B. M., and Guo, S. (2009). Repression of RNA polymerase II elongation in vivo is critically dependent on the C-terminus of Spt5. PloS one 4, e6918.

Cheng, H. M., Chern, Y., Chen, I. H., Liu, C. R., Li, S. H., Chun, S. J., Rigo, F., Bennett, C. F., Deng, N., Feng, Y., et al. (2015). Effects on murine behavior and lifespan of selectively decreasing expression of mutant huntingtin allele by supt4h knockdown. PLoS genetics 11, e1005043.

Crickard, J. B., Fu, J., and Reese, J. C. (2016). Biochemical Analysis of Yeast Suppressor of Ty 4/5 (Spt4/5) Reveals the Importance of Nucleic Acid Interactions in the Prevention of RNA Polymerase II Arrest. The Journal of biological chemistry 291, 9853-9870.

Diamant, G., Amir-Zilberstein, L., Yamaguchi, Y., Handa, H., and Dikstein, R. (2012). DSIF restricts NF-kappaB signaling by coordinating elongation with mRNA processing of negative feedback genes. Cell reports 2, 722-731.

Diamant, G., Bahat, A., and Dikstein, R. (2016a). The elongation factor Spt5 facilitates transcription initiation for rapid induction of inflammatory-response genes. Nat Commun 7, 11547.

Diamant, G., and Dikstein, R. (2013). Transcriptional control by NF-kappaB: elongation in focus. Biochim Biophys Acta 1829, 937-945.

Diamant, G., Eisenbaum, T., Leshkowitz, D., and Dikstein, R. (2016b). Analysis of Subcellular RNA Fractions Revealed a Transcription-Independent Effect of Tumor Necrosis Factor Alpha on Splicing, Mediated by Spt5. Mol Cell Biol 36, 1342-1353.

Emmerson, P. J., Wang, F., Du, Y., Liu, Q., Pickard, R. T., Gonciarz, M. D., Coskun, T., Hamang, M. J., Sindelar, D. K., Ballman, K. K., et al. (2017). The metabolic effects of GDF15 are mediated by the orphan receptor GFRAL. Nat Med 23, 1215-1219.

Fitz, J., Neumann, T., and Pavri, R. (2018). Regulation of RNA polymerase II processivity by Spt5 is restricted to a narrow window during elongation. The EMBO journal 37.

Fujita, T., Piuz, I., and Schlegel, W. (2009). Negative elongation factor NELF controls transcription of immediate early genes in a stimulus-specific manner. Exp Cell Res 315, 274-284.

Gromak, N., West, S., and Proudfoot, N. J. (2006). Pause sites promote transcriptional termination of mammalian RNA polymerase II. Mol Cell Biol 26, 3986-3996.

Henriques, T., Scruggs, B. S., Inouye, M. O., Muse, G. W., Williams, L. H., Burkholder, A. B., Lavender, C. A., Fargo, D. C., and Adelman, K. (2018). Widespread transcriptional pausing and elongation control at enhancers. Genes Dev 32, 26-41.

Hirtreiter, A., Damsma, G. E., Cheung, A. C., Klose, D., Grohmann, D., Vojnic, E., Martin, A. C., Cramer, P., and Werner, F. (2010). Spt4/5 stimulates transcription elongation through the RNA polymerase clamp coiled-coil motif. Nucleic acids research 38, 4040-4051.

Hsu, J. Y., Crawley, S., Chen, M., Ayupova, D. A., Lindhout, D. A., Higbee, J., Kutach, A., Joo, W., Gao, Z., Fu, D., et al. (2017). Non-homeostatic body weight regulation through a brainstem-restricted receptor for GDF15. Nature 550, 255-259.

Ivanov, D., Kwak, Y. T., Guo, J., and Gaynor, R. B. (2000). Domains in the SPT5 protein that modulate its transcriptional regulatory properties. Mol Cell Biol 20, 2970-2983.

Klein, B. J., Bose, D., Baker, K. J., Yusoff, Z. M., Zhang, X., and Murakami, K. S. (2011). RNA polymerase and transcription elongation factor Spt4/5 complex structure. Proceedings of the National Academy of Sciences of the United States of America 108, 546-550.

Komori, T., Inukai, N., Yamada, T., Yamaguchi, Y., and Handa, H. (2009). Role of human transcription elongation factor DSIF in the suppression of senescence and apoptosis. Genes to cells: devoted to molecular & cellular mechanisms 14, 343-354.

Kramer, N. J., Carlomagno, Y., Zhang, Y. J., Almeida, S., Cook, C. N., Gendron, T. F., Prudencio, M., Van Blitterswijk, M., Belzil, V., Couthouis, J., et al. (2016). Spt4 selectively regulates the expression of C9orf72 sense and antisense mutant transcripts. Science 353, 708-712.

Lee, C., Li, X., Hechmer, A., Eisen, M., Biggin, M. D., Venters, B. J., Jiang, C., Li, J., Pugh, B. F., and Gilmour, D. S. (2008). NELF and GAGA factor are linked to promoter-proximal pausing at many genes in *Drosophila*. Mol Cell Biol 28, 3290-3300.

Li, J., and Gilmour, D. S. (2013). Distinct mechanisms of transcriptional pausing orchestrated by GAGA factor and M1BP, a novel transcription factor. The EMBO journal 32, 1829-1841.

Liu, C. R., Chang, C. R., Chern, Y., Wang, T. H., Hsieh, W. C., Shen, W. C., Chang, C. Y., Chu, I. C., Deng, N., Cohen, S. N., et al. (2012). Spt4 is selectively required for transcription of extended trinucleotide repeats. Cell 148, 690-701.

Martinez-Rucobo, F. W., Sainsbury, S., Cheung, A. C., and Cramer, P. (2011). Architecture of the RNA polymerase-Spt4/5 complex and basis of universal transcription processivity. The EMBO journal 30, 1302-1310.

Missra, A., and Gilmour, D. S. (2010). Interactions between DSIF (DRB sensitivity inducing factor), NELF (negative elongation factor), and the *Drosophila* RNA polymerase II transcription elongation complex. Proceedings of the National Academy of Sciences of the United States of America 107, 11301-11306.

Mullican, S. E., Lin-Schmidt, X., Chin, C. N., Chavez, J. A., Furman, J. L., Armstrong, A. A., Beck, S. C., South, V. J., Dinh, T. Q., Cash-Mason, T. D., et al. (2017). GFRAL is the receptor for GDF15 and the ligand promotes weight loss in mice and nonhuman primates. Nat Med 23, 1150-1157.

Narita, T., Yung, T. M., Yamamoto, J., Tsuboi, Y., Tanabe, H., Tanaka, K., Yamaguchi, Y., and Handa, H. (2007). NELF interacts with CBC and participates in 3' end processing of replication-dependent histone mRNAs. Mol Cell 26, 349-365.

Ni, Z., Saunders, A., Fuda, N. J., Yao, J., Suarez, J. R., Webb, W. W., and Lis, J. T. (2008). P-TEFb is critical for the maturation of RNA polymerase II into productive elongation in vivo. Mol Cell Biol 28, 1161-1170.

Pavri, R., Gazumyan, A., Jankovic, M., Di Virgilio, M., Klein, I., Ansarah-Sobrinho, C., Resch, W., Yamane, A., Reina San-Martin, B., Barreto, V., et al. (2010). Activation-induced cytidine deaminase targets DNA at sites of RNA polymerase II stalling by interaction with Spt5. Cell 143, 122-133.

Peng, J., Marshall, N. F., and Price, D. H. (1998). Identification of a cyclin subunit required for the function of *Drosophila* P-TEFb. The Journal of biological chemistry 273, 13855-13860.

Rahl, P. B., Lin, C. Y., Seila, A. C., Flynn, R. A., McCuine, S., Burge, C. B., Sharp, P. A., and Young, R. A. (2010). c-Myc regulates transcriptional pause release. Cell 141, 432-445.

Robson-Dixon, N. D., and Garcia-Blanco, M. A. (2004). MAZ elements alter transcription elongation and silencing of the fibroblast growth factor receptor 2 exon IIIb. The Journal of biological chemistry 279, 29075-29084.

Rougvie, A. E., and Lis, J. T. (1990). Postinitiation transcriptional control in *Drosophila melanogaster*. Mol Cell Biol 10, 6041-6045.

Shetty, A., Kallgren, S. P., Demel, C., Maier, K. C., Spatt, D., Alver, B. H., Cramer, P., Park, P. J., and Winston, F. (2017). Spt5 Plays Vital Roles in the Control of Sense and Antisense Transcription Elongation. Mol Cell 66, 77-88 e75.

Stanlie, A., Begum, N. A., Akiyama, H., and Honjo, T. (2012). The DSIF subunits Spt4 and Spt5 have distinct roles at various phases of immunoglobulin class switch recombination. PLoS genetics 8, e1002675.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.

Tsai, V. W., Zhang, H. P., Manandhar, R., Lee-Ng, K. K. M., Lebhar, H., Marquis, C. P., Husaini, Y., Sainsbury, A., Brown, D. A., and Breit, S. N. (2018). Treatment with the TGF-b superfamily cytokine MIC-1/GDF15 reduces the adiposity and corrects the metabolic dysfunction of mice with diet-induced obesity. Int J Obes (Lond) 42, 561-571.

Wada, T., Takagi, T., Yamaguchi, Y., Ferdous, A., Imai, T., Hirose, S., Sugimoto, S., Yano, K., Hartzog, G. A., Winston, F., et al. (1998a). DSIF, a novel transcription elongation factor that regulates RNA polymerase II processivity, is composed of human Spt4 and Spt5 homologs. Genes Dev 12, 343-356.

Wada, T., Takagi, T., Yamaguchi, Y., Watanabe, D., and Handa, H. (1998b). Evidence that P-TEFb alleviates the negative effect of DSIF on RNA polymerase II-dependent transcription in vitro. The EMBO journal 17, 7395-7403.

Werner, F. (2012). A nexus for gene expression-molecular mechanisms of Spt5 and NusG in the three domains of life. Journal of molecular biology 417, 13-27.

Wu, C. H., Yamaguchi, Y., Benjamin, L. R., Horvat-Gordon, M., Washinsky, J., Enerly, E., Larsson, J., Lambertsson, A., Handa, H., and Gilmour, D. (2003). NELF and DSIF cause promoter proximal pausing on the hsp70 promoter in *Drosophila*. Genes Dev 17, 1402-1414.

Yamada, T., Yamaguchi, Y., Inukai, N., Okamoto, S., Mura, T., and Handa, H. (2006). P-TEFb-mediated phosphorylation of hSpt5 C-terminal repeats is critical for processive transcription elongation. Mol Cell 21, 227-237.

Yamaguchi, Y., Takagi, T., Wada, T., Yano, K., Furuya, A., Sugimoto, S., Hasegawa, J., and Handa, H. (1999a).

NELF, a multisubunit complex containing RD, cooperates with DSIF to repress RNA polymerase II elongation. Cell 97, 41-51.
Yamaguchi, Y., Wada, T., Watanabe, D., Takagi, T., Hasegawa, J., and Handa, H. (1999b). Structure and function of the human transcription elongation factor DSIF. The Journal of biological chemistry 274, 8085-8092.
Yang, L., Chang, C. C., Sun, Z., Madsen, D., Zhu, H., Padkjaer, S. B., Wu, X., Huang, T., Hultman, K., Paulsen, S. J., et al. (2017). GFRAL is the receptor for GDF15 and is required for the anti-obesity effects of the ligand. Nat Med 23, 1158-1166.
Yonaha, M., and Proudfoot, N. J. (1999). Specific transcriptional pausing activates polyadenylation in a coupled in vitro system. Mol Cell 3, 593-600.

What is claimed is:

1. A method of treating a nucleotide repeat disorder in a subject in need thereof, the method comprising administering to the subject a therapeutically effective amount of a compound represented by Formula Ia:

Formula Ia

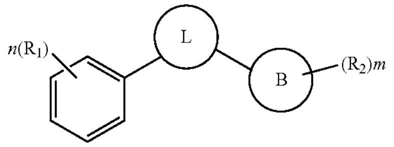

wherein:

n and m are each independently an integer of from 0 to 4;

$R_1$ and $R_2$ are each independently a substituent selected from alkyl, cycloalkyl, aryl, heteroaryl, heteroalicyclic, hydroxy, thiol, alkoxy, thioalkoxy, aryloxy, thioaryloxy, halo, alkyl, amine, amide, nitro, carboxylate and thiocarboxylate;

B is a heteroaryl or a heteroalicyclic; and

L is a linking moiety, comprising from 2 to 12 atoms in length, and comprising a saturated or unsaturated, substituted or unsubstituted hydrocarbon chain, interrupted by at least one S, thereby treating a nucleotide repeat disorder in the subject;

said nucleotide repeat disorder is a trinucleotide repeat disorder selected from Huntington disease, fragile X syndrome, Fragile XE mental retardation, Fragile X-associated tremor/ataxia syndrome, mitotic dystrophy type 1 (DM1), spino-bulbar muscular atrophy (SBMA), Jacobsen syndrome, Spinocerebellar ataxia (SCA) type 1, SCA 2, SCA3 (also known as Machado-Joseph disease), SCA6, SCAT, SCA 7, SCA 8 SCA 12, SCA 17, dentatorubral pallidoluysian atrophy, Friedreich ataxia, Huntington disease-like 2, oculopharyngeal muscular dystrophy, multiple epiphyseal dysplasia, cleidocranial dysplasia, and synpolydactyly.

2. The method of claim 1, wherein L is a substituted, saturated hydrocarbon interrupted by said at least one S, and optionally further interrupted by O.

3. The method of claim 1, wherein the compound inhibits binding of Spt5 to Pol II or changes the conformation of a Spt5-Pol II complex.

4. A method of treating a nucleotide repeat disorder in a subject in need thereof, the method comprising administering to the subject a therapeutically effective amount of a compound selected from the group of compounds presented in Tables 6, 7, 8 and 9-, thereby treating the nucleotide repeat disorder in the subject;

said nucleotide repeat disorder is a trinucleotide repeat disorder selected from Huntington disease, fragile X syndrome, Fragile XE mental retardation, Fragile X-associated tremor/ataxia syndrome, mitotic dystrophy type 1 (DM1), spino-bulbar muscular atrophy (SBMA), Jacobsen syndrome, Spinocerebellar ataxia (SCA) type 1, SCA 2, SCA3 (also known as Machado-Joseph disease), SCA6, SCAT, SCA 7, SCA 8 SCA 12, SCA 17, dentatorubral pallidoluysian atrophy, Friedreich ataxia, Huntington disease-like 2, oculopharyngeal muscular dystrophy, multiple epiphyseal dysplasia, cleidocranial dysplasia, and synpolydactyly.

5. The method of claim 4, wherein said compound inhibits binding of Spt5 to Pol II or changes the conformation of a Spt5-Pol II complex.

6. The method of claim 1, wherein B is an oxazole or a thiazole.

7. The method of claim 1, wherein n is 1 and $R_1$ is an electron-donating group selected from amine, thioalkoxy, and alkoxy.

8. The method of claim 1, wherein said compound is

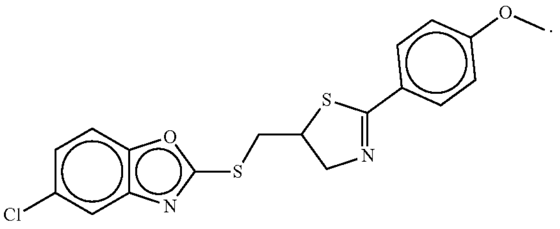

9. The method of claim 1, wherein said trinucleotide repeat disorder is Huntington's disease.

10. The method of claim 4, wherein said trinucleotide repeat disorder is Huntington's disease.

* * * * *

SEQUENCE LISTING

```
<160> NUMBER OF SEQ ID NOS: 95

<210> SEQ ID NO 1
<211> LENGTH: 306
<212> TYPE: PRT
<213> ORGANISM: Artificial sequence
<220> FEATURE:
<223> OTHER INFORMATION: Spt5 NGN  +KOW1 & 2 (175-480aa) amino acid
      sequence

<400> SEQUENCE: 1

Lys Asp Pro Asn Leu Trp Thr Val Lys Cys Lys Ile Gly Glu Glu Arg
1               5                   10                  15

Ala Thr Ala Ile Ser Leu Met Arg Lys Phe Ile Ala Tyr Gln Phe Thr
            20                  25                  30

Asp Thr Pro Leu Gln Ile Lys Ser Val Val Ala Pro Glu His Val Lys
        35                  40                  45

Gly Tyr Ile Tyr Val Glu Ala Tyr Lys Gln Thr His Val Lys Gln Ala
    50                  55                  60

Ile Glu Gly Val Gly Asn Leu Arg Leu Gly Tyr Trp Asn Gln Gln Met
65                  70                  75                  80

Val Pro Ile Lys Glu Met Thr Asp Val Leu Lys Val Val Lys Glu Val
                85                  90                  95

Ala Asn Leu Lys Pro Lys Ser Trp Val Arg Leu Lys Arg Gly Ile Tyr
            100                 105                 110

Lys Asp Asp Ile Ala Gln Val Asp Tyr Val Glu Pro Ser Gln Asn Thr
        115                 120                 125

Ile Ser Leu Lys Met Ile Pro Arg Ile Asp Tyr Asp Arg Ile Lys Ala
    130                 135                 140

Arg Met Ser Leu Lys Asp Trp Phe Ala Lys Arg Lys Lys Phe Lys Arg
145                 150                 155                 160

Pro Pro Gln Arg Leu Phe Asp Ala Glu Lys Ile Arg Ser Leu Gly Gly
                165                 170                 175

Asp Val Ala Ser Asp Gly Asp Phe Leu Ile Phe Glu Gly Asn Arg Tyr
            180                 185                 190

Ser Arg Lys Gly Phe Leu Phe Lys Ser Phe Ala Met Ser Ala Val Ile
        195                 200                 205

Thr Glu Gly Val Lys Pro Thr Leu Ser Glu Leu Glu Lys Phe Glu Asp
    210                 215                 220

Gln Pro Glu Gly Ile Asp Leu Glu Val Val Thr Glu Ser Thr Gly Lys
225                 230                 235                 240

Glu Arg Glu His Asn Phe Gln Pro Gly Asp Asn Val Glu Val Cys Glu
                245                 250                 255

Gly Glu Leu Ile Asn Leu Gln Gly Lys Ile Leu Ser Val Asp Gly Asn
            260                 265                 270

Lys Ile Thr Ile Met Pro Lys His Glu Asp Leu Lys Asp Met Leu Glu
        275                 280                 285

Phe Pro Ala Gln Glu Leu Arg Lys Tyr Phe Lys Met Gly Asp His Val
```

-continued 290 295 300

Lys Val
305

<210> SEQ ID NO 2
<211> LENGTH: 918
<212> TYPE: DNA
<213> ORGANISM: Artificial sequence
<220> FEATURE:
<223> OTHER INFORMATION: Spt5 NGN +KOW1/2 (175-480aa) nucleotide sequence

<400> SEQUENCE: 2
aaggatccca atctgtggac tgtcaaatgt aagattgggg aggaacgggc cacggccatt 60
tccttgatgc gcaagttcat tgcctaccag ttcacagaca cgcccctgca gatcaagtca 120
gtagtggcac cagagcatgt gaagggctac atctacgtgg aggcctacaa gcagacccac 180
gtgaagcagg ccattgaggg ggtgggcaac ctgcggcttg gctactggaa ccagcagatg 240
gtgcccatca aggagatgac agacgtgctc aaagtggtga aggaggtggc caacctgaaa 300
ccaaagtcct gggtccgcct caagcggggc atctacaagg atgacattgc tcaggtggac 360
tacgtggagc ccagccagaa caccatctcc ctgaagatga tcccacgcat cgactacgat 420
cgcatcaagg cccgcatgag cttgaaagac tggtttgcca aaaggaagaa gtttaagcgg 480
cctccacaga ggctgtttga tgctgagaag atcaggtccc tgggggggtga tgttgcctct 540 gatggtgact tcctcatctt tgaggggaac cgttacagcc ggaagggctt tctgttcaag 600
agcttcgcca tgtctgctgt gatcacggag ggtgtgaagc caacactctc tgagctggaa 660
aagtttgagg accagccaga gggcattgac ctggaggtgg tgactgagag cacagggaag 720
gagcgggagc acaacttcca acctggggac aacgtggagg tctgtgaggg tgagctcatc 780
aacctgcagg gcaagatcct cagcgtggat ggcaacaaga tcaccatcat gcccaagcat 840
gaggacctca aggacatgtt ggagttccca gcccaggaac ttagaaaata cttcaagatg 900
ggggaccacg tgaaggtg 918

<210> SEQ ID NO 3
<211> LENGTH: 1635
<212> TYPE: DNA
<213> ORGANISM: Artificial sequence
<220> FEATURE:
<223> OTHER INFORMATION: pRL-Delta-C-spt5 sequence

<400> SEQUENCE: 3
atgacttcga aagtttatga tccagaacaa aggaaacgga tgataactgg tccgcagtgg 60
tgggccagat gtaaacaaat gaatgttctt gattcattta ttaattatta tgattcagaa 120
aaacatgcag aaaatgctgt tattttttta catggtaacg cggcctcttc ttatttatgg 180
cgacatgttg tgccacatat tgagccagta gcgcggtgta ttataccaga ccttattggt 240
atgggcaaat caggcaaatc tggtaatggt tcttataggt tacttgatca ttacaaatat 300
cttactgcat ggtttgaact tcttaattta ccaaagaaga tcatttttgt cggccatgat 360
tggggtgctt gtttggcatt tcattatagc tatgagcatc aagataagat caaagcaata 420
gttcacgctg aaagtgtagt agatgtgatt gaatcatggg atgaatggcc tgatattgaa 480
gaagatattg cgttgatcaa atctgaagaa ggagaaaaaa tggttttgga gaataacttc 540
ttcgtggaaa ccatgttgcc atcaaaaatc atgagaaagt tagaaccaga agaatttgca 600
gcatatcttg aaccattcaa agagaaaggt gaagttcgtc gtccaacatt atcatggcct 660

-continued

```
cgtgaaatcc cgttagtaaa aggtggtggt ggcggaggga gcggtggcgg agggagcaag    720

gatcccaatc tgtggactgt caaatgtaag attggggagg aacgggccac ggccatttcc    780

ttgatgcgca agttcattgc ctaccagttc acagacacgc cctgcagat caagtcagta    840

gtggcaccag agcatgtgaa gggctacatc tacgtggagg cctacaagca gacccacgtg    900

aagcaggcca ttgagggggt gggcaacctg cggcttggct actggaacca gcagatggtg    960

cccatcaagg agatgacaga cgtgctcaaa gtggtgaagg aggtggccaa cctgaaacca   1020

aagtcctggg tccgcctcaa gcggggcatc tacaaggatg acattgctca ggtggactac   1080

gtggagccca gccagaacac catctccctg aagatgatcc cacgcatcga ctacgatcgc   1140

atcaaggccc gcatgagctt gaaagactgg tttgccaaaa ggaagaagtt taagcggcct   1200

ccacagaggc tgtttgatgc tgagaagatc aggtccctgg ggggtgatgt tgcctctgat   1260

ggtgacttcc tcatctttga ggggaaccgt tacagccgga agggctttct gttcaagagc   1320

ttcgccatgt ctgctgtgat cacggagggt gtgaagccaa cactctctga gctggaaaag   1380

tttgaggacc agccagaggg cattgacctg gaggtggtga ctgagagcac agggaaggag   1440

cgggagcaca acttccaacc tggggacaac gtggaggtct gtgagggtga gctcatcaac   1500

ctgcagggca agatcctcag cgtggatggc aacaagatca ccatcatgcc caagcatgag   1560

gacctcaagg acatgttgga gttcccagcc caggaactta gaaaatactt caagatgggg   1620

gaccacgtga aggtg                                                    1635
```

```
<210> SEQ ID NO 4
<211> LENGTH: 363
<212> TYPE: PRT
<213> ORGANISM: Artificial sequence
<220> FEATURE:
<223> OTHER INFORMATION: Pol2 Rpb1 coiled coil domain (8-370aa) amino
      acid sequence

<400> SEQUENCE: 4

Ser Gly Asp Ser Ala Cys Pro Leu Arg Thr Ile Lys Arg Val Gln Phe
1               5                   10                  15

Gly Val Leu Ser Pro Asp Glu Leu Lys Arg Met Ser Val Thr Glu Gly
            20                  25                  30

Gly Ile Lys Tyr Pro Glu Thr Thr Glu Gly Gly Arg Pro Lys Leu Gly
        35                  40                  45

Gly Leu Met Asp Pro Arg Gln Gly Val Ile Glu Arg Thr Gly Arg Cys
    50                  55                  60

Gln Thr Cys Ala Gly Asn Met Thr Glu Cys Pro Gly His Phe Gly His
65                  70                  75                  80

Ile Glu Leu Ala Lys Pro Val Phe His Val Gly Phe Leu Val Lys Thr
                85                  90                  95

Met Lys Val Leu Arg Cys Val Cys Phe Phe Cys Ser Lys Leu Leu Val
            100                 105                 110

Asp Ser Asn Asn Pro Lys Ile Lys Asp Ile Leu Ala Lys Ser Lys Gly
        115                 120                 125

Gln Pro Lys Lys Arg Leu Thr His Val Tyr Asp Leu Cys Lys Gly Lys
    130                 135                 140

Asn Ile Cys Glu Gly Gly Glu Glu Met Asp Asn Lys Phe Gly Val Glu
145                 150                 155                 160

Gln Pro Glu Gly Asp Glu Asp Leu Thr Lys Glu Lys Gly His Gly Gly
                165                 170                 175
```

-continued

```
Cys Gly Arg Tyr Gln Pro Arg Ile Arg Arg Ser Gly Leu Glu Leu Tyr
            180                 185                 190

Ala Glu Trp Lys His Val Asn Glu Asp Ser Gln Glu Lys Lys Ile Leu
        195                 200                 205

Leu Ser Pro Glu Arg Val His Glu Ile Phe Lys Arg Ile Ser Asp Glu
    210                 215                 220

Glu Cys Phe Val Leu Gly Met Glu Pro Arg Tyr Ala Arg Pro Glu Trp
225                 230                 235                 240

Met Ile Val Thr Val Leu Pro Val Pro Pro Leu Ser Val Arg Pro Ala
                245                 250                 255

Val Val Met Gln Gly Ser Ala Arg Asn Gln Asp Asp Leu Thr His Lys
            260                 265                 270

Leu Ala Asp Ile Val Lys Ile Asn Asn Gln Leu Arg Arg Asn Glu Gln
        275                 280                 285

Asn Gly Ala Ala Ala His Val Ile Ala Glu Asp Val Lys Leu Leu Gln
    290                 295                 300

Phe His Val Ala Thr Met Val Asp Asn Glu Leu Pro Gly Leu Pro Arg
305                 310                 315                 320

Ala Met Gln Lys Ser Gly Arg Pro Leu Lys Ser Leu Lys Gln Arg Leu
                325                 330                 335

Lys Gly Lys Glu Gly Arg Val Arg Gly Asn Leu Met Gly Lys Arg Val
            340                 345                 350

Asp Phe Ser Ala Arg Thr Val Ile Thr Pro Asp
        355                 360


<210> SEQ ID NO 5
<211> LENGTH: 1089
<212> TYPE: DNA
<213> ORGANISM: Artificial sequence
<220> FEATURE:
<223> OTHER INFORMATION: Pol2 Rpb1 coiled coil domain (8-370aa)
      nucleotide sequence

<400> SEQUENCE: 5

tcgggggaca gcgcatgccc gctgcgcacc atcaagagag tccagttcgg agtcctgagt      60

ccggatgaac tgaagcgaat gtctgtgacg gagggtggca tcaaataccc agagacgact     120

gagggaggcc gccccaagct tgggggggctg atggacccga ggcagggggt gattgagcgg     180

actggccgct gccaaacatg tgcaggaaac atgacagagt gtcctggcca ctttggccac     240

attgaactgg ccaagcctgt gtttcacgtg ggcttcctgg tgaagacaat gaaagttttg     300

cgctgtgtct gcttcttctg ctccaaactg cttgtggact ctaacaaccc aaagatcaag     360

gatatcctgg ctaagtccaa gggacagccc aagaagcggc tcacacatgt ctacgacctt     420

tgcaagggca aaaacatatg cgagggtggg gaggagatgg acaacaagtt cggtgtggaa     480

caacctgagg gtgacgagga tctgaccaaa gaaaagggcc atggtggctg tgggcggtac     540

cagcccagga tccggcgttc tggcctagag ctgtatgcgg aatggaagca cgttaatgag     600

gactctcagg agaagaagat cctgctgagt ccagagcgag tgcatgagat cttcaaacgc     660

atctcagatg aggagtgttt tgtgctgggc atggagcccc gctatgcacg gccagagtgg     720

atgattgtca cagtgctgcc tgtgcccccg ctctccgtgc ggcctgctgt tgtgatgcag     780

ggctctgccc gtaaccagga tgacctgact cacaaactgg ctgacatcgt gaagatcaac     840

aatcagctgc ggcgcaatga gcagaacggc gcagcggccc atgtcattgc agaggatgtg     900

aagctcctcc agttccatgt ggccaccatg gtggacaatg agctgcctgg cttgccccgt     960
```

```
gccatgcaga agtctgggcg tcccctcaag tccctgaagc agcggttgaa gggcaaggaa   1020

ggccgggtgc gagggaacct gatgggcaaa agagtggact tctcggcccg tactgtcatc   1080

acccccgac                                                           1089


<210> SEQ ID NO 6
<211> LENGTH: 1809
<212> TYPE: DNA
<213> ORGANISM: Artificial sequence
<220> FEATURE:
<223> OTHER INFORMATION: Pol2-pRL-Delta N sequence

<400> SEQUENCE: 6

atgtcggggg acagcgcatg cccgctgcgc accatcaaga gagtccagtt cggagtcctg     60

agtccggatg aactgaagcg aatgtctgtg acggagggtg gcatcaaata cccagagacg    120

actgagggag gccgccccaa gcttgggggg ctgatggacc cgaggcaggg ggtgattgag    180

cggactggcc gctgccaaac atgtgcagga aacatgacag agtgtcctgg ccactttggc    240

cacattgaac tggccaagcc tgtgtttcac gtgggcttcc tggtgaagac aatgaaagtt    300

ttgcgctgtg tctgcttctt ctgctccaaa ctgcttgtgg actctaacaa cccaaagatc    360

aaggatatcc tggctaagtc caagggacag cccaagaagc ggctcacaca tgtctacgac    420

ctttgcaagg gcaaaaacat atgcgagggt ggggaggaga tggacaacaa gttcggtgtg    480

gaacaacctg agggtgacga ggatctgacc aaagaaaagg gccatggtgg ctgtgggcgg    540

taccagccca ggatccggcg ttctggccta gagctgtatg cggaatggaa gcacgttaat    600

gaggactctc aggagaagaa gatcctgctg agtccagagc gagtgcatga gatcttcaaa    660

cgcatctcag atgaggagtg ttttgtgctg ggcatggagc ccgctatgc acggccagag    720

tggatgattg tcacagtgct gcctgtgccc ccgctctccg tgcggcctgc tgttgtgatg    780

cagggctctg cccgtaacca ggatgacctg actcacaaac tggctgacat cgtgaagatc    840

aacaatcagc tgcggcgcaa tgagcagaac ggcgcagcgg cccatgtcat tgcagaggat    900

gtgaagctcc tccagttcca tgtggccacc atggtggaca atgagctgcc tggcttgccc    960

cgtgccatgc agaagtctgg gcgtcccctc aagtccctga agcagcggtt gaagggcaag   1020

gaaggccggg tgcgagggaa cctgatgggc aaaagagtgg acttctcggc ccgtactgtc   1080

atcacccccg acggtggcgg agggagcggt ggcggaggga gcatgacttc gaaagtttat   1140

gatccagaac aaaggaaacg gatgataact ggtccgcagt ggtgggccag atgtaaacaa   1200

atgaatgttc ttgattcatt tattaattat tatgattcag aaaaacatgc agaaaatgct   1260

gttatttttt tacatggtaa cgcggcctct tcttatttat ggcgacatgt tgtgccacat   1320

attgagccag tagcgcggtg tattatacca gaccttattg gtatgggcaa atcaggcaaa   1380

tctggtaatg gttcttatag gttacttgat cattacaaat atcttactgc atggtttgaa   1440

cttcttaatt taccaaagaa gatcattttt gtcggccatg attggggtgc ttgtttggca   1500

tttcattata gctatgagca tcaagataag atcaaagcaa tagttcacgc tgaaagtgta   1560

gtagatgtga ttgaatcatg ggatgaatgg cctgatattg aagaagatat tgcgttgatc   1620

aaatctgaag aaggagaaaa aatggttttg gagaataact tcttcgtgga aaccatgttg   1680

ccatcaaaaa tcatgagaaa gttagaacca gaagaatttg cagcatatct tgaaccattc   1740

aaagagaaag gtgaagttcg tcgtccaaca ttatcatggc ctcgtgaaat cccgttagta   1800

aaaggtggt                                                           1809
```

-continued

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
taaccccatc atcagcggac 20

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 8
agctccaaaa caaaaacagc aa 22

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
cagaggaacg ccactatccc 20

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
actgagttca aaacgcccca 20

<210> SEQ ID NO 11
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 11
ggagggggtt gaggtgtt 18

<210> SEQ ID NO 12
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 12
gtgtgcactt ttattggtct caa 23

<210> SEQ ID NO 13
<211> LENGTH: 21
<212> TYPE: DNA
<213> ORGANISM: Artificial sequence
<220> FEATURE:
<223> OTHER INFORMATION: Single strand DNA oligonucleotide -continued

<400> SEQUENCE: 13
ccatgtcgct tgtgtccttt c 21

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
cttgcaaggc tgagctgacg 20

<210> SEQ ID NO 15
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 15
cctccatctt ctatctgagc ctg 23

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16
ccatgtcgct tgtgtccttt c 21

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
ctcagtctag tcgggcaggt 20

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
ccacaggcag gattctcaca 20

<210> SEQ ID NO 19
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 19
tctgactctg actttgtgcc a 21

<210> SEQ ID NO 20
<211> LENGTH: 21

<212> TYPE: DNA
<213> ORGANISM: Artificial sequence
<220> FEATURE:
<223> OTHER INFORMATION: Single strand DNA oligonucleotide

<400> SEQUENCE: 20
ttctctccag tcacaagcag c 21

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
gaaggaactc tcagccacca 20

<210> SEQ ID NO 22
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 22
agactgtgcc acaatgtttt cac 23

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
cagaaactct tgggcatcgc 20

<210> SEQ ID NO 24
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 24
ttgatgactt tgttgaggca ct 22

<210> SEQ ID NO 25
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 25
gggcccaaga tggctgag 18

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
accctgaaga cttggagcct 20

<210> SEQ ID NO 27
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 27
caaatgtggg attttcccat gagt 24

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 28
cagggctaag gatttcctgc 20

<210> SEQ ID NO 29
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 29
gtacctccag aacagatttg agagt 25

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
gcaggaactg gatcaggact 20

<210> SEQ ID NO 31
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 31
aatggaaagt ggctatgcag t 21

<210> SEQ ID NO 32
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 32
tagccattta tttgaggtaa gcct 24

<210> SEQ ID NO 33
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 33
acttcgcagc ccgacc 16

<210> SEQ ID NO 34
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 34
ctgggggtgt gatctctctt g 21

<210> SEQ ID NO 35
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 35
gtggcgaaga gccctaagaa 20

<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36
tggcctttgc agctttaggt 20

<210> SEQ ID NO 37
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 37
tgctcggaag tctactggtg 20

<210> SEQ ID NO 38
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 38
ccaggcgctg gaaaggtag 19

<210> SEQ ID NO 39
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 39
tggccatccg caacgatga 19

-continued

<210> SEQ ID NO 40
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 40
cttctacttg cccttcgcct tgt 23

<210> SEQ ID NO 41
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 41
ggtgttctga aggtgttcct g 21

<210> SEQ ID NO 42
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 42
ttagccaccg aagccgtaaa 20

<210> SEQ ID NO 43
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 43
ctcgagtggt ccggcg 16

<210> SEQ ID NO 44
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 44
acgatggtga gcagcagaaa 20

<210> SEQ ID NO 45
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 45
ctgagctgaa cgggaagctc 20

<210> SEQ ID NO 46
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 46
cacctggtgc tcagtgtagc 20

<210> SEQ ID NO 47
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 47
gctggcaact ggagtctctc 20

<210> SEQ ID NO 48
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 48
ttgtcccatt catcattcca 20

<210> SEQ ID NO 49
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 49
tccttttcag gtgttggaga gc 22

<210> SEQ ID NO 50
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 50
ccgtatcttc acagctttcc g 21

<210> SEQ ID NO 51
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 51
acaaactcct gaaaccgagc 20

<210> SEQ ID NO 52
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 52
aagaggcgag cttgagagac 20

<210> SEQ ID NO 53

-continued

<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 53
catccaaagt gtgaaggtga ag 22

<210> SEQ ID NO 54
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 54
gctttctgcc cattcttgag 20

<210> SEQ ID NO 55
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 55
accaggactt gggactttgc 20

<210> SEQ ID NO 56
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 56
aggagcgctg caaaaccaac 20

<210> SEQ ID NO 57
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 57
tcttctcctc ctttctgtcc 20

<210> SEQ ID NO 58
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 58
tgagatttga gagactccag 20

<210> SEQ ID NO 59
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 59
ctggctcata gactgcaatg 20

<210> SEQ ID NO 60
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 60
tgaggtgctt tgtgtggttc 20

<210> SEQ ID NO 61
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 61
gctctgtgtg aaggtgcagt 20

<210> SEQ ID NO 62
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 62
tctgtgttgg cgcagtgt 18

<210> SEQ ID NO 63
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 63
catgtgtgaa agcagcaaag a 21

<210> SEQ ID NO 64
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 64
cctcaaactc caaaagacca gt 22

<210> SEQ ID NO 65
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 65
gagtttgctc ctggctgct 19

<210> SEQ ID NO 66
<211> LENGTH: 21
<212> TYPE: DNA

<213> ORGANISM: Artificial sequence
<220> FEATURE:
<223> OTHER INFORMATION: Single strand DNA oligonucleotide

<400> SEQUENCE: 66
gttgcttgct gcttctgatt c 21

<210> SEQ ID NO 67
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 67
agcggtggcg gagggagcaa ggatcccaat ctgtggac 38

<210> SEQ ID NO 68
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 68
gaagcggccg ctctagaatt acaccttcac gtggtccccc atc 43

<210> SEQ ID NO 69
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 69
ctcactatag gctagccacc atggagcgag tgcatgagat cttc 44

<210> SEQ ID NO 70
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 70
caccgctccc tccgccaccg tcgggggtga tgacagtac 39

<210> SEQ ID NO 71
<211> LENGTH: 52
<212> TYPE: DNA
<213> ORGANISM: Artificial sequence
<220> FEATURE:
<223> OTHER INFORMATION: Single strand DNA oligonucleotide

<400> SEQUENCE: 71
catcaccatc atcaccacag ccaggatccg atgacttcga aagtttatga tc 52

<210> SEQ ID NO 72
<211> LENGTH: 51
<212> TYPE: DNA
<213> ORGANISM: Artificial sequence
<220> FEATURE:
<223> OTHER INFORMATION: Single strand DNA oligonucleotide

<400> SEQUENCE: 72
tcgacttaag cattatgcgg ccgcaagctt ctaggtcttt atagctgtgt c 51

<210> SEQ ID NO 73
<211> LENGTH: 55
<212> TYPE: DNA
<213> ORGANISM: Artificial sequence
<220> FEATURE:
<223> OTHER INFORMATION: Single strand DNA oligonucleotide

<400> SEQUENCE: 73
attagttaag tataagaagg agatatacat atgtcggggg acagcgcatg cccgc 55

<210> SEQ ID NO 74
<211> LENGTH: 51
<212> TYPE: DNA
<213> ORGANISM: Artificial sequence
<220> FEATURE:
<223> OTHER INFORMATION: Single strand DNA oligonucleotide

<400> SEQUENCE: 74
cgcagcagcg gtttctttac cagactcgag ttattgttca tttttgagaa c 51

<210> SEQ ID NO 75
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 75
gatgggggac cacgtgaagg tgggtggcgg agggagcggt g 41

<210> SEQ ID NO 76
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 76
gaagcggccg ctctagaact aggtctttat agctgtgtc 39

<210> SEQ ID NO 77
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 77
catcaccaca gccaggatcc gatgaaggat cccaatctgt ggac 44

<210> SEQ ID NO 78
<211> LENGTH: 51
<212> TYPE: DNA
<213> ORGANISM: Artificial sequence
<220> FEATURE:
<223> OTHER INFORMATION: Single strand DNA oligonucleotide

<400> SEQUENCE: 78
tcgacttaag cattatgcgg ccgcaagctt ctaggtcttt atagctgtgt c 51

<210> SEQ ID NO 79
<211> LENGTH: 55
<212> TYPE: DNA
<213> ORGANISM: Artificial sequence
<220> FEATURE:

<223> OTHER INFORMATION: Single strand DNA oligonucleotide

<400> SEQUENCE: 79
attagttaag tataagaagg agatatacat atgtcggggg acagcgcatg cccgc 55

<210> SEQ ID NO 80
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 80
gcagcggttt ctttaccaga ctcgagttag tcgggggtga tgacagtacg 50

<210> SEQ ID NO 81
<211> LENGTH: 1305
<212> TYPE: DNA
<213> ORGANISM: Artificial Sequence
<220> FEATURE:
<223> OTHER INFORMATION: Spt5-Spt4 fusion sequence

<400> SEQUENCE: 81
atgaaggatc ccaatctgtg gactgtcaaa tgtaagattg gggaggaacg ggccacggcc 60
atttccttga tgcgcaagtt cattgcctac cagttcacag acacgcccct gcagatcaag 120
tcagtagtgg caccagagca tgtgaagggc tacatctacg tggaggccta caagcagacc 180
cacgtgaagc aggccattga gggggtgggc aacctgcggc ttggctactg gaaccagcag 240
atggtgccca tcaaggagat gacagacgtg ctcaaagtgg tgaaggaggt ggccaacctg 300
aaaccaaagt cctgggtccg cctcaagcgg ggcatctaca aggatgacat tgctcaggtg 360
gactacgtgg agcccagcca gaacaccatc tccctgaaga tgatcccacg catcgactac 420
gatcgcatca aggcccgcat gagcttgaaa gactggtttg ccaaaaggaa gaagtttaag 480
cggcctccac agaggctgtt tgatgctgag aagatcaggt ccctgggggg tgatgttgcc 540
tctgatggtg acttcctcat ctttgagggg aaccgttaca gccggaaggg ctttctgttc 600
aagagcttcg ccatgtctgc tgtgatcacg gagggtgtga agccaacact ctctgagctg 660
gaaaagtttg aggaccagcc agagggcatt gacctggagg tggtgactga gagcacaggg 720
aaggagcggg agcacaactt ccaacctggg gacaacgtgg aggtctgtga gggtgagctc 780
atcaacctgc agggcaagat cctcagcgtg gatggcaaca agatcaccat catgcccaag 840
catgaggacc tcaaggacat gttggagttc ccagcccagg aacttagaaa atacttcaag 900
atgggggacc acgtgaaggt gggtggcgga gggagcggtg gcggagggag catggccctg 960
gagacggtgc cgaaggacct gcggcatctg cgggcctgtt tgctgtgttc gctggtcaag 1020
actatagacc agtttgaata tgatggttgt gacaattgtg atgcatatct acaaatgaag 1080
ggtaaccgag agatggtata tgactgcact agctcttcct ttgatggaat cattgcgatg 1140
atgagtccag aggacagctg ggtctccaag tggcagcgag tcagtaactt taagccaggt 1200
gtatatgcgg tgtcagtcac tggtcgcctg ccccaaggaa tcgtgcggga gctgaaaagt 1260
cgaggagtgg cctacaaatc cagagacaca gctataaaga cctag 1305

<210> SEQ ID NO 82
<211> LENGTH: 8
<212> TYPE: DNA
<213> ORGANISM: Artificial sequence
<220> FEATURE:
<223> OTHER INFORMATION: regulatory motif sequence

<400> SEQUENCE: 82 gggaggrr 8

<210> SEQ ID NO 83
<211> LENGTH: 6
<212> TYPE: DNA
<213> ORGANISM: Artificial sequence
<220> FEATURE:
<223> OTHER INFORMATION: regulatory motif sequence

<400> SEQUENCE: 83 caggtg 6

<210> SEQ ID NO 84
<211> LENGTH: 6
<212> TYPE: DNA
<213> ORGANISM: Artificial sequence
<220> FEATURE:
<223> OTHER INFORMATION: regulatory motif sequence

<400> SEQUENCE: 84 tggaaa 6

<210> SEQ ID NO 85
<211> LENGTH: 6
<212> TYPE: DNA
<213> ORGANISM: Artificial sequence
<220> FEATURE:
<223> OTHER INFORMATION: regulatory motif sequence

<400> SEQUENCE: 85 aacttt 6

<210> SEQ ID NO 86
<211> LENGTH: 7
<212> TYPE: DNA
<213> ORGANISM: Artificial sequence
<220> FEATURE:
<223> OTHER INFORMATION: regulatory motif sequence
<220> FEATURE:
<221> NAME/KEY: misc_feature
<222> LOCATION: (4)..(4)
<223> OTHER INFORMATION: n is a, c, g, or t

<400> SEQUENCE: 86 tgantca 7

<210> SEQ ID NO 87
<211> LENGTH: 7
<212> TYPE: DNA
<213> ORGANISM: Artificial sequence
<220> FEATURE:
<223> OTHER INFORMATION: regulatory motif sequence

<400> SEQUENCE: 87 gggcggr 7

<210> SEQ ID NO 88
<211> LENGTH: 6
<212> TYPE: DNA
<213> ORGANISM: Artificial sequence
<220> FEATURE:
<223> OTHER INFORMATION: regulatory motif sequence

<400> SEQUENCE: 88 ttgttt 6

<210> SEQ ID NO 89
<211> LENGTH: 6
<212> TYPE: DNA
<213> ORGANISM: Artificial sequence
<220> FEATURE:
<223> OTHER INFORMATION: regulatory motif sequence

<400> SEQUENCE: 89 tataaa 6

<210> SEQ ID NO 90
<211> LENGTH: 6
<212> TYPE: DNA
<213> ORGANISM: Artificial sequence
<220> FEATURE:
<223> OTHER INFORMATION: regulatory motif sequence

<400> SEQUENCE: 90 ctttgt 6

<210> SEQ ID NO 91
<211> LENGTH: 7
<212> TYPE: DNA
<213> ORGANISM: Artificial sequence
<220> FEATURE:
<223> OTHER INFORMATION: regulatory motif sequence

<400> SEQUENCE: 91 rtaaaca 7

<210> SEQ ID NO 92
<211> LENGTH: 7
<212> TYPE: DNA
<213> ORGANISM: Artificial sequence
<220> FEATURE:
<223> OTHER INFORMATION: regulatory motif sequence
<220> FEATURE:
<221> NAME/KEY: misc_feature
<222> LOCATION: (4)..(4)
<223> OTHER INFORMATION: n is a, c, g, or t

<400> SEQUENCE: 92 ttantca 7

<210> SEQ ID NO 93
<211> LENGTH: 7
<212> TYPE: DNA
<213> ORGANISM: Artificial sequence
<220> FEATURE:
<223> OTHER INFORMATION: regulatory motif sequence

<400> SEQUENCE: 93 tgtttgy 7

<210> SEQ ID NO 94
<211> LENGTH: 8
<212> TYPE: DNA
<213> ORGANISM: Artificial sequence
<220> FEATURE:
<223> OTHER INFORMATION: regulatory motif sequence

<400> SEQUENCE: 94 gggtggrr 8

-continued

```
<210> SEQ ID NO 95
<211> LENGTH: 6
<212> TYPE: DNA
<213> ORGANISM: Artificial sequence
<220> FEATURE:
<223> OTHER INFORMATION: regulatory motif sequence

<400> SEQUENCE: 95

cacgtg                                                                  6
```